(12) United States Patent
Jordan et al.

(10) Patent No.: US 10,932,710 B2
(45) Date of Patent: Mar. 2, 2021

(54) CARRIERS FOR STORAGE AND TRANSPORT OF BIOLOGICAL SAMPLES

(71) Applicant: Drawbridge Health, Inc., San Diego, CA (US)

(72) Inventors: Brett L. Jordan, San Francisco, CA (US); Masao Drexel, Mountain View, CA (US); Dagmar Beyerlein, San Francisco, CA (US); Alicia Jackson, Menlo Park, CA (US); Kara Juneau, Palo Alto, CA (US)

(73) Assignee: Drawbridge Health, Inc., San Diego, CA (US)

( * ) Notice: Subject to any disclaimer, the term of this patent is extended or adjusted under 35 U.S.C. 154(b) by 0 days.

(21) Appl. No.: 16/685,893

(22) Filed: Nov. 15, 2019

(65) Prior Publication Data
US 2020/0164362 A1 May 28, 2020

Related U.S. Application Data

(63) Continuation of application No. 16/104,846, filed on Aug. 17, 2018, now Pat. No. 10,638,963, which is a (Continued)

(51) Int. Cl.
*A61B 5/15* (2006.01)
*A61B 5/151* (2006.01)
(Continued)

(52) U.S. Cl.
CPC .... *A61B 5/150099* (2013.01); *A61B 5/15016* (2013.01); *A61B 5/150022* (2013.01);
(Continued)

(58) Field of Classification Search
CPC ................ B01L 3/508; B01L 2200/18; B01L 2300/021; B01L 2300/06;
(Continued)

(56) References Cited

U.S. PATENT DOCUMENTS 3,623,475 A 11/1971 Sanz et al.
3,645,692 A 2/1972 Stork et al.
(Continued)

FOREIGN PATENT DOCUMENTS

CN 1278649 C 10/2006
CN 101203177 B 5/2010
(Continued)

OTHER PUBLICATIONS

BEGOLO, et al. A microfluidic device for dry sample preservation in remote settings. Lab Chip, 2013,13, 4331-4342, published Sep. 17, 2013.
(Continued)

*Primary Examiner* — Dennis White
(74) *Attorney, Agent, or Firm* — Wilson Sonsini Goodrich & Rosati

(57) ABSTRACT

Disclosed herein are devices, apparatus, systems, methods and kits for collecting and storing a fluid sample from a subject. A device for collecting the fluid sample can include a housing comprising a recess having an opening, a vacuum chamber in the housing and in fluidic communication with the recess, and one or more piercing elements that are extendable through the opening to penetrate skin of the subject. The vacuum chamber can be configured for having a vacuum that draws the skin into the recess. The recess can be configured having a size or shape that enables an increased volume of the fluid sample to be accumulated in the skin drawn into the recess.

28 Claims, 64 Drawing Sheets

Related U.S. Application Data continuation of application No. PCT/US2018/013223, filed on Jan. 10, 2018.

(60) Provisional application No. 62/444,764, filed on Jan. 10, 2017, provisional application No. 62/468,906, filed on Mar. 8, 2017.

(51) Int. Cl.
| | |
|---|---|
| *B01L 3/00* | (2006.01) |
| *B01L 3/02* | (2006.01) |
| *G01N 33/487* | (2006.01) |
| *G01N 33/543* | (2006.01) |
| *G01N 35/00* | (2006.01) |

(52) U.S. Cl.
CPC ...... *A61B 5/15113* (2013.01); *A61B 5/15117* (2013.01); *A61B 5/15142* (2013.01); *A61B 5/150251* (2013.01); *A61B 5/150305* (2013.01); *A61B 5/150343* (2013.01); *A61B 5/150427* (2013.01); *A61B 5/150442* (2013.01); *A61B 5/150977* (2013.01); *A61B 5/150984* (2013.01); *B01L 3/0296* (2013.01); *B01L 3/508* (2013.01); *B01L 3/5023* (2013.01); *G01N 33/487* (2013.01); *G01N 33/54386* (2013.01); *G01N 35/00732* (2013.01); *A61B 5/1513* (2013.01); *A61B 5/150236* (2013.01); *A61B 5/150244* (2013.01); *A61B 5/150503* (2013.01); *A61B 5/150969* (2013.01); *B01L 2200/026* (2013.01); *B01L 2200/18* (2013.01); *B01L 2300/021* (2013.01); *B01L 2300/041* (2013.01); *B01L 2300/06* (2013.01); *B01L 2300/0609* (2013.01); *B01L 2300/0825* (2013.01); *B01L 2300/0864* (2013.01); *B01L 2400/0406* (2013.01); *B01L 2400/049* (2013.01)

(58) Field of Classification Search
CPC ....... B01L 2300/0609; B01L 2300/041; B01L 3/0296; B01L 3/5023; B01L 2300/0825; B01L 2200/026; B01L 2400/0406; B01L 2400/049; B01L 2300/0864; G01N 33/487; G01N 33/54386; G01N 35/00732; A61B 5/150099; A61B 5/15016; A61B 5/150251; A61B 5/150977; A61B 5/15113; A61B 5/150442; A61B 5/150305; A61B 5/15142; A61B 5/150984; A61B 5/150427; A61B 5/150343; A61B 5/150022; A61B 5/15117; A61B 5/150503; A61B 5/150236; A61B 5/150244; A61B 5/1513; A61B 5/150969

See application file for complete search history.

(56) References Cited

U.S. PATENT DOCUMENTS

| | | |
|---|---|---|
| 4,257,426 A | 3/1981 | Bailey |
| 4,972,843 A | 11/1990 | Broden |
| 5,141,850 A | 8/1992 | Cole et al. |
| 5,252,489 A | 10/1993 | Macri |
| 5,320,607 A | 6/1994 | Ishibashi |
| 5,494,646 A | 2/1996 | Seymour |
| 5,496,562 A | 3/1996 | Burgoyne |
| 5,636,640 A | 6/1997 | Staehlin |
| 5,662,127 A | 9/1997 | De Vaughn |
| 5,680,872 A | 10/1997 | Sesekura et al. |
| 5,701,910 A | 12/1997 | Powles et al. |
| 5,709,699 A | 1/1998 | Warner |
| 5,725,774 A | 3/1998 | Neyer |
| 5,756,126 A | 5/1998 | Burgoyne |
| 5,807,527 A | 9/1998 | Burgoyne |
| 5,906,742 A | 5/1999 | Wang et al. |
| 5,938,679 A | 8/1999 | Freeman et al. |
| 5,939,259 A | 8/1999 | Harvey et al. |
| 5,951,582 A | 9/1999 | Thorne et al. |
| 5,971,941 A | 10/1999 | Simons et al. |
| 5,972,386 A | 10/1999 | Burgoyne |
| 5,984,940 A | 11/1999 | Davis et al. |
| 5,985,327 A | 11/1999 | Burgoyne |
| 6,004,278 A | 12/1999 | Botich et al. |
| 6,036,659 A | 3/2000 | Ray et al. |
| 6,036,924 A | 3/2000 | Simons et al. |
| 6,063,039 A | 5/2000 | Cunningham et al. |
| 6,093,156 A | 7/2000 | Cunningham et al. |
| 6,132,449 A | 10/2000 | Lum et al. |
| 6,152,942 A | 11/2000 | Brenneman et al. |
| 6,155,992 A | 12/2000 | Henning et al. |
| 6,261,245 B1 | 7/2001 | Kawai et al. |
| 6,283,926 B1 | 9/2001 | Cunningham et al. |
| 6,309,887 B1 | 10/2001 | Ray |
| 6,332,871 B1 | 12/2001 | Douglas et al. |
| 6,334,856 B1 | 1/2002 | Allen et al. |
| 6,340,354 B1 | 1/2002 | Rambin |
| 6,419,661 B1 | 7/2002 | Kuhr et al. |
| 6,485,439 B1 | 11/2002 | Roe et al. |
| 6,506,168 B1 | 1/2003 | Fathallah et al. |
| 6,558,361 B1 | 5/2003 | Yeshurun |
| 6,591,124 B2 | 7/2003 | Sherman et al. |
| 6,602,718 B1 | 8/2003 | Augello et al. |
| 6,645,717 B1 | 11/2003 | Smith et al. |
| 6,719,771 B1 | 4/2004 | Crossman |
| 6,743,211 B1 | 6/2004 | Prausnitz et al. |
| 6,752,817 B2 | 6/2004 | Flora et al. |
| 6,776,959 B1 | 8/2004 | Helftenbein |
| 6,794,140 B1 | 9/2004 | Goldsborough |
| 6,866,675 B2 | 3/2005 | Perez et al. |
| 6,890,319 B1 | 5/2005 | Crocker |
| 6,988,996 B2 | 1/2006 | Roe et al. |
| 7,025,774 B2 | 4/2006 | Freeman et al. |
| 7,047,070 B2 | 5/2006 | Wilkinson et al. |
| 7,056,306 B1 | 6/2006 | Halseth et al. |
| 7,077,828 B2 | 7/2006 | Kuhr et al. |
| 7,163,515 B2 | 1/2007 | McNenny |
| 7,211,052 B2 | 5/2007 | Roe |
| 7,235,056 B2 | 6/2007 | Duchon et al. |
| D546,440 S | 7/2007 | Burnside |
| 7,250,270 B2 | 7/2007 | Goldrick et al. |
| D548,339 S | 8/2007 | Stonier et al. |
| 7,258,693 B2 | 8/2007 | Freeman et al. |
| 7,282,371 B2 | 10/2007 | Helftenbein |
| 7,291,497 B2 | 11/2007 | Holmes et al. |
| 7,344,499 B1 | 3/2008 | Prausnitz et al. |
| 7,374,546 B2 | 5/2008 | Roe et al. |
| 7,380,480 B1 | 6/2008 | Chen |
| 7,455,663 B2 | 11/2008 | Bikovsky |
| 7,473,397 B2 | 1/2009 | Griffin et al. |
| 7,589,184 B2 | 9/2009 | Hogan et al. |
| 7,666,150 B2 | 2/2010 | Douglas et al. |
| 7,682,318 B2 | 3/2010 | Alden et al. |
| 7,695,442 B2 | 4/2010 | Wong et al. |
| 7,758,516 B2 | 7/2010 | Perez |
| 7,758,518 B2 | 7/2010 | Perez et al. |
| 7,766,846 B2 | 8/2010 | Wong et al. |
| 7,828,749 B2 | 11/2010 | Douglas et al. |
| 7,833,170 B2 | 11/2010 | Matsumoto et al. |
| 7,833,486 B2 | 11/2010 | Fielden et al. |
| 7,892,185 B2 | 2/2011 | Freeman et al. |
| 7,955,347 B2 | 6/2011 | Stout |
| 8,025,850 B2 | 9/2011 | Chan et al. |
| 8,062,608 B2 | 11/2011 | Pankow |
| 8,142,723 B2 | 3/2012 | Menon et al. |
| 8,234,767 B2 | 8/2012 | Roeper et al. |
| 8,283,165 B2 | 10/2012 | Hogan et al. |
| 8,333,712 B2 | 12/2012 | Imamura et al. |
| 8,337,419 B2 | 12/2012 | Freeman et al. |
| 8,337,464 B2 | 12/2012 | Young et al. |

(56) References Cited

U.S. PATENT DOCUMENTS

| | | |
|---|---|---|
| 8,469,986 B2 | 6/2013 | Schraga |
| 8,519,125 B2 | 8/2013 | Whitney et al. |
| 8,561,795 B2 | 10/2013 | Schott et al. |
| 8,574,169 B2 | 11/2013 | Hoenes |
| 8,636,673 B2 | 1/2014 | Freeman et al. |
| 8,657,763 B2 | 2/2014 | Jacobs |
| 8,708,928 B2 | 4/2014 | Videbaek et al. |
| 8,808,202 B2 | 8/2014 | Brancazio et al. |
| 8,821,412 B2 | 9/2014 | Gonzalez-Zugasti et al. |
| 8,827,971 B2 | 9/2014 | Gonzalez-Zugasti et al. |
| 8,835,146 B2 | 9/2014 | Battrell et al. |
| 8,852,123 B2 | 10/2014 | Roe et al. |
| 8,900,856 B2 | 12/2014 | Muller-Cohn et al. |
| 8,932,313 B2 | 1/2015 | Weiss et al. |
| 8,961,787 B2 | 2/2015 | Wood et al. |
| 9,023,292 B2 | 5/2015 | Rostaing et al. |
| 9,033,898 B2 | 5/2015 | Chickering, III et al. |
| 9,040,236 B2 | 5/2015 | Hill et al. |
| 9,040,675 B2 | 5/2015 | Bales et al. |
| 9,040,679 B2 | 5/2015 | Kvam et al. |
| 9,041,541 B2 | 5/2015 | Levinson et al. |
| D732,686 S | 6/2015 | Lui |
| 9,044,738 B2 | 6/2015 | Li et al. |
| 9,113,836 B2 | 8/2015 | Bernstein et al. |
| 9,119,578 B2 | 9/2015 | Haghgooie et al. |
| 9,176,126 B2 | 11/2015 | Holmes et al. |
| 9,289,763 B2 | 3/2016 | Berthier et al. |
| 9,295,417 B2 | 3/2016 | Haghgooie et al. |
| 9,359,649 B2 | 6/2016 | Lloyd, Jr. et al. |
| 9,380,972 B2 | 7/2016 | Fletcher et al. |
| 9,408,568 B2 | 8/2016 | Fletcher et al. |
| 9,415,392 B2 | 8/2016 | Ismagilov et al. |
| 9,427,184 B2 | 8/2016 | Holmes et al. |
| 9,480,966 B2 | 11/2016 | Kovacs et al. |
| 9,480,981 B2 | 11/2016 | Lenigk et al. |
| 9,517,026 B2 | 12/2016 | Gelfand et al. |
| 9,534,214 B2 | 1/2017 | Li et al. |
| 9,554,736 B2 | 1/2017 | Gupta et al. |
| 9,623,409 B2 | 4/2017 | Khattak et al. |
| 9,629,579 B2 | 4/2017 | Volkmuth et al. |
| 9,636,062 B2 | 5/2017 | Holmes et al. |
| 9,707,384 B2 | 7/2017 | La Fontaine |
| 9,718,058 B2 | 8/2017 | Khattak et al. |
| 9,730,624 B2 | 8/2017 | Gonzalez-Zugasti et al. |
| 9,730,625 B2 | 8/2017 | Krasnow et al. |
| 9,775,551 B2 | 10/2017 | Bernstein et al. |
| 9,795,960 B2 | 10/2017 | Maillefer et al. |
| 9,845,489 B2 | 12/2017 | Whitney et al. |
| 9,901,922 B2 | 2/2018 | Lenigk et al. |
| 9,950,321 B2 | 4/2018 | Griffin et al. |
| 10,188,335 B2 | 1/2019 | Haghgooie et al. |
| 10,335,078 B2 | 7/2019 | Kvam et al. |
| 10,335,784 B2 | 7/2019 | Maillefer et al. |
| 10,350,592 B2 | 7/2019 | Lenigk et al. |
| 10,371,608 B2 | 8/2019 | Algotsson et al. |
| D870,264 S | 12/2019 | Fedor et al. |
| 10,492,716 B2 | 12/2019 | Berthier et al. |
| 10,543,310 B2 | 1/2020 | Bernstein et al. |
| 10,597,697 B2 | 3/2020 | Nelson et al. |
| 10,625,242 B2 | 4/2020 | Kovacs et al. |
| 10,638,963 B2 | 5/2020 | Beyerlein et al. |
| 10,655,167 B2 | 5/2020 | Heller et al. |
| D892,310 S | 8/2020 | Jordan et al. |
| 2001/0039010 A1 | 11/2001 | Burgoyne |
| 2002/0146696 A1 | 10/2002 | Burgoyne et al. |
| 2003/0134312 A1 | 7/2003 | Burgoyne |
| 2003/0198968 A1 | 10/2003 | Matson |
| 2003/0212345 A1 | 11/2003 | McAllister et al. |
| 2003/0215358 A1 | 11/2003 | Schulman et al. |
| 2004/0087990 A1 | 5/2004 | Boecker et al. |
| 2004/0096914 A1 | 5/2004 | Fang et al. |
| 2004/0101895 A1 | 5/2004 | Fomovskaia et al. |
| 2004/0202576 A1 | 10/2004 | Aceti et al. |
| 2005/0065466 A1 | 3/2005 | Vedrine |
| 2005/0112034 A1 | 5/2005 | McCormick |
| 2005/0222539 A1 | 10/2005 | Gonzales et al. |
| 2005/0245844 A1 | 11/2005 | Mace et al. |
| 2006/0030790 A1 | 2/2006 | Braig et al. |
| 2006/0068399 A1 | 3/2006 | McMillan et al. |
| 2006/0099567 A1 | 5/2006 | Muller-Cohn et al. |
| 2006/0200044 A1 | 9/2006 | Freeman et al. |
| 2006/0234251 A1 | 10/2006 | Akhavan-Tafti |
| 2006/0293722 A1 | 12/2006 | Slatkine et al. |
| 2007/0087357 A1 | 4/2007 | Clark et al. |
| 2007/0088248 A1 | 4/2007 | Glenn et al. |
| 2007/0117173 A1 | 5/2007 | Levison et al. |
| 2007/0123803 A1 | 5/2007 | Fujiwara et al. |
| 2008/0081976 A1 | 4/2008 | Hodges et al. |
| 2008/0145272 A1 | 6/2008 | Feaster et al. |
| 2008/0176209 A1 | 7/2008 | Muller et al. |
| 2009/0024098 A1 | 1/2009 | Bizup et al. |
| 2009/0053704 A1 | 2/2009 | Novoradovskaya et al. |
| 2009/0104637 A1 | 4/2009 | Ismagilov et al. |
| 2009/0155838 A1 | 6/2009 | Hale |
| 2009/0208919 A1 | 8/2009 | Utermohlen et al. |
| 2009/0221976 A1 | 9/2009 | Linden |
| 2009/0246750 A1 | 10/2009 | Lloyd et al. |
| 2009/0299224 A1 | 12/2009 | Yoo |
| 2010/0010374 A1 | 1/2010 | Escutia et al. |
| 2010/0042073 A1 | 2/2010 | Oster et al. |
| 2010/0099074 A1 | 4/2010 | Nolan et al. |
| 2010/0121283 A1 | 5/2010 | Hamatake et al. |
| 2010/0144836 A1 | 6/2010 | Van Engeland et al. |
| 2010/0173392 A1 | 7/2010 | Davis et al. |
| 2010/0209957 A1 | 8/2010 | Hogan et al. |
| 2010/0256524 A1 | 10/2010 | Levinson et al. |
| 2010/0261988 A1 | 10/2010 | Tamir |
| 2010/0323343 A1 | 12/2010 | Egan et al. |
| 2011/0009847 A1 | 1/2011 | Levinson et al. |
| 2011/0070585 A1 | 3/2011 | Ollikka et al. |
| 2011/0091990 A1 | 4/2011 | Dastane et al. |
| 2011/0105872 A1 | 5/2011 | Chickering, III et al. |
| 2011/0105951 A1 | 5/2011 | Bernstein et al. |
| 2011/0105952 A1 | 5/2011 | Bernstein et al. |
| 2011/0118677 A1 | 5/2011 | Wiley et al. |
| 2011/0125058 A1 | 5/2011 | Levinson et al. |
| 2011/0125059 A1 | 5/2011 | Petrich et al. |
| 2011/0172508 A1 | 7/2011 | Chickering, III et al. |
| 2011/0172510 A1 | 7/2011 | Chickering, III et al. |
| 2011/0194996 A1 | 8/2011 | Selinfreund et al. |
| 2011/0212002 A1 | 9/2011 | Curry et al. |
| 2011/0288389 A9 | 11/2011 | Levinson et al. |
| 2011/0306853 A1 | 12/2011 | Black et al. |
| 2012/0010529 A1 | 1/2012 | Chickering, III et al. |
| 2012/0039809 A1 | 2/2012 | Levinson et al. |
| 2012/0041338 A1 | 2/2012 | Chickering, III et al. |
| 2012/0052572 A1 | 3/2012 | Whitney et al. |
| 2012/0149128 A1 | 6/2012 | Manneh |
| 2012/0152743 A1 | 6/2012 | Finehout et al. |
| 2012/0158100 A1 | 6/2012 | Schomacker |
| 2012/0237939 A1 | 9/2012 | Reed et al. |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0288889 A1 | 11/2012 | Miyamura |
| 2012/0289690 A1 | 11/2012 | Page et al. |
| 2013/0018279 A1 | 1/2013 | Plante et al. |
| 2013/0102501 A1 | 4/2013 | Craighead et al. |
| 2013/0150811 A1 | 6/2013 | Horgan |
| 2013/0158468 A1 | 6/2013 | Bernstein et al. |
| 2013/0158482 A1 | 6/2013 | Davis et al. |
| 2013/0172698 A1 | 7/2013 | Reynolds et al. |
| 2013/0190578 A1 | 7/2013 | Freeman et al. |
| 2013/0211289 A1 | 8/2013 | Moga et al. |
| 2013/0280725 A1 | 10/2013 | Ismagilov et al. |
| 2013/0309679 A1 | 11/2013 | Ismagilov et al. |
| 2013/0323723 A1 | 12/2013 | Horton et al. |
| 2013/0330750 A1 | 12/2013 | Horton et al. |
| 2013/0337432 A1 | 12/2013 | Cook et al. |
| 2014/0038172 A1 | 2/2014 | De la Rosa et al. |
| 2014/0039172 A1 | 2/2014 | Nelson et al. |
| 2014/0080112 A1 | 3/2014 | Ryan et al. |
| 2014/0100525 A1 | 4/2014 | Freeman |
| 2014/0207086 A1 | 7/2014 | Stats et al. |

(56) References Cited

U.S. PATENT DOCUMENTS

| | | |
|---|---|---|
| 2014/0227686 A1 | 8/2014 | Saghbini et al. |
| 2014/0234942 A1 | 8/2014 | Kovacs et al. |
| 2014/0272925 A1 | 9/2014 | Menon et al. |
| 2014/0273058 A1 | 9/2014 | Menon et al. |
| 2014/0302521 A1 | 10/2014 | Algotsson et al. |
| 2014/0305823 A1 | 10/2014 | Gelfand et al. |
| 2014/0308164 A1 | 10/2014 | Wilkinson et al. |
| 2014/0309557 A1 | 10/2014 | Fletcher et al. |
| 2014/0323911 A1 | 10/2014 | Sloan et al. |
| 2014/0342371 A1 | 11/2014 | Holmes |
| 2014/0343481 A1 | 11/2014 | Ignon |
| 2014/0358036 A1 | 12/2014 | Holmes |
| 2015/0031035 A1 | 1/2015 | Kvam et al. |
| 2015/0076054 A1 | 3/2015 | Anekal et al. |
| 2015/0125882 A1 | 5/2015 | Bornheimer et al. |
| 2015/0164398 A1 | 6/2015 | Ko et al. |
| 2015/0165346 A1 | 6/2015 | Puleo et al. |
| 2015/0211967 A1 | 7/2015 | Gooley et al. |
| 2015/0259671 A1 | 9/2015 | Puleo et al. |
| 2015/0273467 A1 | 10/2015 | Sloan et al. |
| 2015/0299693 A1 | 10/2015 | Chen et al. |
| 2016/0029936 A1 | 2/2016 | Kvam et al. |
| 2016/0030895 A1 | 2/2016 | Griffin et al. |
| 2016/0143568 A1 | 5/2016 | List |
| 2016/0174888 A1 | 6/2016 | Berthier et al. |
| 2016/0313298 A1 | 10/2016 | Wright et al. |
| 2016/0349221 A1 | 12/2016 | Goldman et al. |
| 2017/0021067 A1 | 1/2017 | Todd et al. |
| 2017/0021333 A1 | 1/2017 | Li et al. |
| 2017/0035337 A1 | 2/2017 | Wilkinson et al. |
| 2017/0067803 A1 | 3/2017 | Jackson et al. |
| 2017/0095190 A1 | 4/2017 | Sloan et al. |
| 2017/0282177 A1 | 10/2017 | Bedrio |
| 2017/0354968 A1 | 12/2017 | Maillefer et al. |
| 2018/0008183 A1 | 1/2018 | Chickering, III et al. |
| 2018/0074042 A1 | 3/2018 | Kelso et al. |
| 2018/0078241 A1 | 3/2018 | Moga et al. |
| 2018/0078751 A1 | 3/2018 | Fedor et al. |
| 2019/0000365 A1 | 1/2019 | Beyerlein et al. |
| 2019/0144919 A1 | 5/2019 | Jackson et al. |

FOREIGN PATENT DOCUMENTS

| | | |
|---|---|---|
| CN | 1968652 B | 6/2010 |
| CN | 101674773 B | 7/2012 |
| CN | 101454038 B | 11/2012 |
| CN | 103370007 A | 10/2013 |
| CN | 102405018 B | 11/2014 |
| CN | 102497814 B | 1/2015 |
| CN | 102309330 B | 4/2015 |
| CN | 102791197 B | 3/2016 |
| CN | 103068308 B | 3/2016 |
| CN | 103874460 B | 6/2016 |
| CN | 102648015 B | 10/2016 |
| CN | 102405015 B | 1/2017 |
| CN | 102811754 B | 5/2017 |
| CN | 103260516 B | 5/2017 |
| CN | 103874461 B | 5/2017 |
| CN | 107115115 A | 9/2017 |
| CN | 107260186 A | 10/2017 |
| CN | 107708560 A | 2/2018 |
| EP | 1437093 A1 | 7/2004 |
| EP | 1484111 A1 | 12/2004 |
| EP | 1746419 A1 | 1/2007 |
| GB | 1601283 A | 10/1981 |
| JP | H0350212 A | 7/1991 |
| JP | 2002085384 A | 3/2002 |
| JP | 2008022988 A | 2/2008 |
| JP | 2008099988 A | 5/2008 |
| JP | 2008099991 A | 5/2008 |
| JP | 2008099992 A | 5/2008 |
| JP | 2010536377 A | 12/2010 |
| JP | 2011521709 A | 7/2011 |
| JP | 2012523851 A | 10/2012 |
| JP | 2014516644 A | 7/2014 |
| JP | 6058063 B2 | 1/2017 |
| JP | 2017522117 A | 8/2017 |
| WO | WO-9118091 A1 | 11/1991 |
| WO | WO-9202175 A1 | 2/1992 |
| WO | WO-9624062 A1 | 8/1996 |
| WO | WO-9640077 A2 | 12/1996 |
| WO | WO-9824493 A1 | 6/1998 |
| WO | WO-0066606 A1 | 11/2000 |
| WO | WO-0074763 A2 | 12/2000 |
| WO | WO-0143643 A1 | 6/2001 |
| WO | WO-03086443 A1 | 10/2003 |
| WO | WO-03094770 A1 | 11/2003 |
| WO | WO-2005066636 A1 | 7/2005 |
| WO | WO-2005095653 A2 | 10/2005 |
| WO | WO-2005107594 A2 | 11/2005 |
| WO | WO-2006118622 A1 | 11/2006 |
| WO | WO-2006118707 A2 | 11/2006 |
| WO | WO-2008075213 A2 | 6/2008 |
| WO | WO-2009027950 A2 | 3/2009 |
| WO | WO-2010031007 A2 | 3/2010 |
| WO | WO-2010123908 A1 | 10/2010 |
| WO | WO-2011019656 A1 | 2/2011 |
| WO | WO-2011026169 A1 | 3/2011 |
| WO | WO-2012113906 A2 | 8/2012 |
| WO | WO-2012113907 A2 | 8/2012 |
| WO | WO-2012113911 A1 | 8/2012 |
| WO | WO-2013066249 A1 | 5/2013 |
| WO | WO-2014088606 A2 | 6/2014 |
| WO | WO-2014099121 A1 | 6/2014 |
| WO | WO-2014153181 A1 | 9/2014 |
| WO | WO-2014172245 A1 | 10/2014 |
| WO | WO-2015022410 A1 | 2/2015 |
| WO | WO-2015108598 A2 | 7/2015 |
| WO | WO-2015162093 A1 | 10/2015 |
| WO | WO-2015191633 A1 | 12/2015 |
| WO | WO-2016019388 A1 | 2/2016 |
| WO | WO-2016134324 A1 | 8/2016 |
| WO | WO-2016180990 A1 | 11/2016 |
| WO | WO-2017044887 A1 | 3/2017 |
| WO | WO-2017083252 A1 | 5/2017 |
| WO | WO-2017214338 A1 | 12/2017 |
| WO | WO-2018022535 A1 | 2/2018 |
| WO | WO-2018090027 A1 | 5/2018 |
| WO | WO-2018132515 A1 * | 7/2018 ......... A61B 5/150022 |

OTHER PUBLICATIONS

Co-pending U.S. Appl. No. 29/655,964, filed Jul. 9, 2018.

Dauner, et al. Evaluation of nucleic acid stabilization products for ambient temperature shipping and storage of viral RNA and antibody in a dried whole blood format. Am J Trop Med Hyg. Jul. 2015;93(1):46-53. Epub May 4, 2015.

EP16845220.9 Extended European Search Report dated Apr. 18, 2019.

Fetzer, Susan Jane. Reducing the Pain of Venipuncture. J Perianesth Nurs 14 (2), 95-112. Apr. 1999.

Gay, et al. Accuracy of a filter paper method for measuring glycosylated hemoglobin. Diabetes Care. Jan. 1992;15(1):108-10.

Harvey, et al. Impregnated 903 blood collection paper A tool for DNA preparation from dried blood spots for PCR amplification. 1995. Clinical Chemistry 41(S6 Part 2): S108.

Hewitt, et al. Tissue handling and specimen preparation in surgical pathology: issues concerning the recovery of nucleic acids from formalin-fixed, paraffin-embedded tissue. Arch Pathol Lab Med. Dec. 2008;132(12):1929-35. doi: 10.1043/1543-2165-132.12.1929.

Hogan et al. Next-Generation Biospecimen Preservation at Ambient Temperature Based on the Use of Micron-Scale Scaffolds. integenX (Mar. 14, 2012). 21 slides.

Homsy, et al. Development and validation of a low cost blood filtration element separating plasma from undiluted whole blood. Biomicrofluidics. Mar. 2012;6(1):12804-128049. doi: 10.1063/1.3672188. Epub Mar. 15, 2012.

http://www.whatman.com/DMPK.aspx and FTA DMPK Card Selection. 2017. URL:< http://www.gelifesciences.com/webapp/wcs/stores/servlet/CategoryDisplay?categoryId=104363&catalogId=10101&productId=&top=Y&storeId=11787&langId=-1>.

(56) References Cited

OTHER PUBLICATIONS

Hu, et al. Validation and Modification of Dried Blood Spot-Based Glycosylated Hemoglobin Assay for the Longitudinal Aging Study in India. Am J Hum Biol. Jul. 8, 2015; 27(4): 579-581. Published online Dec. 3, 2014. doi: 10.1002/ajhb.22664.
Innovac Quick Draw: Available at http://www.innovativemedtech.com/products/innovac-quick-draw/. Captured: Sep. 1, 2015; Accessed: Nov. 1, 2016.
International search report with written opinion dated Jan. 10, 2017 for PCT/US2016/051157.
Jeppsson, et al. Capillary blood on filter paper for determination of HbA1c by ion exchange chromatography. Diabetes Care. Feb. 1996;19(2):142-5.
Jones, et al. Analysis of Hemoglobin A1c from Dried Blood Spot Samples with the Tina-quant® II Immunoturbidimetric Method.J Diabetes Sci Technol. Mar. 2010; 4(2): 244-249. Published online Mar. 1, 2010. doi: 10.1177/193229681000400203.
Little, et al. Collection of blood on filter paper for measurement of glycated hemoglobin by affinity chromatography. Clin Chem. May 1986;32(5):869-71.
Maleska, et al. Comparison of HbA1c detection in whole blood and dried blood spots using an automated ion-exchange HPLC system. Bioanalysis. Mar. 2017;9(5):427-434. doi: 10.4155/bio-2016-0278. Epub Feb. 13, 2017.
Mastronardi, et al. The use of dried blood spot sampling for the measurement of HbA1c: a cross-sectional study. BMC Clinical Pathology, Jul. 8, 2015, 15:13. DOI: 10.1186/s12907-015-0013-5.
Matsubara, et al. Dried blood spot on filter paper as a source of mRNA. Nucleic Acids Research, vol. 20, Issue 8, Apr. 25, 1992. p. 1998, 1 page.
McDade, et al. What a drop can do: dried blood spots as a minimally invasive method for integrating biomarkers into population-based research. Demography. Nov. 2007;44(4):899-925.
MicroPoint: One-step body fluid sampling platform. Available at http://www.micropoint-tech.com/our-products/one-step-blood-sampling-platform; Captured: Aug. 1, 2015; Accessed: Nov. 1, 2015 .
Microsafe capillaries from Safe-Tec, LLC: available at http://www.safe-tecinc.com/microsafe. Captured: May 5, 2015. Accessed: Nov. 1, 2016.
Miles, et al. Improved Elution of DNA from Whatman FTA Cards Using PrepGEM/ForensicGEM Storage Card Extraction Kits. ZyGEM, Oct. 1, 2012. 2 Pages.
Miller, et al. Collection and laboratory methods for dried blood spots for hemoglobin A1c and total and high-density lipoprotein cholesterol in population-based surveys. Clin Chim Acta. May 20, 2015;445:143-54. doi: 10.1016/j.cca.2015.03.028. Epub Mar. 27, 2015.
Nabatiyan, et al. Membrane-based plasma collection device for point-of-care diagnosis of HIV. J Virol Methods. Apr. 2011;173(1):37-42. Epub Jan. 8, 2011.
Natarajan, et al. Paper-based archiving of mammalian and plant samples for RNA analysis. BioTechniques, 2000, 29 pages, 1328-1333.
Notification of Reasons for Refusal dated Feb. 7, 2017 for Japanese Patent Application No. JP2015-510354.
Office Action dated Jan. 6, 2016 for U.S. Appl. No. 13/985,089.
Office Action dated Feb. 24, 2017 for U.S. Appl. No. 13/985,089.
Office Action dated Apr. 25, 2017 for U.S. Appl. No. 15/261,707.
Office Action dated Jun. 6, 2017 for U.S. Appl. No. 15/285,986.
Office Action dated Jun. 18, 2015 for U.S. Appl. No. 13/985,089.
Office Action dated Aug. 11, 2017 for U.S. Appl. No. 15/261,707.
Patel, Prachi. Paper Diagnostics That Cost Pennies. Scientific American 315, 40 (2016); Published online: Nov. 15, 2016; doi:10.1038/scientificamerican1216-40.
PCT/US2018/013223 International Search Report and Written Opinion dated May 31, 2018.
Senese, Fred. What is cellulose? General Chemistry Online. Accessed Jun. 1, 2015. URL:< http://antoine.frostburg.edu/chem/senese/101/consumer/faq/what-is-cellulose.shtml>.
Tao, et al. Evaluation of a solid matrix for collection and ambient storage of RNA from whole blood. BMC Clin Pathol. 2014; 14: 22. Published online May 13, 2014. doi: 10.1186/1472-6890-14-22.
Tasso and GenTegra simplify blood draws, awarded $3M expansion. GenTegra website Apr. 7, 2015. Accessed Jun. 28, 2018. URL:< http://www.gentegra.com/tasso-and-gentegra-simplify-blood-draws-awarded-3m-expansion/>.
University of Wisconsin—Madison. Biomedical engineers offer much-needed update for blood-sampling process. Published May 15, 2014, available at:< https://www.engr.wisc.edu/biomedical-engineers-offer-much-needed-update-for-blood-sampling-process/>.
U.S. Appl. No. 15/261,707 Office Action dated Mar. 1, 2019.
U.S. Appl. No. 15/261,707 Office Action dated Jul. 31, 2018.
U.S. Appl. No. 15/261,707 Office Action dated Mar. 27, 2018.
Wang et al. Minimally invasive extraction of dermal interstitial fluid for glucose monitoring using microneedles. Diabetes Technol Ther. Feb. 2005;7(1):131-41.
Weigl et al. Point-of-Care Diagnostics in Low-Resource Settings and Their Impact on Care in the Age of the Noncommunicable and Chronic Disease Epidemic. J Lab Autom. Jun. 2014; 19(3):248-57.
Yan et al. Evaluation needle length and density of microneedle arrays in the pretreatment of skin for transdermal drug delivery. Int J Pharm. May 31, 2010;391(1-2):7-12.
EP18738600.8 Extended European Search Report dated Sep. 23, 2020.
GB2008501.5 Office Action and Search Report dated Jun. 30, 2020.
Vivid Plasma Separation Membrane. Product Data. PALL Life Sciences (Copyright 2009). 6 pages.
Co-pending U.S. Appl. No. 29/740,373, filed Jul. 2, 2020.
GB2000728.2 Office Action dated Jan. 28, 2020.
U.S. Appl. No. 15/261,707 Office Action dated Feb. 19, 2020.
U.S. Appl. No. 16/104,846 Notice of Allowance dated Feb. 24, 2020.
U.S. Appl. No. 15/463,943 Office Action dated Mar. 5, 2020.
U.S. Appl. No. 16/685,999 Office Action dated Jul. 22, 2020.
U.S. Appl. No. 29/655,964 Notice of Allowance dated Apr. 15, 2020.
Co-pending U.S. Appl. No. 16/685,954, filed Nov. 15, 2019.
Co-pending U.S. Appl. No. 16/685,999, filed Nov. 15, 2019.
European Office Action dated Sep. 27, 2018 for European Patent Application No. EP15717489.7, 5 Pages.
GB1615387.6 Office Action dated Jun. 14, 2019.
GB1911162.4 Office Action dated Dec. 17, 2019.
PCT/US2018/013223 International Preliminary Report on Patentability dated Jul. 16, 2019.
U.S. Appl. No. 16/104,846 Office Action dated Feb. 27, 2019.
U.S. Appl. No. 15/285,986 Notice of Allowance dated Nov. 7, 2019.
U.S. Appl. No. 15/285,986 Office Action dated Feb. 26, 2019.
U.S. Appl. No. 15/463,943 Office Action dated Oct. 15, 2019.
U.S. Appl. No. 16/104,846 Office Action dated Jul. 19, 2019.
U.S. Appl. No. 16/685,954 Office Action dated Feb. 6, 2020.
U.S. Appl. No. 16/685,999 Office Action dated Feb. 4, 2020.
U.S. Appl. No. 15/261,707 Office Action dated Oct. 23, 2020.
U.S. Appl. No. 16/685,954 Office Action dated Oct. 21, 2020.
U.S. Appl. No. 16/685,999 Notice of Allowance dated Oct. 21, 2020.

\* cited by examiner

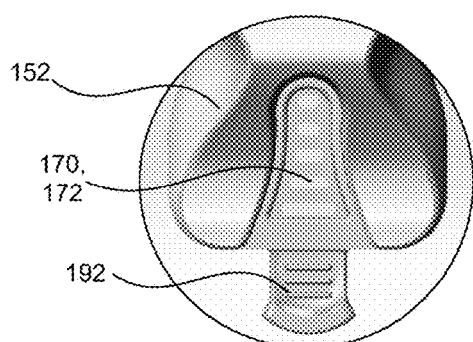
FIG. 1C
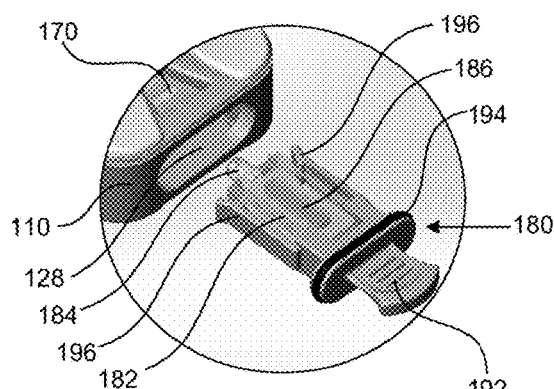
FIG. 1D
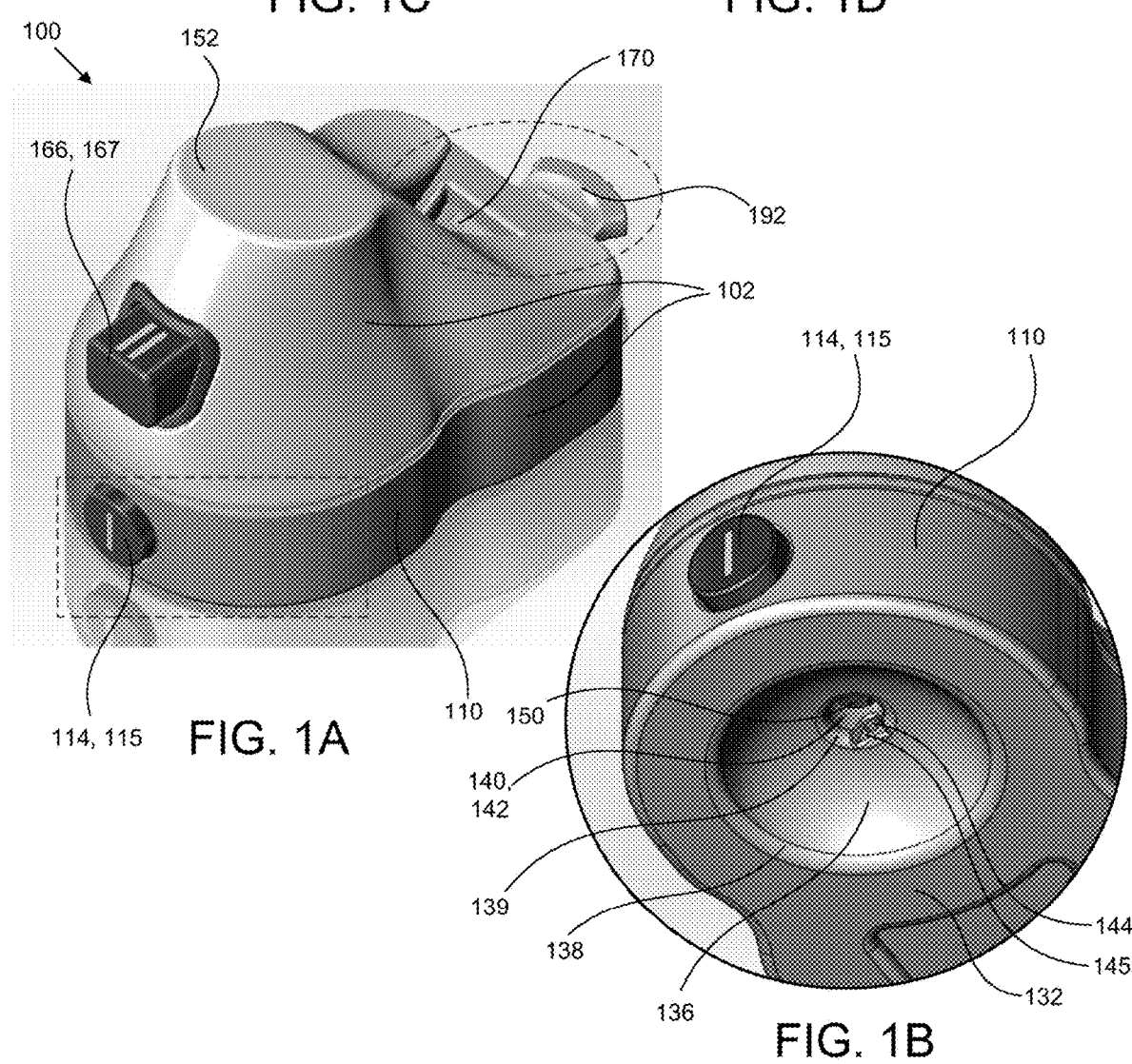
FIG. 1A
FIG. 1B

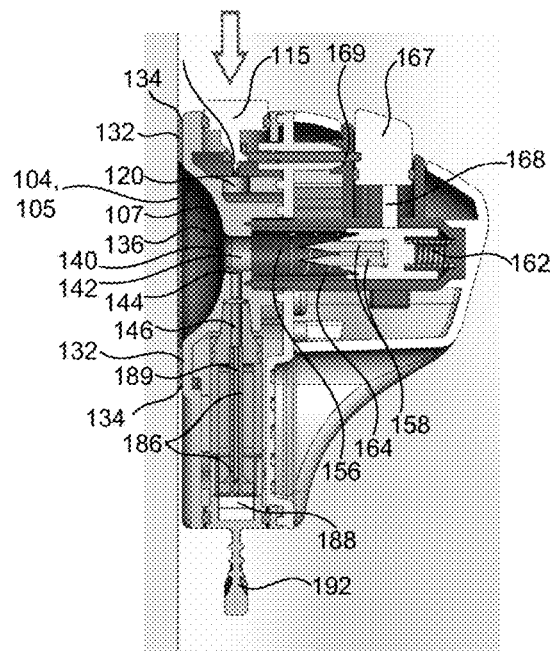
FIG. 5A
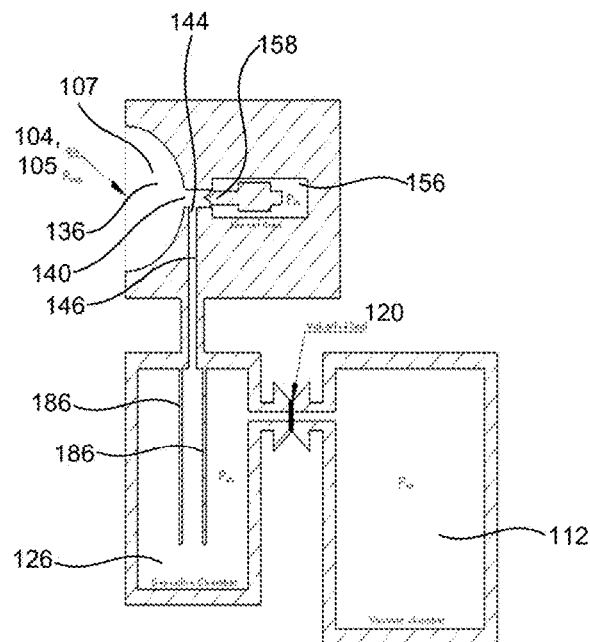
FIG. 5B
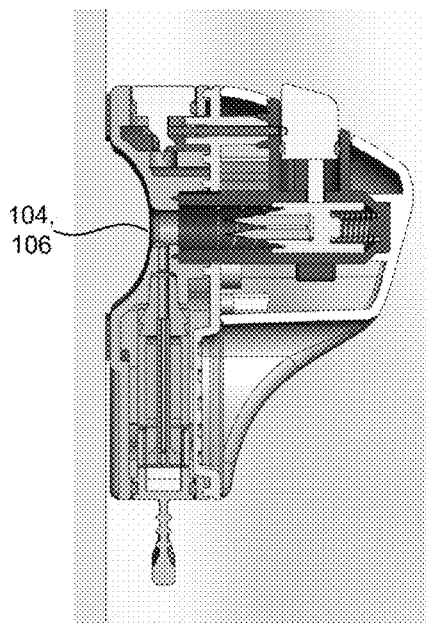
FIG. 6A
FIG. 6B

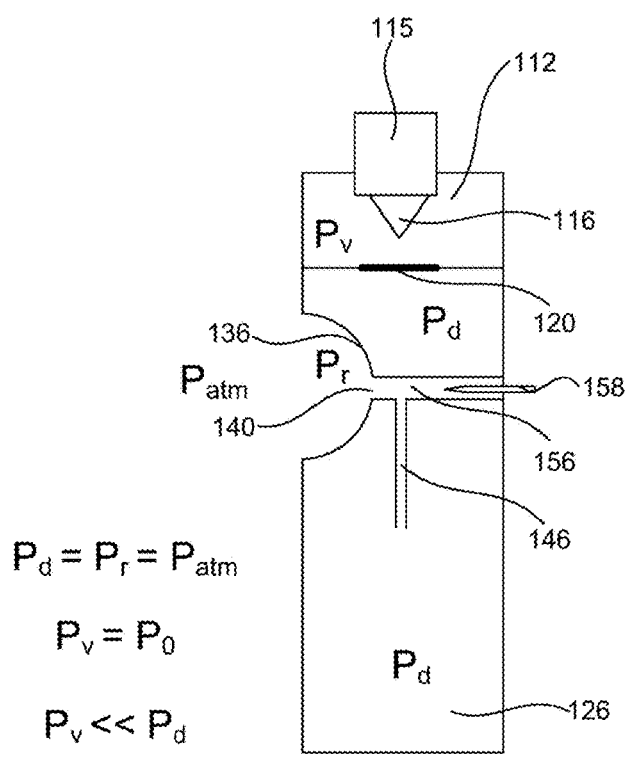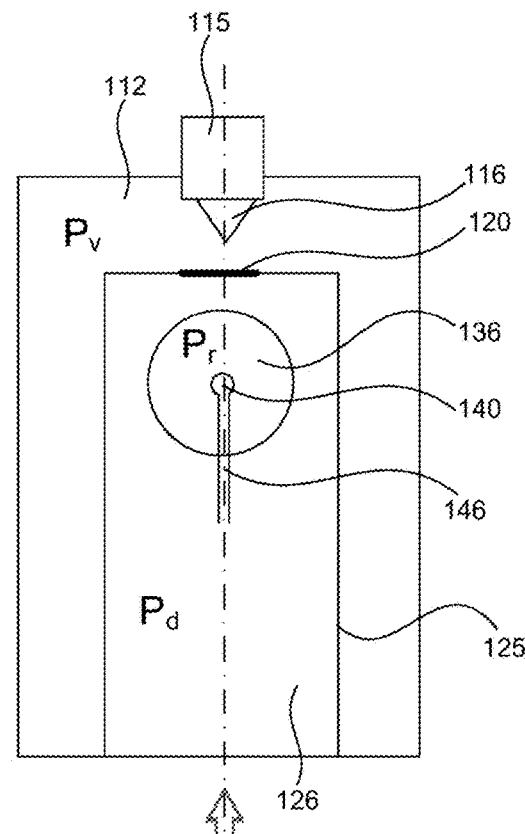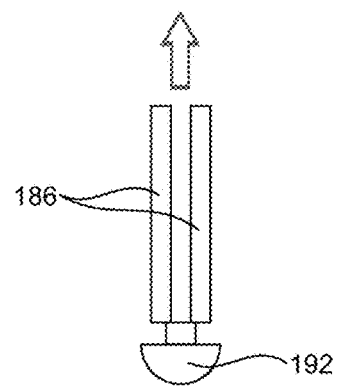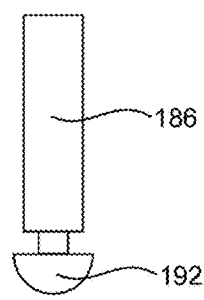
FIG. 11A          FIG. 11B

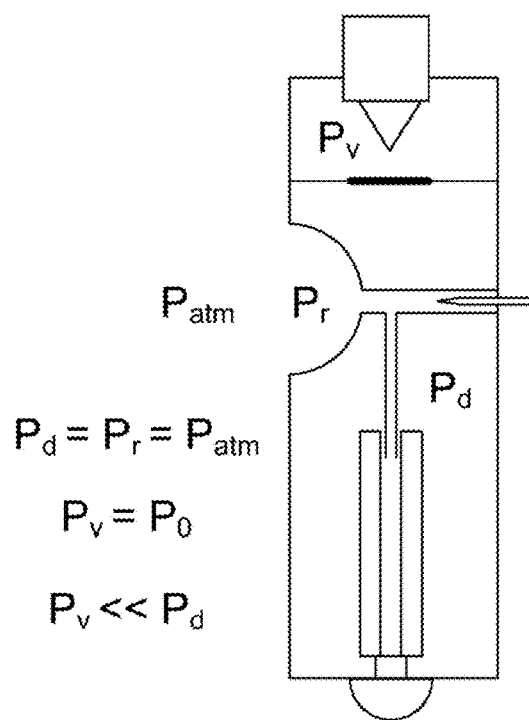
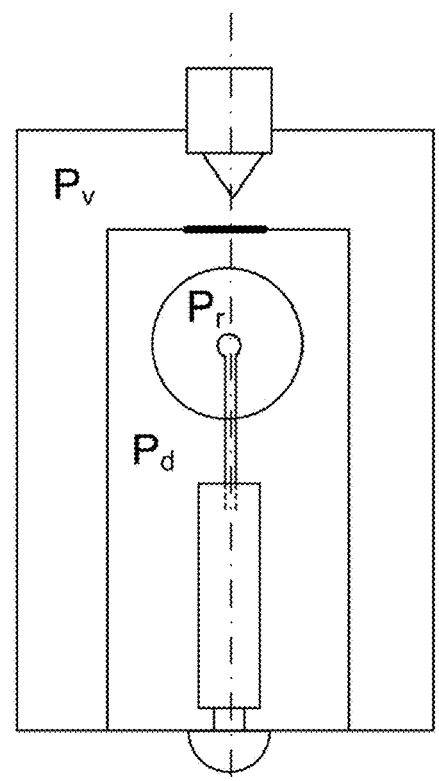
FIG. 12A    FIG. 12B
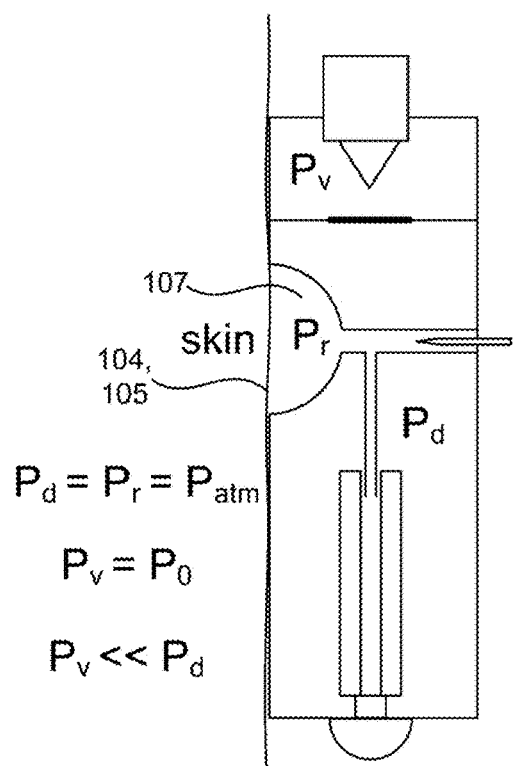
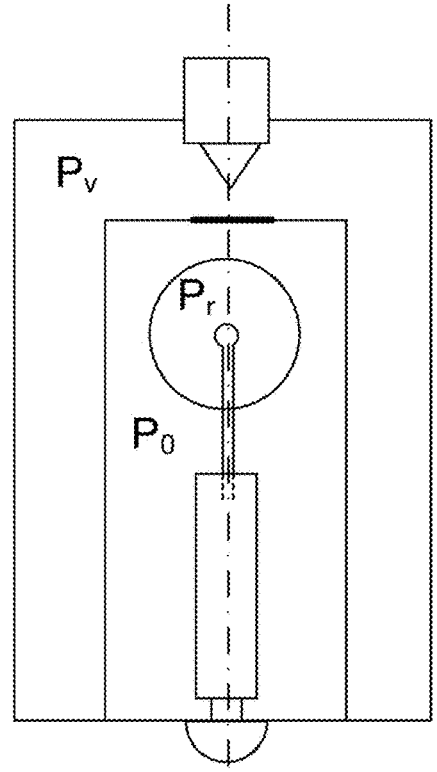
FIG. 13A    FIG. 13B

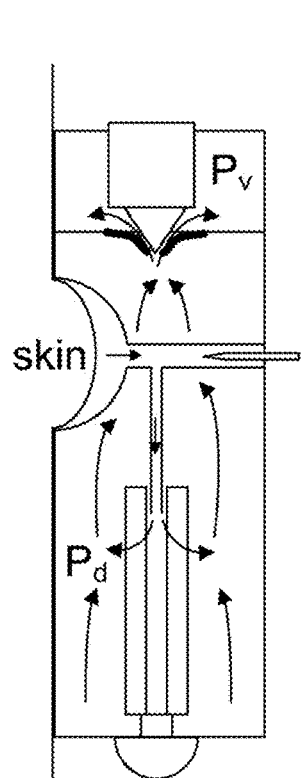
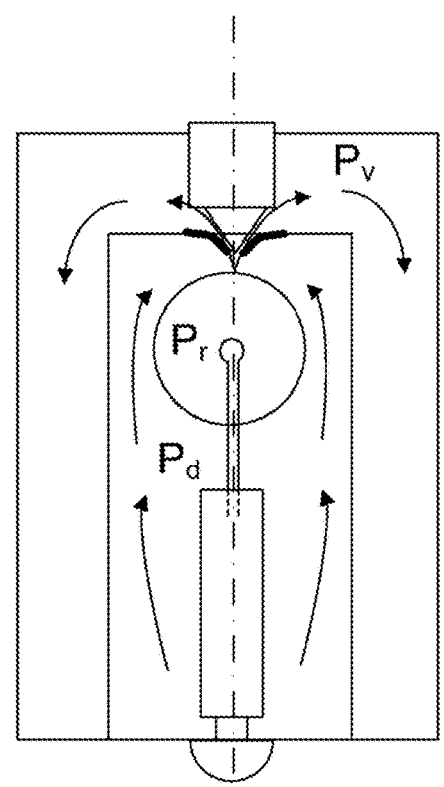
$P_d$ and $P_r$ decrease
$P_v$ increases
FIG. 14A  FIG. 14B
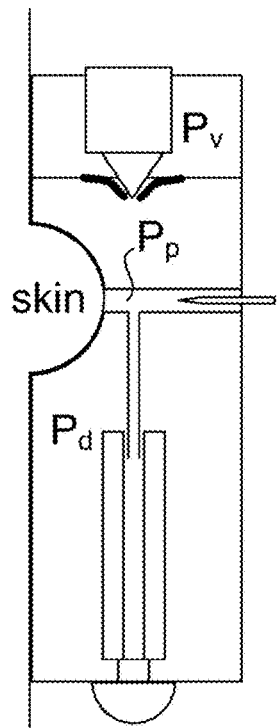
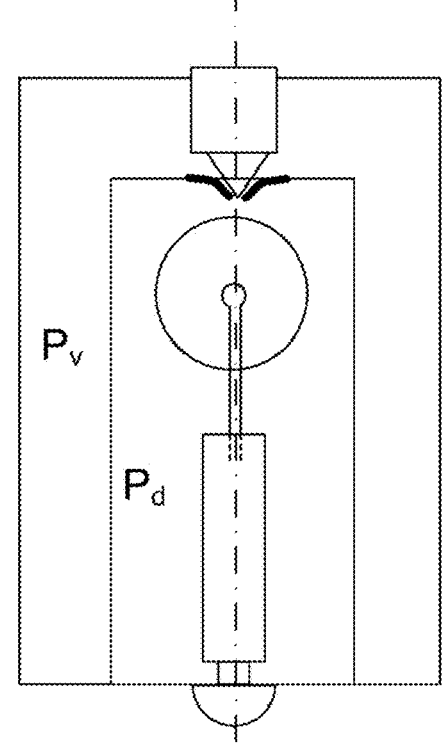
$P_d = P_v = P_p = P_1$
$P_0 < P_1 < P_{atm}$
FIG. 15A  FIG. 15B $P_d = P_v = P_p = P_1$ $P_0 < P_1 < P_{atm}$ $P_c > P_{atm} > P_1$ $P_p = P_2$
$P_d = P_v = P_3$
$P_2 \gg P_3$
$P_3 < P_{atm}$ $P_d = P_v = P_3$
$P_3 < P_{atm}$ $P_d = P_v = P_3$
$P_3 < P_{atm}$

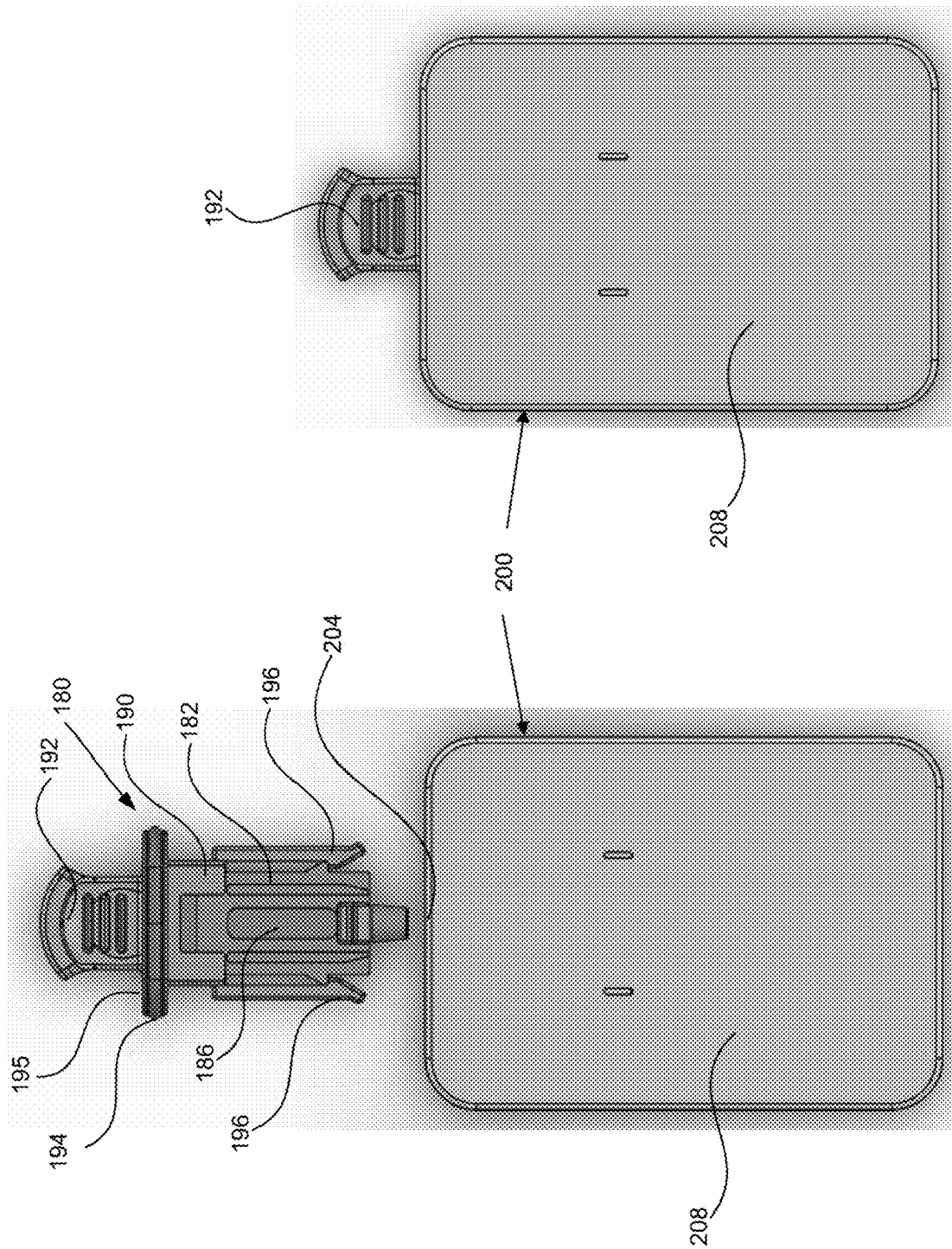

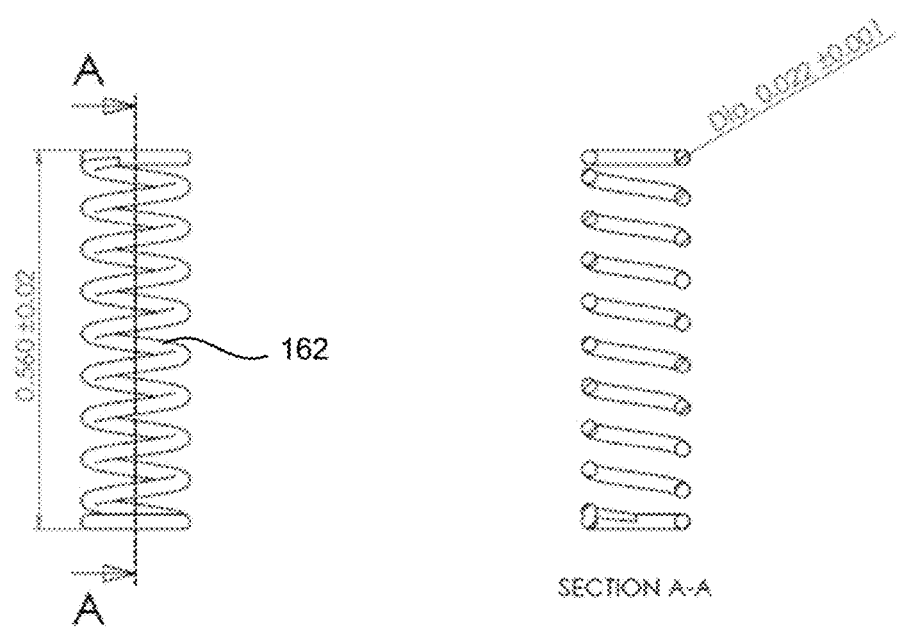
FIG. 28A
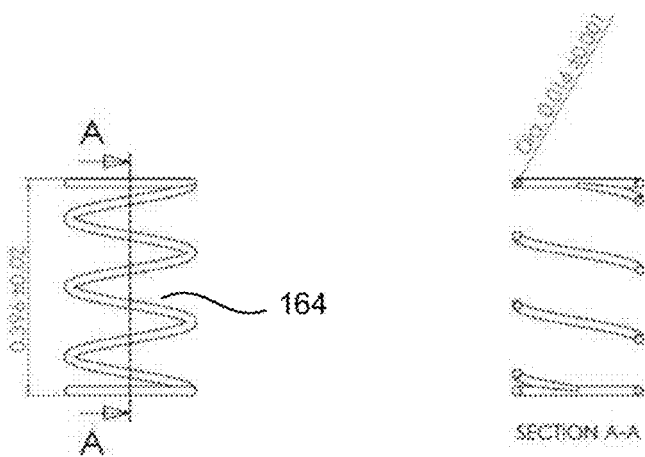
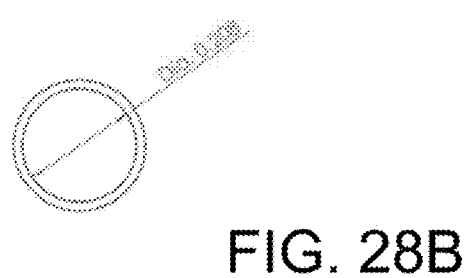
FIG. 28B

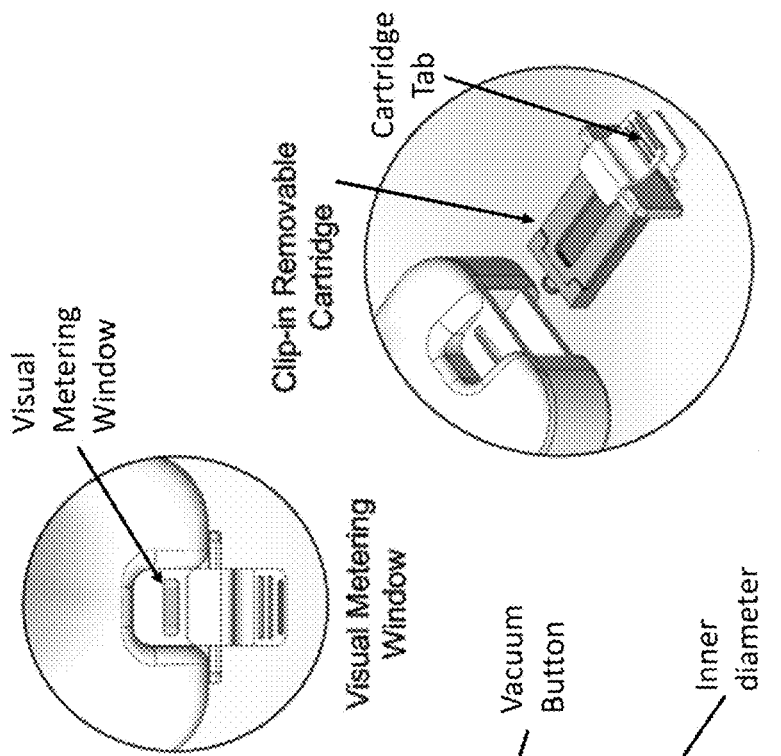
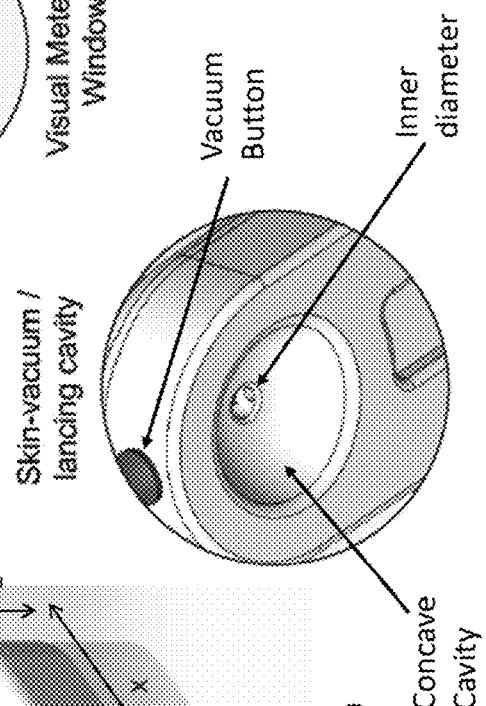
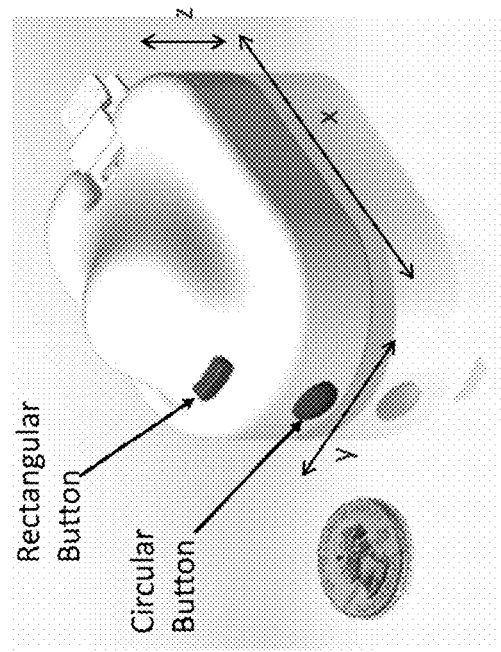
FIG. 31A, FIG. 31B, FIG. 31C, FIG. 31D

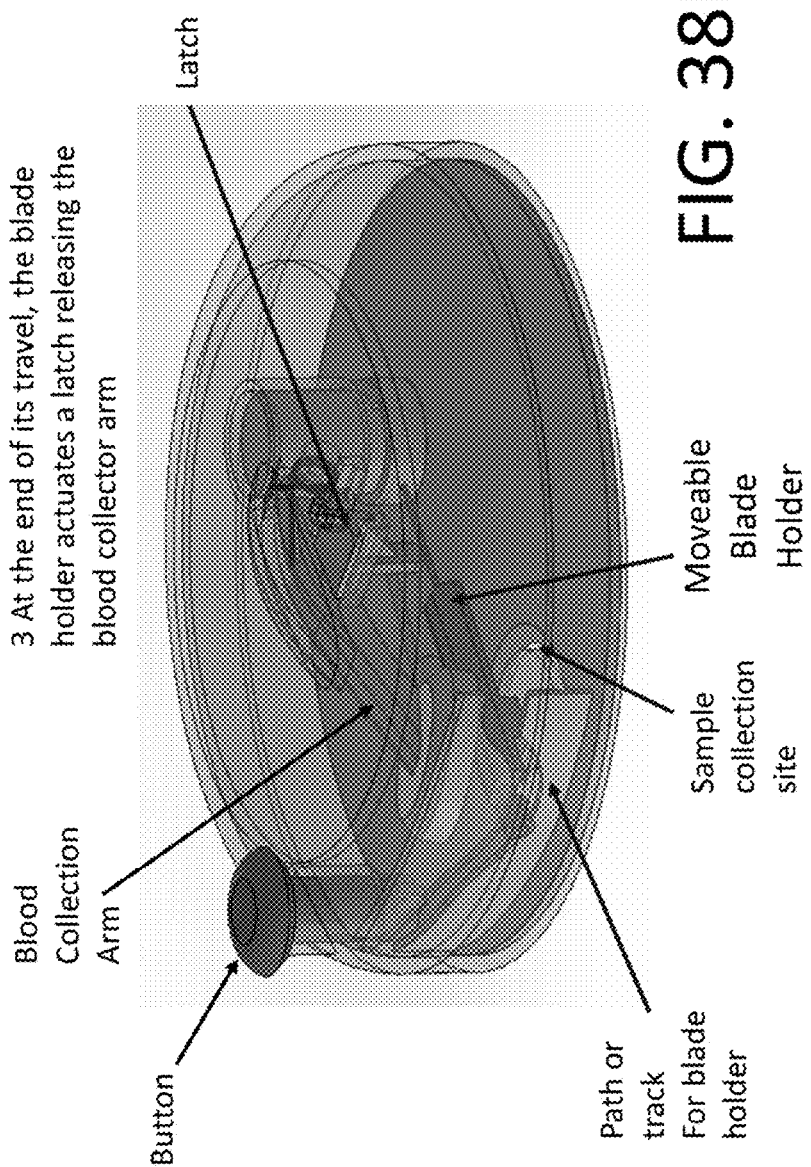

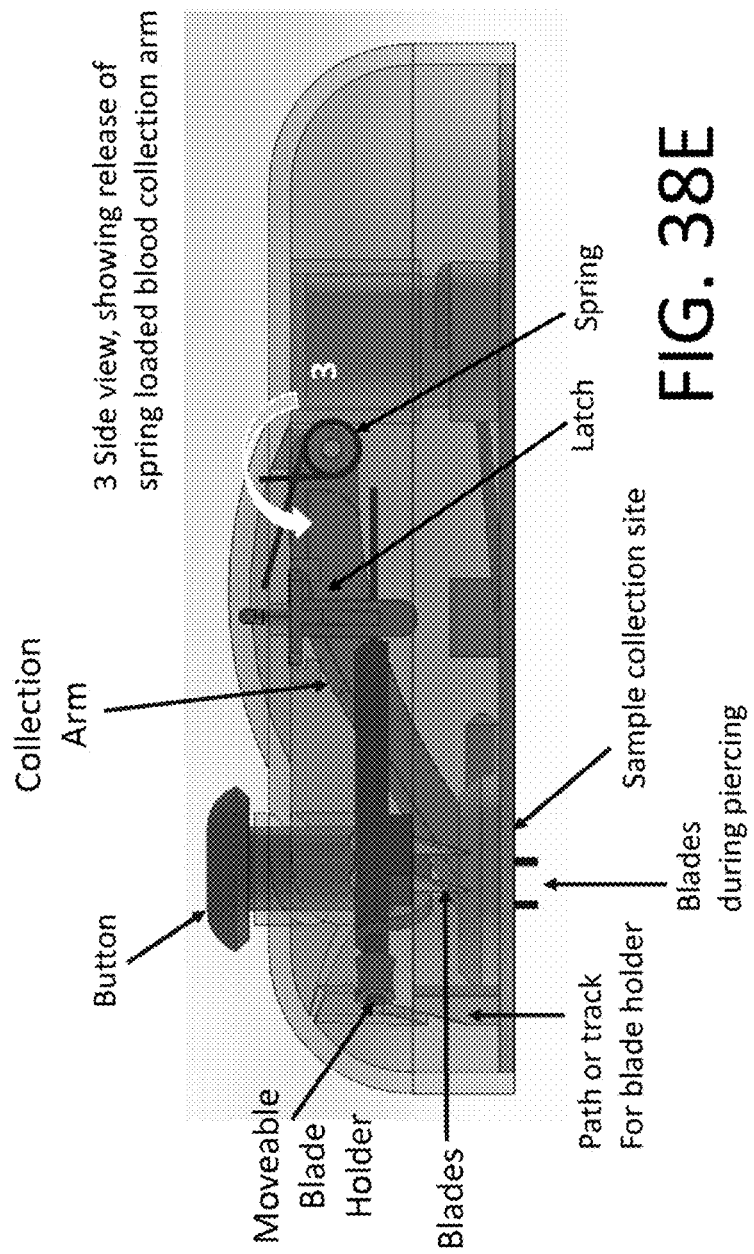

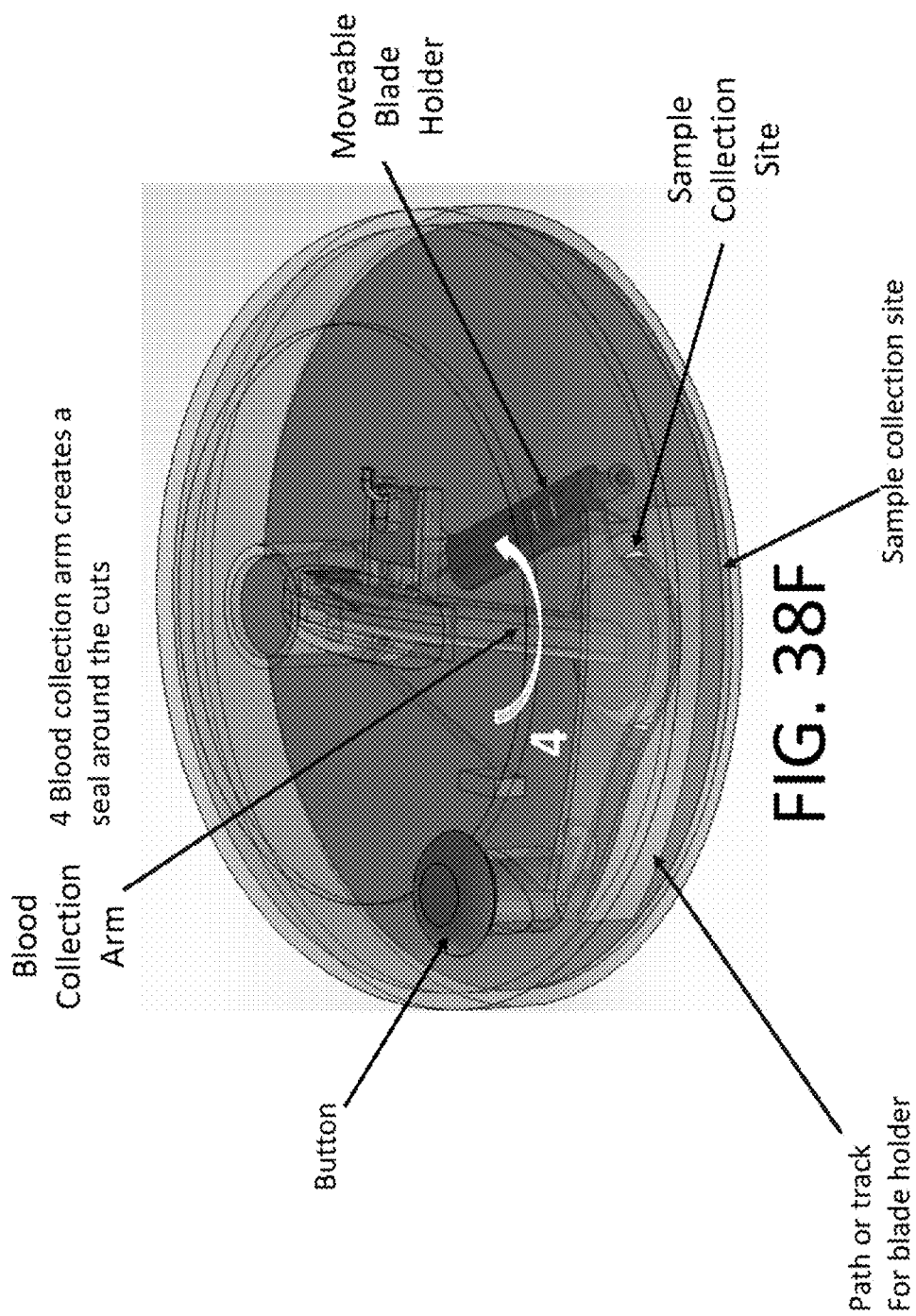

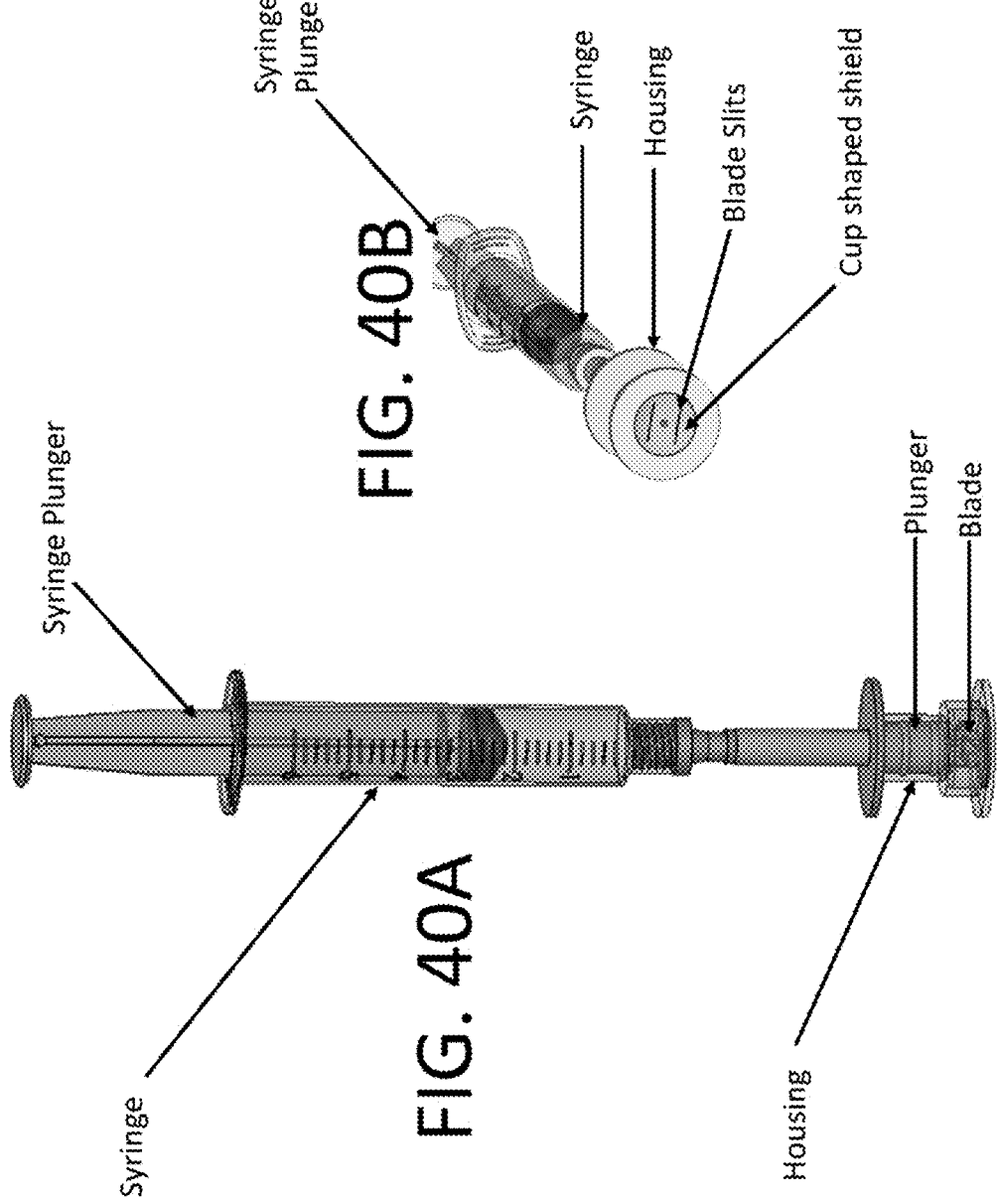

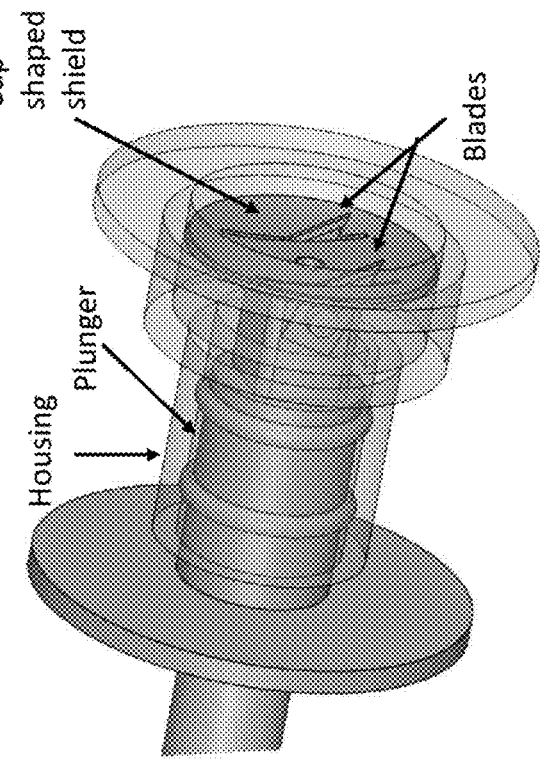
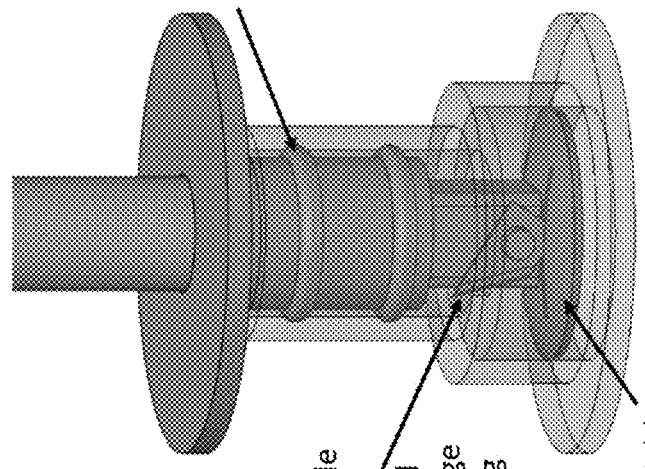
FIG. 40D
FIG. 40C

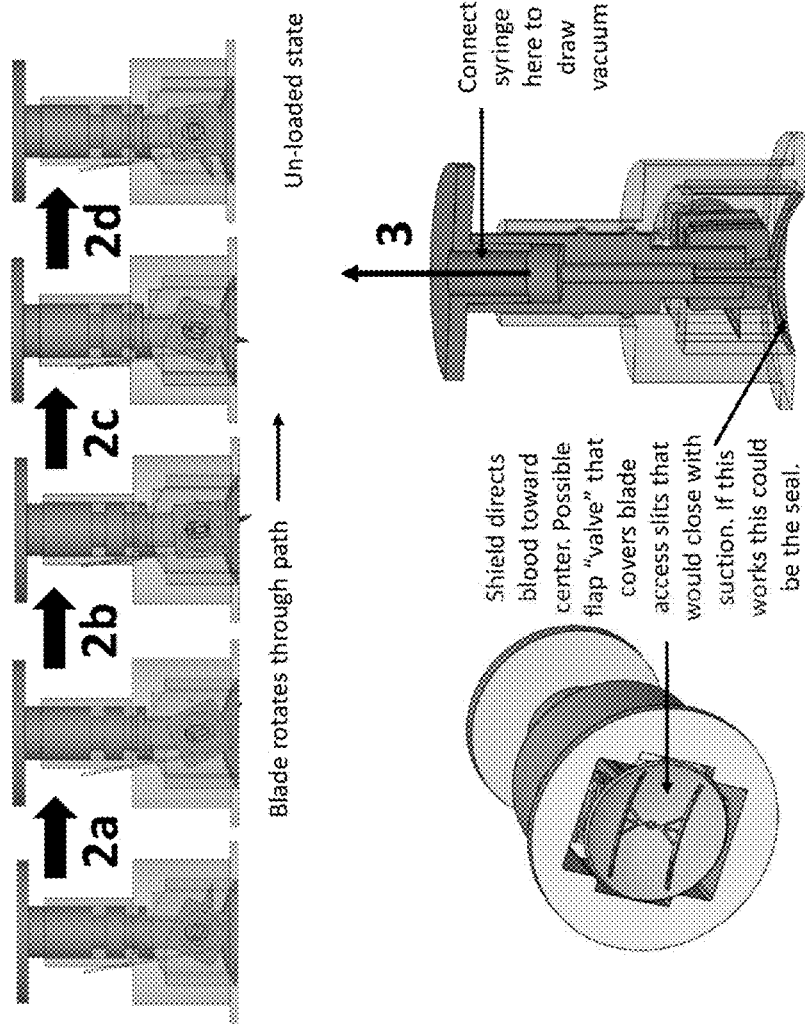
FIG. 42B
FIG. 42C
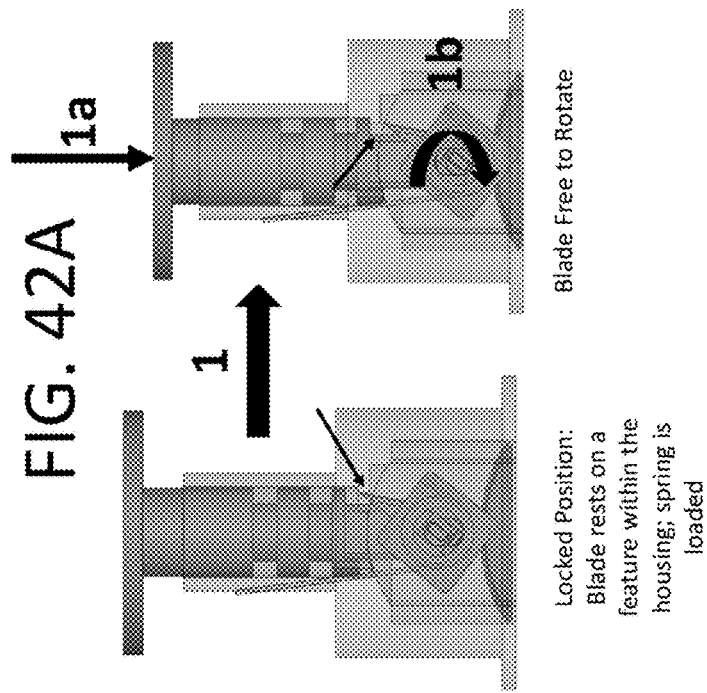
FIG. 42A

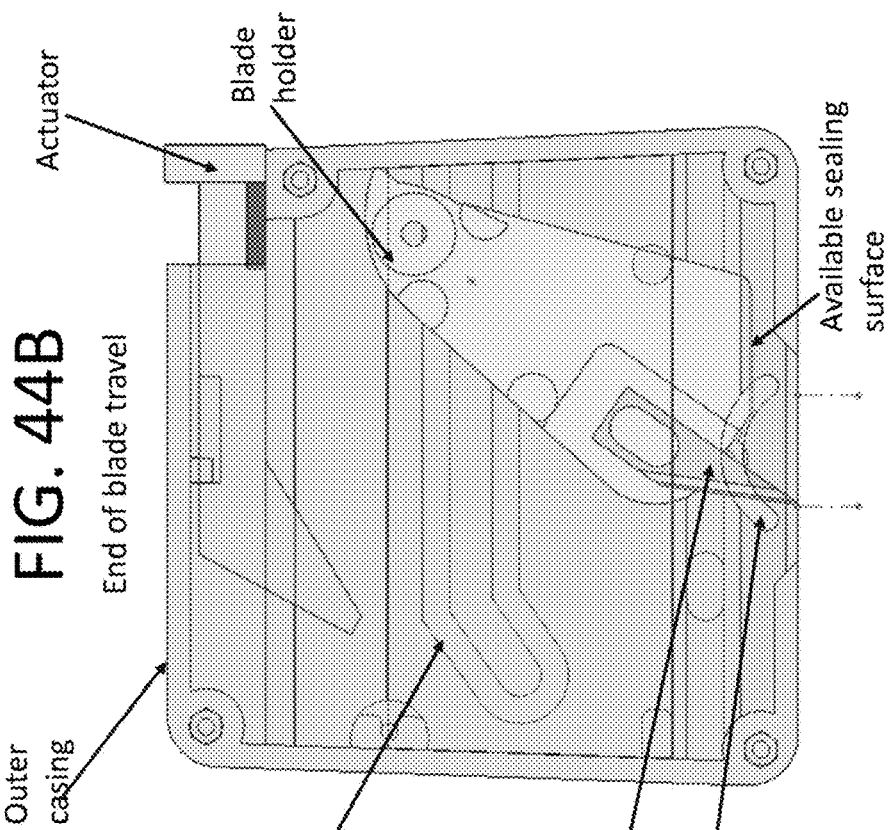
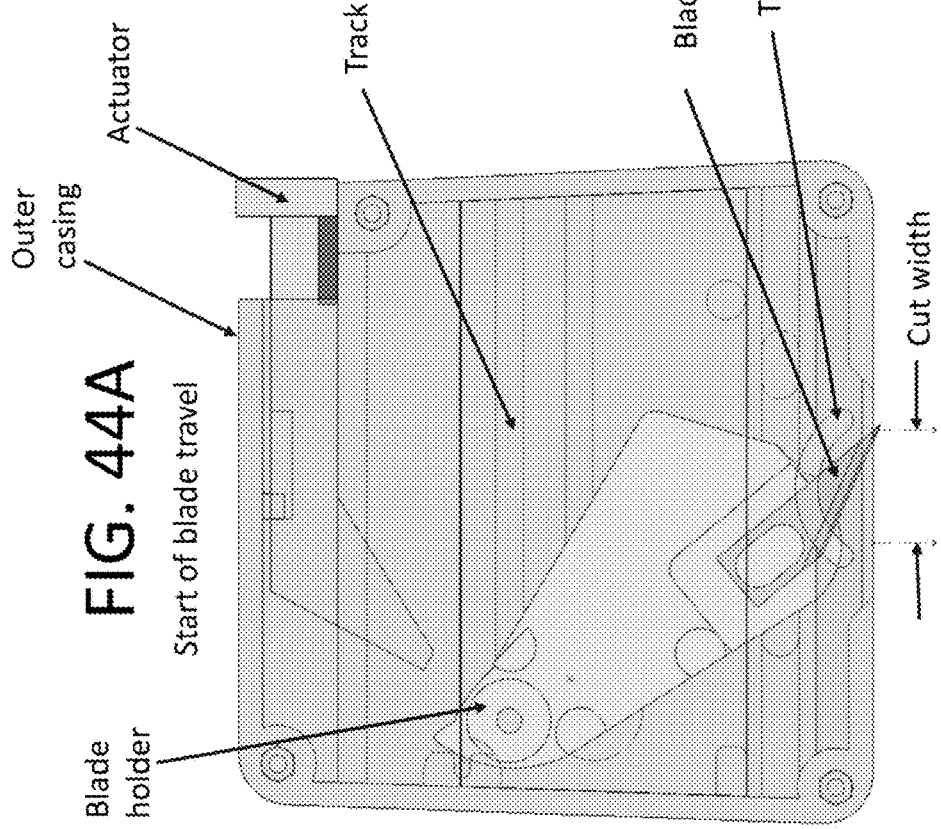

FIG. 52

120 subjects,
3 blood collection sites,
~40 subjects/site

Method Comparison
120 BAT devices vs.
120 venipunctures
Linear Fit: slope of 1.0±0.22; intercept 0.0±3.0; $R^2 > 0.92$

Site 1: Device Lot-to-Lot Variability
20 of 40 subjects
2 additional BAT lots/subject
60 BAT devices total
HbA1C% CV < 6%

Site 2: Inter-operator Variability
20 of 40 subjects
2 additional HCPs/subject
60 BAT devices total
HbA1C% CV < 6%

| Study | Subjects | # Lots | # Devices |
|---|---|---|---|
| Method Comparison | 120 | 1 | 120 |
| Lot-to-Lot | 20 | 3 | 60 |
| Inter-operator | 20 | 1 | 60 |

FIG. 56

Step 1. Complete sleeve label

Record or transfer patient information onto the sleeve label

Step 2. Location Selection – Upper arm

Select collection location on upper arm two fingers below clavicle bone.

Step 3. Clean collection area

Clean collection area starting from center of collection location and moving outwards. Do not blow or fan the cleaned collection area to speed up drying with alcohol wipe and allow to dry.

Step 3. Clean collection area

Clean collection area starting from center of collection location and moving outwards. Do not blow or fan the cleaned collection area to speed up drying with alcohol wipe and allow to dry.

Step 4. Wipe collection area

Wipe the collection area with clean gauze from center of collection location and moving outwards.

Step 5. Adhesive liner removal

Remove adhesive protection liner on the bottom of the device.

FIG. 56
*Continued*

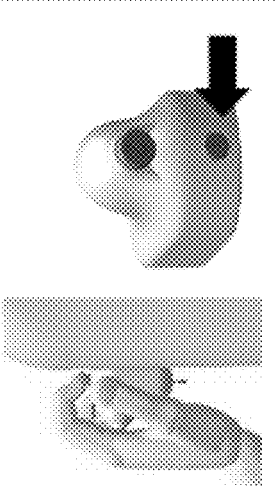

Step 7. *Vacuum activation (button 1)*
Press button labeled "1" to activate vacuum.

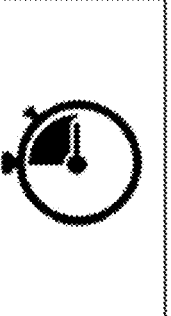

Step 8. *Wait 5 seconds*
Wait 5 seconds to allow vacuum application to skin.

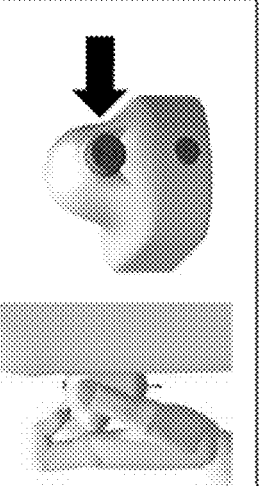

Step 9. *Lancet activation (button 2)*
Press button labeled "2" to activate the lancet.

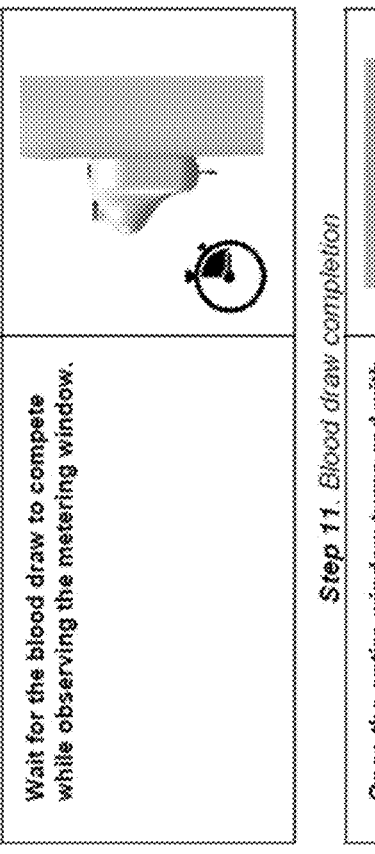

Step 10. *Wait during blood draw period*
Wait for the blood draw to compete while observing the metering window.

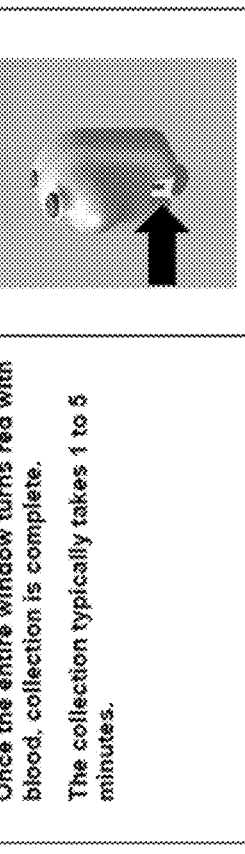

Step 11. *Blood draw completion*
Once the entire window turns red with blood, collection is complete.

The collection typically takes 1 to 5 minutes.

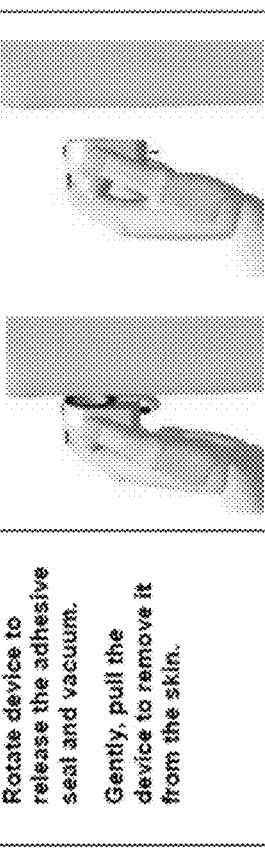

Step 12. *Device removal*
Rotate device to release the adhesive seal and vacuum.

Gently, pull the device to remove it from the skin.

FIG. 56 *Continued*
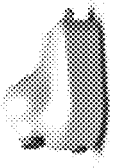

CARRIERS FOR STORAGE AND TRANSPORT OF BIOLOGICAL SAMPLES

CROSS-REFERENCE

This application is a continuation application of U.S. Ser. No. 16/104,846, filed on Aug. 17, 2018, which is a continuation of International Application Serial No. PCT/US2018/013223, filed on Jan. 10, 2018, which claims the benefit of U.S. Provisional Application Ser. No. 62/468,906, filed on Mar. 8, 2017 and U.S. Provisional Application Ser. No. 62/444,764, filed on Jan. 10, 2017, all of which are incorporated herein by reference in their entirety.

BACKGROUND

Body fluid collection, for example collection of blood samples for performing diagnostic tests, can be used to assess and inform the health of individuals. Early detection and reliable diagnosis can play a central role in making effective therapeutic decisions for treatment of diseases or managing certain physiological conditions. Detection can involve identification of disease-specific biomarkers in human body fluids that can indicate irregularities in cellular regulatory functions, pathological responses, or intervention to therapeutic drugs.

Many individuals, however, may not relish the process of having blood drawn from their bodies, possibly due to association with pain, cuts, bleeding, sharp objects, sight of blood, fear of infections, etc. Typically, venous blood collection of a subject is performed at external facilities such as hospitals, skilled nursing facilities, and outpatient environments such as primary care physician (PCP) & specialty hospital clinics, surgery centers, occupational health clinics, or physician offices. The blood collection process can be tedious and time consuming for individuals who have to visit those facilities for blood draw, and for healthcare personnel who can have to attend to multiple patient encounters within a single day.

Thus, a need exists for improved devices and methods that enable blood collection to be performed easily and conveniently by users, and that can decrease users' reliance on traditional healthcare facilities for blood draw.

SUMMARY

The present disclosure addresses at least the above needs. Various embodiments of the present disclosure address the demand for devices and methods, that enable individuals to easily, conveniently, and reliably collect and store blood samples outside of traditional healthcare facilities, for example in their own homes, in remote locations, while traveling, etc. Individuals who have minimal to no medical training can use the disclosed devices and methods to efficiently collect and store blood on their own or with the help of others, without the need for trained healthcare personnel. The embodiments described herein can obviate the need for individuals to schedule, or make special or frequent trips to healthcare facilities for blood sample collection, which helps to free up the individuals' time and reduce patient load on healthcare resources. Nonetheless, it should be appreciated that the disclosed devices and methods are also suitable for use by healthcare or non-healthcare personnel in a variety of environments or applications, for example in personalized point-of-care (POC), Emergency Medical Services (EMS), ambulatory care, hospitals, clinics, emergency rooms, patient examination rooms, acute care patient rooms, field environments, nurse's offices in educational settings, occupational health clinics, surgery or operation rooms, etc.

Blood samples collected using the devices and methods described herein can be analyzed to determine a person's physiological state, for detecting diseases and also for monitoring the health conditions of the user. In some instances, individuals can rapidly evaluate their physiological status since blood samples can be quickly collected using the devices and methods described herein, and either (1) analyzed on the spot using for example immunoassays or (2) shipped promptly to a testing facility. The reduced lead-time for blood collection, analysis and quantification can be beneficial to many users, especially users who have certain physiological conditions/diseases that require constant and frequent blood sample collection/monitoring. Taking diabetes as an example, hemoglobin A1c (HbA1c) can make up 60% of all glycohemoglobins and can be used for monitoring glycemic control. The amount of HbA1c, as a percentage of total hemoglobin, can reflect the average blood glucose concentration in a patient's blood over the preceding 120 days. Generally it is recommended that diabetic patients test their HbA1c levels every three to six months. The glycemic recommendation for non-pregnant adults with diabetes can be <7.0%, while HbA1c levels of >8% can indicate that medical action can be required to control diabetic complications, including cognitive impairment and hypoglycemic vulnerability.

The various embodiments described herein are capable of drawing blood at increased flowrates and higher sample volumes beginning from time of skin incision, compared to traditional non-venous blood collection devices and method. The disclosed devices and methods can be used to collect blood samples of predefined volumes, for example through the use of custom matrices for sample collection, and absorbent pads for holding and metering out excess blood. Additionally, the blood collection devices and methods described herein are minimally invasive and permit lower levels of pain (or perception of pain) in a subject, which can help to improve the overall blood collection experience for the subject.

In some aspects, a handheld user-activable device or method disclosed herein can be configured or capable of collecting at least 150 uL of blood from a subject in less than 3 minutes beginning from time of incision or penetration of a skin portion of the subject.

In some aspects, a device for collecting fluid sample from a subject is provided. The device can comprise a recess and a pre-evacuated vacuum chamber located within the device. The recess can be configured to maintain contact with at least 5.0 cm$^2$ of a skin surface area of the subject under vacuum pressure, prior to and as the fluid sample is being collected from the skin of the subject.

In some aspects, a device for collecting fluid sample from a subject can comprise: a housing comprising a recess having an opening; a vacuum chamber in the housing in fluidic communication with the recess; and one or more piercing elements that are extendable through the opening to penetrate skin of the subject. The vacuum chamber can be configured for having a vacuum that draws the skin into the recess, and the recess can be configured having a size or shape that enables an increased volume of the fluid sample to be accumulated in the skin drawn into the recess.

In some aspects, a method for collecting a fluid sample from a subject can comprise: providing a device having a housing, said housing configured to support a vacuum chamber and a piercing module, the housing comprising a recess having an opening; placing the recess of the housing adjacent to skin of the subject; activating the vacuum in the vacuum chamber to draw the skin into the recess; accumulating an increased volume of the fluid sample in the skin drawn into the recess, wherein the recess is configured having a size or shape that enables the increased volume of the fluid sample to be accumulated; extending one or more piercing elements through the opening to penetrate the skin; and maintaining the device adjacent to the skin for a sufficient amount of time to draw the fluid sample into the device.

In some embodiments, the fluid sample can comprise blood from the subject. The recess can serve as a suction cavity for drawing the skin and increasing capillary pressure differential. The increased volume of the fluid sample can depend on a volume and/or surface area of the skin that is drawn into the recess. In some cases, the volume of the skin enclosed by the recess can range from about 0.4 cm$^3$ to about 4.0 cm$^3$. The surface area of the skin in contact with the recess can range from about 3.2 cm$^2$ to about 7.2 cm$^2$. The increased volume of the fluid sample can depend on a pressure of the vacuum in the vacuum chamber. The pressure of the vacuum in the vacuum chamber can range from about −4 psig to about −15 psig. The increased volume of the fluid sample in the skin drawn into the recess can be at least about 50 μL prior to the penetration of the skin. In some cases, the increased volume of the fluid sample in the skin drawn into the recess, an increased capillary pressure, and with aid of the vacuum, can permit the fluid sample to be drawn from the skin and collected at an average flowrate of at least 30 μL/min. In some cases, the fluid sample can be collected at an average flowrate of at least 100 μL/min. In some cases, the fluid sample can be collected at an average flowrate of at least 150 μL/min. In some cases, the average flowrate can be sustained at least until about 150-300 μL of the fluid sample has been collected. The size and/or shape of the recess can be configured to permit the skin to substantially conform to the recess. A gap between the skin and the recess can be negligible when the skin is drawn into the recess. A surface of the recess can be substantially in contact with the skin drawn into the recess. In some cases, a size of the recess can be at least two times a size of the opening within the recess. In some cases, the size of the opening within the recess can range from about 1.5 mm to about 6 mm, and the size of the recess at its outermost periphery can range from about 10 mm to about 60 mm. A surface area of the recess can be substantially greater than an area of the opening. In some cases, the surface area of the recess can be at least ten times the area of the opening. In some cases, the surface area of the recess can range from about 75 mm$^2$ to about 2900 mm$^2$, and the area of the opening can range from about 1.5 mm$^2$ to about 30 mm$^2$. In some cases, an area of the skin directly under the opening can be at least 1.5 times smaller than a total area of the skin drawn into the recess. In some cases, the area of the skin directly under the opening can be at least 5 times smaller than the total area of the skin drawn into the recess.

In some embodiments, the recess can comprise a concave cavity. In some cases, the concave cavity can have a volume ranging from about 1.0 cm$^3$ to about 5.0 cm$^3$. The recess can be in the shape of a spherical cap. In some cases, a base diameter of the spherical cap can range from about 10 mm to about 60 mm, and a height of the spherical cap can range from about 3 mm to about 30 mm. The spherical cap can be a hemisphere. The opening can be at an apex of the spherical-capped recess. In some embodiments, the recess can comprise one or more fillets configured to improve vacuum suction to the skin and reduce vacuum leak. The one or more fillets can extend continuously along a periphery of the recess. The one or more fillets of the recess can be configured to be in contact with the skin when the skin is drawn into the recess.

In some embodiments, a vacuum pressure of at least about −1 psig can be provided in order to draw the skin into and completely fill the recess. In some cases, the skin can be drawn into the recess by the vacuum and can completely fill the recess in less than 1 second. In some cases, the skin can be drawn into the recess by the vacuum and can completely fill the recess in no more than 5 seconds.

In some embodiments, (1) the size or shape of the recess or (2) a pressure of the vacuum can be configured to achieve a minimum capillary pressure in the skin drawn into the recess. In some cases, (1) the size or shape of the recess or (2) a pressure of the vacuum can be configured to achieve a minimum tension in the skin drawn into the recess. The device can be supported and held in place on the skin of the subject with the aid of an adhesive. The device can be supported and held in place on the skin of the subject with the aid of the vacuum. The device can be supported and held in place on the skin of the subject primarily with the aid of the vacuum. The device can be configured for use on an upper portion of the subject's arm. The device can be configured to remain in its position on the subject's arm independent of any movement or changes in orientation of the subject's arm.

In some embodiments, the device can be capable of collecting 250 uL of fluid sample from the subject in less than 1 minute 45 seconds. In some cases, the device can be capable of collecting at least 175 uL to 300 uL of fluid sample from the subject in less than 3 minutes. In some cases, the device can be capable of collecting at least 200 μL of fluid sample from the subject in less than 5 minutes. The device can be configured to collect the fluid sample at a rate that is dependent on the size or shape of the recess and/or vacuum pressure. The recess can be configured having a size and shape that enables an increased volume of the fluid sample to be accumulated in the skin drawn into the recess. The recess can be configured having a size and shape that enables the increased volume of the fluid sample to be accumulated. In some cases, (1) the size and shape of the recess and (2) a pressure of the vacuum can be configured to achieve a minimum capillary pressure in the skin drawn into the recess. In some cases, (1) the size and shape of the recess and (2) a pressure of the vacuum can be configured to achieve a minimum tension in the skin drawn into the recess. The device can be configured to collect the fluid sample at a rate that is dependent on the size and shape of the recess.

In some other aspects, a device for collecting a fluid sample from a subject is provided. The device can comprise: a housing comprising a piercing activator configured to activate one or more skin piercing elements, and a vacuum activator separate from the piercing activator and configured to activate an evacuated vacuum chamber prior to the activation of the one or more piercing elements by the piercing activator.

In some aspects, a method for collecting a fluid sample from a subject can comprise: placing a device packaged with an evacuated vacuum chamber and one or more piercing elements on skin area of the subject; activating the evacuated vacuum chamber to effectuate vacuum pressure on the skin area; piercing the skin area after vacuum activation; and maintaining the vacuum pressure during and after penetrating the skin area of the subject, in order to draw the fluid sample from the skin into device.

In some embodiments, the piercing activator and the vacuum activator can be two separate components. The vacuum activator can comprise a first input interface on the housing, and the piercing activator can comprise a second input interface on the housing. In some cases, at least one of the first input interface or the second input interface can comprise a button. In some alternative cases, the vacuum activator can comprise a first input interface and the piercing activator can comprise a second input interface, and at least one of the first input interface or the second input interface can be remote from the housing.

In some embodiments, the piercing activator can be configured to activate the one or more piercing elements after the skin is drawn into the recess. The piercing activator can be configured to activate the one or more piercing elements after the skin is drawn into the recess by the vacuum for a predetermined length of time. In some cases, the predetermined length of time can range from about 1 second to about 60 seconds. In some embodiments, the housing can comprise the pre-evacuated vacuum chamber, and the vacuum activator can be configured to activate the vacuum in the pre-evacuated vacuum chamber. In some cases, the piercing activator can be configured to activate the one or more piercing elements only after the vacuum has been activated. In some cases, the piercing activator can be locked and incapable of activating the one or more piercing elements prior to activation of the vacuum. The piercing activator can comprise a locking mechanism coupled to the vacuum activator. The locking mechanism can be configured such that the piercing activator is initially in a locked state. The vacuum activator can serve as a key for unlocking the piercing activator, and the piercing activator can be simultaneously unlocked when the vacuum activator is activated. The vacuum activator can be configured to activate the vacuum by establishing fluidic communication to the pre-evacuated vacuum chamber. For example, the vacuum activator can be configured to pierce a foil seal or open a valve to establish the fluidic communication to the pre-evacuated vacuum chamber.

In some embodiments, the vacuum activator can be located on the housing such that the vacuum activator is configured to be pressed in a first direction, and the piercing activator can be located on the housing such that the piercing activator is configured to be pressed in a second direction. In some cases, the first direction and the second direction can be substantially the same. Alternatively, the first direction and the second direction can be substantially different. In some cases, the first direction and the second direction can be substantially parallel to each other. In some cases, at least one of the first direction or the second direction does not extend toward the skin of the subject. For example, the second direction does not extend toward the skin of the subject. In some cases, at least one of the first direction or the second direction can extend substantially parallel to the skin of the subject. In some cases, the first direction and the second direction can both extend substantially parallel to the skin of the subject. In some cases, at least one of the first direction or the second direction can extend in a direction of gravitational force. In some cases, the first direction and the second direction can both extend in the direction of gravitational force. In some embodiments, the piercing activator and the vacuum activator can be located on a same side of the housing, and can be ergonomically accessible by the subject when the device is mounted onto an arm of the subject. For example, the piercing activator can be located on a cover of the housing, and the vacuum activator can be located on a base of the housing where the vacuum chamber is located. Alternatively, the piercing activator and the vacuum activator can be located on different sides of the housing, and can be ergonomically accessible by the subject when the device is mounted onto an arm of the subject.

In some further aspects, a method for collecting a fluid sample from a subject is provided. The method can comprise: with aid of a fluid acquisition device: piercing skin of the subject and delivering the fluid sample from the subject to a matrix disposed within a deposition chamber of the fluid acquisition device, wherein the delivery of the fluid sample is assisted or enhanced using (1) gravitational force, (2) vacuum force, (3) a pressure difference between capillary pressure and internal pressure of the device, and (4) wicking behavior of the fluid sample along the matrix.

In some aspects, a device for collecting a fluid sample from skin of a subject and delivering it to a deposition chamber is provided, wherein fluid flow from the skin to a matrix in the deposition chamber can be preferably enhanced by (1) gravitational force, (2) vacuum force, (3) a pressure differential between capillary pressure and internal pressure of the device, and (4) wicking behavior of the fluid sample along the matrix.

In some embodiments, the device can comprise an enclosure for holding one or more piercing elements, and the enclosure can be in fluidic communication with the deposition chamber. The deposition chamber and the enclosure can be initially at ambient pressure, prior to activation of a vacuum from a pre-evacuated vacuum chamber located onboard the device. In some cases, the deposition chamber, the vacuum chamber, and the enclosure can be configured to equalize to an internal pressure that is less than the ambient pressure after the vacuum has been activated. The internal pressure can be higher than the initial evacuated vacuum pressure of the vacuum chamber. In some cases, the internal pressure can be about −5.5 psig, and the sealed vacuum pressure can be about −12 psig. The internal pressure can be configured to draw the skin into a recess of the housing. The internal pressure can be configured to draw blood from capillary beds to the skin that is being drawn into the recess. A pressure differential can be created between capillary pressure and the internal pressure when the skin is penetrated by one or more piercing elements of the device. The internal pressure can increase as the fluid sample is drawn from the skin towards the deposition chamber and the enclosure. In some cases, the internal pressure in the enclosure can increase more rapidly compared to a collective internal pressure of the deposition chamber and the vacuum chamber. The internal pressure in the enclosure can increase substantially more than the collective internal pressure of the deposition chamber and the vacuum chamber. The substantially increased internal pressure of the enclosure can inhibit the flow of the fluid sample into the enclosure. The substantially increased internal pressure of the enclosure can result in preferential flow of the fluid sample towards the deposition chamber instead of towards the enclosure. The substantially increased internal pressure of the enclosure can cause the flow of the fluid sample into the enclosure to slow or stop, while the fluid sample can continue to flow towards the deposition chamber under the influence of the pressure differential. In some cases, (1) a volume of the enclosure and (2) a collective volume of the deposition chamber and the vacuum chamber, can be configured such that minimal amounts of the fluid sample flows towards and into the enclosure. In some cases, a ratio of the volume of the enclosure to the collective volume of the deposition chamber and the vacuum chamber can range from about 1:5 to about 1:15. In some cases, the one or more piercing elements can be configured to penetrate the skin to generate cuts, and the pressure differential can enable deeper cuts and the cuts to be held open under tension. The pressure differential can be configured to increase the size of the cuts to enable a higher flowrate and volume of the fluid sample to be collected from the skin.

In some further aspects, a device for penetrating skin of a subject is provided. The device can comprise: one or more piercing elements supported by a piercing holder movable by two or more spring elements; a deployment spring positioned to deploy the one or more piercing elements through an opening in the device; and a retraction spring positioned to retract the one or more piercing elements back into the device, wherein a length of the one or more piercing elements is less than about 20 mm, and the depth of penetration of the one or more piercing elements is about 2 mm. In some cases, the length of the one or more piercing elements is about 12.7 mm.

In some aspects, a method for penetrating skin of a subject can comprise providing the aforementioned device; drawing the skin of the subject into a recess of the device; activating the deployment spring and deploying the one or more piercing elements through the opening in the device; penetrating the skin of the subject using the one or more piercing elements; and using the retraction spring to retract the one or more spring elements back into the device.

In some embodiments, two or more piercing elements can be supported by a holder in a random configuration. In some cases, the two or more piercing elements can have random orientations relative to each other. The two or more piercing elements can comprise beveled edges that are randomly oriented relative to each other. The beveled edges of the two or more piercing elements can be non-symmetrical to each other. The beveled edges of the two or more piercing elements can be at an acute or oblique angle relative to each other.

In some cases, two or more piercing elements can be supported by a holder in a predefined configuration. The two or more piercing elements can have predefined orientations relative to each other. The two or more piercing elements can comprise beveled edges that are oriented relative to each other in a predefined manner. The beveled edges of the two or more piercing elements can be symmetrical to each other.

In some embodiments, the piercing elements can comprise two or more lancets. Optionally, the piercing elements can comprise needles and/or microneedles. In some cases, two or more lancets can have a same bevel angle. Alternatively, two or more lancets can have different bevel angles. In some cases, the bevel angle(s) can range from about 10 degrees to about 60 degrees. In some cases, the two or more lancets can comprise beveled faces having a same bevel length. Alternatively, the two or more lancets can comprise beveled faces having different bevel lengths. In some cases, the bevel length(s) can range from about 2 mm to about 10 mm.

In some embodiments, two or more piercing elements can be configured to generate cuts on the skin that extend in different directions along the skin and that are non-parallel to each other.

In some embodiments, the deployment spring can be configured to move and cause the piercing elements to penetrate the skin of the subject at speeds ranging from about 0.5 m/s to about 2.0 m/s. The deployment spring can be configured to move and cause the piercing elements to penetrate the skin of the subject with a force ranging from about 1.3 N to about 24.0 N. A spring-force of the retraction spring can be less than a spring-force of the deployment spring. In some cases, the deployment spring can have a spring-rate of about 2625 N/m, and the retraction spring can have a spring-rate of about 175 N/m. The deployment spring can be configured to cause the one or more piercing elements to penetrate the skin to depths ranging from about 0.5 mm to about 3 mm. The retraction spring can be configured to retract the piercing elements from the skin of the subject at speeds ranging from about 0.1 m/s to about 1.0 m/s.

In some embodiments, the device can further comprise: a vacuum activator configured to activate a vacuum for drawing the skin into a recess of the device. In some cases, a piercing activator can be configured to activate the deployment spring only after the vacuum activator is activated.

In some further aspects, a device for monitoring fluid sample collection from a subject is provided. The device can comprise: a housing comprising a cartridge chamber; a cartridge operably coupled to the cartridge chamber; components for penetrating skin of the subject and drawing the fluid sample from the skin into the cartridge; and a flow meter on the housing that enables the subject or a user to monitor a progress of the fluid sample collection in real-time as the fluid sample is collected into the cartridge.

In some aspects, a method for monitoring fluid sample collection from a subject can comprise: providing (1) a housing comprising a cartridge chamber, (2) a cartridge operably coupled to the cartridge chamber, (3) components for penetrating skin of the subject and drawing the fluid sample from the skin into the cartridge, and (4) a flow meter on the housing; and monitoring, with aid of the flow meter, a progress of the fluid sample collection in real-time as the fluid sample is collected into the cartridge.

In some embodiments, the flow meter can be provided on a lid covering a base of the housing. The flow meter is not obscured by a cover of the housing. The flow meter can be in proximity to the cartridge chamber. The flow meter can be substantially aligned with a cartridge located within the cartridge chamber. In some embodiments, the flow meter can comprise a plurality of windows disposed parallel to a longitudinal axis of the cartridge. The plurality of windows can be made of an optically transparent material. The fluid sample can be visible through the windows and sequentially fills each window as the fluid sample is being collected into the cartridge. Each window can be indicative of a known amount of fluid sample that is collected. The fluid sample collection is complete when the fluid sample is visible in all of the windows. The plurality of windows can comprise three or more windows.

In some embodiments, the flow meter can comprise a single window disposed parallel to a longitudinal axis of the cartridge. The window can be made of an optically transparent material. The fluid sample can be visible through the window and continuously fills the window as the fluid sample is being collected into the cartridge. The fluid sample collection is complete when the fluid sample is visible throughout the window.

In some further aspects, a cartridge assembly is provided. The cartridge assembly can comprise: a cartridge for holding one or more matrices for storing a fluid sample thereon; a cartridge holder releasably coupled to the cartridge, wherein the cartridge assembly is releasably coupled to a device used for collecting the fluid sample.

In some embodiments, a device for collecting a fluid sample from a subject is provided. The device can comprise: a housing comprising a deposition chamber and a pre-evacuated vacuum chamber, wherein the deposition chamber is configured to receive and releasably couple to the cartridge assembly, and the deposition chamber is in fluidic communication with the vacuum chamber.

In some embodiments, a fluid sample collection kit can comprise the device and the cartridge assembly. In some embodiments, a fluid sample collection assembly can comprise the device and the cartridge assembly releasably coupled to said device. In some embodiments, an input port of the cartridge can be releasably coupled to and in fluidic communication with a channel of the device, and the fluid sample can be collected from penetrated skin of the subject and transported through the channel into the cartridge.

In some embodiments, a method for collecting a fluid sample from a subject can comprise: releasably coupling the cartridge assembly to the device; placing the device adjacent to skin of the subject; activating vacuum in the vacuum chamber to draw the skin into a recess of the housing; using one or more piercing elements of the device to penetrate the skin; maintaining the device adjacent to the skin for a sufficient amount of time to draw the fluid sample into the device and collect the fluid sample into the cartridge; and decoupling the cartridge assembly from the device after a certain amount of the fluid sample has been collected in the cartridge.

In some embodiments, the cartridge holder can be releasably coupled to the cartridge via a quick release mechanism. In some cases, the quick release mechanism can comprise one or more spring-clips on the cartridge holder. The cartridge assembly can be capable of being coupled to and detached from the deposition chamber without use of tools. The cartridge assembly can be capable of being coupled to and detached from the deposition chamber using no more than two motion steps. The cartridge assembly can be coupled to the deposition chamber prior to the collection of the fluid sample from the subject. The cartridge assembly can be decoupled from the deposition chamber after the fluid sample from the subject has been collected into the cartridge.

In some embodiments, the cartridge can comprise two or more matrices for collecting and storing the fluid sample thereon. The two or more matrices can be disposed in a configuration that permits the fluid sample to wick between and along the two or more matrices. For example, the two or more matrices can be disposed substantially parallel to each other. In some cases, the two or more matrices can be separated by a gap of about 0.5 mm. In some cases, at least one of the matrices can be capable of collecting at least 60 uL of fluid sample. In some cases, each of two or more matrices can be capable of collecting at least 60 uL of fluid sample.

In some embodiments, the cartridge can further comprise one or more absorbent pads configured to be in fluidic communication with the one or more matrices, wherein the one or more absorbent pads can be used to hold excess fluid sample. The one or more absorbent pads can aid in ensuring that a predefined volume of the fluid sample can be collected and maintained on the one or more matrices, regardless of an input volume of the fluid sample into the cartridge up to a predefined range. In some cases, the one or more matrices can include two matrices that are each configured to hold up to about 7 uL of the fluid sample. Each of the two matrices can be configured to hold and maintain about 75 uL of the fluid sample as the input volume of the fluid sample to the cartridge increases beyond 150 uL up to the predefined range. In some cases, the predefined range can be from about 150 uL to about 300 uL. In other cases, the predefined range can be greater than 300 uL. In some cases, the one or more absorbent pads can be capable of holding at least 100 uL of excess fluid sample.

In some embodiments, the cartridge holder can comprise a cartridge tab that is configured to be releasably coupled to a distal end of the deposition chamber. The cartridge tab can be configured such that the subject or a user is able to (1) support the cartridge assembly by holding the cartridge tab, (2) couple the cartridge assembly to the device by pushing the cartridge tab, and/or (3) decouple the cartridge assembly from the device by pulling the cartridge tab.

In some further aspects, a transportation sleeve is provided. The sleeve can comprise: an opening configured to couple to a cartridge tab included with the cartridge; and a dual support-release mechanism within the sleeve, wherein the dual support-release mechanism can comprise: (a) a retention element configured to engage with a corresponding mating feature on the cartridge and secure the cartridge within the sleeve, and (b) a release element configured to cause the spring-clips on the cartridge holder to release and thereby decouple the cartridge from the cartridge holder. The dual support-release mechanism can permit the cartridge holder to be removed from the opening of the sleeve while the cartridge is secured in place within the sleeve, without exposure of the strips to the ambient environment. In some cases, the transportation sleeve can further comprise a desiccant within the sleeve. In some cases, the sleeve can be sized and shaped to accommodate user or patient identity (ID) labels.

In some embodiments, a transportation assembly can comprise: the transportation sleeve, and the cartridge coupled to said transportation sleeve. In some cases, the cartridge tab can be configured to hermetically seal the opening of the sleeve.

In some embodiments, the cartridge can be oriented such that the flow of the fluid sample into the cartridge is further aided with gravity. In some cases, the cartridge can comprise a luer-type fitting that can engage with the device when the cartridge is inserted into the deposition chamber.

In some embodiments, the one or more matrices can comprise absorbent paper. In some cases, one or more of the matrices can comprise stabilization chemistry. In some cases, a first matrix can comprise a first stabilization chemistry and a second matrix can comprise a second stabilization chemistry different from the first stabilization chemistry. In some alternative cases, one or more of the matrices does not comprise stabilization chemistry.

Provided herein are medical systems, devices, and methods for sample collection and storage. The disclosed systems, devices, and methods can comprise structure features that facilitate sample collection (e.g. blood collection devices) as well as components for collecting blood sample on to substrate for storage and transport.

Any of the devices disclosed herein can rely on the generation of a vacuum to apply negative pressure to deform the skin of a subject and to apply local suction directly to the sample collection site, thereby facilitating sample flow and collection. Any of the devices disclosed herein can comprise a concave cavity that can be placed at the surface of the skin of the subject, this concave cavity can be configured to deliver vacuum (e.g. negative pressure, suction etc.) to the skin of the subject. Any of the devices disclosed herein can comprise an opening disposed at the apex of or other surface of the concave cavity, the inner diameter can be configured to allow a piercing element to pierce the skin of the subject; and a piercing element can be configured to pass through the inner diameter. Local suction can be applied to the sample collection site through the inner diameter.

In some embodiments, a vacuum can be configured to deform the skin of the subject using different mechanisms, for example the vacuum can be configured to draw the skin of the subject into the concave cavity. A concave cavity can be configured to constrain the surface of the skin against its entire or a portion of its concave surface of the subject at which point the piercing element can be configured to pierce the skin of the subject. An opening contiguous with a cylinder (e.g. a cylinder in fluid contact with a cartridge) can be configured to draw the blood from the subject into the device when the vacuum is applied to the skin of the subject and after an incision has been made in the skin of the subject.

Vacuum pressure can be generated using an evacuated vacuum chamber configured such that activation of the device pierces the evacuated vacuum chamber forming negative pressure that draws the blood from the subject through the opening and channels and into a cartridge and onto a solid matrix for sample storage vacuum pressures can be in the range of between 1-20 psi. The vacuum pressure can be about 5 psi. Vacuum chamber volume can be within a 10%-100% margin of twice the volume of the combined concave cavity, opening, channel and cartridge volume. Any of the devices disclosed herein can comprise a vacuum activation actuator configured to activate the vacuum upon actuation of the vacuum activation actuator. The vacuum activation actuator can comprise a button.

Any of the devices disclosed herein can be configured for drawing a specific volume (e.g. greater than 20 μL, greater than 40 μL, greater than 60 μL, greater than 80 μL, greater than 100 μL, greater than 150 μL, or greater than 200 μL) of blood (e.g. capillary blood) from a subject in defined period of time (e.g. less than 4 minutes), can have specific vacuum and device parameters. The structure of the concave cavity can have an impact on blood collection, for example the rate of blood sample collection can be dependent on the curvature and size of the concave cavity and the vacuum pressure.

To facilitate blood collection the surface area acted on by the vacuum can have specific parameters, for example the surface area of the skin under vacuum and in contact with the concave cavity can be within a 10% margin of 500 mm$^2$ and the opening in fluid contact with a cylinder (e.g. a cylinder in fluid contact with a cartridge) can have a diameter can be within a 10% margin of 8 mm$^2$. Any of the devices, systems and methods herein for collecting sample (e.g. blood samples) can be configured with a removable cartridge. The removable cartridge can be held in fluid communication with the cylinder (e.g. the cylinder in contact with the opening in the concave cavity). Any of the devices disclosed herein can comprise a visual metering window configured to permit visualization of the removable cartridge while the removable cartridge is in the device. Any of the devices disclosed herein can comprise a piercing module, wherein the piercing module comprises one or more piercing elements. The piercing elements can be actuated with a button. Before and after actuation, the piercing element can be withdrawn when the piercing element is in an unactivated state.

Also disclosed herein are cartridges configured to collect sample from the device and transfer it to solid substrate such that precise volumes of sample are collected on and metered by the absorbency of the solid substrate. For example, the standardized quantity of blood saturating each strip of the substrate can be within the range of 50-100 uL on a substrate with surface area within the range of 100-300 square millimeters. A cartridge can comprise a channel disposed between two strips of substrate configured for transferring a blood sample to the two strips of substrate. A cartridge can comprise a spacer disposed between a portion of each of the two strips of substrate. A spacer can be configured to adjust the space between the two strips of substrate depending on one or more conditions. Cartridges can be removable from the device, for example using methods to clip the cartridge into place. Cartridges can further comprise a wicking tail. A wicking tail can be configured for standardizing the quantity of blood saturated on the two strips of substrate.

Collecting standardized quantities of blood on substrate of specific surface area can be performed using various methods. Methods for applying blood to at least two solid supports can comprise the steps of providing a cartridge comprising at least two solid supports. The provided cartridge can comprise at least two solid supports are substantially the same size, such that a surface of each of the at least two solid supports face each other and the surface at least two solid supports are substantially parallel to each other. The at least two solid supports can be separated by a defined distance (e.g. within 10% margin of 0.4 mm), and the cartridge can be configured so that a channel is formed between the two solid supports. Blood can be passing into the tunnel between the at least two solid supports, wherein the blood is absorbed to each of the at least two solid supports as it passes through the tunnel between the at least two solid supports. Solid supports used in these methods can comprise fixed dimensions (e.g. width between 3 mm and 10 mm and length between 3 mm and 26 mm). The cartridge used in the method can further comprise a wicking element configured for metering blood flow through the device.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A is a perspective view of a sample acquisition device in accordance with some embodiments;

FIG. 1B shows a recess of the device for skin suction;

FIG. 1C shows a flow meter of the device for monitoring the progress of sample collection;

FIG. 1D shows a removable cartridge assembly for sample collection;

FIG. 5A shows a side sectional view of the device placed on a subject's skin without vacuum activation;

FIG. 5B shows a schematic block diagram corresponding to the device of FIG. 5A;

FIG. 6A shows the subject's skin being drawn into the recess under vacuum pressure;

FIG. 6B shows a schematic block diagram corresponding to the device of FIG. 6A;

FIGS. 11A and 11B show schematic block diagrams of a sample acquisition device prior to insertion of a cartridge assembly;

FIGS. 12A and 12B show schematic block diagrams of the device after insertion of the cartridge assembly;

FIGS. 13A and 13B show the device of FIGS. 12A/12B being placed on a subject's skin;

FIGS. 14A and 14B show the equalization of pressures and the subject's skin being drawn into the recess, upon piercing the foil separating the vacuum chamber and the deposition chamber;

FIGS. 15A and 15B show the subject's skin being completely drawn into the recess by negative pressure;

FIG. 22B shows a top view of the transportation sleeve and a filled cartridge assembly prior to its insertion into the sleeve;

FIG. 22C shows the filled cartridge assembly inserted into the transportation sleeve;

FIG. 28A shows different views of a deployment spring;

FIG. 28B shows different views of a retraction spring;

FIG. 31A, FIG. 31B, FIG. 31C, and FIG. 31D illustrates features that can be included in a device or device for collecting a blood sample;

FIG. 38D illustrates internal workings of a device provided herein at an end of a travel path of a blade holder, where the collection arm is released by a latch that makes contact with the blade holder at the end of the travel path;

FIG. 38E shows a side view of a device provided herein, providing a view of a release mechanism for a blood collection arm;

FIG. 38F illustrates a released blood collection arm creating a seal around cuts created by blades shown in FIG. 38E;

FIG. 40A, FIG. 40B, FIG. 40C, and FIG. 40D illustrate various views of a blood collection device and components thereof configured for lancing a subject using vertical cutting, and extracting a sample from the subject using a syringe;

FIG. 42A, FIG. 42B, and FIG. 42C illustrates a device and mechanism for collecting a sample using a spring loaded blade rotatable blade to perform vertical cutting;

FIG. 44A and FIG. 44B illustrate two views of a device for simultaneously lancing a subject and forming a seal;

FIG. 50B illustrates a wicking pad capturing excess blood. FIG. 50C illustrates varying levels of blood deposition on matrix strips.);

FIG. 52 illustrates a flow chart of a clinical trial to access precision of blood tests done using blood drawn with devices disclosed herein compared to venipunctures;

FIG. 56 illustrates an exemplary procedure to collect and store blood using a device described herein.

DETAILED DESCRIPTION

Figure 2A:
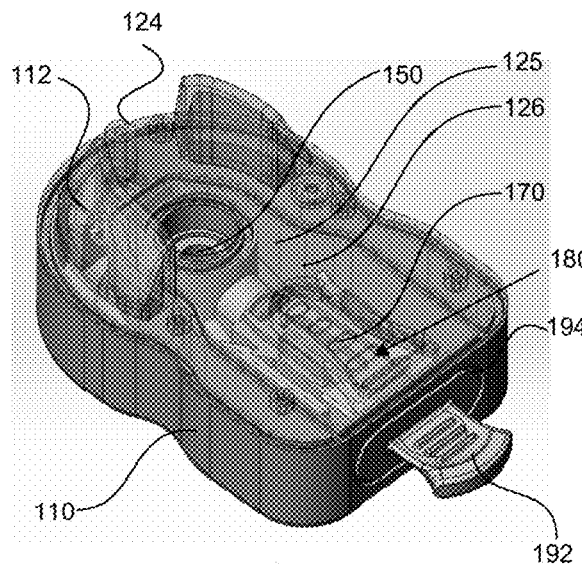
FIG. 2A shows a perspective view of a housing base assembly of the device.

Reference will now be made in detail to exemplary embodiments of the disclosure, examples of which are illustrated in the accompanying drawings. Wherever possible, the same reference numbers will be used throughout the drawings and disclosure to refer to the same or like parts.

I. General

Provided herein are devices, methods, and kits for collecting a fluid sample, e.g., from a subject's body. The fluid sample can be, for example, blood drawn from penetrated skin of the subject. The devices disclosed herein can be handheld and user-activable, and suitable for use outside of traditional healthcare facilities, for example in homes, in remote locations, while a subject is traveling, etc. The devices can be portable and easy to use, and allow individuals to efficiently and reliably collect their own blood samples, without relying on trained healthcare personnel, and without requiring the individual to have any prior blood draw training experience. The devices and methods described herein can be minimally invasive and permit lower levels of pain (or perception of pain) in a subject relative to use of other devices and methods, which can help to improve the overall blood draw experience for the subject. Kits can be provided with detailed instructions that guide users on how the devices can be used for blood sample collection and storage. Optionally in any of the embodiments disclosed herein, the kits can include transportation sleeves and pouches for shipping/transportation of cartridges to testing facilities. A cartridge can be configured to support one or more matrices configured to hold at least a predefined volume of collected blood.

Notably, the sample acquisition devices and methods disclosed herein can enhance collection of a fluid sample (e.g., blood) from the subject. The disclosed sample acquisition devices and methods can be capable of drawing blood at increased flowrates and higher sample volumes beginning from time of skin incision, compared to currently available non-venous blood collection devices and methods. According to various embodiments of the present disclosure, an average collection flowrate and collected sample volume can be increased with aid of a number of features, e.g., a recess that is configured or optimally designed for skin suction, vacuum, pressure differentials, aid of gravitational force, wicking or capillary effects, as described in further detail herein. Additionally, the embodiments disclosed herein are advantageous over currently available non-venous blood collection devices and methods, in that the disclosed devices and methods can permit stabilization of controlled volumes of blood samples to be deposited on one more matrix strips. Further advantages of the disclosed embodiments can include ease of sample removal from a sample acquisition device, and the packaging of the removed sample for subsequent transportation to testing facilities.

Samples, e.g., blood samples, collected using the sample acquisition devices and methods described herein can be analyzed to determine a person's physiological state, for detecting diseases and also for monitoring a health condition of the user. Individuals can rapidly evaluate their physiological status, since samples, e.g., blood samples can be quickly collected using the disclosed devices and methods, and the samples, e.g., blood samples can be either (1) analyzed on the spot using, for example, immunoassays or (2) shipped promptly to a testing facility. The reduced lead-time for blood collection, analysis and quantification can be beneficial to many users, e.g., users who have certain physiological conditions/diseases that require constant and frequent blood sample collection/monitoring.

Various aspects of the devices, methods, and kits described herein can be applied to any of the particular applications set forth herein and for any other types of fluid sample devices, in addition to blood collection devices. The devices, methods, and kits can be used in any system that requires a fluid sample to be drawn from the subject's body. The devices, methods, and kits described herein can be applied as a standalone apparatus or method, or as part of a medical system in a healthcare environment. It shall be understood that different aspects of the devices, methods, and kits described herein can be appreciated individually, collectively, or in combination with each other.

II. Sample Acquisition Devices

FIGS. 1A-1D illustrate sample acquisition device 100 in accordance with some embodiments. A sample acquisition device as described herein can refer to any apparatus, device or system that is designed, configured, or used for collecting, storing, and/or stabilizing a fluid sample, e.g., a fluid sample drawn from a subject. In various aspects, the sample is a biological sample. Non-limiting examples of biological samples suitable for use with the devices of the disclosure can include whole blood, blood serum, blood plasma, and the like.

The devices herein can be used in a variety of environments and applications including an individual's own home, remote locations, on-site or while traveling, personalized healthcare, point-of-care (POC), hospitals, clinics, emergency rooms, patient examination rooms, acute care patient rooms, ambulatory care, pediatrics, field environments, nurse's offices in educational settings, occupational health clinics, surgery or operation rooms.

In some of the embodiments described herein, a sample acquisition device is preferably used to collect and store a sample, e.g., blood, drawn from a subject. A subject as described herein can be an individual, a user, an end user, a patient, and the like. A subject can be an animal, preferably a primate or a non-primate. A subject can be a male or female. A subject can be pregnant, suspected of being pregnant, or planning to become pregnant. A subject can be ovulating. A subject can have a condition, e.g., cancer, autoimmune disease, or diabetes. A human can be an infant, child, teenager, adult, or elderly person. In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100, or over 12 years old, over 16 years old, over 18 years old, or over 21 years old.

The sample acquisition devices herein can be easily and conveniently used by a subject to draw a sample, e.g., blood sample, without the help or aid of others. Optionally in some cases, the device can be used by a third party to collect blood from a subject. A third party can include, for example a family member of the subject, trained medical professionals such as physicians and nurses, Emergency Medical Technicians (EMTs), clinicians, laboratory technicians, untrained medical personnel, etc. Optionally in any of the embodiments disclosed herein, a third party can be a non-living entity, e.g. a robot.

The device can be designed such that it is minimally invasive and generates a low level of pain (or reduced perception of pain) in the users. For example, the device can include a low number (e.g. one or two) piercing elements, instead of an array of multiple (three, four, five or more) needles or microneedles for penetrating the skin. Optionally, a device need not be pre-packaged with one or more piercing elements. For example, a variety of piercing elements can be operably and releasably coupled to the device, and/or interchanged onto the device e.g., after each use. In some alternate cases, a device can be operated without using piercing elements. For example, a subject's skin can have one or more pre-existing cuts, and the device can be placed over the one or more pre-existing cuts to draw blood using skin suction and vacuum pressure.

The device can be portable, disposable and designed for use in a single patient encounter. Optionally in any of the embodiments disclosed herein, the device can be re-usable. For example, a device can be used more than once, for example twice, three, four, five, five, six, seven, eight, nine, ten or more times. Optionally in any of the embodiments disclosed herein, a single device can be used in multiple patient encounters, either with a same subject or with a plurality of different subjects. The device can be of a form factor and ergonomically designed to facilitate the sample collection process. Sample collection, treatment and storage can be performed on a single device. In some cases, sample collection, treatment and storage can be performed using multiple components or devices (e.g., a piercing module and a vacuum module can be provided as separate devices that are operably connected or coupled together via one or more channels).

In some embodiments, a sample acquisition device can be configured or capable of collecting at least 150 uL of blood from a subject within a time window beginning from time of incision or penetration of a skin portion of the subject. The time window can be less than 5 minutes, preferably less than 3 minutes. In some embodiments, the time window can be under 2 minutes. Optionally in any of the embodiments disclosed herein, the time window can be under one minute. The device is capable of collecting a larger volume of blood at higher average flowrates compared to currently available non-venous collection devices.

In some other embodiments, a sample acquisition device can be configured to collect smaller amounts of blood (e.g. less than 150 uL, 140 uL, 130 uL, 120 uL, 110 uL, 100 uL, 90 uL, 80 uL, 70 uL, 60 uL, 50 uL, 40 uL, 30 uL, or 25 uL) of blood from a subject within a time window beginning from time of incision or penetration of a skin portion of the subject. The time window can be less than 5 minutes, preferably less than 3 minutes. In some embodiments, the time window can be under 2 minutes. Optionally in any of the embodiments disclosed herein, the time window can be under one minute.

FIGS. 1A, 1B, 1C, and 1D illustrate different views of an exemplary sample acquisition device 100. Specifically, FIG. 1A shows an overall perspective view of the device. The device can include a housing 102. The housing can include a housing base 110 and a housing cover 152 operably coupled to each other. The housing base can encompass a vacuum chamber and a deposition chamber as described further herein.

Optionally in any of the embodiments disclosed herein, a housing can be provided separately from the components of the device, and the housing need not be part of or integrated with the components. For example, a vacuum chamber, deposition chamber, cartridge chamber, and/or cartridge assembly as described elsewhere herein can be operably coupled to a separately provided housing. A recess as described herein can be provided on a portion of the housing. A housing can include a casing, enclosure, shell, box, and the like. A housing can include one or more hollow chambers, cavities or recesses. The housing may be formed having any shape and/or size. The housing can be configured to support one or more components as described elsewhere herein. Additionally or optionally, one or more of the components can serve or function as the housing. The housing can be integrated with one or more of the components herein, or one or more of the components can be integrated with or into the housing. The housing can be configured for mounting onto a surface such as, for example, skin of a subject. Optionally in any of the embodiments disclosed herein, a bracket or strap can be provided that allows the housing to be mounted to a surface.

The device can include a vacuum activator 114. The vacuum activator can include a button 115 located on the housing base. In some cases, the device does not have a vacuum activator or need not have a vacuum activator (e.g., the device can be configured to automatically configured to provide a vacuum upon sensing contact to an appropriate surface, without requiring a user to manually or semi-manually activate a vacuum activator). The device can further include a piercing activator 166. The piercing activator can include a button 167 located on the housing cover. In some cases, the device does not have a piercing activator or need not have a piercing activator (e.g., the device can be used to draw blood from skin that has already been penetrated or pre-cut by other discrete stand-alone piercing elements). The piercing activator can be preferably activated after the vacuum activator has been activated. In some cases, the piercing activator can be activated independently of the vacuum activator or vacuum state of the device. In some embodiments, the piercing activator can be locked prior to use of the device, and the piercing activator can be activated only after the vacuum activator has been activated. In some cases, the vacuum activator is locked prior to use of the device, and the vacuum activator can be activated only after the piercing activator has been activated. The piercing activator (e.g., button 115) and vacuum activator (e.g., button 167) can be located on the same side or face of the housing. Alternatively, the piercing activator (e.g., button 115) and vacuum activator (e.g., button 167) can be located on different sides or faces of the housing. The device 100 or any of the devices herein can further include a cartridge assembly 180. Such cartridge assembly can be releasably coupled to the device and detached from the device. As shown in FIG. 1A, a cartridge tab 192 of the cartridge assembly can protrude from an edge of the device. Optionally in any of the embodiments disclosed herein, the cartridge tab and the piercing activator/vacuum activator (e.g., buttons 115/167) can be located on different sides (e.g. opposite ends) of the housing. Additional details about the vacuum activator and the piercing activator are described herein.

FIG. 1B shows a bottom perspective view of the device, in particular a recess 136 provided on the housing base 110. The recess can be a concave cavity. The recess can have a cup-like shape. Optionally in any of the embodiments disclosed herein, the recess can have a substantially hemispherical shape. The housing base can be configured to be placed and releasably attached onto a portion of a subject's body, for example on the subject's upper arm. A portion of a subject's skin can be drawn into the recess with aid of vacuum pressure, e.g., as described elsewhere herein. The recess can be configured having a shape and/or size that enables an increased volume of a fluid sample (e.g., blood) to be collected from a subject. The housing base can include a planar portion 132 to be placed on the subject's skin. The planar portion can surround the periphery of the recess. The planar portion of the housing base can have any shape. Optionally in any of the embodiments disclosed herein, the planar portion can include an annular ring-like shape. An adhesive (not shown) can be placed on the planar portion of the housing base to promote adhesion of the device to the subject's skin, and to create an airtight hermetic seal after the device has been placed onto the skin. Optionally in any of the embodiments disclosed herein, a fillet 138 can be provided between the periphery of the recess and the planar portion of the housing base. The fillet can improve vacuum suction to the skin and reduce leaks. As shown in FIG. 1B, the recess can include an opening 140. The opening can be located anywhere in the recess. For example, the opening can be located at an innermost portion of the recess. Optionally in any of the embodiments disclosed herein, a fillet 139 can be provided at the periphery of the opening. Additional details about the recess, the opening, and suction of skin into the recess are described herein.

The opening 140 can be an opening of a lumen 142. The lumen can include a port 144 leading to a deposition chamber (not shown) located in the housing base. Optionally in any of the embodiments disclosed herein, the lumen can include a cutout 145, and the port 144 can be provided within or proximal to the cutout. The cutout 145 can help to reduce or prevent occlusion of the port 144 by a subject's skin when the skin is drawn into the recess of the housing base. Keeping access to the port 144 open (e.g. by not having the port occluded or blocked by skin) can help to ensure that blood drawn from a subject's skin is able to flow through the port 144 into the deposition chamber. The lumen can further include a port 150 leading to an enclosure for holding one or more piercing elements (not shown). The one or more piercing elements can be configured to extend out of the opening to penetrate the subject's skin when (or after) the skin is drawn into the recess by vacuum pressure. The one or more piercing elements can be subsequently retracted back into the housing after penetrating the skin. Additional details about the one or more piercing elements and their actuation are described herein.

Blood can be drawn from cuts made on the skin. The blood can flow from the cuts through the port 144 towards a cartridge (not shown) located in a deposition chamber in the housing base. The flowrate and volume of the blood collection can be enhanced (e.g. increased) with aid of the vacuum, pressure differentials, gravitational force, and wicking/capillary effects, e.g., as described in detail elsewhere herein. The cartridge can include one or more matrices for collecting and storing a predefined volume of the blood. Additional details about the enhanced fluid collection are described in various parts of the Specification, for example in Section II Part G.

FIG. 1C shows a flow meter 170 of the device. The flow meter can include one or more optically transparent windows 172. The flow meter can be substantially aligned with the cartridge (specifically the matrices in the cartridge) when the cartridge assembly is inserted into the device. The flow meter can allow the subject or another user to monitor a progress of the sample (e.g., blood) collection in real-time as the sample is being collected into the cartridge. In some embodiments, the flow meter can be provided on a lid of the housing base. For example, the flow meter can be formed as part of the lid. The lid can be an intervening layer between the housing base and the housing cover. The lid can cover the housing base, and seal a vacuum chamber in the housing base. In some embodiments, the lid can be ultrasonically welded to the housing base. The lid can provide an airtight hermetic seal. Additional details about the flow meter are described, e.g., in Section II Part F of the Specification.

FIG. 1D shows a cartridge assembly 180 that can be releasably coupled to the device. The cartridge assembly can be part of the device, and can be decoupled from the device. The cartridge assembly can be inserted into a deposition chamber (or cartridge chamber) of the housing base via an opening 128. The cartridge assembly can include a cartridge 182 and a cartridge holder 190. The cartridge holder is configured to support the cartridge. The cartridge holder can include a cartridge tab 192, a seal/gasket 194, and spring clips 196. A subject or user can handle or hold the cartridge assembly using the cartridge tab. For example, the subject can insert the cartridge assembly into the deposition chamber (cartridge chamber) of the device by pushing in the cartridge tab. After the sample collection has been completed, the subject can remove the cartridge assembly from the deposition chamber (cartridge chamber) of the device by pulling the cartridge tab. The subject can also hold the cartridge assembly by the cartridge tab to avoid contamination to the cartridge and/or sample. The seal/gasket 194 can hermetically seal the deposition chamber (cartridge chamber) once the cartridge assembly is properly inserted into the device. The spring clips 196 allow the cartridge to be held in place by the cartridge holder.

The cartridge can be configured to support one or more matrices 186 on which the fluid sample (e.g., blood) is collected. In some embodiments, the cartridge can support two or more matrices. The two or more matrices can separated by one or more spacers. The cartridge can include a cartridge port 184 and a channel (not shown) leading to the matrices. The cartridge can be configured to support one or more absorbent pads (not shown) for holding excess fluid. The absorbent pads help to ensure that a predefined volume of fluid can be collected on each of the matrices. Additional details about the cartridge assembly are described, e.g., in Section II Part C of the Specification.

Figure 2B:
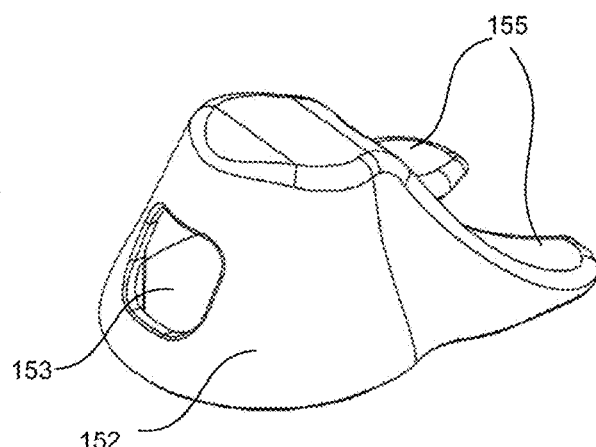
FIG. 2B shows a perspective view of a housing cover of the device.
Figure 2C:
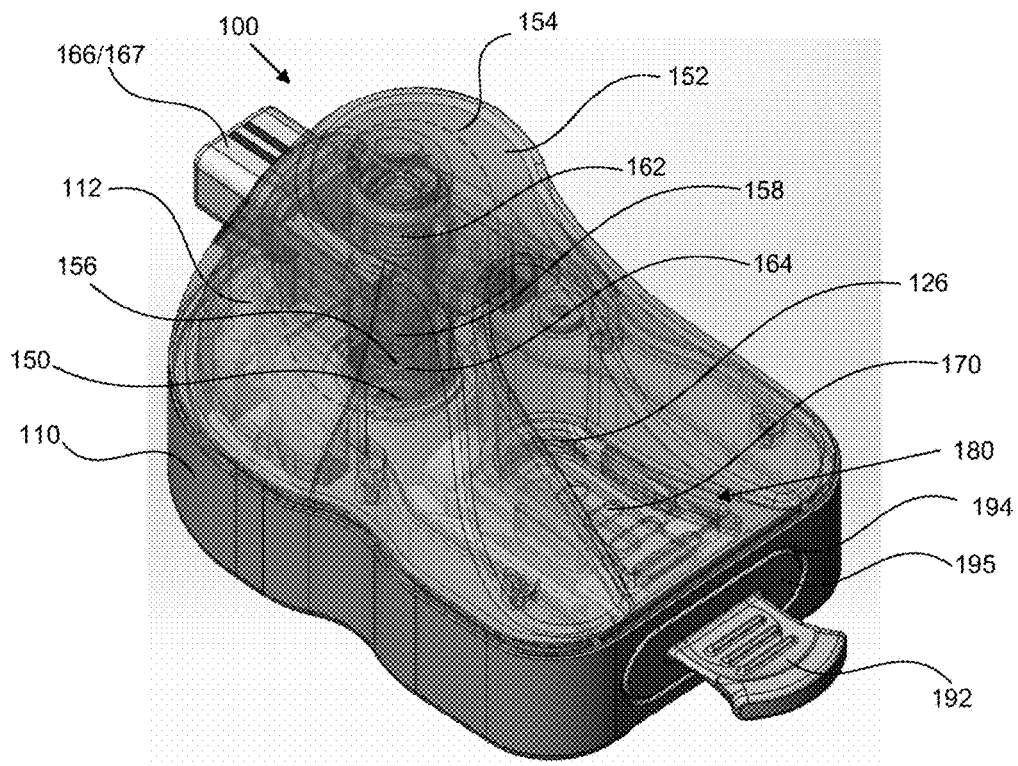
FIG. 2C shows another perspective view of the device.

The housing base 110 and the housing cover 152 can each be separately provided, and coupled together to form the housing. For example, FIG. 2A shows a perspective view of the housing base 110 with a lid 124 covering/sealing the housing base. The housing base can include a vacuum chamber 112 and a deposition chamber 126. The vacuum chamber and the deposition chamber can be separated by one or more walls 125. The walls can be substantially impermeable to fluids (e.g. gases and liquids). The lid 124 can hermetically seal the vacuum chamber and the deposition chamber. The lid can include the flow meter 170. The deposition chamber can also serve as a cartridge chamber, and can be interchangeably referred to as such herein. A cartridge assembly 180 is shown inserted into the deposition chamber (or cartridge chamber). The seal/gasket 194 can hermetically seal the deposition chamber once the cartridge assembly is fully inserted into the deposition chamber. FIG. 2B shows a perspective view of the housing cover 152. The housing cover can include a through-hole 153 through which the button 167 of the piercing activator 166 can be inserted. The housing cover can include wings 155 having a U or V-like shape to prevent obscuring the flow meter on the lid of the housing base. Accordingly, the housing cover can be shaped in a manner that allows a subject or another user to view the flow meter and monitor the progress of the fluid sample collection. The housing cover can have sufficient vertical (Z-height) clearance to permit placement of a piercing module 154 therein. The piercing module can comprise one or more piercing elements that are configured to extend and retract through the opening of the recess. FIG. 2C shows a perspective view of the assembled device 100 whereby the housing cover and the housing base are coupled together. Exemplary means of attachment of the housing cover to the housing base can include snapfits, ultrasonic welding, nuts and bolts, rivets, screws, nails, locks, latches, wires, joints, soldering, welding, gluing and the like. In some alternative embodiments, the housing base and housing cover can be monolithically and collectively formed as a single component.

The housing of the device can be formed having any shape and/or size. The housing or any components thereof can be formed using any number of techniques known in the art such as injection molding, blow molding, three-dimensional (3D) printing, etc. The housing can include materials suitable for healthcare applications (e.g., the housing material is compatible for use with biological materials), depending on the particular application. For example, components of the housing can include or be fabricated from materials such as cellophane, vinyl, acetate, polyethylene acrylic, butyl rubber, ethylene-vinyl acetate, natural rubber, a nitrile, silicone rubber, a styrene block copolymer, a vinyl ether, or a tackifier. Optionally in any of the embodiments disclosed herein, the device can include antimicrobial and/or antiseptic materials, for example sodium bicarbonate; hydrogen peroxide; benzalkonium chloride; chlorohexidine; hexachlorophene; iodine compounds; and combinations thereof.

Optionally in any of the embodiments disclosed herein, one or more components of the device can include or can be fabricated from materials such as polyvinyl chloride, polyvinylidene chloride, low density polyethylene, linear low density polyethylene, polyisobutene, poly[ethylene-vinylacetate] copolymer, lightweight aluminum foil and combinations thereof, stainless steel alloys, commercially pure titanium, titanium alloys, silver alloys, copper alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-housing based ceramics, composites of PEEK and calcium housing based ceramics, composites of PEEK with resorbable polymers, totally resorbable materials, such as, for example, calcium housing based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The housing of the device can comprise acrylobutadiene styrene (ABS), polypropylene (PP), polystyrene (PS), polycarbonate (PC), polysulfone (PS), polyphenyl sulfone (PPSU), polymethyl methacrylate (acrylic) (PMMA), polyethylene (PE), ultra high molecular weight polyethylene (UHMWPE), lower density polyethylene (LPDE), polyamide (PA), liquid crystal polymer (LCP), polyaryl amide (PARA), polyphenyl sufide (PPS), polyether etherketone (PEEK), polyvinyl chloride (PVC), polyethylene terephthalate (PET), polytetra flouroethylene (PTFE), polyaryletherketone (PAEK), polyphenyl sulfone (PPSU), or a combination thereof. In some embodiments, a device disclosed herein can comprise polypropylene, polycarbonate, glass filled polycarbonate, a low permeability copolyester (e.g. Eastman MN211), polyisoprene rubber, and/or TPE injection moldable seals.

Various components of the device can have material composites, including one or more of the above materials, to achieve various desired characteristics such as strength, rigidity, elasticity, compliance, biomechanical performance, durability and/or radiolucency preference. One or more of the components of the device can comprise antimicrobial and/or antiseptic materials. The components of the device, individually or collectively, can also be fabricated from a heterogeneous material such as a combination of two or more of the above-described materials. The components of the device can be monolithically formed or integrally connected.

The device can be ergonomically designed such that a subject or user is able to hold the device comfortably with one hand or both hands. The device can have a compact form factor that makes it highly portable (e.g. easy to be carried around in a user's bag or purse). Exemplary dimensions (e.g. length, width and height) of the device can be given as follows. In some embodiments, the length is about 1.5 inches, about 2.0 inches, about 2.5 inches, about 3.0 inches, or about 3.5 inches. The length can be between about 2.0 inches and about 3.0 inches. The length can be between about 1.5 inches and about 3.5 inches. In some embodiments, the width is about 1.25 inches, about 1.5 inches, about 1.75 inches, about 2.0 inches, or about 2.25 inches. The width can be between about 1.5 inches and about 2.0 inches. The width can be between about 1.25 inches and about 2.25 inches. In some embodiments, the height is about 1.25 inches, about 1.5 inches, about 1.65 inches, about 2.0 inches, or about 2.25 inches. The height can be between about 1.5 inches and about 2.0 inches. The height can be between about 1.25 inches and about 2.25 inches. The length by width by height can be about 2.5 inches by about 1.75 inches by about 1.65 inches.

Figure 3A:
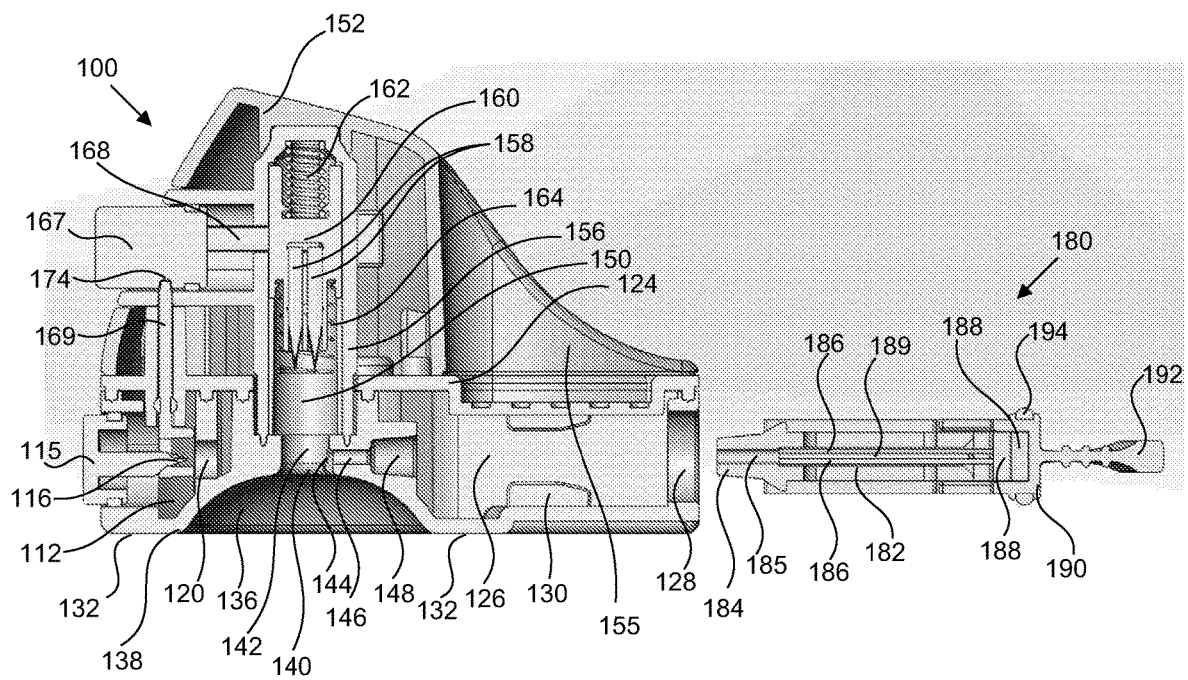
FIG. 3A shows a side sectional view of the device prior to insertion of the cartridge assembly.
Figure 3B:
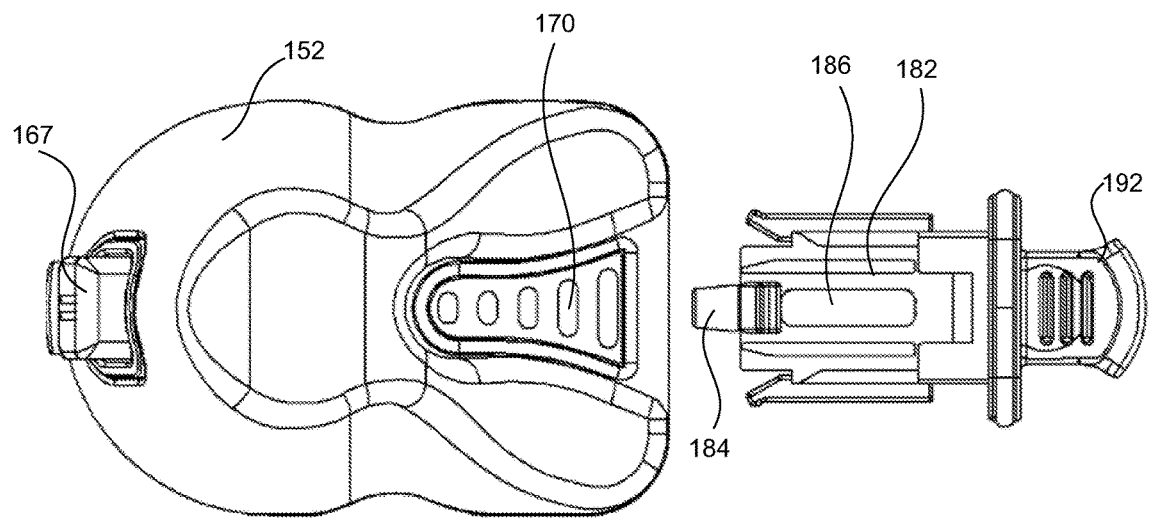
FIG. 3B shows a top view of the device of FIG. 3A.
Figure 4A:
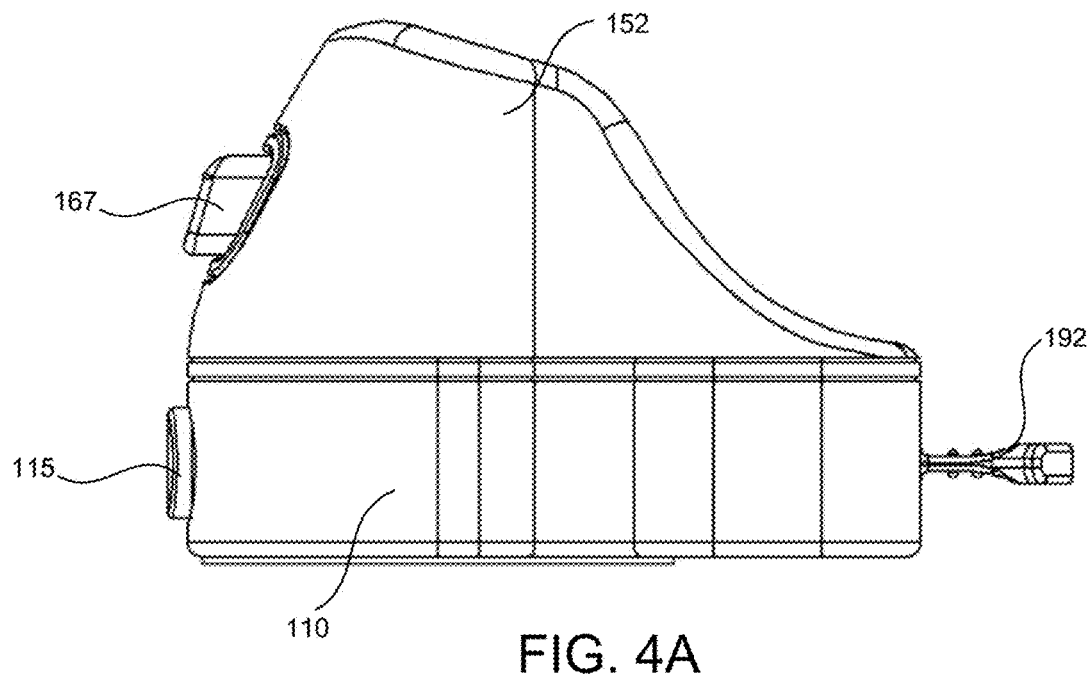
FIG. 4A shows a side view of the device after insertion of the cartridge assembly.
Figure 4B:
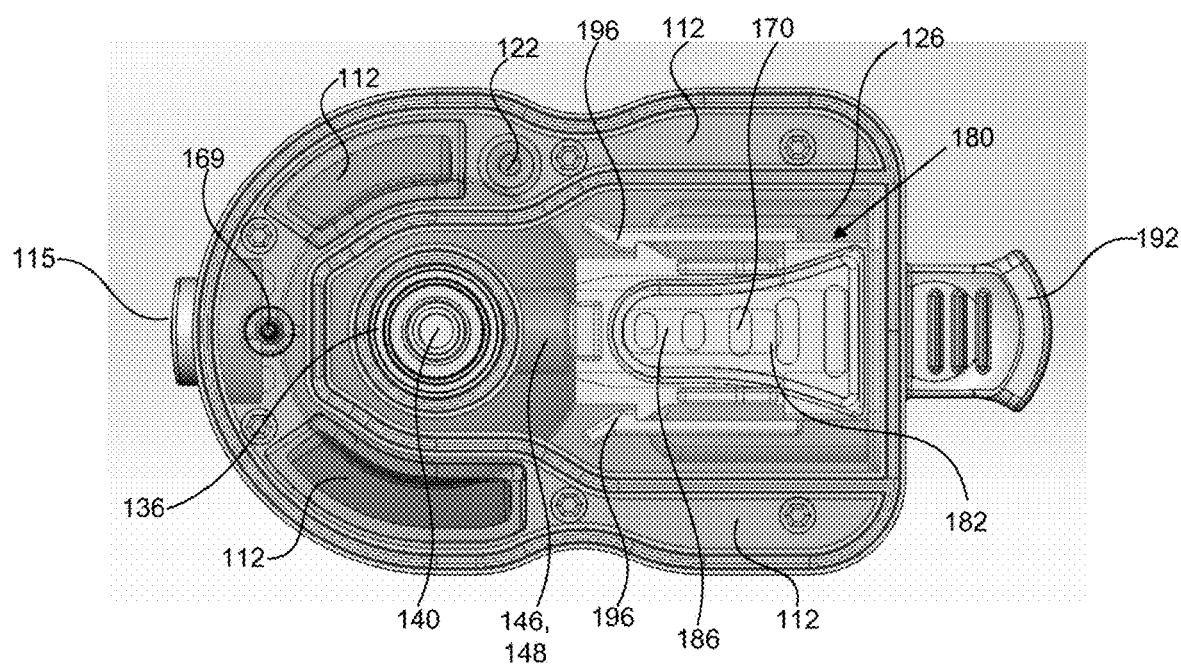
FIG. 4B shows a top sectional view of the device of FIG. 4A.

FIG. 3A shows a side sectional view of the device 100 prior to insertion of the cartridge assembly 180 into the device, and FIG. 3B shows a corresponding top view. FIG. 4A shows a side view of the device with the cartridge assembly inserted therein, and FIG. 4B shows a corresponding top sectional view. Various features of the device 100 and the cartridge assembly 180 are next described in detail with reference to the above figures and other relevant figures.

A. Recess for Skin Suction

Referring to FIGS. 1B and 3A, the housing base 102 of the device can include the recess 136. The recess can be provided on a portion (e.g. bottom surface) of the housing base. The recess can be formed as a sunken cavity or trench on the housing base. In some cases, the recess can be formed as a molded extrusion into the housing base. The recess can be shaped like a cup and configured to provide a skin "cupping" effect with aid of vacuum pressure. The recess can be sized and/or shaped to receive a portion of a surface, e.g., subject's skin therein, and to permit the surface, e.g., skin to substantially conform to the recess under application of vacuum pressure. A surface of the recess can be substantially in contact with the skin drawn into the recess. A gap between the skin and the recess can be negligible when the skin is drawn into the recess. The recess can serve as a suction cavity for drawing the skin therein and for increasing capillary pressure differential. The recess can be configured having a size and/or shape that enables an increased volume of blood to be accumulated in the skin drawn into the recess. The increased volume of the fluid sample can depend in part on a volume and/or surface area of the skin that is drawn into the recess.

In some alternative embodiments, the device can be configured to draw other types of objects (e.g. objects that are not skin or skin surfaces) into the recess under vacuum, and to further draw a fluid sample from those objects. Examples of those other types of objects can include sponges, clothes, fabrics, paper, porous materials, organic produce such as fruits or vegetables, or any solid materials that are holding (or capable of holding) fluid samples therein or thereon. Additional non-limiting examples of biological samples suitable for use with the devices of the disclosure can include sweat, tears, urine, saliva, feces, vaginal secretions, semen, interstitial fluid, mucus, sebum, crevicular fluid, aqueous humour, vitreous humour, bile, breast milk, cerebrospinal fluid, cerumen, enolymph, perilymph, gastric juice, peritoneal fluid, vomit, and the like. In some embodiments, a fluid sample can be a solid sample that has been modified with a liquid medium. In some instances, a biological sample can be obtained from a subject in a hospital, laboratory, clinical or medical laboratory.

The recess can be configured to maintain contact with a skin surface area of the subject under vacuum pressure, prior to and as blood is being collected from penetrated skin of the subject. In some embodiments, the skin surface area of the subject in contact with the recess can be at least 3 $cm^2$, 4 $cm^2$, 5 $cm^2$, 6 $cm^2$, 7 $cm^2$, 8 $cm^2$, 9 $cm^2$, or 10 $cm^2$, or any value therebetween. In some preferred embodiments, at least 5 $cm^2$ of the skin surface area of the subject can be in full contact with the surface of the recess when the skin is drawn into the recess under vacuum pressure. In some embodiments, the volume of the skin enclosed within the recess can be at least about 1.0 $cm^3$, 1.1 $cm^3$, 1.3 $cm^3$, 1.4 $cm^3$, 1.4 $cm^3$, 1.5 $cm^3$, 1.6 $cm^3$, 1.7 $cm^3$, 1.8 $cm^3$, 1.9 $cm^3$, 2.0 $cm^3$, 2.1 $cm^3$, 2.2 $cm^3$, 2.3 $cm^3$, 2.4 $cm^3$, 2.5 $cm^3$, 2.6 $cm^3$, 2.8 $cm^3$, 2.9 $cm^3$, 3.0 $cm^3$, or any value therebetween. In some embodiments, at least 1.8 $cm^3$ of the subject's skin can be enclosed within the recess when the skin is drawn into the recess under vacuum pressure. In some embodiments, the volume of the enclosed within the recess can be substantially the same as an inner volume of the recess.

Optionally in any of the embodiments disclosed herein, the housing base of the device can have more than one recess, e.g. 2, 3, 4, 5, 6, 7, 8, 9, 10 or more recesses. The recesses can be connected to one another, for example by one or more channels. Alternatively, the recesses need not be connected to one another. The recesses can be in fluidic communication with one or more of the vacuum chambers and deposition chambers described elsewhere herein. The plurality of recesses can be configured to permit suction to occur on multiple portions of a surface (e.g. skin surface). In some cases, the plurality of recesses can enable blood to be drawn from different portions of a user's skin (that is drawn into the plurality of recesses).

The recess can be formed having any shape, design, depth, surface area, and/or size. The recess can have any convenient shape, such as a curved shape, hemispherical, spherical cap, square, circle, cuboid, trapezoidal, disc, etc. The recess can be symmetrical, for example a hemisphere. Alternatively, the recess can have an irregular shape and need not be symmetrical. The recess can have rounded corners or edges. Additional examples of possible shapes or designs include but are not limited to: mathematical shapes, two-dimensional geometric shapes, multi-dimensional geometric shapes, curves, polygons, polyhedral, polytopes, minimal surfaces, ruled surfaces, non-orientable surfaces, quadrics, pseudospherical surfaces, algebraic surfaces, riemann surfaces, geometric shapes, and so forth. Optionally in any of the embodiments disclosed herein, the recess can have a substantially circular or elliptical shape. The surface of the recess can be smooth. In some embodiments, the recess can be configured to have a shape and/or size that can reduce or eliminate bruising on the skin when the skin is drawn into the recess by vacuum pressure. Optionally, the surface of the recess can take on a variety of alternative surface configurations. For example, in some cases, the surface of the recess can contain raised or depressed regions.

Referring to FIG. 1B, the recess can comprise a concave cavity. The concave cavity can enclose an interior volume of at least about 1.0 $cm^3$, 1.1 $cm^3$, 1.3 $cm^3$, 1.4 $cm^3$, 1.4 $cm^3$, 1.5 $cm^3$, 1.6 $cm^3$, 1.7 $cm^3$, 1.8 $cm^3$, 1.9 $cm^3$, 2.0 $cm^3$, 2.1 $cm^3$, 2.2 $cm^3$, 2.3 $cm^3$, 2.4 $cm^3$, 2.5 $cm^3$, 2.6 $cm^3$, 2.8 $cm^3$, 2.9 $cm^3$, 3.0 $cm^3$, or any value therebetween. In some embodiments, the concave cavity can preferably enclose an interior volume of about 1.85 $cm^3$.

The recess can have a depth ranging from about 2 mm to about 30 mm, or preferably at least deep enough such that a skin portion of the subject is drawn into and completely fills the recess under vacuum pressure. The depth can be a height of the recess. The depth can be measured relative to an innermost portion of the recess. In some other embodiments, the recess can have a depth that is less than 2 mm or greater than 10 mm.

The recess can have a rigid surface (e.g. a rigid concave surface) that does not deform when skin of a subject is drawn into the recess under vacuum pressure. Alternatively, the recess can have a flexible surface (e.g. a flexible concave surface). For example, the bottom of the recess can include an elastic material such as an elastomer. The elastic material can be configured to conform to the skin when the skin is drawn into the recess. The elastic material can compress or press against the skin when the skin is drawn into the recess. The compression can help to improve the contact area between the skin and the recess. Increased contact area can allow the skin to completely fill the recess with reduced gaps or creases inbetween. This can help to ensure that the skin is sufficiently taut (under tension) prior to penetration of the skin for blood collection. Holding the skin taut can enable deeper cuts to be made in the skin. Furthermore, holding the skin taut can also hold the cuts open better compared to loose skin.

As shown in FIGS. 1B and 3A, the recess can be in the shape of a spherical cap. The spherical cap can be, for example a hemisphere or part of a hemisphere. In some embodiments, a housing base diameter of the spherical cap can range from about 10 mm to about 60 mm, preferably about 25 mm. A height of the spherical cap can range from about 2 mm to about 30 mm, preferably about 6 mm. A volume of a hemisphere formed by the concave surface can be equivalent to, or about half, or about a quarter, of a volume of a vacuum chamber in the device.

Referring to FIGS. 1B and 3A, the recess can include the opening 140. The opening can be located at an innermost portion of the recess. For example, the opening can be located at an apex of the spherical-shaped recess. The opening can be formed having any shape and/or size. In some embodiments, the opening can have a substantially circular or elliptical shape. In some cases, the recess can have more than one opening, e.g., 1, 2, 3, 4, 5, 6, 7, 8, 9, 10, 25, 50, 100, 1000, or more openings. One or more of the openings can be in fluidic communication with a vacuum source and/or an enclosure holding one or more piercing elements. In some cases, one or more openings, e.g., connected to a vacuum source, can be found throughout the surface of the recess, or at least 10%, 25%, or 50% of the surface of the recess. Optionally in any of the embodiments disclosed herein, a plurality of openings can be distributed across the surface of the recess, for example in a manner similar to a showerhead. A vacuum can be applied via the plurality of openings to draw a subject's skin into the recess. In some cases, one or more of the plurality of the openings can be further configured to permit one or more piercing elements to extend and retract therethrough, and to pierce the skin that is drawn into the recess.

The opening 140 can provide access to/from the lumen 142. The device can include one or more piercing elements that are configured to extend through the lumen and out of the opening into the recess, to penetrate skin that is drawn into the recess under vacuum pressure. The penetration of the skin can permit blood to be drawn from the subject, e.g., as described in detail elsewhere herein. The lumen can include two or more ports. For example, the lumen can include a first port 144 leading to the deposition chamber 126 located in the housing base, and a second port 150 leading to an enclosure 156 located in the housing cover. A piercing module 154 comprising one or more piercing elements 158 can be provided in the enclosure 156.

A size of the recess 136 can be substantially greater than a size of the opening 140. For example, a size of the recess can be at least twice a size of the opening. In some embodiments, the size (e.g. diameter) of the opening can range from about 1.5 mm to about 6 mm, and the size (e.g. base diameter or width) of the recess can range from about 10 mm to about 60 mm. In some preferred embodiments, a diameter of the opening can be about 5 mm, and a base diameter of the recess can be about 25 mm.

In some embodiments, a ratio of the size (e.g. diameter) of the opening to the size (e.g. base diameter) of the recess can be about 1:2, about 1:3, about 1:4, about 1:5, about 1:6, about 1:7, about 1:8, about 1:9, about 1:10, about 1:20, about 1:25, about 1:50, or about 1:100, or any ratios therebetween. In some embodiments, a ratio of the size (e.g. diameter) of the opening to the size (e.g. base diameter) of the recess can be about 1:2 to about 1:10, or from about 1:5 to about 1:50, or from about 1:10 to about 1:100. The aforementioned ratio can be also less than about 1:2, 1:3, 1:4, 1:5, 1:10, 1:15, 1:20; 1:25; 1:30; 1:50, or 1:100. In some embodiments, the ratio of the size (e.g. diameter) of the opening to the size (e.g. base diameter) of the recess can be preferably at least about 1:5.

A surface area of the recess 136 can be substantially greater than an area of the opening 140. The surface area of the recess can be associated with the interior of the recess (excluding the opening), and can be measured across a 3D (e.g. a concave hemispherical) plane. The area of the opening can be measured across a substantially 2D or quasi-2D plane defined by the opening. In some embodiments, the surface area of the recess can be at least five times, six times, seven times, eight times, nine times, ten times, or twenty times the area of the opening. In some embodiments, the surface area of the recess can range from about 75 mm$^2$ to about 2900 mm$^2$, and the area of the opening can range from about 1.5 mm$^2$ to about 30 mm$^2$. In some embodiments, the area of the opening can preferably be about 0.2 cm$^2$, and the surface area of the recess can preferably be about 5.2 cm$^2$.

In some embodiments, an area of the skin directly under the opening 140 can be at least 1.5 times smaller than a total area of the skin drawn into the recess 136. In some embodiments, the area of the skin directly under the opening can be preferably at least 5 times smaller than the total area of the skin drawn into the recess.

Referring to FIG. 1B, the planar portion 132 of the housing base can be configured to be placed onto the skin (e.g., on the upper arm) of the subject. The planar portion can be provided surrounding the recess. An adhesive (not shown) can be placed on the planar portion of the housing base. The adhesive can create an airtight hermetic seal on the skin that prevents air from the ambient environment from entering the recess after the device is placed onto the subject's skin. The seal can also prevent fluids (e.g., blood, gas, etc.) from escaping out of the recess into the ambient environment after the device is placed onto the subject's skin. An appropriate biocompatible adhesive material or gasket material can be placed on the planar portion on the housing base, to promote adhesion of the device onto the subject's skin for improved contact. Any suitable adhesive can be used. The adhesive can be a hydrogel, an acrylic, a polyurethane gel, a hydrocolloid, or a silicone gel.

The adhesive can be a hydrogel. Optionally in any of the embodiments disclosed herein, the hydrogel can comprise a synthetic polymer, a natural polymer, a derivative thereof, or a combination thereof. Examples of synthetic polymers include, but are not limited to poly(acrylic acid), poly(vinyl alcohol) (PVA), poly(vinyl pyrrolidone) (PVP), poly (ethylene glycol) (PEG), and polyacrylamide. Examples of natural polymers include, but are not limited to alginate, cellulose, chitin, chitosan, dextran, hyaluronic acid, pectin, starch, xanthan gum, collagen, silk, keratin, elastin, resilin, gelatin, and agar. The hydrogel can comprise a derivatized polyacrylamide polymer.

In some embodiments, the adhesive can be a 3-layer laminate comprising of (1) hydrogel for applying to the skin side), (2) Tyvek™, and (3) a secondary adhesive for bonding to the planar portion of the housing base of the device.

In some embodiments, the adhesive can be pre-attached to the planar portion on the housing base of the device 100. The device can comprise a protective film or backing covering the adhesive on the planar portion. The protective film can be removed prior to use of the device and placement of the device on the subject's skin. In another embodiment, an adhesive in the form of a gel, a hydrogel, a paste, or a cream can be applied to skin of the subject or to the planar portion on the housing base of the device, prior to placement of the device on the subject's skin. The adhesive can then be placed in contact with the subject's skin for a predetermined amount of time (e.g., on the order of several seconds to several minutes) in order to form an adhesion layer between the skin and device. The adhesive can be a pressure-sensitive adhesive or a heat-sensitive adhesive. In some embodiments, the adhesive can be hypoallergenic.

In some embodiments, the adhesive can be a peelable adhesive, and can have a shape and size corresponding to the planar portion on the housing base of the device. In the example shown in FIG. 1B, the planar portion on the housing base can be in the shape of an annular ring, although any shape can be contemplated. Accordingly, the peelable adhesive can be provided as an annular ring corresponding to the planar portion on the housing base.

In some embodiments, a fillet 138 can be provided at an interface between the planar portion and the recess. For example, the fillet 138 can extend continuously along a periphery of the recess adjoining the planar portion of the housing base. The fillet can be configured having a radius or curvature that can help to improve vacuum suction to the skin and to reduce vacuum leak. For example, the fillet of the recess can conform to and be substantially in contact with the skin of the subject when the skin is drawn into the recess. In some embodiments, a fillet 139 can be provided along the periphery of the opening, for example as shown in FIGS. 1B and 3A. The use of fillets can also eliminate sharp edges and reduce unwanted cuts or bruises to the skin when the skin is drawn into the recess under vacuum pressure.

Optionally in any of the embodiments disclosed herein, the recess can be coated or sprayed with a copper, silver, titanium or other metal, coating, or any other antimicrobial material, anti-viral material, surfactants or agents that are designed to reduce microorganisms, disease, virus, cellular, bacteria, or airborne or surface particulates from clinging onto the surface and/or edges of the recess. Optionally in any of the embodiments disclosed herein, one or more walls of the recess can be impregnated with an antimicrobial material. For example, the antimicrobial material can be integrally formed with the recess of the housing to help control the bacterial level present on or within the recess.

B. Vacuum Chamber and Deposition Chamber

The device can include a vacuum chamber 112 and a deposition chamber 126, for example as shown in FIGS. 2A, 2C, 3A and 4B. The vacuum chamber and the deposition chamber can be provided in the housing (e.g. integrated into the housing base). Optionally, the vacuum chamber and the deposition chamber can be operably coupled to a separately provided housing. The vacuum chamber can be configured to be in fluidic communication with the recess and the deposition chamber. The vacuum chamber and the deposition chamber can be part of the housing base. The vacuum chamber and the deposition chamber can be located in different sections (e.g. compartments) of the housing base, and provided having various shapes or configurations. For example, in some embodiments, the vacuum chamber can be shaped like a horse-shoe surrounding the deposition chamber, as shown in FIGS. 2A and 4B. The vacuum chamber and the deposition chamber can be separated by one or more walls 125. The walls can be substantially impermeable to fluids (e.g. gases and liquids) and can prevent leaks between the chambers. The walls can be made materials having very low permeability values. For example, polypropylene can have a permeability coefficient of $9 \times 10^{-11}$ $(cm^3$ $cm)/(sec \cdot cm^2 \cdot cm \cdot Hg)$ to oxygen, and $4.5 \times 10^{-11}$ $(cm^3$ $cm)/(sec \cdot cm^2 \cdot cm \cdot Hg)$ to air. As an example, PETG can have a permeability coefficient of $1.5 \times 10^{-11}$ $(cm^3$ $cm)/(sec \cdot cm^2 \cdot cm \cdot Hg)$ to oxygen, and $7.5 \times 10^{-12}$ $(cm^3$ $cm)/(sec \cdot cm^2 \cdot cm \cdot Hg)$ to air. In some alternative cases, the vacuum chamber and the deposition chamber need not be separated, e.g., by walls. For example, the vacuum chamber and the deposition chamber can be the same chamber in a device as packaged. The combined vacuum chamber and the deposition chamber can be a monolithic chamber. A chamber can have more than one function or purpose, for example 2, 3, 4, 5, 6, 7, 8, 9, 10 or more functions or purposes. For example, in some cases, a vacuum chamber can also serve the function of a deposition chamber. Likewise, in some cases, a deposition chamber can also serve the function of a vacuum chamber.

The deposition chamber can be interchangeably referred to as a cartridge chamber, since the deposition chamber can be configured to receive a cartridge assembly 180 therein. Blood can be collected from the subject, and transported from the recess into the deposition chamber for collection and storage onto a cartridge 182. In some cases, the device comprises more than one vacuum chamber, e.g., 2, 3, 4, 5, 6, 7, 8, 9, 10, or more vacuum chambers (each vacuum chamber can be connected to a different recess or the same recess), and/or more than one deposition chamber, e.g., 2, 3, 4, 5, 6, 7, 8, 9, 10, or more deposition chambers (each deposition chamber can be connected to the same vacuum chamber or a different vacuum chamber). Any number of vacuum chambers and/or deposition chambers can be contemplated for depending on design applications and needs.

The housing base can include a lid 124 that covers and hermetically seals the vacuum chamber. The lid can serve as a vacuum chamber lid. The lid can also cover the deposition chamber or a portion thereof. The vacuum chamber can be an evacuated chamber, and can be referred to interchangeably as such. Referring to FIG. 4B, the vacuum chamber can include a self-sealing septum 122 through which air can be drawn out of the vacuum chamber. A vacuum state can be generated in the vacuum chamber, for example by inserting a distal end of a syringe through the septum 122, and using the syringe to draw air out of the vacuum chamber. The distal end of the syringe can comprise a needle that is inserted through the septum into the vacuum chamber. The septum can be made of any appropriate airtight flexible or elastomeric material. In some embodiments, the septum can be made of polyisoprene. The septum can be in a naturally sealed state, and can revert to its sealed state when the needle is removed from the septum.

In some other embodiments, a mechanical device such as a vacuum pump can be used to evacuate the vacuum chamber (e.g., before or after packaging). The mechanical device can include components such as pistons, motors, blowers, pressure regulators, and the like. In some cases, non-mechanical means, such as chemicals or other reactants, can be introduced to the vacuum chamber and can undergo reaction to decrease pressure within the vacuum chamber (e.g., create a vacuum state).

The housing base can include a separation interface 120 that separates the vacuum chamber from the deposition chamber. The separation interface can be, for example a foil. In some embodiments, the separation interface can be a multi-layer foil laminate. The separation interface can include any materials or means that can serve as a fluidic barrier between the vacuum chamber and the deposition chamber. The separation interface can be "opened" to enable fluidic communication between the vacuum chamber and the deposition chamber. Other non-limiting examples of a separation interface include diaphragms, caps, seals, lids, membranes, valves, and the like. The separation interface can be bonded to the housing base using any of the attachment means described herein. The separation interface can include any suitable polymer or composite material that can be pierced by a sharp object. The separation interface can be impermeable or semipermeable to gas or liquids. For example, suitable materials for use in the separation interface can include polymer thin films, polyethylene, latex, etc.

The separation interface, e.g., foil, can help to maintain the vacuum pressure in the vacuum chamber, and the pressure difference between the vacuum chamber and the deposition chamber. Piercing the separation interface, e.g., foil, can result in pressure equalization between the vacuum chamber and the deposition chamber, and create a pressure differential (negative pressure) that (1) draws the skin into the recess and (2) further draws blood from skin of the subject after the skin has been penetrated. In some embodiments, a vacuum pressure of at least about −1 psig to −2 psig is provided, in order to draw the surface, e.g., skin into the recess and completely fill the recess. In some embodiments, the skin is drawn into the recess by the vacuum and completely fills the recess in less than 2 seconds, preferably less than 1 second. In some embodiments, the skin is drawn into the recess by the vacuum and completely fills the recess in no more than 5 seconds.

In some cases, the vacuum chamber and the deposition chamber need not be separated, i.e., the vacuum chamber and the deposition chamber can be the same chamber, or can collectively constitute a same chamber. In those cases, the combined vacuum chamber/deposition chamber can be separated from an opening of the recess by a separation interface, e.g., foil. As an example, the separation interface can be provided at or proximal to the opening of the recess, and can be used to establish fluidic communication between the recess and the combined vacuum chamber/deposition chamber.

As previously described, the recess of the device can be configured having a size and/or shape that enables higher average flowrate, and an increased volume of blood to be accumulated and collected. The collection flowrate can be dependent on the shape and/or size of the recess. For example, the recess shown in FIG. 1B can aid in enhancing the flowrate of blood collected from the subject.

The increased volume and flowrate of the blood collection can also depend on a starting or initial vacuum pressure of the vacuum chamber. The starting or initial vacuum pressure can correspond to the pressure of the vacuum chamber post evacuation. In some embodiments, the initial vacuum pressure of the vacuum chamber can range from about −4 psig to about −15 psig, preferably about −8 psig to about −12 psig. In some preferred embodiments, the initial vacuum pressure of the vacuum chamber can be about −12 psig. In some other embodiments, the initial vacuum pressure of the vacuum chamber can be less than −15 psig, for example −16 psig, −17 psig, −18 psig, −19 psig, −20 psig, −21 psig, −22 psig, −23 psig, −24 psig or lower.

The vacuum chamber can have a volume V1 ranging from about 3 $cm^3$ to about 30 $cm^3$. The deposition chamber can have a volume V2 ranging from about 1 $cm^3$ to about 20 $cm^3$.

In some embodiments, the volume V1 of the vacuum chamber is preferably about 10 $cm^{3'}$ and the volume V2 of the deposition chamber is preferably about 6 $cm^3$." The volumes of the vacuum chamber and the deposition chamber can be designed such that the pressure in both chambers equalizes to a desired value when the separation interface, e.g., foil, separating the two chambers is pierced. For example, the vacuum chamber can have an initial starting vacuum pressure of about −12 psig, and the ratio of V1 to V2 can be configured such that the equalized pressure in both chambers is about −4 psig after the foil is pierced. Any ratio of V1:V2 can be contemplated, for example 1:1, 1:2, 1:3 and so forth.

In some embodiments, the increased volume of the blood in the skin drawn into the recess is at least about 20 μL, 30 μL, 40 μL, 50 μL, 60 μL, or 70 μL prior to the penetration of the skin. Higher flowrates and blood sample collection volumes can be achieved in part due to the increased volume of blood in the skin drawn into the recess, increased capillary pressure, and with aid of the vacuum pressure. In some embodiments, the device is capable of drawing blood from penetrated skin and collecting the blood at a flowrate of at least about 30 μL/min. In some embodiments, the device can be capable of drawing blood from penetrated skin and collecting the blood at a flowrate of more than 600 μL/min. Generally, the device is capable of drawing blood from penetrated skin and collecting the blood at an average flowrate of at least about 100 μL/min, 125 μL/min, 150 μL/min, or any values or ranges therebetween. In some embodiments, the device can sustain the aforementioned average flowrate(s) at least until a substantial amount of blood has been collected (e.g. ranging from about 150 μL to about 1000 μL of blood, or in some cases more than 1 mL of blood). In some embodiments, the device is capable of collecting about 250 uL of fluid sample from the subject in less than 1 min 45 secs. In some cases, the device is capable of collecting at least 175 uL to 300 uL of fluid sample from the subject in less than 2 mins. In some cases, the device is capable of collecting at least 200 μL of fluid sample from the subject in less than 4 minutes.

In some other embodiments, the device 100 can be configured to collect smaller amounts of blood (e.g. less than 150 uL, 140 uL, 130 uL, 120 uL, 110 uL, 100 uL, 90 uL, 80 uL, 70 uL, 60 uL, 50 uL, 40 uL, 30 uL, or 25 uL) of blood from a subject within a time window beginning from time of incision or penetration of a skin portion of the subject. The time window can be less than 5 minutes, preferably less than 3 minutes. In some embodiments, the time window can be under 2 minutes. In some embodiments, the time window can be under one minute.

In some embodiments, (1) the size and/or shape of the recess and/or (2) the vacuum pressure can be configured to achieve a minimum capillary pressure in the skin drawn into the recess. Similarly, (1) the size and/or shape of the recess and/or (2) the vacuum pressure can be configured to achieve a minimum tension in the skin drawn into the recess. As an example, the tension of the skin can be about 0.8 lbs/force at a vacuum pressure of about −1 psig.

An area of skin under vacuum when the device is applied to the skin can be about 100 to about 1000 $mm^2$, or about 100, 200, 300, 400, 500, 600, 700, 800, or 900 $mm^2$. An area of skin under the opening can be about 0.1 $mm^2$ to about 20 $mm^2$, or about 2, 4, 6, 8, 10, 12, 14, 16, 18, or 20 $mm^2$. An area of skin under vacuum when the device is applied to the skin can be at least 100, 200, 300, 400, 500, 600, 700, 800, or 900 $mm^2$, or less than 100, 200, 300, 400, 500, 600, 700, 800, or 900 $mm^2$, or about 100 to about 900 $mm^2$, or about 200 to 800 $mm^2$.

In some embodiments, an area of skin under vacuum is an area of skin encompassed by the area of the concave cavity at the housing base of the device. In some embodiments, an area of skin under vacuum is an area skin under the opening. In some embodiments, an area of the skin under the opening is at least 5 times smaller than an area of skin under vacuum when the device is applied to the skin. In some embodiments, an area of skin under the opening is about 5, about 10, about 20, about 30, about 40, about 50, about 60, about 70, about 80, about 90, about 100 times, about 200, about 300, about 400, about 500, about 600, about 700, about 800, about 900, about 1000, about 2000, about 3000, about 4000, about 5000, about 6000, about 7000, about 8000, about 9000, or about 10,000 times smaller than an area of skin under the vacuum. An area of skin under the opening can be less than 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 times smaller than an area of skin under the vacuum.

C. Piercing Module

Figure 26:
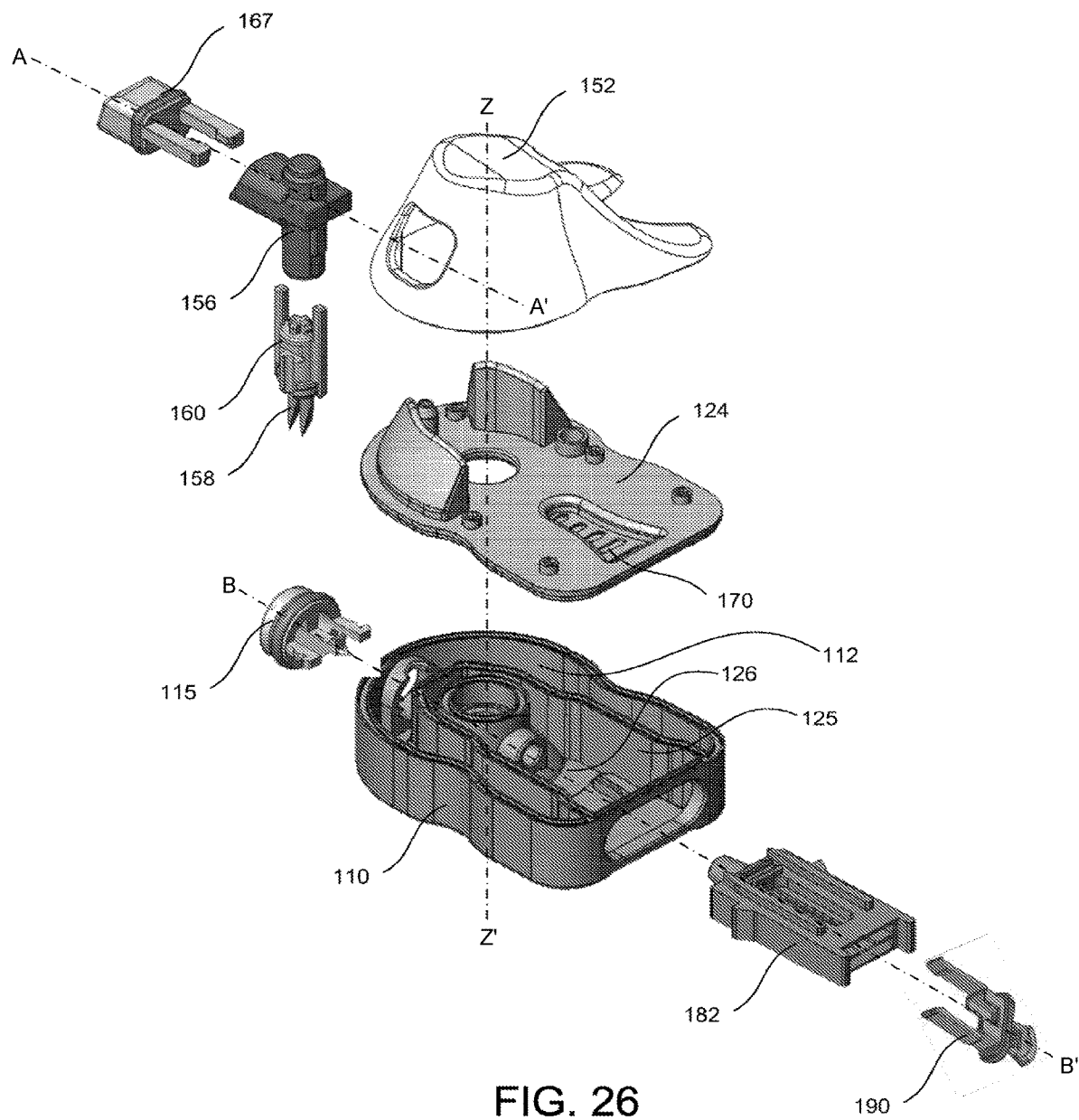
FIG. 26 shows an exploded view of certain components of the sample acquisition device.
Figure 27A:
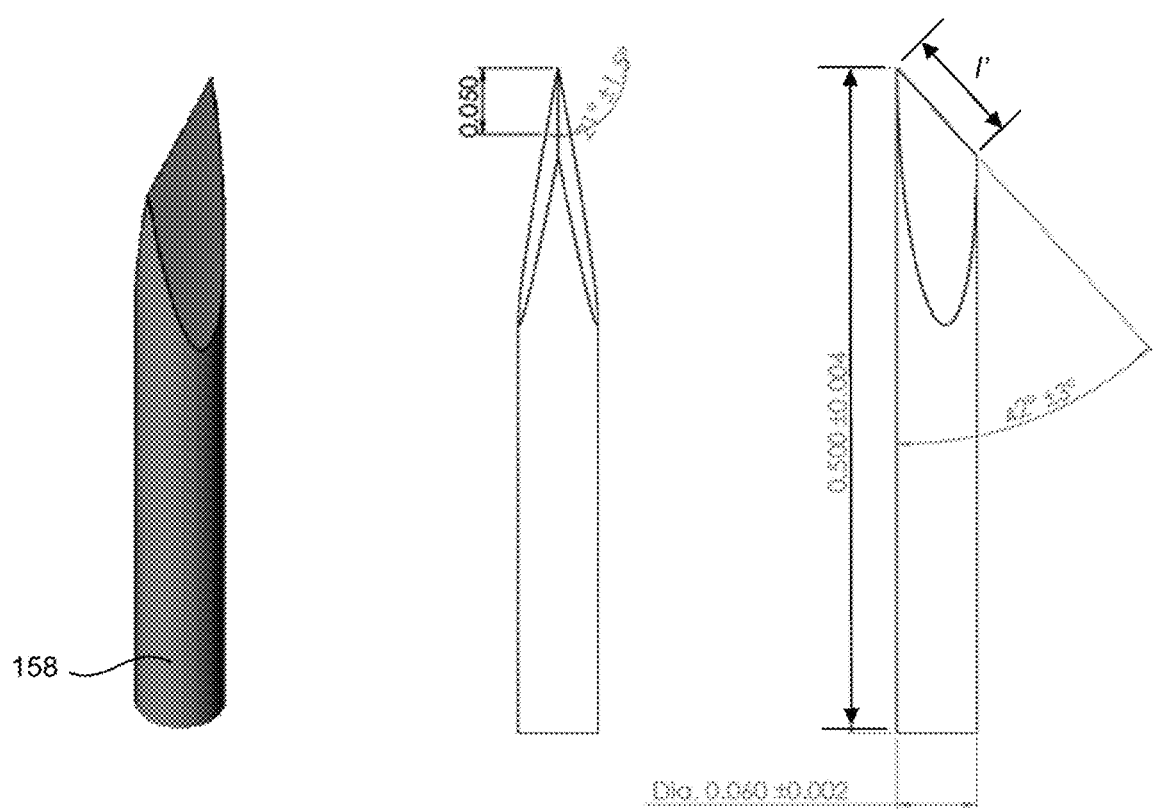
FIG. 27A shows different views of a piercing elements.
Figure 27B:
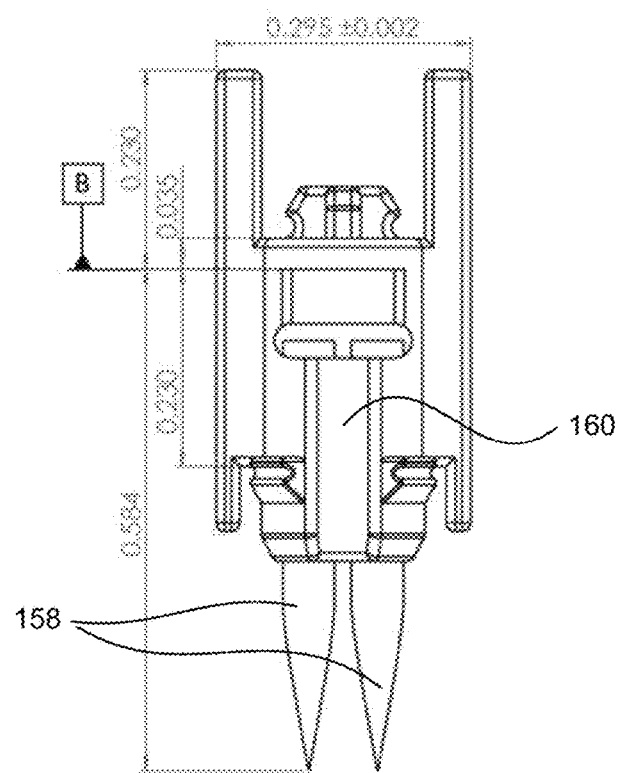
FIG. 27B shows the piercing elements being supported by a holder.

The device can include a piercing module 154 for penetrating skin of the subject when the skin is drawn into the recess under vacuum pressure. In some alternative cases, the device need not comprise a piercing module. The piercing module 154 can be provided in an enclosure 156. The enclosure can be located within the housing cover 152. The enclosure can be provided as a separate component that is coupled to the housing cover (see, e.g. FIG. 26). FIG. 26 show a vertical axis Z-Z' extending through housing cover 152, lid 124 and housing base 110. FIG. 26 also shows an axis A-A' extending through button 167 and enclosure 156. FIG. 26 further shows an axis B-B' extending through button 115, deposition chamber 126, cartridge 182, and cartridge holder 190. The piercing module can include one or more piercing elements 158 supported by a holder 160, for example as shown in FIGS. 27A and 27B. The piercing elements can include lancets, lances, blades, needles, microneedles, surgical knives, sharps, rods, and the like. Any number of piercing elements (e.g., at least 1, 2, 3, 4, 5, 6, 7, 8, 9, 10 or more piercing elements) can be contemplated. In some embodiments, the piercing elements can preferably comprise two lancets.

The piercing elements can comprise tempered steel, high carbon steel, or stainless steel. Examples of stainless steel include, but are not limited to 304 stainless steel, 316 stainless steel, 420 stainless steel, and 440 stainless steel. In some embodiments, the piercing elements can be coated with a surface finish. The surface finish can increase lubricity during a skin cut. The surface finish can also improve sharpness or penetration ability of the piercing elements. In some embodiments, the surface finish can be a zirconium nitride coating or a titanium nitride coating.

The piercing elements can be made of a biocompatible plastic or a biocompatible metal. The biocompatible plastic can include a number of suitable types of polymeric materials including, but not limited to, thermosets, elastomers, or other polymeric materials. Further, suitable biocompatible metals can include, for example, stainless steel, titanium, etc. Additionally or optionally, the piercing elements can be formed from various composite materials. The piercing elements can be manufactured using a number of suitable production processes. For example, the piercing elements can be fabricated using known metal processing techniques, such as casting or forging, or for the case of polymeric materials, any suitable polymer processing system can be used, including, for example, injection molding. A piercing element can have a sharp, pointed end that can be used to pierce a user's skin in order to collect blood.

The piercing module can further comprise one or more actuation elements (e.g., spring elements) for actuating the holder and moving the piercing elements. Other non-limiting examples of actuation elements can include magnets, electromagnets, pneumatic actuators, hydraulic actuators, motors (e.g. brushless motors, direct current (DC) brush motors, rotational motors, servo motors, direct-drive rotational motors, DC torque motors, linear solenoids stepper motors, ultrasonic motors, geared motors, speed-reduced motors, or piggybacked motor combinations), gears, cams, linear drives, belts, pulleys, conveyors, and the like. Non-limiting examples of spring elements can include a variety of suitable spring types, e.g., nested compression springs, buckling columns, conical springs, variable-pitch springs, snap-rings, double torsion springs, wire forms, limited-travel extension springs, braided-wire springs, etc. Further, the actuation elements (e.g., spring elements) can be made from any of a number of metals, plastics, or composite materials.

In some embodiments, the spring elements can include a deployment spring 162 positioned to deploy the one or more piercing elements through the opening of the recess, to penetrate the skin of the subject. An example of a deployment spring is shown in FIG. 28A. In some embodiments, the deployment spring can be configured to move and cause the piercing elements to penetrate the skin at speeds ranging from about 0.5 m/s to about 1.5 m/s, preferably about 1 m/s, and with a force ranging from about 1.3N to about 18N. The deployment spring can be configured to cause the one or more piercing elements to penetrate the skin to depths ranging from about 0.5 mm to about 3 mm.

The spring elements can further include a retraction spring 164 positioned to retract the one or more piercing elements through the opening back into the device, after the skin of the subject has been penetrated. An example of a retraction spring is shown in FIG. 28B. The retraction spring can be configured to retract the piercing elements from the skin of the subject at a speed of about 0.2 m/s. A spring-force of the retraction spring can be less than a spring-rate of the deployment spring. In some embodiments, the deployment spring can have a spring-rate of about 2625 N/m, and the retraction spring can have a spring-force of about 175 N/m.

A piercing element can have a length of about 1.0 mm to about 40.0 mm, or about 1.0 mm, about 1.5 mm, about 2.0 mm, about 4.0 mm, about 6.0 mm, about 8.0 mm, about 10.0 mm, about 15.0 mm, about 20.0 mm, about 25.0 mm, about 30.0 mm, about 35.0 mm, about 40.0 mm; a width of about 0.01 mm to about 3.0 mm, or about 0.01 mm, about 0.05 mm, about 0.1 mm, about 0.5 mm, about 1.0 mm, about 1.5 mm, about 2.0 mm, about 2.5 mm, about 3.0 mm. The length of a piercing element can be measured along a longitudinal direction, for example as shown by length l in FIG. 27A.

Each of the one or more piercing elements can be configured to pierce the skin of the subject to a depth of about 1.0 mm to about 25.0 mm, or about 1.0 mm, 1.5 mm, 2.0 mm, 3.0 mm, 4.0 mm, 5.0 mm, about 6.0 mm, about 7.0 mm, about 8.0 mm, about 9.0 mm, about 10.0 mm, about 15.0 mm, about 20.0 mm or about 25 mm. In some embodiments, a penetration depth of the one or more piercing elements can be preferably about 2 mm into the skin of the subject.

In some embodiments, the piercing elements can include lancets, and a length l of the lancet can be preferably less than about 13 mm. This length can be relatively shorter than currently commercially available lancets, and the shorter length of the lancets in the embodiments described herein can help to reduce the form factor of the device, as well as the type of spring and spring forces for actuating those lancets. For example, a shorter spring with lower spring-rate is needed to actuate a shorter lancet, as compared to longer lancets which tend to require longer springs and higher spring-rates. Shorter springs and lancets can help to reduce the size of the piercing module, which leads to a corresponding reduction in the size of the housing cover and the overall size of the device.

In some embodiments, two or more piercing elements can be supported by the holder in a random configuration. For example, two or more piercing elements can have random orientations relative to each other. The two or more piercing elements can comprise beveled edges that are randomly oriented relative to each other. The beveled edges of the two or more piercing elements can be non-symmetrical to each other. For example, the beveled edges of the two or more piercing elements can be at an acute or oblique angle relative to each other. Accordingly, the two or more piercing elements in the above configuration can be configured to generate cuts on the skin that extend in different directions along the skin, and that are non-parallel to each other.

In some alternative embodiments, two or more piercing elements can be supported by the holder in a predefined configuration. The two or more piercing elements can have predefined orientations relative to each other. For example, the two or more piercing elements can comprise beveled edges that are oriented relative to each other in a predefined manner. The beveled edges of the two or more piercing elements can be symmetrical to each other.

In some embodiments, the piercing elements can include two or more lancets. The lancets can have a same bevel angle, or different bevel angles. An example of a lancet and a bevel angle is shown in FIG. 27A. The bevel angle(s) can range from about 10 degrees to about 60 degrees. In some embodiments, the bevel angle of the lancets can be preferably about 42 degrees. The two or more lancets can have a same bevel length. Alternatively, the two or more lancets can have different bevel lengths. The bevel length of a lancet as described herein can refer to a length of the sharp beveled or slanted edge of the lancet, as shown by l' in FIG. 27A. In some embodiments, the bevel length of a lancet can range from about 1.6 mm to about 2.2 mm.

A method for penetrating the skin of a subject using the device 100 can be provided as follows. The method can include (1) placing the device onto the skin of the subject, (2) drawing skin into the recess of the device using vacuum, (3) activating an actuation element (e.g., a deployment spring) and deploying the one or more piercing elements through the opening in the device; (4) penetrating the skin of the subject using the one or more piercing elements; and (5) using another actuation element (e.g., a retraction spring) to retract the one or more piercing elements back into the device.

D. Vacuum Activator and Piercing Activator

The device can include a vacuum activator 114 configured to activate the (evacuated) vacuum chamber, which generates a vacuum pressure that can draw the skin into the recess and subsequently facilitate collection of blood from the penetrated skin. The device can also include a piercing activator 166 configured to activate the deployment spring, for actuating the piercing elements. The vacuum activator can be separate from the piercing activator. For example, the vacuum activator and the piercing activator can be two separate discrete components of the device. In some alternative embodiments (not shown), the vacuum activator and the piercing activator can be integrated together as a single component that can be used to simultaneously or sequentially activate the vacuum and the piercing elements.

The vacuum activator can include a first input interface, and the piercing activator can include a second input interface. The first and second input interfaces can be located on different parts of the housing. Examples of suitable input interfaces can include buttons, knobs, finger triggers, dials, touchscreens, keyboards, mice, or joysticks. In some embodiments, at least one of the first input interface or the second input interface can comprise a button. For example, the vacuum activator can include a button 115 located on the housing base 110, and the piercing activator can include a button 167 located on the housing cover 152. In some embodiments, the vacuum activator and the piercing activator can be located on a same side of the housing, and the buttons 115/167 can be ergonomically accessible by the subject when the device is mounted onto an arm of the subject. The buttons can have distinct or different shapes and/or sizes, and can be ergonomically located for ease of use (e.g. easy identification by the user and well placed locations for simple activation).

In some alternative embodiments (not shown), at least one of the first or second input interfaces can be remote from the housing of the device. For example, one or both of the first and second input interfaces can be located on a user terminal (e.g. a mobile device or remote controller) that is connected with the device 100 via one or more wired or wireless communication channels.

Examples of wireless communication channels can include Bluetooth®, WiFi, Near Field Communication (NFC), 3G, and/or 4G networks. Signals for activating the vacuum and/or the piercing elements can be transmitted remotely from the user terminal to the device 100 over the one or more communication channels.

Figure 7A:
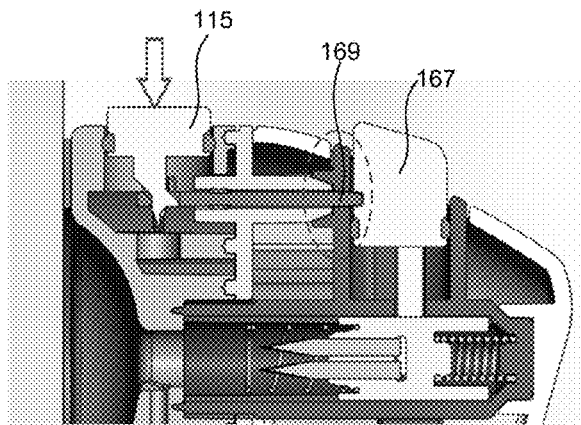
FIG. 7A shows a piercing activator of the device in a locked state.
Figure 7B:
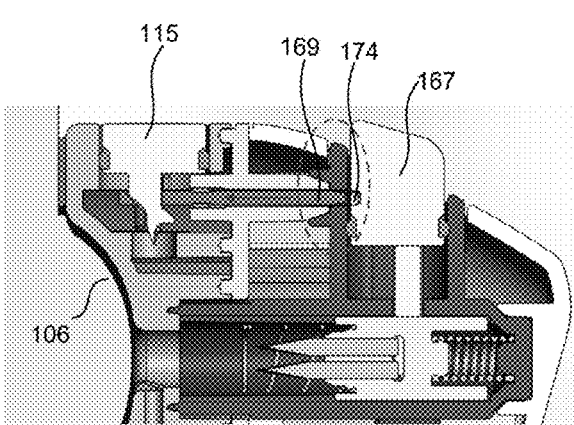
FIG. 7B shows the piercing activator of the device in an unlocked state.

In some embodiments, the vacuum activator can be activated first, followed by the piercing activator. In other words, vacuum pressure can be activated prior to activation of the piercing elements. In certain embodiments, the piercing activator can be activated only after the vacuum activator and vacuum have been activated. For example, the piercing activator can be initially in a locked state, and incapable of activating the one or more piercing elements prior to activation of the vacuum. The piercing activator can be unlocked only after the vacuum activator has been activated. The above effect can be achieved by providing a locking mechanism that couples the piercing activator to the vacuum activator. The locking mechanism can be configured such that the piercing activator is initially in the locked state. The vacuum activator can function as a key for unlocking the piercing activator, and the piercing activator can be simultaneously unlocked when the vacuum activator is activated. Referring to FIGS. 7A and 7B, the locking mechanism can include a locking pin 169 coupled to the button 115 of the vacuum activator. Prior to use of the device for sample collection, the locking pin can be engaged in a slot or hole 174 located on the button 167 of the piercing activator, which prevents the button 167 from being pressed down by a user. Accordingly, the piercing activator is incapable of being activated when the button 167 is in the locked position. When the user presses the button 115, the locking pin 169 retracts in the direction shown in FIG. 7B and disengages from the slot 174, thus unlocking the button 167. Pressing the button 115 also pierces the foil 120 separating the vacuum chamber and the deposition chamber which causes the vacuum to be activated. Specifically, the chambers equalize to a negative pressure which draws the subject's skin into the recess. The user can then press down the unlocked button 167 to activate the piercing elements 158 for penetrating the subject's skin that is drawn into the recess.

In some embodiments, the piercing activator can be configured to activate the one or more piercing elements after the skin is drawn into the recess. The piercing activator can be configured to activate the one or more piercing elements after the skin is drawn into the recess by the vacuum for a predetermined length of time. The predetermined length of time can range, for example from about 1 second to about 60 seconds.

The vacuum activator can be configured to activate the vacuum by piercing the foil, which establishes fluidic communication between the vacuum chamber, deposition chamber, and the recess, and introduces negative pressure in the recess and the deposition chamber.

In some embodiments (not shown), the foil can be replaced by a valve, and the vacuum activator can be configured to open the valve to establish the fluidic communication. A valve can be a flow control valve having a binary open and closed position. Alternatively, a flow control valve can be a proportional valve that can control the flow rate of the air that flows between the vacuum chamber and the deposition chamber. For example, a proportional valve can have a wide open configuration that can permit a greater rate of flow than a partially open configuration that can permit a lesser rate of flow. Optionally, regulating, throttling, metering or needle valves can be used. Return or non-return valves can be used. A valve can have any number of ports. For example, a two-port valve can be used. Alternatively, a three-port, four-port or other type of valve can be used in alternative configurations. Any description herein of valves can apply to any other type of flow control mechanism. The flow control mechanisms can be any type of binary flow control mechanism (e.g., containing only an open and closed position) or variable flow control mechanism (e.g., which can include degrees of open and closed positions).

In some embodiments, the vacuum activator can be located on the housing such that the button 115 is configured to be pressed in a first direction when the device is mounted onto the subject's arm. The piercing activator can be located on the housing such that the button 167 is configured to be pressed in a second direction when the device is mounted onto the subject's arm. In some embodiments, the first direction and the second direction can be substantially the same. The first direction and the second direction can be substantially parallel to each other. In some embodiments, the first direction and the second direction can be substantially different, e.g. orthogonal or oblique to each other.

In some embodiments, at least one of the first direction or the second direction does not extend toward the skin of the subject. For example, the second direction may not extend toward the skin of the subject. At least one of the first direction or the second direction can extend substantially parallel to the skin of the subject. In some embodiments, the first direction and the second direction can both extend substantially parallel to the skin of the subject. At least one of the first direction or the second direction can extend in a direction of gravitational force. In some embodiments, the first direction and the second direction can both extend in the direction of gravitational force.

It is noted that pressing the button 167 of the piercing activator (which activates the piercing elements) in a direction away from the skin, for example downwards as opposed to against the skin, can be advantageous in reducing the perception of fear and pain associated with skin penetration. By locating the piercing activator and the button 167 on the housing in the configuration as shown, the overall user experience with the device can be improved.

In some alternative embodiments (not shown), the vacuum activator can be configured to generate one or more visual, audio, tactile, and/or message signals to indicate the status of the vacuum to a user. The signals can indicate to the user, for example that (1) the vacuum has been activated, (2) the pressure(s) within the different chamber(s), (3) the vacuum post internal pressure equalization, (4) that the piercing activator is next ready for activation, and the like. The visual signals can be generated using visible markers that are viewable to the naked eye. A visible marker can include an image, shape, symbol, letter, number, bar code (e.g., 1D, 2D, or 3D barcode), quick response (QR) code, or any other type of visually distinguishable feature. A visible marker can include an arrangement or sequence of lights that can be distinguishable from one another. For examples, lights of various configurations can flash on or off. Any light source can be used, including but not limited to, light emitting diodes (LEDs), OLEDs, lasers, plasma, or any other type of light source. The visible markers can be provided in black and white or in different colors. The visible markers can be substantially flat, raised, indented, or have any texture. In some instances, the visible markers can emit heat or other IR spectrum radiation, UV radiation, radiation along the electromagnetic spectrum.

The audio signals can include vibrations or sounds of different frequencies, pitches, harmonics, ranges, or patterns of sounds that can be detected by the user. For example, the sounds can include words, or musical tones. The vibrations/sounds can be discernible by the human ear. The vibrations/sounds can be used to indicate the status of the vacuum. For example, a first vibration/sound can be generated when the vacuum is properly activated, and a second vibration/sound different from the first can be generated if the vacuum is improperly activated or below a minimum internal pressure differential.

In some alternative embodiments (not shown), the piercing activator can be configured to generate one or more visual, audio, tactile, and/or message signals to a user. Such signals can be useful, for example in preparing the user's state of mind for an impending penetration of the skin by one or more piercing elements. Such signals can be used to distract the user prior to, during and/after the cuts on the skin are made. For example, lights and/or music emitted by the device can be used to attract the user's attention, which can potentially help to reduce the pain level (or perception of pain) during and after the cuts are made.

Optionally in any of the embodiments disclosed herein, the vacuum activation can be semi-automatic or fully automatic. In some embodiments, the device need not require manual vacuum activation. For example, the device can be configured to automatically apply the vacuum upon sensing or detecting that the device has been placed on a surface (e.g., on a subject's skin), or that the recess of the device is properly placed over the surface. Optionally in any of the embodiments disclosed herein, activation of the piercing elements can be semi-automatic or fully automatic. For example, the piercing elements can be automatically activated to penetrate the surface (e.g., a subject's skin) upon sensing or detecting that the surface is drawn into the recess of the device, and/or that the surface is in proximity to the opening (e.g., 140) of the recess. The above sensing or detection (for the vacuum activation and/or piercing activation) can be enabled using any variety or number of sensors. The sensors can be included with the device (e.g., onboard the device) or remote from the device. Non-limiting examples of sensors that can be used with any of the embodiments herein include proximity sensors, tactile sensors, acoustic sensors, motion sensors, pressure sensors, interferometric sensors, inertial sensors, thermal sensors, image sensors, and the like. In some cases, if the vacuum activation and/or piercing activation is configured to be semi-automatic or fully automatic, the buttons for the piercing activator and/or piercing activator can be optionally included (or omitted) from the device.

E. Cartridge Assembly

As previously described, the deposition chamber of the device can also function as a cartridge chamber, and these two terms can be interchangeably used herein. The cartridge chamber can be configured to receive a cartridge assembly. The cartridge assembly can include a cartridge configured hold one or more matrices for storing a fluid sample (e.g., blood) thereon, and a cartridge holder. The cartridge holder can be releasably coupled to the cartridge using for example spring-clips. The cartridge assembly can be configured to releasably couple to the device 100 used for collecting blood from the subject. The cartridge holder can include a cartridge tab that is configured to be releasably coupled to a distal end of the cartridge chamber. The cartridge tab can be designed such that the subject or a user is able to (1) support the cartridge assembly by holding the cartridge tab, (2) couple the cartridge assembly to the device by pushing in the cartridge tab, and/or (3) decouple the cartridge assembly from the device by pulling the cartridge tab.

Referring to FIG. 3A, the cartridge can include a cartridge port 184 that is configured to be releasably coupled to an output port 148 in the deposition chamber 126. Fluidic communication can be established between a channel 146 of the device and a channel 185 of the cartridge when the ports 148 and 184 are coupled to each other. As shown in FIG. 3A, the channel 146 can extend towards the port 144 which is adjacent to the opening 140 of the recess 136. Blood can be drawn from the penetrated skin of the subject, and transported through the channels 146 and 185 into the cartridge with aid of vacuum, pressure differentials, and gravitational force.

The cartridge chamber can include cartridge guides 130 for guiding and holding the cartridge inside the cartridge chamber. The cartridge assembly can be releasably coupled to the cartridge chamber via a quick release mechanism. A quick release coupling mechanism can enable a user to rapidly mechanically couple (attach) and/or decouple (remove) the cartridge assembly from the cartridge chamber with a short sequence of simple motions (e.g., rotating or twisting motions; sliding motions; depressing a button, switch, or plunger, etc.). For example, a quick release coupling mechanism can require no more than one, two, three, or four user motions to perform a coupling and/or decoupling action. In some instances, a quick release coupling mechanism can be coupled and/or decoupled manually by a user without the use of tools. In some embodiments, the quick release coupling mechanism can include a luer-type fitting that mechanically engages with the cartridge when the cartridge assembly is inserted into the cartridge chamber.

The cartridge assembly can be coupled to the cartridge chamber prior to the collection of blood from the subject, and decoupled from the cartridge chamber after blood from the subject has been collected into the cartridge. The cartridge can include one or more matrices for collecting, storing, and/or stabilizing the collected blood sample. The matrices can be provided in strip form (as strips). A strip as used herein can refer to a solid matrix that is sized to maximize blood collection volume while still fitting into commonly used containers (e.g., a 3 ml BD vacutainer, deep well plate or 2 ml Eppendorf tube). A matrix as used herein can be interchangeably referred to herein as a matrix strip, a strip, a solid matrix, a solid matrix strip, and the like. A solid matrix can be configured to meter out, collect and stabilize fixed volumes of blood or plasma (e.g., greater than 25 uL, greater than 50 uL, greater than 75 uL, greater than 100 uL, greater than 125 uL, greater than 150 uL, greater than 175 uL, greater than 200 uL, or greater than 500 uL of blood or plasma). The cartridge assembly can be configured to hold any number of matrices (e.g., 1, 2, 3, 4, 5, 6, 7, 8, 9, 10 or more strips) and in various configurations.

The matrices can also enable lateral transport/flow of the blood. Non-limiting examples of the matrices can include absorbent paper strips, or a membrane polymer such as nitrocellulose, polyvinylidene fluoride, nylon, Fusion 5™, or polyethersulfone. In some embodiments, the matrices can comprise cellulose housing based paper (e.g. Whatman™ 903 or 226 paper), paper treated with chemicals or reagents for stabilizing the sample or one or more components of the sample (e.g., RNA stabilization matrix or Protein Stabilization Matrix). In some embodiments, the matrix comprises a cellulose filter paper. Any suitable commercially available filter paper can be used. Examples of commercially available filter paper include, but are not limited to, filter paper from Whatman®, such as 903 sample collection cards and fast transit analysis (FTA®) card. In some embodiments, the matrix can comprise a nitrocellulose filter paper. In some embodiments, the matrix does not comprise glass fiber filter paper.

The collection of the fluid sample can be aided by the natural wicking or capillary action associated with the matrix, which can enhance and accelerate the absorption or collection of the fluid sample onto the matrix. For a matrix having a surface area within the range of 100-300 square millimeters, a standardized quantity of blood saturating the matrix can be within a range of about 50-100 uL. In some embodiments, the quantity of blood absorbed by each matrix is about 30 to about 100 µL. In some embodiments, the quantity of blood absorbed by each matrix is about 67 to about 82 µL. In some embodiments, the quantity of blood absorbed by each matrix is 30 µL. In some embodiments, the quantity of blood absorbed by each matrix is about 45 µL. In some embodiments, the quantity of blood absorbed by each matrix is about 60 µL. In some embodiments, the quantity of blood absorbed by each matrix is about 75 µL. In some embodiments, the quantity of blood absorbed by each matrix is about 100 µL. In some cases, the matrices can be composed of a material comprising a plurality of capillary beds such that, when contacted with a fluid sample, the fluid sample is transported laterally across the matrices. The fluid sample fluid can flow along a flow path from a proximal end to a distal end of the matrices, for example by wicking or capillarity.

Figure 29:
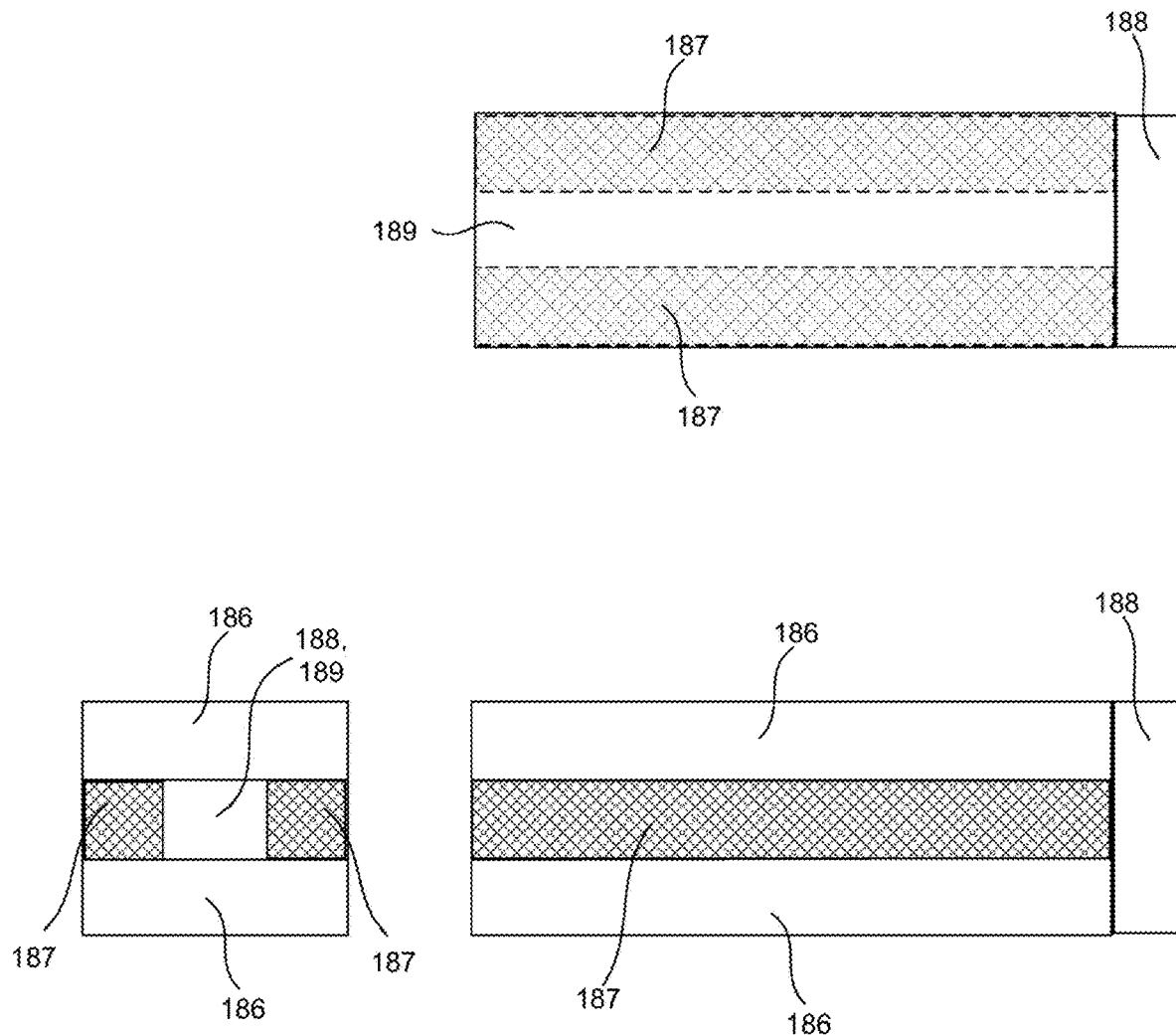
FIG. 29 shows different views of two matrices separated by spacers with an absorbent pad on one end.
Figure 30:
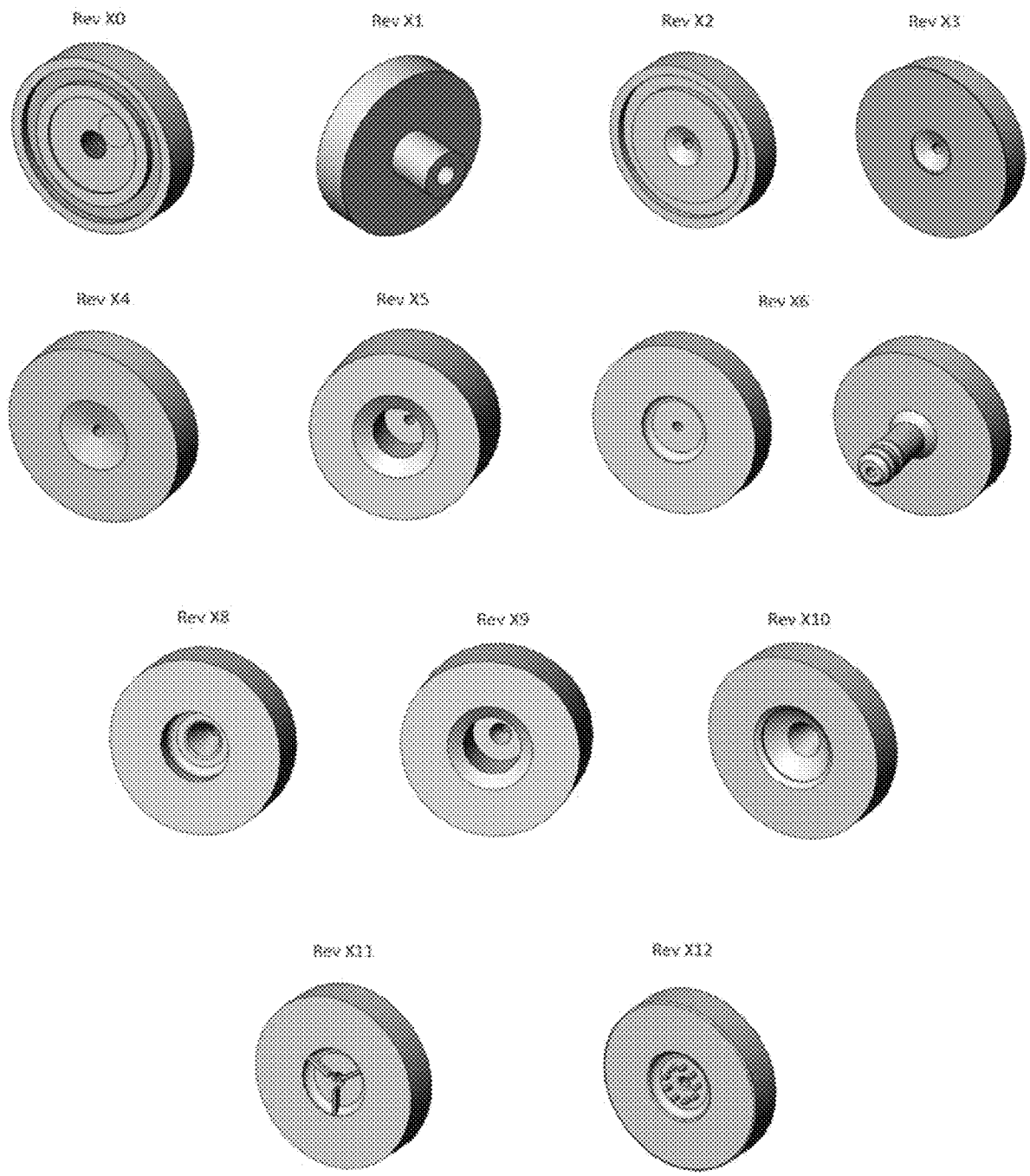
FIG. 30 shows examples of different types of recesses that can be used in a sample acquisition device.

In some embodiments, two or more matrices are disposed in a configuration within the cartridge that permits the blood to wick between and flow along the matrices. The two or more matrices can be disposed substantially parallel to each other. The two or more matrices can be separated by spacers. The spacers can be made of an appropriate biocompatible material. Two or more spacers can be placed between two matrices to form a channel through the blood can flow via capillary action and wicking. In the example of FIGS. 3A and 29, the two matrices 186 can be separated by a pair of spacers 187. The spacers can be positioned on opposing lengths of the matrices to form a channel 189 through the blood can flow via capillary action and wicking. In some embodiments, the two or more matrices can be separated by a gap of about 0.5 mm (i.e. the spacers can have a thickness of about 0.5 mm). Any gap size may be contemplated. The spacers between the matrices can be adjustable and removable, depending on other relevant aspect (e.g. the needs and application of the sample being collected, stability of the analyte, rate of absorption requirements etc). The spacers can comprise a range of widths and coatings. Exemplary widths include widths in the millimeter to centimeter range (e.g., greater than 2 mm, greater than 4 mm, greater than 6 mm, greater than 8 mm, greater than 10 mm, greater than 0.2 cm, greater than 0.4 cm etc.). In further embodiments, the spacers can be coated with materials including hydrophobic coatings, hydrophilic coatings, antimicrobial coatings, coatings that bind to one or more components of a sample, coatings for binding to or inhibiting enzymes that can degrade or otherwise impact the quality of one or more analytes on the sample.

In some embodiments, at least one of the matrices is capable of collecting at least 60 uL of blood. In some cases, each of the two or more matrices is capable of collecting at least 60 uL of blood. The volume of blood collected can depend on the number of the matrices in the cartridge. For example, providing two matrices each with 60 uL holding capacity can yield a total blood sample volume of about 120 uL.

Referring to FIGS. 3A and 29, the cartridge assembly 180 can include one or more absorbent pads 188 for holding excess fluid sample (e.g. excess blood flowing beyond the matrices). The absorbent pads can serve as a wicking tail that can be used to absorb excess sample, and standardize or meter the volume of blood deposited on the saturated matrices. The absorbent pads can be placed at a distal end of the channel 189 opposite to the cartridge port 184, and can be placed in contact with end portions of the matrices 186. The absorbent pads can be supported or held in place by the cartridge holder 190. For example, the absorbent pads can be placed in a slot in the cartridge holder. The absorbent pads can be configured to absorb excess sample overflow. Each absorbent pad can be capable of holding at least about 10 uL of excess fluid sample. In some cases, each absorbent pad can be capable of holding at least about 20 uL, 30 uL, 40 uL, 50 uL, 60 uL, 70 uL, 80 uL, 90 uL, 100 uL, or more than 100 uL of excess fluid sample. The absorbent pads can be used to enable controlled metering of the matrices. The absorbent pads and their ability to contain the blood beyond the saturation volume of the matrices can enable consistent volumes of blood on the matrices, independent of varying input volumes to the device and cartridge. The absorbent pads can be configured (e.g., composition adjusted) so that the absorbent pads can be used as a means to control the volume of the sample absorbed on the matrices.

The cartridge assembly can comprise self-metering capability which can be advantageous for collecting a predefined volume of blood on the matrix strips for each individual, regardless of varying input volumes of blood flow to the cartridge for different individuals. The variations in input blood volume can occur since capillary pressures and blood flow can often vary from individual to individual (e.g., due to age, gender, health, etc.). The design of the cartridge assembly can ensure that matrix strips consistently contain a target blood volume independent of the volume of the blood that enters the cartridge (within or up to a predefined range). In the example of FIG. 29, the two matrix strips (e.g. 186) are in contact with one or more absorbent pads (e.g. 188) at the ends opposite the inlet port (e.g. 184) of the cartridge. As blood enters the cartridge via the port 184 during the draw, the matrix strips gradually saturate and during this time, the volume contained within the strips can increase (e.g. linearly) with the volume of blood that enters the cartridge. In some embodiments, once the matrix strips are saturated at ~75 uL, the excess blood can wick onto the absorbent pad(s). By using the absorbent pads to absorb excess blood, the blood contained within the two matrix strips can be maintained at about 75 uL on each strip, even if (or as) the input volume of blood flowing into the cartridge increases beyond 150 uL. The volume of blood on the matrix strips can be metered/maintained unless or until the absorbent pads saturate with blood. In some embodiments, any input volume of blood between ~150 uL and 300 uL to the cartridge can still result in the same volume (~75 uL) of blood contained on each of the two matrix strips, with aid of the absorbent pad(s). In some embodiments, a range of blood volume collected on the matrix strips can be increased or decreased, for example by adding one or more additional absorbent pads, increasing or decreasing the strip size/saturation level, etc.

The collection of blood on the matrix strips can occur in phases. For example, during an initial phase, while the input volume of blood to the cartridge is between 0-150 uL, the two strips are filling but have not yet saturated, and the blood volume on each of the two strips increases gradually from 0-75 uL. During a subsequent phase, as the input volume of blood to the cartridge increases beyond 150 uL (e.g. 150 uL-300 uL), the strips are saturated at constant blood volume of ~75 uL per strip, with excess blood flowing into the absorbent pads. The above-described passive metering mechanism can be advantageous in maintaining a predefined blood volume (e.g. 75 uL per strip) with varying blood input volumes within a target range.

It should be appreciated that the cartridge can include any number of matrix strips. The matrix strips can have the same saturation volumes or have different saturation volumes. The cartridge can also include any number of absorbent pads. The number of absorbent pads may or may not be the same as the number of matrix strips. The saturation volumes for the absorbent pads can be the same or different. The cartridge can be designed such that the matrix strips and absorbent pads have a self-metering capability as described above. For example, the sample volumes collected on the matrix strips can increase until the matrix strips reach their saturation volumes. After the matrix strips are saturated, any excess fluid is collected the absorbent pads. Accordingly, controlled well-defined volumes of the sample can be collected on the matrix strips, even though the input volume to the cartridge can and often exceeds the total saturation volumes of the matrix strips.

The use of the matrices with absorbent pads can facilitate accurate and precise sample collection. Two or more matrices can be stacked or arranged in ways that facilitate blood collection, distribution, precision and reproducible volumes of sample or analyte per surface area of each matrix. In some embodiments, the matrices can have different compositions or purposes. For example, a first matrix(es) can be used to separate cells from a cell free component and collect the cell free component on one matrix, and a second matrix(es) can be used collect raw unseparated sample. In some embodiments, the absorbent pads can be used as or incorporated into an indicator or be visible through a viewing window (of a flow meter) to inform a user that the collection procedure is complete.

In some embodiments, a method for collecting a fluid sample (e.g., blood) from a subject can be provided. The method can include: (1) releasably coupling the cartridge assembly to a device (e.g. device 100); (2) placing the device adjacent to skin of the subject; (3) activating vacuum in the pre-evacuated vacuum chamber to draw the skin into a recess of the housing; (4) using one or more piercing elements of the device to penetrate the skin; (5) maintaining the device adjacent to the skin for a sufficient amount of time to draw the fluid sample into the device and collect the fluid sample into the cartridge; and (6) decoupling the cartridge from the device after a certain amount of the fluid sample has been collected in the cartridge.

In some embodiments, one or more of the matrices can be designed and fabricated on a substrate. The substrate can be rigid or flexible. Examples of suitable substrates can include silicon, glass, printed circuit boards, polyurethane, polycarbonate, polyamide, polyimide, and the like.

The cartridges described herein generally depict fluid samples stored on solid matrices. However, this should not be taken to limit the devices disclosed herein. For example, the devices can include cartridges or means for collecting, treating, stabilizing and storing sample in either a liquid or a solid state. In some embodiments (not shown), the cartridge can include a vessel for storing liquid sample. The vessel can be used in conjunction with one or more matrices. Alternatively, the vessel can be used in place of matrices. Any number of vessels for storing liquid sample can be contemplated.

In some embodiments, the device disclosed herein can have multiple vacuum chambers (e.g. 2, 3, 4, 5 or more vacuum chambers) and multiple piercing modules (e.g., 2, 3, 4, 5 or more piercing modules). The device can be reusable and can be used to collect multiple samples in multiple cartridges. For example, a first vacuum chamber and a first piercing module can be activated to fill a first cartridge, a second vacuum chamber and a second piercing module can be activated to fill a second cartridge, a third vacuum chamber and a third piercing module can be activated to fill a third cartridge, and so forth. In some embodiments, a same vacuum chamber and piercing module can be used to fill a plurality of different cartridges, either within a same sample procedure or multiple procedures performed at different points in time.

F. Flow Meter

In some embodiments, the device can include a flow meter 170 on the housing. The flow meter can be interchangeably referred to herein as a metering window (or metering windows). The flow meter can enable a subject or a user to monitor a progress of the fluid sample collection (e.g. blood sample collection) in real-time as the fluid sample is collected into the cartridge. For example, the subject or user can rely on the flow meter to determine whether the fluid sample collection is complete or near completion. In some embodiments, the flow meter can be provided on the housing base 110. For example, the flow meter can be a part of, or integrated into the lid 124 of the housing base. The flow meter can be in proximity to the deposition chamber 126 (or cartridge chamber). The flow meter can be located directly above the deposition chamber (or cartridge chamber). The flow meter can be substantially aligned with the cartridge 182 when the cartridge assembly is inserted into the cartridge chamber, for example as shown in FIGS. 3B, 4B, 20A, and 20B.

Figure 17A:
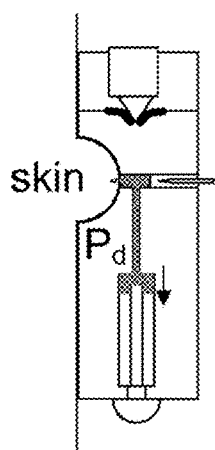
FIGS. 17A, 18A, and 19A show schematic block diagrams of blood flow along the matrices in the cartridge at different stages of the blood collection.
Figure 17B:
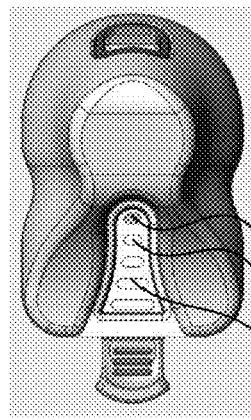
FIGS. 17B, 18B, and 19B illustrate a flow meter indicating the progress of the blood collection in accordance with some embodiments.
Figure 18A:
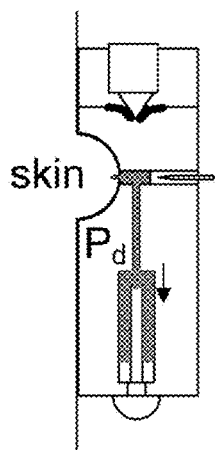
Figure 18B:
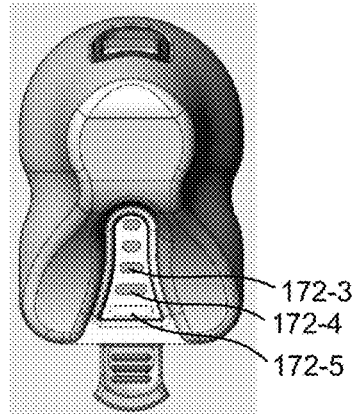
Figure 19A:
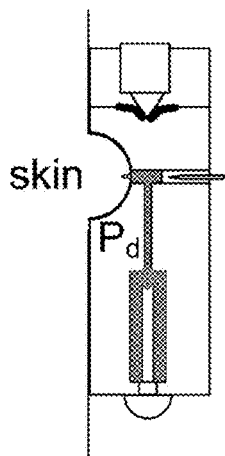
Figure 19B:
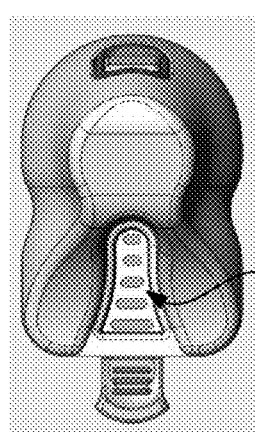

In some embodiments, the flow meter 170 can include a plurality of windows 172 disposed parallel to a longitudinal axis of the cartridge chamber. The plurality of windows can include three, four, five or more windows. In the example of FIGS. 17B, 18B, and 19B, the flow meter 170 can include windows 172-1, 172-2, 172-3, 172-4, and 172-5. The windows can line up with the matrices 186 of the cartridge when the cartridge assembly is inserted into the cartridge chamber. The windows can be made of an optically transparent material that allows the subject or user to see the underlying matrices in the cartridge. The fluid sample that is collected on the matrices can be visible through the windows. The fluid sample and the matrices of the cartridge can have different colors, preferably highly contrasting colors to permit easy viewing of the flow of the fluid sample along the matrices. The color of the fluid sample (e.g. red color for blood) can sequentially fill each window as the fluid sample is being collected on the matrices in the cartridge. Each window can be indicative of a known amount of fluid sample that is collected. For example, in FIG. 17B, the window 172-1 can have a visible color that indicates to the user that the matrices are about 20% filled. In FIG. 18B, the windows 172-1, 172-2, 172-3, and 172-4 can have a visible color that indicates to the user that the matrices are about 80% filled. In FIG. 19B, all of the windows 172-1, 172-2, 172-3, 172-4, and 172-5 can have a visible color that indicates to the user that the matrices are 100% filled. Accordingly, the user is able to determine that the sample collection is complete when the color of the fluid sample is visible in all of the windows.

Figure 17C:
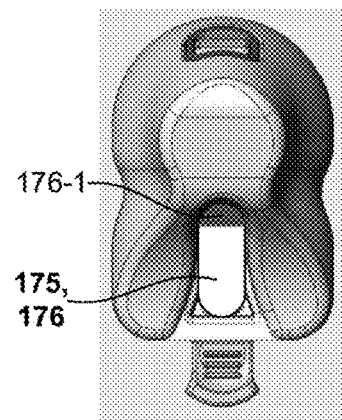
FIGS. 17C, 18C, and 19C illustrate a flow meter indicating the progress of the blood collection in accordance with some other embodiments.
Figure 18C:
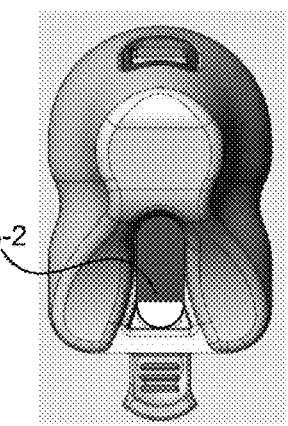
Figure 19C:
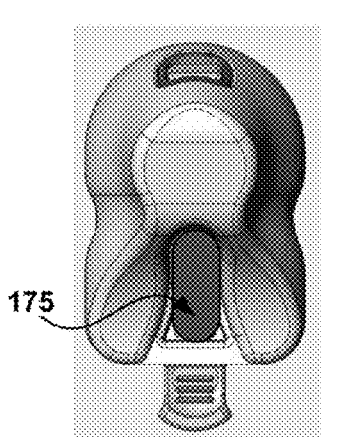

FIGS. 17C, 18C, and 19C show a flow meter 175 in accordance with some other embodiments. The flow meter 175 can consist of a single window 176 disposed parallel to a longitudinal axis of the cartridge chamber. The single window can line up with the matrices 186 of the cartridge when the cartridge assembly is inserted into the cartridge chamber. The single window can be made of an optically transparent material. The fluid sample can be visible through the single window. The color of the fluid sample (e.g. red color for blood) can continuously fill the window as the fluid sample is being collected in the cartridge. In some embodiments, the window can include one or more markers that indicate a known amount of fluid sample that is collected. A user can be able to determine that the fluid sample collection is complete when the color of the fluid sample is visible throughout the entire window.

In some alternative embodiments (not shown), the flow meter can include one or more visible markers. The visible markers can replace the windows of the flow meter, or can be used in conjunction with the metering windows. The visible markers can be viewable to the naked eye. A visible marker can include an image, shape, symbol, letter, number, bar code (e.g., 1D, 2D, or 3D barcode), quick response (QR) code, or any other type of visually distinguishable feature. A visible marker can include an arrangement or sequence of lights that can be distinguishable from one another. For examples, lights of various configurations can flash on or off. Any light source can be used, including but not limited to, light emitting diodes (LEDs), OLEDs, lasers, plasma, or any other type of light source. The visible markers can be provided in black and white or in different colors. The visible markers can be substantially flat, raised, indented, or have any texture.

In some instances, the visible markers can emit heat or other IR spectrum radiation, UV radiation, radiation along the electromagnetic spectrum. In another example, the device or flow meter can emit vibrations or sounds of different frequencies, pitches, harmonics, ranges, or patterns of sounds that can be detected by the user. For example, the sounds can include words, or musical tones. The vibrations/sounds can be discernible by the human ear. The vibrations/sounds can be used to indicate a progress of the fluid sample collection process. For example, a first vibration/sound can be generated when the fluid sample starts flowing onto the matrices, and a second vibration/sound different from the first can be generated when the fluid sample has completely filled the matrices.

In some embodiments, the flow meter can be used to detect (e.g. enable the subject or a user to view) a feature, colorimetric change, display of a symbol, masking of a symbol, or other means of indicating the progress of the fluid sample collection, and to indicate that the fluid sample collection has been completed.

In some embodiments, one or more graphical user interfaces (GUIs) can be provided on the device. The GUIs can complement the use of the flow meter. In some embodiments, the function of the flow meter can be incorporated into the GUIs. The GUIs can be rendered on a display screen on the device. A GUI is a type of interface that allows users to interact with electronic devices through graphical icons and visual indicators such as secondary notation, as opposed to text-housing based interfaces, typed command labels or text navigation. The actions in a GUI can be performed through direct manipulation of the graphical elements. In addition to computers, GUIs can be found in hand-held devices such as MP3 players, portable media players, gaming devices and smaller household, office and industry equipment. The GUIs can be provided in a software, a software application, etc. The GUIs can be provided through a mobile application. The GUIs can be rendered through an application (e.g., via an application programming interface (API) executed on the device). The GUIs can allow a user to visually monitor the progress of the sample collection. In some embodiments, the GUIs can allow a user to monitor levels of analytes of interest in the collected sample.

In some embodiments, the device can be capable of transmitting data to a remote server or mobile devices. The data can include for example, user details/information, the date/time/location at which the sample is collected from the subject, the amount/volume of sample collected, time taken to complete the sample collection, maximum/minimum/average flowrates during sample collection, position of the subject's arm during sample collection, whether any errors or unexpected events occurred during the sample collection, etc. In some cases, the data can be transmitted to a mobile device (e.g., a cell phone, a tablet), a computer, a cloud application or any combination thereof. The data can be transmitted by any means for transmitting data, including, but not limited to, downloading the data from the system (e.g., USB, RS-232 serial, or other industry standard communications protocol) and wireless transmission (e.g., Bluetooth®, ANT+, NFC, or other similar industry standard). The information can be displayed as a report. The report can be displayed on a screen of the device or a computer. The report can be transmitted to a healthcare provider or a caregiver. In some instances, the data can be downloaded to an electronic health record. Optionally, the data can comprise or be part of an electronic health record. For example, the data can be uploaded to an electronic health record of a user of the devices and methods described herein. In some cases, the data can be transmitted to a mobile device and displayed for a user on a mobile application.

G. Sample Collection

Next, exemplary methods of use of the devices herein for sample collection are described with detail with reference to various figures. Referring to FIG. 5A, the device 100 having cartridge assembly 180 can be placed on a subject's skin 104 (e.g. on the subject's upper arm). The subject's skin can be initially in a free state 105 (i.e. the skin is not under tension or drawn into the recess by vacuum pressure). The planar portion 132 of the housing base 110 can be in contact with the subject's skin, and attached to the skin with aid of an adhesive 134 as described elsewhere herein. The device can be configured for use in the orientation as shown in FIG. 5A, with the channels 146 and 189 and matrices 186 substantially aligned in the direction of gravity to aid sample flow.

FIG. 5B shows a schematic block diagram corresponding to FIG. 5A, and depicts the different chambers and enclosure. Referring to FIG. 5A, the device 100 can include the (1) deposition chamber 126, (2) vacuum chamber 112, (3) enclosure 156 for holding the piercing module 154, and (4) a cavity 107 enclosed between the skin and the surface of the recess. The vacuum chamber and the deposition chamber can be separated by the foil 120. The deposition chamber can be in fluidic communication with the cavity 107 and the enclosure 156 via channel 146. Prior to vacuum activation, the pressures within the deposition chamber 126 ($P_{dc}$), enclosure 156 ($P_{1a}$), and channel 146 can be at atmospheric pressure (or ambient pressure). The pressure $P_{vc}$ within the vacuum chamber 112 can be at its maintained pressure which is below atmospheric while the separation interface 120 is closed (e.g. when the foil is intact). In some embodiments, the pressure $P_{vc}$ can be about −12 psig prior to breaking of the foil 120. The capillary blood pressure within the skin ($P_{cap}$) is at a pressure greater than atmospheric. In some embodiments (not shown), the separation interface 120 can include a valve which can be opened to establish fluidic communication between the vacuum chamber and the deposition chamber. In some cases, the foil can be replaced by the valve, or used in conjunction with the valve.

Referring to FIGS. 6A and 6B, the vacuum in the vacuum chamber 112 can be activated by opening the separation interface 120, for example by breaking the foil (or in some cases, opening a valve). The vacuum activator can comprise a sharp protrusion 116 coupled to the button 115. The vacuum can be activated by pressing the button 115 downwards (FIG. 5A), which causes the protrusion 116 to break the foil (FIG. 6A). Subsequently, the pressure within the vacuum chamber, deposition, chamber, the enclosure and the internal channel equalizes at a pressure ($P_{int}$) which is below atmospheric but greater than the initial pressure of the vacuum chamber. In some embodiments, the equalized pressure can be about −4 psig. This negative gauge pressure can draw the skin into the recess 136 and dras blood to that region within the capillary beds. This action can result in an increase in the capillary blood pressure within the skin which is now under tension within the recess.

Figure 8A:
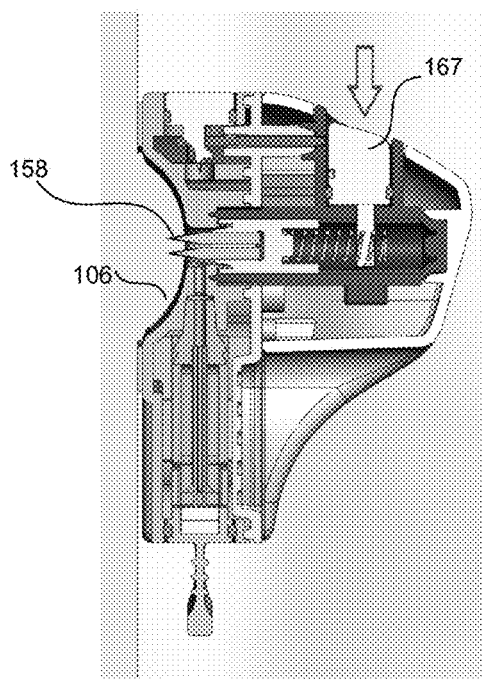
FIG. 8A shows the subject's skin being penetrated by piercing elements after the piercing elements have been deployed.
Figure 8B:
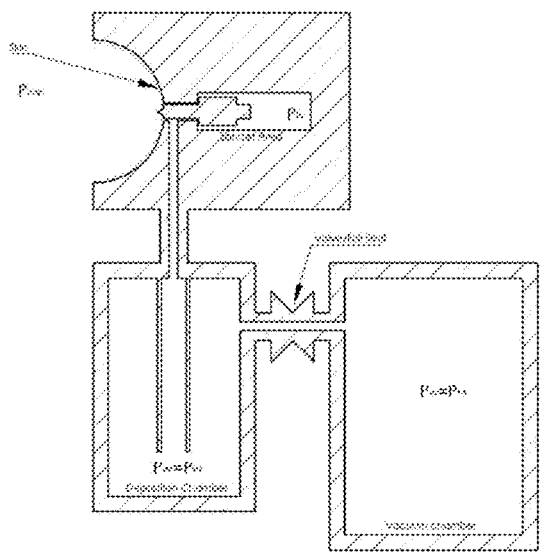
FIG. 8B shows a schematic block diagram corresponding to the device of FIG. 8A.
Figure 9A:
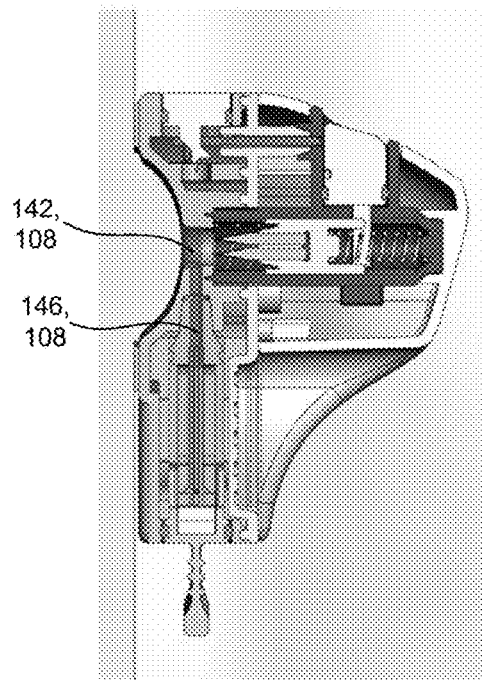
FIG. 9A shows blood being drawn from the cuts on the skin after the piercing elements have been retracted.
Figure 9B:
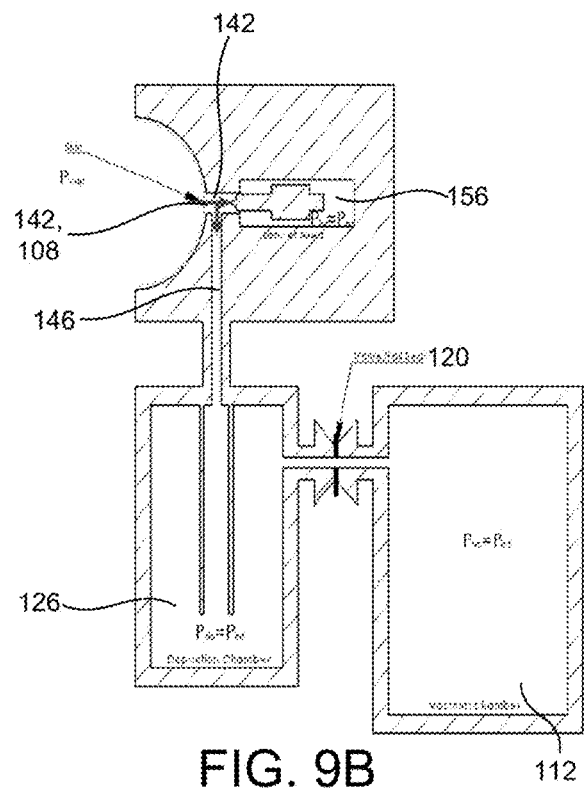
FIG. 9B shows a schematic block diagram corresponding to the device of FIG. 9A.

As previously described, activation of the vacuum can release the lock on the button 167 of the piercing activator. Referring to FIGS. 8A and 8B, when the button 167 is pressed downwards, the deployment spring 162 (which can be initially in a compressed state) is deployed, and extends the piercing elements 158 towards the opening 140 to penetrate the skin at the opening. In some embodiments (not shown), the deployment spring can be initially in an uncompressed state, and compressed by one or more actuating elements in preparation for deployment of the piercing elements. Referring to FIGS. 9A and 9B, the piercing elements are retracted from the skin by the retraction spring 164 after the skin has been penetrated. The initial flow of blood is driven by the pressure differential between the capillary blood pressure ($P_{cap}$) and the internal pressure of the device ($P_{int}$). As previously mentioned, the internal pressure can be about −4 psig, and the capillary blood pressure is greater than atmospheric. Initially, a small amount of blood can travel towards and into the enclosure 156 while blood can also enter the channel 146 guiding it towards the deposition chamber 126.

Figure 10A:
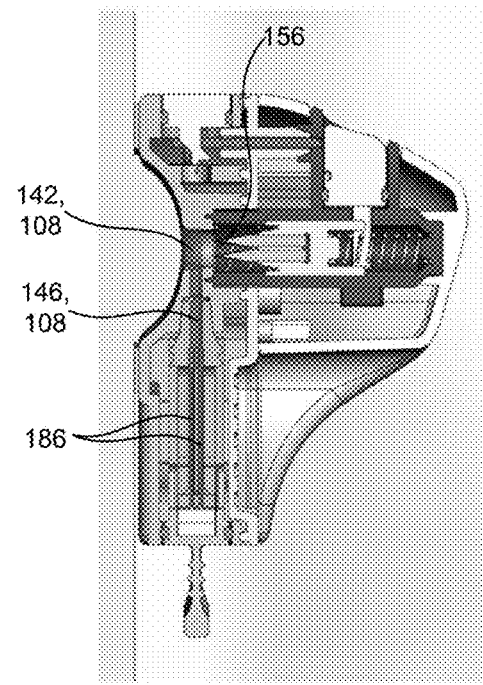
FIG. 10A shows the preferential and enhanced flow of blood from the cuts towards the cartridge in the deposition chamber of the device.
Figure 10B:
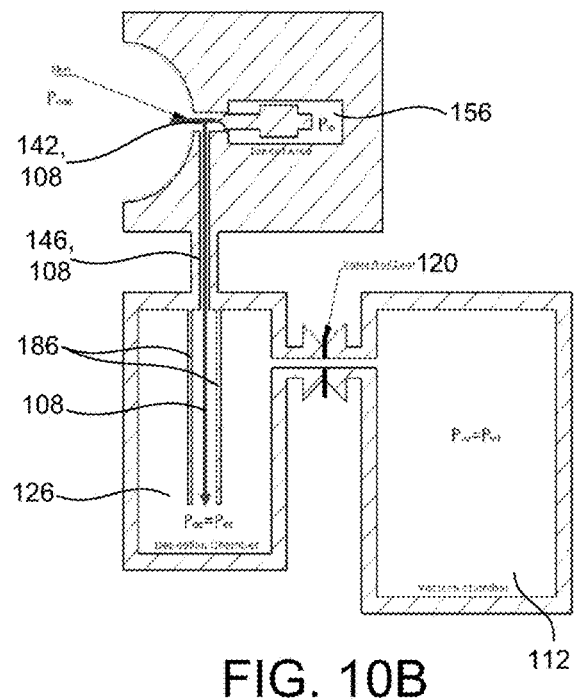
FIG. 10B shows a schematic block diagram corresponding to the device of FIG. 10A.

Referring to FIGS. 10A, 10B, and 11, the flow of blood can quickly reach a "steady state." As blood enters the device, the volume of the blood present naturally causes the internal pressure to increase due to its negative gauge internal pressure. The volume V1a of the enclosure 156 can be substantially smaller than the combined volume $V_{dc+vc}$ of the deposition chamber 126 and vacuum chamber 112. In some embodiments, a ratio of $V_1a$ to $V_{dc+vc}$ can be about 1:10. The enclosure 156 can have an internal pressure $P_{int\_1a}$, and the deposition chamber 126 and vacuum chamber 112 can collectively have an internal pressure $P_{int\_dc+vc}$. Due to the substantially smaller internal volume of the enclosure, the internal pressure $P_{int\_1a}$ within the enclosure increases with the presence of blood much more rapidly than the internal pressure $P_{int\_dc+vc}$ within the deposition chamber and vacuum chamber which increases a very small amount. The internal pressure buildup in the enclosure causes the flow of blood into the enclosure to slow or stop, while the blood continues to be drawn into the deposition chamber by the pressure differential between the internal pressures $P_{int\_1a}$ and $P_{int\_dc+vc}$ and the capillary blood pressure ($P_{cap}$). Blood flow towards the deposition chamber can further be aided by gravitational force, and by capillary action along the channels 146 of the device and the channel 189 of the cartridge. The blood flow can be further aided by wicking along the matrices 186 as the blood flows through the channel 189 of the cartridge.

The preferential flow of blood towards the deposition chamber 126 allows more blood to be collected in the deposition chamber. Minimal blood flowing into the enclosure 156 can also help to reduce wastage of blood, since blood in the enclosure is not collected and used. Accordingly, the above-described device configurations can help to increase the flowrate and volume of blood collected in the deposition chamber.

FIGS. 11A through 16F are schematic block diagrams showing the same operating principles as the embodiments described in FIGS. 5A through 10B. The schematic block diagrams are simplified generalized views of the device and the cartridge assembly, to show the change in pressures between the chambers and the flow of fluids. As such, some of the elements can be omitted in the interest of clarity. Like reference numerals refer to like elements throughout.

FIG. 11A shows a side sectional view of the device prior to insertion of the cartridge assembly, and FIG. 11B shows the corresponding front view. The cartridge assembly can include the matrices 186 and the cartridge tab 192. The device can include the (1) vacuum chamber 116, (2) deposition chamber 126, (3) recess 136, (4) enclosure 158 for the piercing element 158, and (5) channel 146 leading to the deposition chamber. The deposition chamber and the vacuum chamber can be separated by the foil 120. As shown in the FIG. 11B, the vacuum chamber can surround the deposition chamber in a U-like shape, and the two chambers can be separated by one or more walls 125. The pressures in the vacuum chamber, deposition chamber, and recess can be given by $P_v$, $P_d$, and $P_r$, respectively. Initially, $P_d$ and $P_r$ can be at atmospheric pressure ($P_{atm}$). The pressure $P_v$ within the vacuum chamber can be at a pre-evacuated vacuum pressure ($P_0$) which is below atmospheric while the foil 120 is closed (i.e. the foil is intact). Initially, $P_0$ can be substantially less than $P_d$. In some embodiments, $P_0$ can be about −12 psig. In some embodiments (not shown), the foil 120 can be replaced by a valve which can be opened to establish fluidic communication between the vacuum chamber and the deposition chamber.

FIGS. 12A and 12B show the cartridge assembly inserted into the deposition chamber. Next, the device can be placed onto a subject's skin 104, as shown in FIG. 13A. The skin can be initially in a free state 105 (i.e. not under tension due to vacuum suction). A cavity 107 can be enclosed between the skin 104 and the surface of the recess 136. The initial pressures within the chambers and various compartments can remain the same since there is no fluidic communication causing any pressure changes.

Referring to FIGS. 14A and 14B, the vacuum in the vacuum chamber 112 can be activated by breaking the foil 120 (or in some cases, opening a valve). The vacuum activator can comprise a sharp protrusion 116 coupled to the button 115. The vacuum can be activated by pressing the button 115 downwards, which can causes the protrusion 116 to break the foil. Air from the deposition chamber 126, cavity 107, enclosure 156, and channel 146 can be drawn into the vacuum chamber to equalize the pressures, as shown in FIGS. 14A and 14B. As a result, $P_d$ and $P_r$ will decrease while $P_v$ increases. At the same time, the skin can be drawn into the recess by the pressure differentials.

Referring to FIGS. 15A and 15B, the skin can be completely drawn into the recess. The pressure $P_p$ in the enclosure 156, $P_v$ and $P_d$, and the pressure in the channel 146 equalize at a pressure $P_1$, whereby $P_0 < P_1 < P_{atm}$. In some embodiments, $P_1$ can be about −4 psig. This negative gauge pressure can draw and holds the skin in the recess 136, and draws blood to the skin region within the capillary beds. This can result in an increase in the capillary blood pressure $P_c$ within the skin which can now be under tension.

Figure 16A:
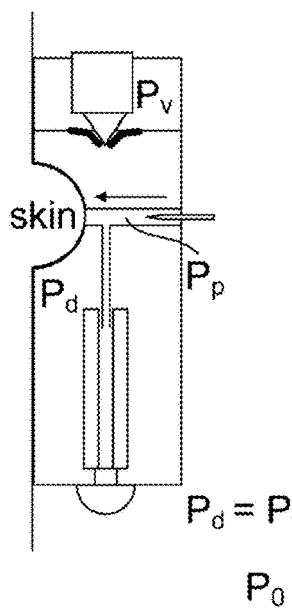
FIG. 16A shows the deployment of the piercing elements and penetration of the subject's skin in the recess.
Figure 16B:
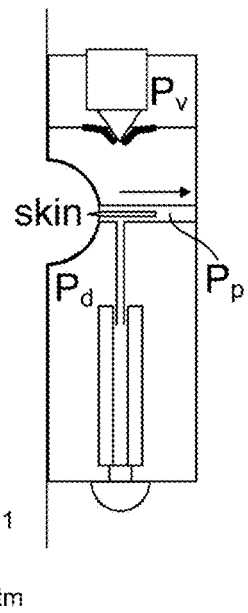
FIG. 16B shows the subject's skin being penetrated and the retraction of the piercing elements.
Figure 16C:
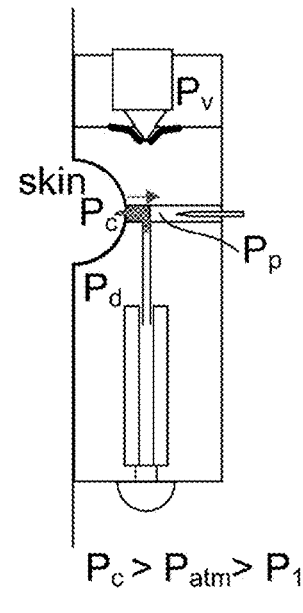
FIG. 16C shows the initial flow of blood from the cuts on the skin.
Figure 16D:
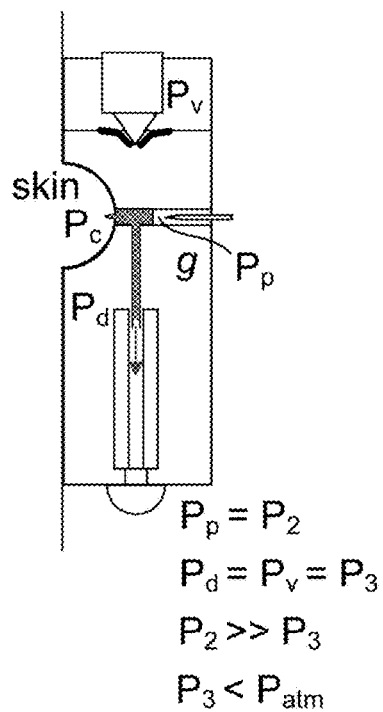
FIG. 16D shows the blood being drawn towards the cartridge in the deposition chamber with aid of the vacuum, pressure differentials, and gravitational force.
Figure 16E:
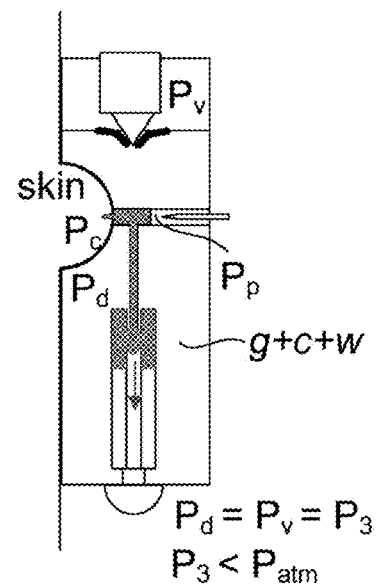
FIG. 16E shows the preferential flow of blood towards the deposition chamber, and the wicking of blood along matrices in the cartridge.
Figure 16F:
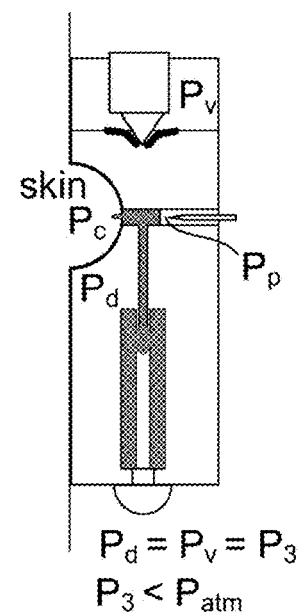
FIG. 16F shows the blood absorbed onto the matrices, and completion of the blood collection.

Next, referring to FIGS. 16A and 16B, the piercing element 158 can be deployed and penetrate the skin at the opening 140 of the recess, and retracted from the skin as shown in FIG. 16C. The initial flow of blood can be driven by the pressure differential between $P_c$ and $P_{int}$, whereby $P_c > P_{atm} > P_1$. Initially, a small amount of blood can travel towards and into the enclosure 156 while blood also enters the channel 146 guiding it towards the deposition chamber 126, as shown in FIG. 16C.

The volume $V_{1a}$ of the enclosure 156 can be substantially smaller than the combined volume $V_{dc+vc}$ of the deposition chamber 126 and vacuum chamber 112. In some embodiments, a ratio of $V_{1a}$ to $V_{dc+vc}$ can be about 1:10. As blood flows into the enclosure and towards the deposition chamber, the pressure $P_p$ of the enclosure increases to $P_2$, and the pressures $P_d$ and $P_v$ of the deposition chamber and the vacuum chamber can increase to $P_3$. However, $P_2$ can be substantially greater than $P_3$ since $V_{1a}$ can be substantially smaller than $V_{dc+vc}$. In other words, the pressure in the enclosure 156 increases much more rapidly than the pressure within the deposition chamber and vacuum chamber which increases by a very small amount. The internal pressure buildup in the enclosure causes the flow of blood into the enclosure to slow or stop, while the blood continues to be drawn into the deposition chamber by the pressure differential between the internal pressures $P_{int\_1a}$ and $P_{int\_dc+vc}$ and the capillary blood pressure $P_{cap}$. Accordingly, the flow of blood reaches a "steady state" in which the blood is drawn only towards the deposition chamber. Blood flow towards the deposition chamber can be further aided by gravitational force g, and by capillary action c along the channels 146 of the device and the channel 189 of the cartridge. The blood flow can be further aided by wicking w along the matrices 186 as the blood flows through the channel 189 of the cartridge.

As previously described, the preferential flow of blood towards the deposition chamber 126 can allow more blood to be collected in the deposition chamber. Minimal blood flowing into the enclosure 156 can also help to reduce wastage of blood, since in some cases blood in the enclosure is not collected and used. Accordingly, the above-described device configurations can help to increase the flowrate and volume of blood collected in the deposition chamber.

III. Packaging and Transportation of Cartridge Post Sample Collection

Figure 20A:
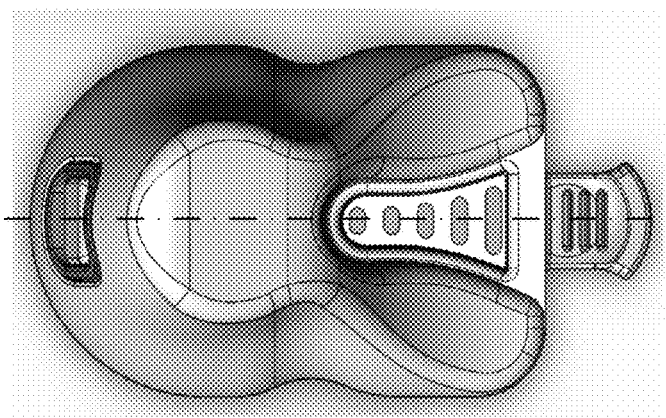
FIG. 20A shows a top view of a device with the flow meter indicating that the blood collection has been completed.
Figure 20B:
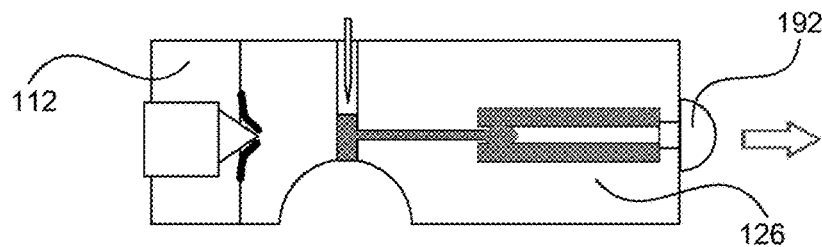
FIG. 20B is a schematic block diagram corresponding to the device of FIG. 20A prior to removal of the filled cartridge assembly.
Figure 21A:
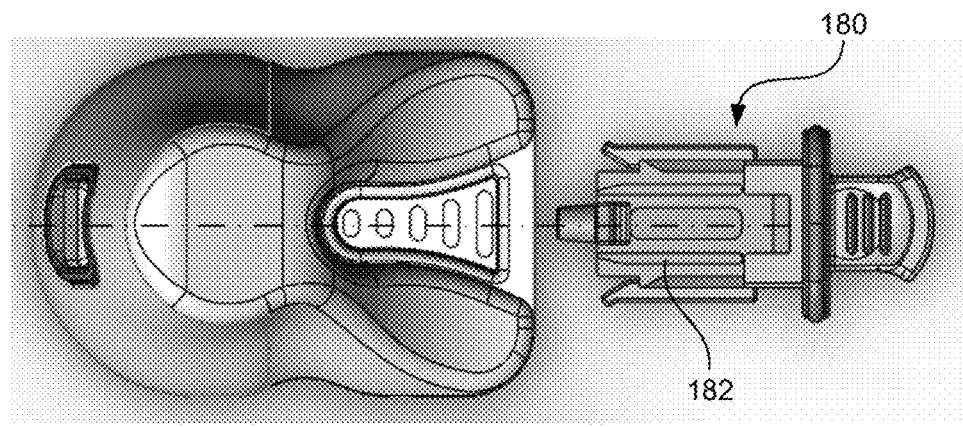
FIG. 21A shows a top view of the device with the filled cartridge assembly removed.
Figure 21B:
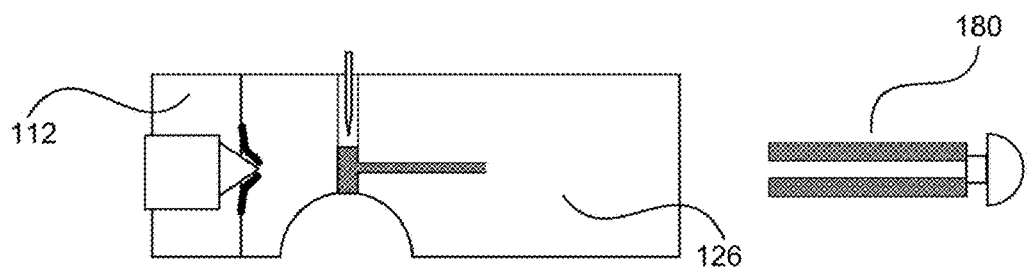
FIG. 21B is a schematic block diagram corresponding to the device of FIG. 21A with the filled cartridge assembly removed.

As previously described with reference to FIGS. 17A-19A, 17B-19B, and 17C-19C, the use of flow meters on the device can allow a user to monitor the progress of the sample collection, and to know when the sample collection has been completed. FIG. 20A shows a top view of the device with a completely filled cartridge, and FIG. 21A shows a top view with the filled cartridge removed from the device. The cartridge assembly can be removed from the deposition chamber of the device by pulling the cartridge tab. The filled cartridge can be subsequently packaged and transported to an external facility for further processing. For example, the sample can be treated, stabilized and stored. In any of the embodiments described herein, the devices can be configured to collect, treat, and store the sample. Samples drawn by the device can be stored in liquid or solid form. The sample can undergo optional treatment before being stored. Storage can occur on the device, off the device, or in a removable container, vessel, compartment, or cartridge within the device.

Figure 22A:
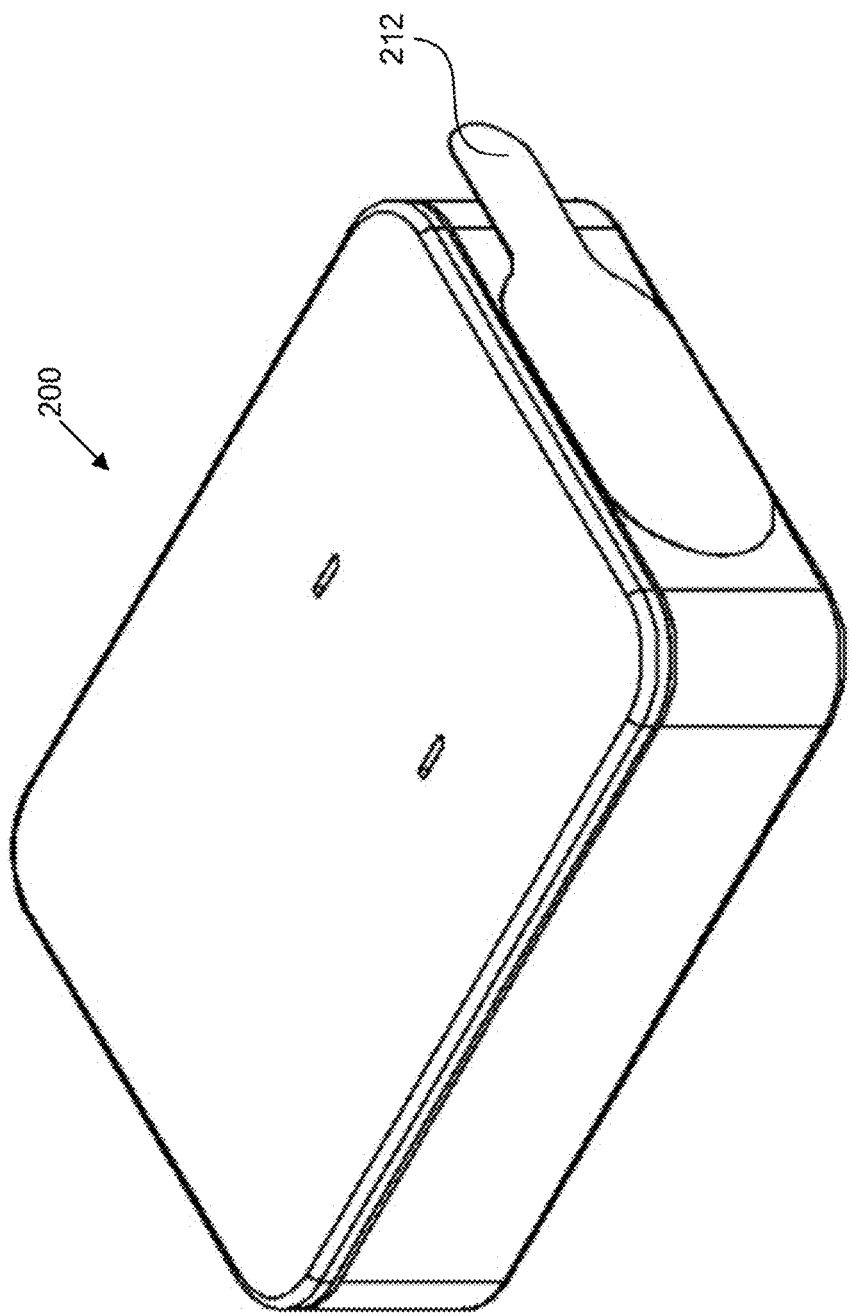
FIG. 22A shows a perspective view of a transportation sleeve.

FIG. 22A shows a perspective view of a transportation sleeve 200 that can be used for packaging of a filled cartridge or samples within the cartridge. The sleeve can include a hollow interior for storing the filled cartridge or samples during shipment/transportation. The sleeve can include an opening for receiving the cartridge. In some embodiments, the sleeve can include a cover 212 for covering the opening prior to use of the sleeve. The cover 212 can be, for example a peel foil that can be attached to the opening via an adhesive, and peeled off by a user prior to use of the sleeve. A dessicant (not shown) can be disposed within the sleeve, and used for keeping the samples dry. The peel foil can help to protect the interior of the sleeve from moisture and contamination prior to use.

Figure 23:
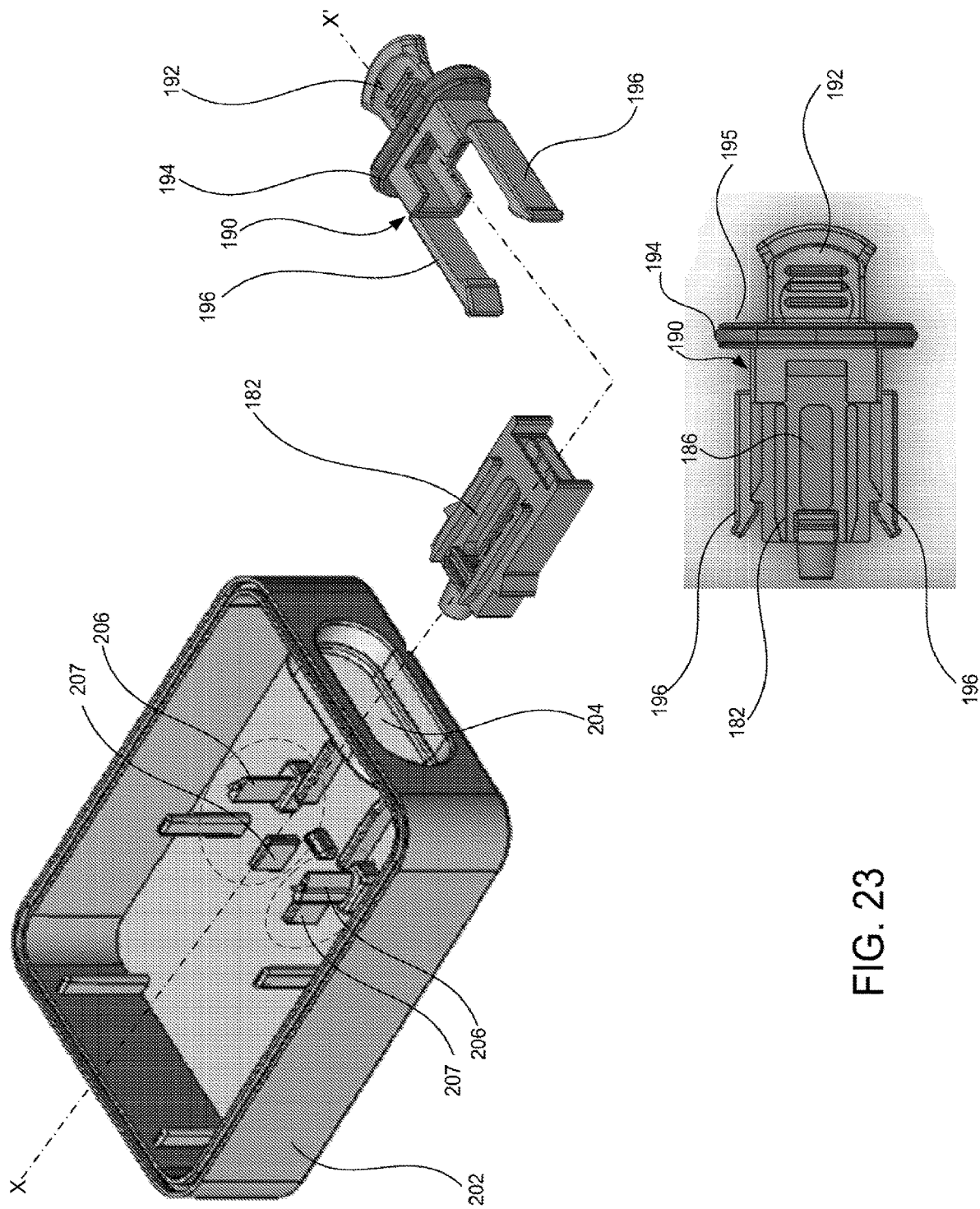
FIG. 23 shows an exploded view of the transportation sleeve and cartridge assembly.

FIG. 22B shows a top view of the transportation sleeve and a filled cartridge assembly prior to its insertion into the sleeve. FIG. 22C shows the filled cartridge assembly inserted into the transportation sleeve, with the cartridge tab 192 extending from an edge of the sleeve. FIG. 23 shows an exploded view of the transportation sleeve and cartridge assembly with an axis X-X' extending through the aforementioned components. Referring to the above figures, the sleeve can include a sleeve base 202 and a sleeve lid 208 configured to be operably coupled to each other. The sleeve base can include an opening 204 for receiving the cartridge assembly. The opening can be configured to couple to the cartridge holder (e.g. proximal to the cartridge tab). The sleeve can include a dual support-release mechanism comprising (a) a retention element configured to engage with a corresponding mating feature on the cartridge and secure the cartridge within the sleeve, and (b) a release element configured to cause the spring-clips on the cartridge holder to release and thereby decouple the cartridge from the cartridge holder. In some embodiments, the dual support-release mechanism can be implemented using a plurality of posts 206 and 207.

Figure 24A:
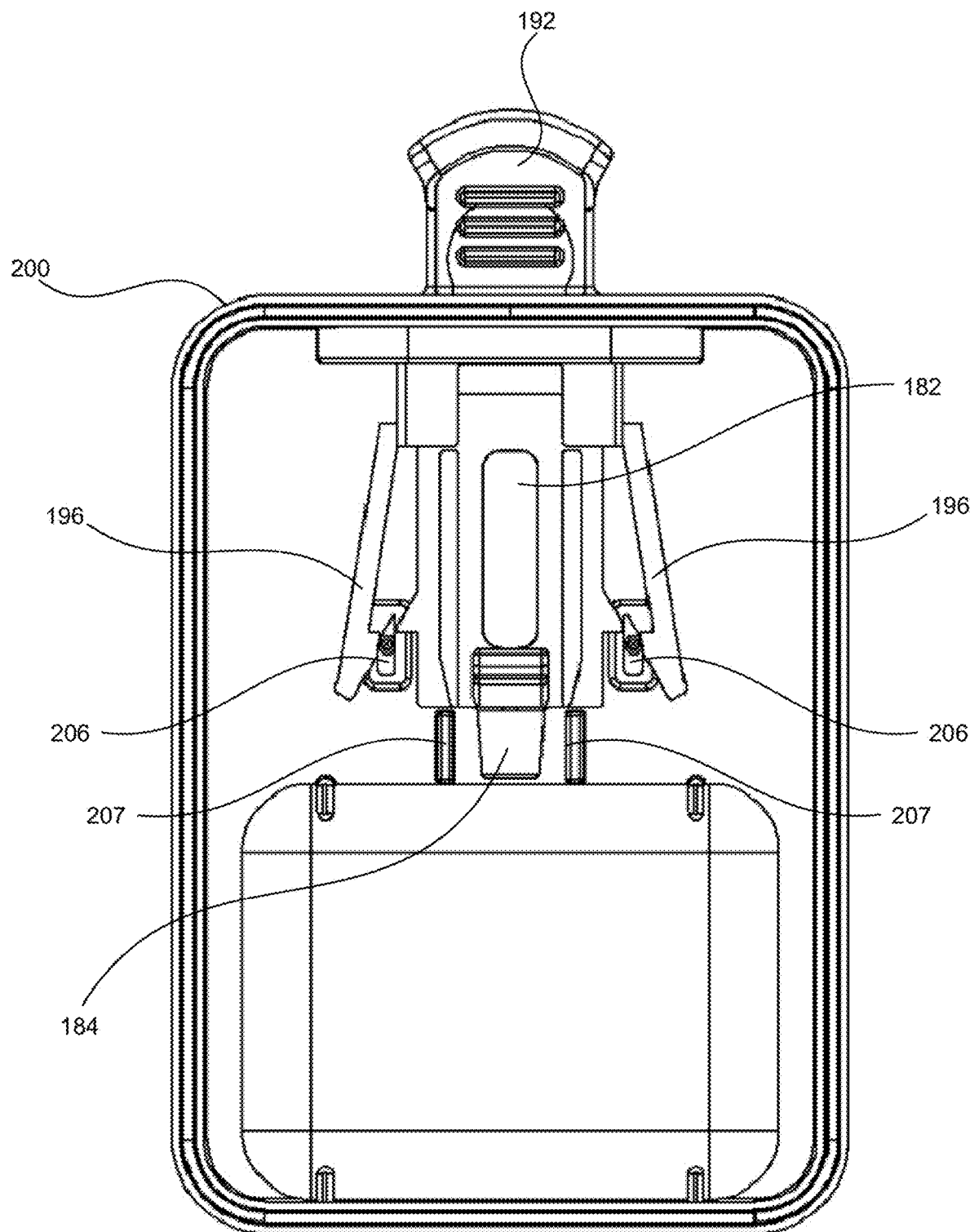
FIG. 24A shows a side sectional view of the transportation sleeve with cartridge assembly inserted therein.
Figure 24B:
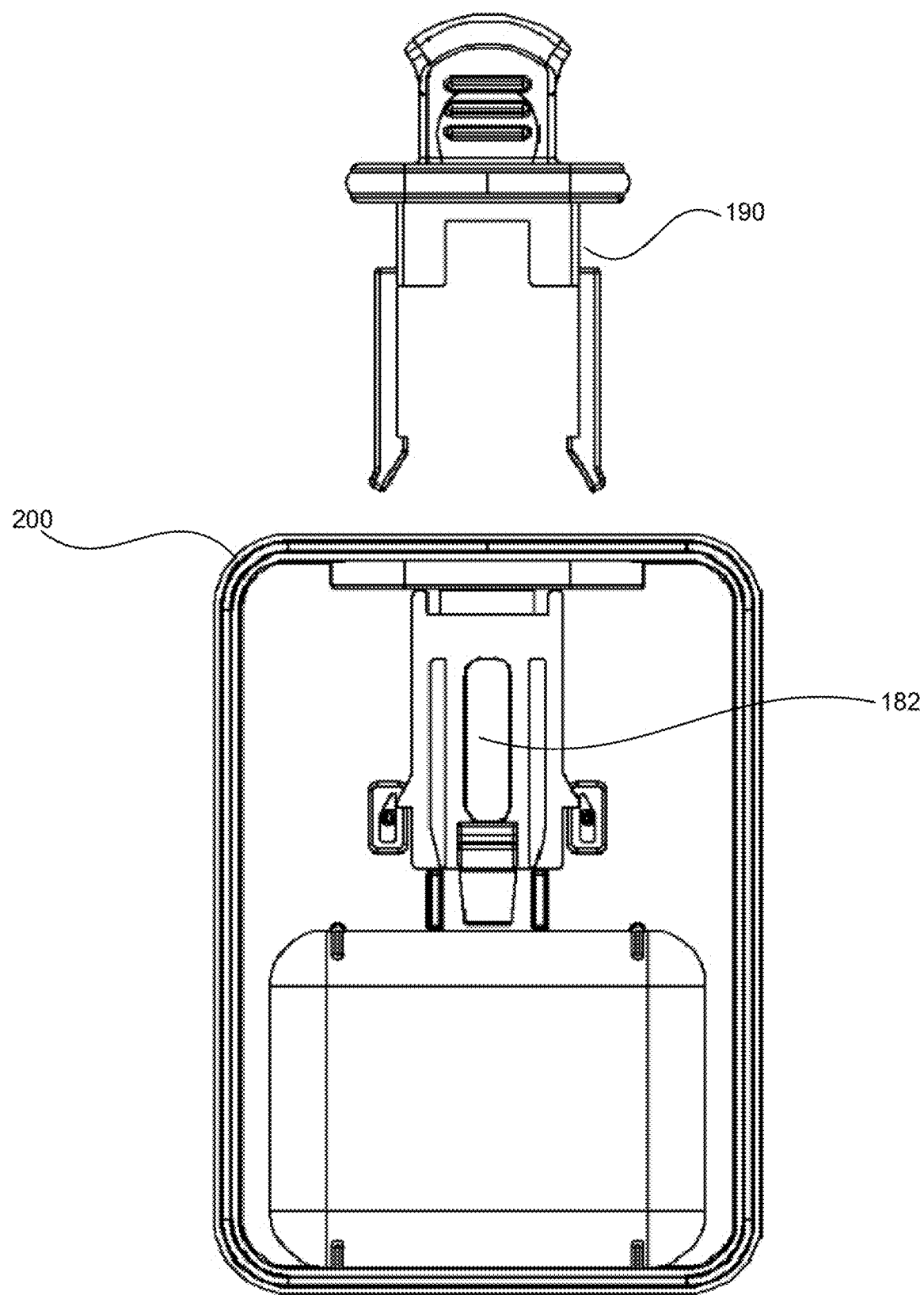
FIG. 24B shows a side sectional view with the cartridge holder removed, leaving the cartridge within the transportation sleeve.

FIG. 24A shows a side sectional view of the transportation sleeve with the cartridge assembly inserted therein. FIG. 24B shows a side sectional view with the cartridge holder removed, leaving the cartridge within the transportation sleeve. As shown in the above figures, the cartridge assembly is inserted into the opening 204 of the sleeve 200 by pushing the cartridge tab 192 until a rear portion of the cartridge holder and the seal/gasket 194 comes into contact with and seals the opening 204. The posts 206 can be configured to engage and release the spring clips 196 on the cartridge holder when the cartridge assembly is properly inserted into the sleeve. The release of the spring clips decouples the cartridge from the cartridge holder. The posts 207 can serve as stoppers, and come into contact with a portion of the cartridge adjacent to the cartridge port 184. As shown in FIG. 24B, the cartridge holder can be subsequently removed from the sleeve, leaving the cartridge held in place by posts 206 and 207 within the sleeve. As described above, the post 206 and 207 can provide the dual support-release mechanism. The decoupling of the cartridge from the cartridge holder via the dual support-release mechanism can permit the cartridge holder to be removed from the opening of the sleeve while the cartridge is secured in place within the sleeve, without exposure of the strips to the ambient environment.

In some embodiments, additional treatment and/or stabilization of the sample on the matrices 186 can take place within the transportation sleeve following the release of the cartridge from the cartridge holder. In some embodiments, a desiccant can be provided within the sleeve for drying the sample on the matrices. In some embodiments, the sleeve can be placed in a carrier pouch 220 and shipped for further processing (see e.g., steps 13 and 14 of FIG. 25B).

Figure 25A:
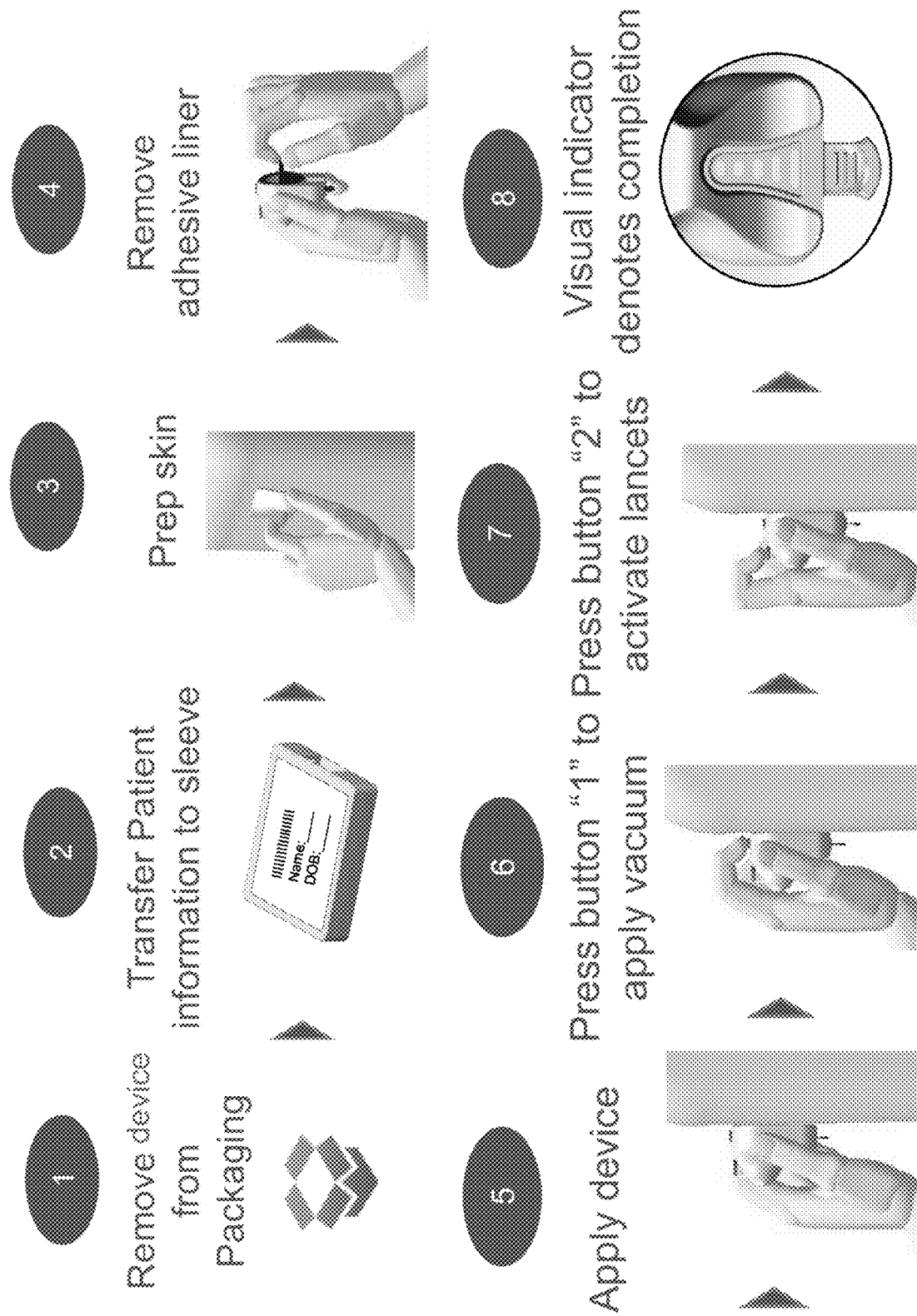
FIGS. 25A and 25B show an exemplary procedure of collecting blood samples from a subject using a sample acquisition device, and packaging of the blood samples for shipment.
Figure 25B:
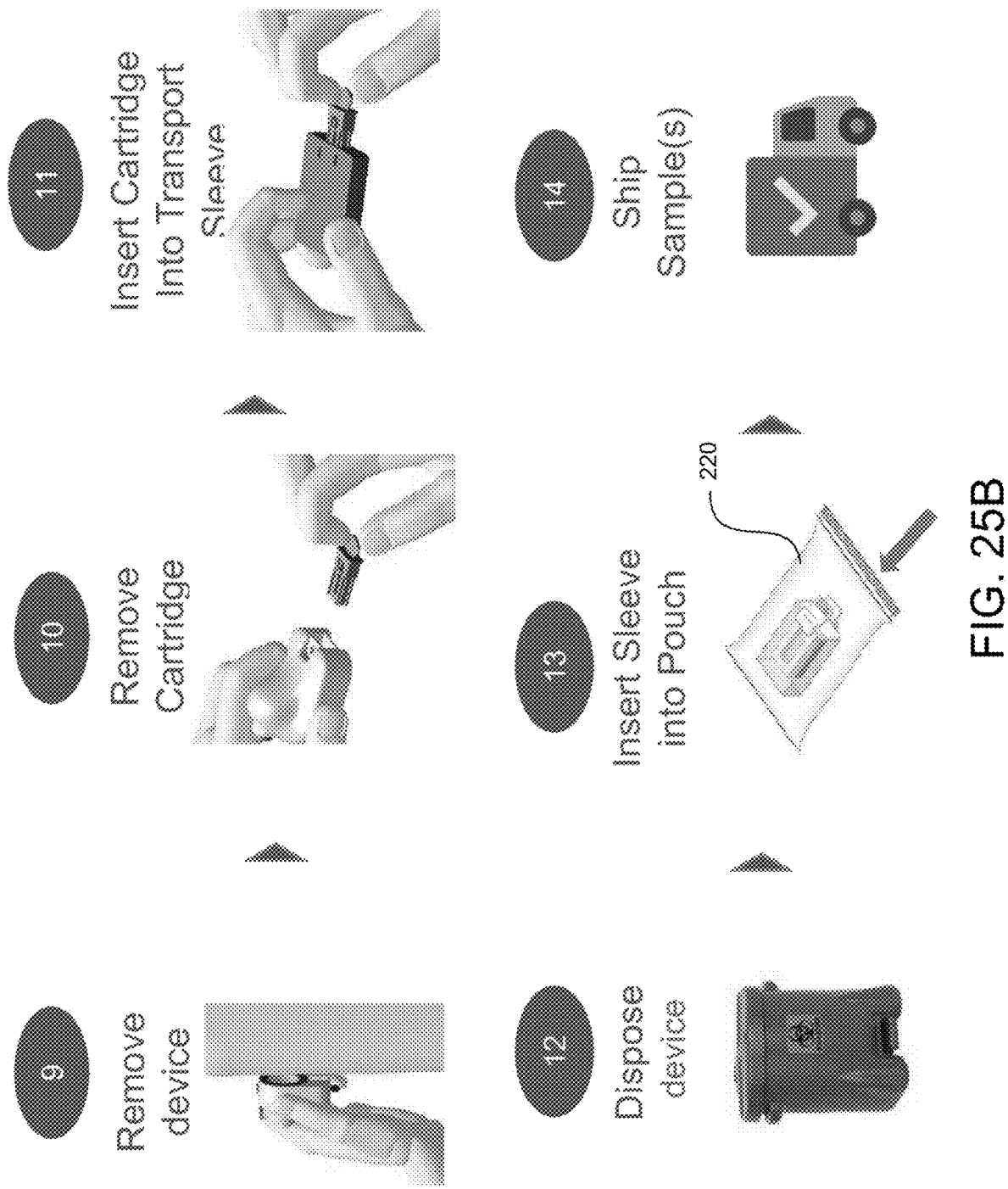

FIGS. 25A and 25B illustrate exemplary procedures to collect and store blood samples using any of the devices described herein (e.g. device 100). Referring to FIG. 25A, the device can first be removed from its packaging (step 1). A subject or another user (e.g. a healthcare personnel) can record the patient's information on a sleeve label (step 2). An alcohol swab is then used to clean the skin on the patient's upper arm where the device will be applied (step 3). Next, an adhesive liner is removed from the planar portion on the housing base of the device to reveal a hydrogel adhesive (step 4). Next, the device is placed and adhered to the patient's skin with the hydrogel adhesive (step 5). The button labeled "1" on the device is pressed to activate the vacuum to drawn the patient's skin into the recess (step 6). The button labeled "2" on the device is next pressed to activate one or more piercing elements to penetrate the patient's skin at the opening of the recess (step 7). Blood is absorbed by one or more matrices in the cartridge of the device. As blood is absorbed, the flow meter on the device can indicate the progress of the blood collection, and indicate when the matrices are full (step 8). Once the matrices are full, the device is removed (step 9). The cartridge is removed from the device (step 10) and inserted into a transportation sleeve (step 11). The device is no longer needed and can be disposed appropriately in a sharps container (step 12). The sleeve can be placed into a pouch (step 13) which is used to ship the sample to a lab for processing (step 14).

IV. Additional Embodiments

Provided herein are devices, methods, and kits for collecting blood from a subject. Devices, methods, and kits provided herein can permit application of a vacuum to skin of a subject, followed by piercing of the skin of the subject under vacuum (e.g., with one or more blades). Application of the vacuum can enhance blood flow to a region of skin under vacuum and can increase the rate and volume of blood collection in the device. The vacuum can be generated using a cupping action via, e.g., a rigid concave surface or flexible concave surface, e.g., a concave cavity (see, e.g., FIGS. 31A-31D). A volume of a hemisphere formed by the concave surface can be equivalent to, or about half, or about a quarter, of a volume of a vacuum chamber in the device. The concave cavity can comprise an opening with an inner diameter, and the concave cavity can comprise a diameter at a base of the device.

Any of the devices provided herein can comprise one or more piercing elements, e.g., blades. The one or more piercing elements, e.g., blades, can be configured to pass through the opening of the device and pierce the skin of a subject. Each of one or more blades can comprise a length of about 1 mm to about 10 mm, or about 1 mm, 1.5 mm, 2 mm, 4 mm, 6 mm, 8 mm, 10 mm, a width of about 0.01 to about 2 mm, or about 0.01 mm, 0.05 mm, 0.1 mm, 0.5 mm, 1 mm, 2 mm, and a depth of about 1 to about 20 mm, or about 1, 5, 10, 15, or 20 mm. The devices can comprise one or more piercing elements, e.g., at least 1, 2, 3, 4, 5, 6, or 7 piercing elements (e.g., lancets, needles, or blades).

A method for collecting blood from a subject is provided herein, the method comprising applying a vacuum to skin of a subject using a device; after applying the vacuum, piercing the skin of the subject under which the vacuum is applied, wherein the device is used to pierce the skin of the subject, thereby generating an incision in the skin under which the vacuum is applied; and collecting the blood from the incision under the vacuum, wherein the collecting occurs in the device. The vacuum can deform skin, enhance perfusion and draw blood from the smaller incision area. The vacuum can be a global vacuum. A local vacuum can also be used, but the skin deformation and perfusion can be much less.

In some embodiments, the subject has diabetes. In some embodiments, collecting blood from a subject further comprises stabilizing a component or analytes of interest from the blood. In some embodiments, the analyte of interest is hemoglobin A1c (HbA1c).

The device can be configured with user friendly features. FIG. 31A, FIG. 31B, FIG. 31C, and FIG. 31D illustrate features that can be integrated into devices disclosed in the present application. Such features can include single or multiple (e.g., 2, 3, 4, 5) actuators or activators (e.g., which can include buttons) for device activation, with positions that can be readily activatable by the user given the shape of the device and location of the actuator. Actuators or activators can have distinct shapes, sizes, and locations configured (e.g. positioned or structured on the device) for ease of use (e.g. easy identification by the user and well placed locations for simple activation). An example of a device with actuators or activators for performing one or more user direct actions is shown in FIG. 31A, wherein two buttons are shown each with an easily identified shape and comfortable to use location. The circular button shown in FIG. 31A can be used for activating a vacuum and the rectangular button can activate a piercing element (e.g., lancet) for piercing the skin. In some cases, a single actuator or activator can be used to activate a vacuum and a piercing element. The device can comprise a lancet activation actuator configured to activate the lancet upon actuation of the lancet activation actuator. The lancet activation actuator can comprise a button.

Features, e.g., user friendly features, can comprise mechanisms for expediting blood collection by enhancing a rate or means of collecting a sample, thus reducing the time it takes to collect a sample. One such feature is illustrated in FIG. 31B, which depicts a device with a skin-vacuum and lancing cavity for reducing the amount of time required to collect a sample. The skin-vacuum and lancing cavity can comprise a concave cavity into which the skin of the subject can be drawn (e.g., under negative pressure), and an opening comprising an inner opening through which a one or more piercing elements (e.g., lancets), e.g., 1, 2, 3, 4, 5, 6, 7, 8, 9, or 10 piercing elements, can exit and pierce skin so that a blood sample can be drawn from the subject. In some embodiments the device can comprise a vacuum actuator (e.g., button) for activating the vacuum.

FIG. 31C shows additional features. For example a device for collecting a blood sample can comprise a visual metering window that can allow a user to monitor sample collection and determine when the sample collection is complete. When the sample collection is complete, a visual metering window can be used to detect (e.g., visualize) a feature, colorimetric change, display of a symbol, masking of a symbol, or other means of indicating that collection is complete. Further user friendly features can comprise a removable cartridge (e.g., clip-in removable cartridge) for collecting and transporting a blood sample, as shown in FIG. 31D. A removable cartridge (e.g., clip-in removable cartridge) can comprise a cartridge tab for releasing and removing the cartridge. In some embodiments a removable cartridge (e.g., clip-in removable cartridge) can comprise a solid matrix for collecting, storing, and/or stabilizing a collected sample, and the removable cartridge can facilitate easy transport (e.g. transport at room temperature), and transport without the need for subsequent sample preparation or stabilization procedures.

Figure 50B:
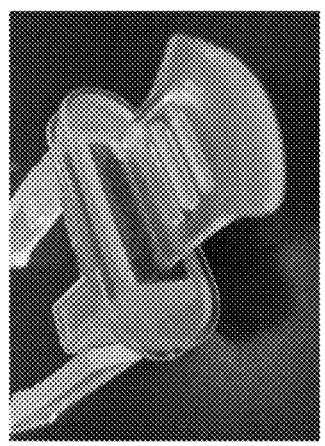
FIG. 50A, FIG. 50B, and FIG. 50C illustrate a visual metering window permitting a user to view draw progress (FIG. 50A illustrates visually tracking by the health care provider (HCP) as the stabilization matrix strip fills. When the final window fills, the draw is complete.
Figure 50C:
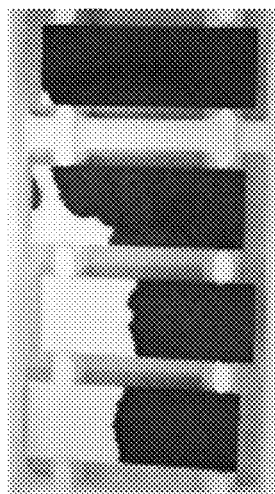
Figure 50A:
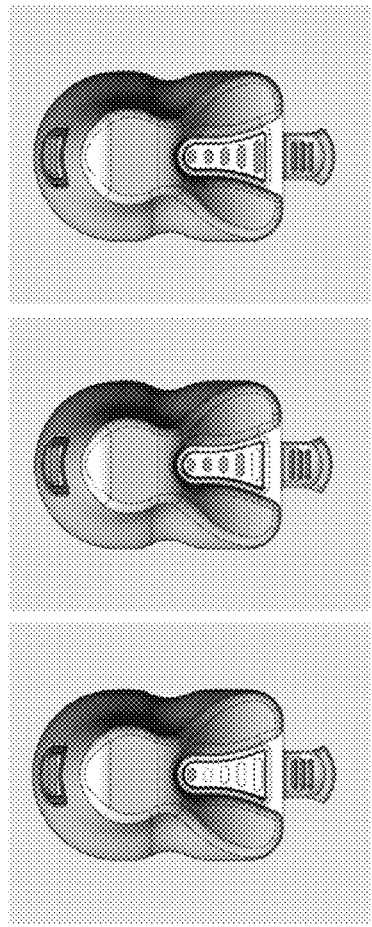
Figure 51:
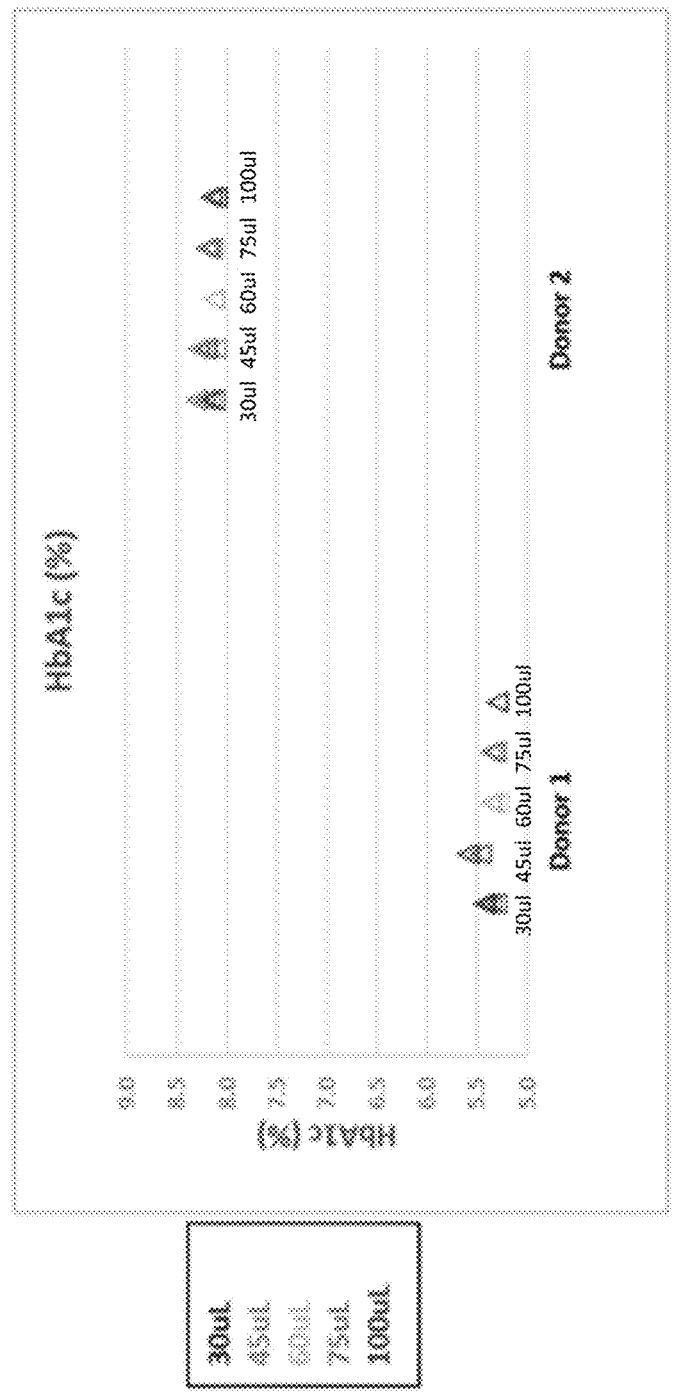
FIG. 51 illustrates the percentage of HbA1c in blood samples of five different volumes (30 µL, 45 µL, 60 µL, 75 µL, 100 µL) drawn from two different donors.

FIG. 50A shows an additional embodiment of the visual metering window and illustrates how blood absorption on the matrix strips can appear. In some embodiments a wicking pad captures excess blood unable to be absorbed by the matrix strips (FIG. 50B). Blood absorption on the matrix strips is illustrated in FIG. 50C.

Figure 32A:
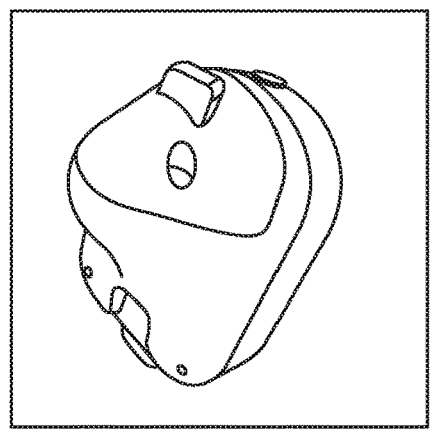
FIG. 32A, FIG. 32B, FIG. 32C, and FIG. 32D illustrate front, side, and back views of a device that can be used to collect a sample of defined volume and store it on a removable stabilization matrix.
Figure 32B:
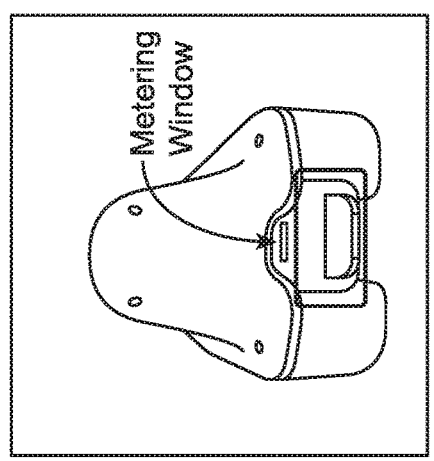
Figure 32C:
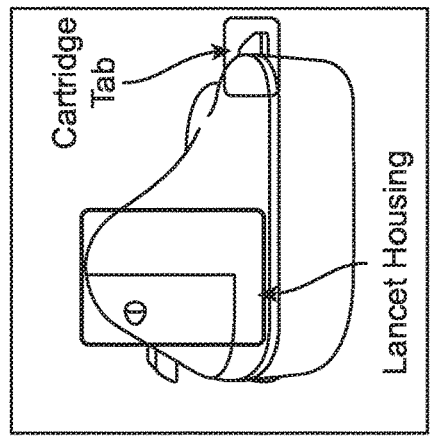
Figure 32D:
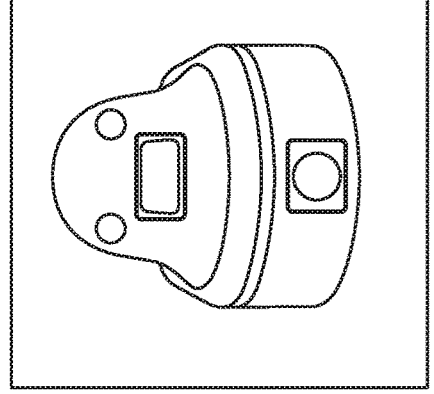

FIG. 32A, FIG. 32B, FIG. 32C, and FIG. 32D illustrate an integrated device with several of the user features described in FIG. 31A, FIG. 31B, FIG. 31C, and FIG. 31D. FIG. 32A illustrates a front view of a device with a dual button configuration. In some embodiments one button can be responsible for activating a vacuum and a second button can be responsible for activating a piercing (e.g., lancet piercing) mechanism; for example, the lower round button or vacuum button can be configured to cause a vacuum (negative gauge pressure) to be applied to the skin, and the upper rectangular button or lancet button can be configured to activate a vertical lancing mechanism to pierce the skin. In alternate embodiments buttons can be activated using a variety of methods; for example the buttons can be activated separately, in a specific sequence or order, or the two buttons can be combined into one button so that only a single button is needed to activate the collection mechanisms on the device. Buttons can perform different functions, and have different shapes, sizes, colors, or locations that support the function of each button. FIG. 32B illustrates a side view of the device depicted in FIG. 32A. FIG. 32B illustrates a device with a lancet housing, the lancet housing in this embodiment comprises a raised area for houses the lancing mechanism. Also depicted is a removable cartridge for storing a solid matrix, with a cartridge tab for removing the removable matrix cartridge. FIG. 32C depicts an alternate view of the device illustrated in FIGS. 32A and 32B. Illustrated features include the rear cartridge lid closure and cartridge tab, as well a visual metering widow configured to alert the user when the draw is complete. FIG. 32D illustrates a side perspective view of the device illustrated in FIG. 32A, FIG. 32B, and FIG. 32C.

Figure 33B:
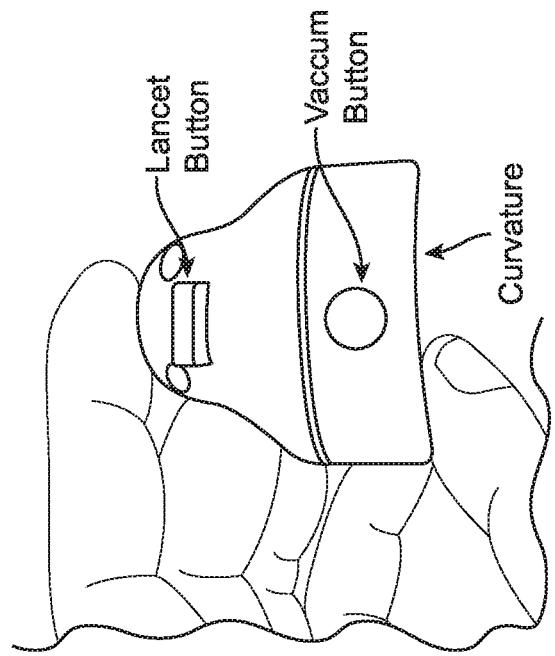
FIG. 33A, FIG. 33B, and FIG. 33C illustrate features of a device that can be used to enhance sample collection.
Figure 33A:
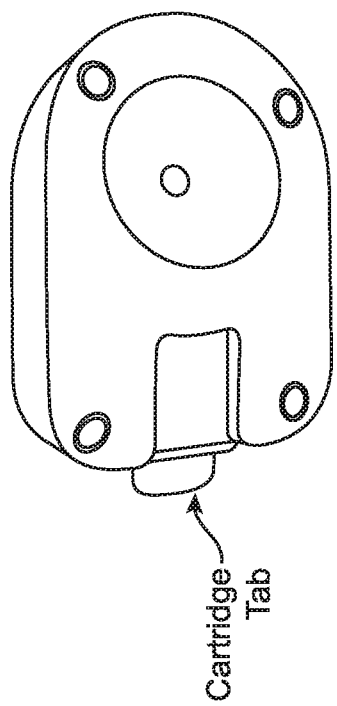

FIG. 33A depicts the bottom view of a device for collecting a blood sample, the depicted bottom region is the site of the device configured for making contact with the skin of the subject. As shown, the bottom of the device can comprise a concave cavity, for example a concave hemispherical cavity as shown here, although other shapes can also be used. The concave cavity in this embodiment forms a hemispherical cup disposed within the bottom of the device. The cupped skin area can be substantially larger than the lanced area. In some embodiments the ratio of the cupped skin to the lanced area can be greater than 20:1, greater than 30:1, greater than 40:1, greater than 50:1, greater than 60:1, greater than 70:1, greater than 80:1, greater than 90:1, or greater than 100:1. In some embodiments the cupped area can be within 20% margin of 500 mm2 and the lanced area can be within a 20% margin of 8 mm$^2$. The lanced area can comprise a hole in the center of the concave cavity from which lancets can protrude; this area can additionally act as a vacuum channel and as part of the blood path to the deposition cartridge. The lancets or other piercing element can be held in a cylinder shaped lancet actuator. The lancet actuator can have a diameter of 1-10 mm (e.g. 1, 2, 3, 4, 5, 6, 7, 9, 10 mm). The area of the lancet actuator can be between 5 and 100 mm$^2$ (e.g. 5, 10, 13.2, 15, 20, 40, 60, 80, 100 mm$^2$). The lancets or blades held by the lancet actuator can generate an incision area of between 1and 20 mm$^2$ (e.g. 1, 3, 5, 9, 11, 15, 17, 20 mm$^2$).

Any of the sample acquisition devices herein can also be referred to as the "device," The housing, outer housing, upper housing, lower housing, or lancet housing of the device can comprise acrylobutadiene styrene (ABS), polypropylene (PP), polystyrene (PS), polycarbon (PC), polysulfone (PS), polyphenyl sulfone (PPSU), polymethyl methacrylate (acrylic) (PMMA), polyethylene (PE), ultra high molecular weight polyethylene (UHMWPE), lower density polyethylene (LPDE), polyamide (PA), liquid crystal polymer (LCP), polyaryl amide (PARA), polyphenyl sufide (PPS), polyether etherketone (PEEK), polyvinyl chloride (PVC), polyethylene terephthalate (PET), polytetra flouroethylene (PTFE), polyaryletherketone (PAEK), polyphenyl sulfone (PPSU), or a combination thereof. In some embodiments, the outer housing comprises polypropylene.

After the device is placed on the skin of the subject and the device is activated, a vacuum or pressure differential can form between the surface of the skin as well as components disposed within the device. Skin can be pulled into the cavity by the pressure differential and can be constrained by the walls of the cavity. At some point after the vacuum is formed between the device and the skin, a piercing element (e.g., a lancet) can be activated to pierce the skin. As such, the vacuum "cupping" can be configured to enhance blood flow to the lanced area and also aspirate blood from the opening collection site, through the device and into a collection cartridge.

A side view of the device depicted in FIG. 33A is illustrated in FIG. 33B. In some embodiments the bottom of the device can comprise a curved base. Slight curvature at the base of the device can allow the device to better conform to the patient's anatomy (e.g., arm, e.g., upper arm) and can guide orientation of the device. In some embodiments, the device described herein is used to draw blood from the arm. In some embodiments, the device is not used to draw blood from the fingertip. In some embodiments, the device is not used to draw blood from a neonate.

Collection of the sample can comprise steps and components configured for piercing (e.g., lancing) the subject's skin and providing or creating a vacuum to facilitate extraction of the sample. In some instances a vacuum can be provided before lancing of the skin; in other instances the vacuum can be provided after lancing of the subject's skin, and in still other instances the vacuum can be provided simultaneously with lancing the subject's skin. FIG. 33A and FIG. 33B illustrate features of a device that can facilitate efficient blood collection using application of a vacuum to the skin of the subject. The vacuum can operate as a means of deforming the skin, and this action coupled with lancing of the deformed skin can facilitate sample collection. In further instances the device can be configured to perform one or more additional processing steps (e.g. treatment, stabilization, and storage of the collected sample).

Figure 33C:
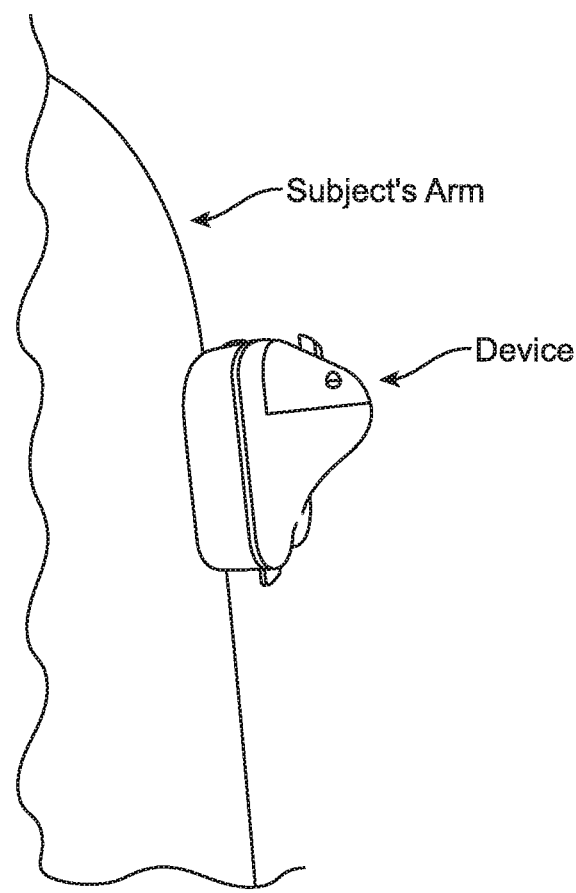

FIGS. 33A and 33B illustrates an embodiment of a device for collecting a sample using global vacuum and local suction. Methods for using the device can comprise multiple steps. For example, a device as depicted in FIG. 33A and FIG. 33B can be placed on the arm of a subject using the orientation illustrated in FIG. 33C. The global vacuum cavity can be placed in contact with the skin, and a seal can be created with an adhesive material or gasket material placed on the foot of the device (e.g. in curved surface of the device show in FIG. 33B). Vacuum can be applied with the press of a button or other mechanism. Thereafter, lancing can be applied, for example utilizing a spring loaded plunging mechanism which cause two (can be more or fewer) lancets to penetrate the skin and retract. Lancing can be performed by a single blade or multiple blades (e.g. two or more, three or more, four or more, five or more, or ten or more blades). Blades can have various tip sized and shapes (e.g. slanted, triangular, circular, pointed, blunt, serrated). In instances where more than one blade is present, blades can be configured or arranged into patters with different shapes or orientations (e.g. ring, star, hash, square, rectangular etc.)

After sample is collected additional processing steps can be performed on the sample. Once blood is collected using a sample acquisition device, the sample can be treated, stabilized and stored. In some embodiments collection devices, e.g. devices disclosed in the present application, can be configured to collect, treat, and store the sample. Sample drawn by the device can be stored in liquid or solid form. The sample can undergo optional treatment before being stored. Storage can occur on the device, off the device, or in a removable container, vessel, compartment, or cartridge within the device.

A sample acquisition device can be configured to collect, treat, stabilize, and store a collected sample. Additional processing (e.g. treatment, stabilization, and storage) can comprise steps or methods and device components configured for concentrating the sample, adjusting or metering the flow of the sample, exposing the sample to one or more reagents, and depositing the sample on a solid substrate or matrix. Methods for using a sample acquisition device can include steps to perform one or more of the following processes: collection, treatment, stabilization, and storage of the sample. Collection, treatment, stabilization, and storage can be performed within a single device. Treatment can comprise filtration of the sample to separate components or analytes of interest. In some embodiments, the collected sample can be collected, treated, and stabilized prior to transfer to a removable cartridge for storage. In other embodiments, one or more steps comprising collecting, treating, and stabilizing, can occur on a removable cartridge.

In some embodiments, single action (e.g. activation using a button) can activate alternate processing steps including sample treatment, stabilization, and storage. Additional processing steps can be performed on the device in response to single action, or in some instances two or more user actions can be necessary to move the sample through one or more different processes (e.g. collection, treatment, stabilization, and storage). User actions can comprise pressing a single button, pressing multiple buttons, pressing two or more buttons at the same time, and pressing two or more buttons in a prescribed sequence (e.g. based on a prescribed sequence to perform a set of treatment steps desired by the user.)

Sample collected on a device can undergo a treatment step prior to being deposited on a solid substrate. A cartridge containing the two or more deposition strips can be maintained in a near vertical orientation to reduce deposition speed and increase sample deposition consistency. Vacuum can be released by the user and device can be removed when a visual (or other) metering mark is observed. The sample cartridge containing the two or more solid matrix strips can be removed from the device.

In some embodiments, solid matrix strips can be sized to maximize blood collection volume while still fitting into commonly used containers (e.g. a 3 ml BD vacutainer, deep well plate or 2 ml Eppendorf tube). Solid matrix can be configured to meter out, collect and stabilize fixed volumes of blood or plasma (e.g. greater than 25 uL, 50 uL, greater than 75 uL, greater than 100 uL, greater than 125 uL, greater than 150 uL, greater than 175 uL, greater than 200 uL, or greater than 500 uL of blood or plasma). A solid matrix can comprise cellulose based paper (e.g. Whatman™ 903 or 226 paper), paper treated with chemicals or reagents for stabilizing the sample or one or more components of the sample (e.g. RNA stabilization matrix or Protein Stabilization Matrix). In some embodiments, the solid matrix comprises a cellulose filter paper. In some embodiments, any suitable commercially available filter paper is used. Examples of commercially available filter paper include, but are not limited to, filter paper from Whatman®, such as 903 sample collection cards and fast transit analysis (FTA®) card. In some embodiments, the solid matrix comprises a nitrocellulose filter paper. In some embodiments, the solid matrix does not comprise glass fiber filter paper.

Figure 34A:
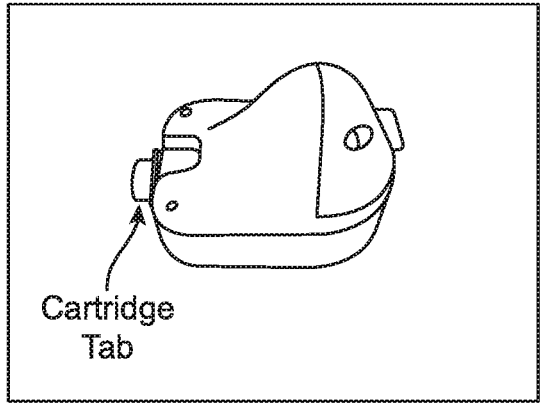
FIG. 34A, FIG. 34B, FIG. 34C, and FIG. 34D illustrate an embodiment of a device for collecting a blood sample from a subject, and means for storing the sample in a removable cartridge.

Sample acquisition devices (e.g. the devices depicted in FIGS. 31A-D, FIGS. 32A-D, and FIGS. 33A-C) can comprise a removable cartridge or enclosure for storing a liquid sample or solid matrix for removing the sample once it has been collected. FIG. 34A, FIG. 34B, FIG. 34C, and FIG. 34D illustrate steps for removing a removable cartridge from an exemplary devices configured with a removable cartridge (e.g. the devices depicted in FIGS. 31A-D, FIGS. 32A-D, and FIGS. 33A-C). A device can come with a cartridge pre-loaded in the device, as shown in FIG. 34A, or a device can come without the cartridge such that a cartridge can be acquired separately and installed into the device by the user prior to sample collection. The device illustrated in FIG. 34A is shown with the cartridge loaded in the device and with the cartridge tab projecting from the back of the device. After a draw is complete the cartridge can be removed as shown. The cartridge can comprise one or more solid matrix strips, or a vessel for storing liquid sample. Alternatively, the cartridge can be empty. In some cases, the cartridge can include liquid handling reagents. In some embodiments, the cartridge/device interface can contain a seal (e.g. gasket or other type) to maintain internal pressure during the draw period.

Figure 34B:
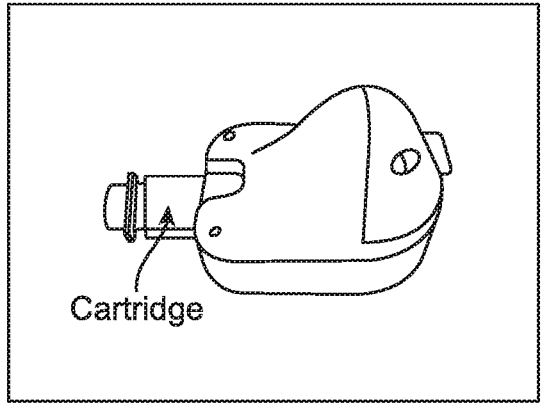
Figure 34C:
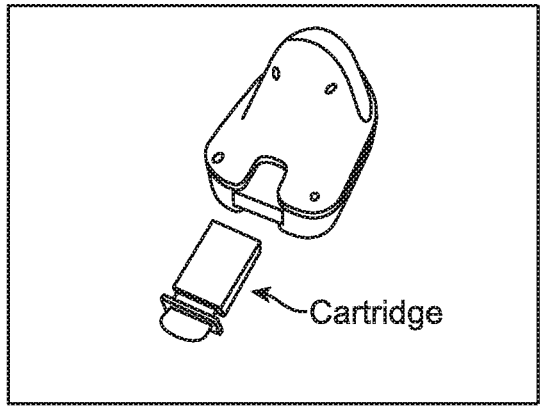
Figure 34D:
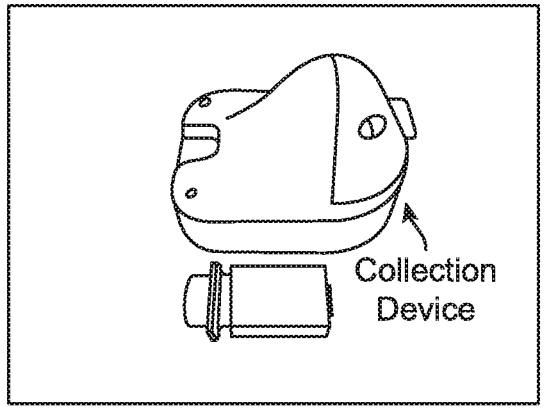

FIG. 34B illustrates the partially removed cartridge. Removal of the cartridge can be performed using the cartridge tab shown in FIG. 34A. In FIG. 34C, the cartridge depicted in FIG. 34B has been completely removed and is placed at the back of the collection device in an orientation by which it was removed. FIG. 34D illustrates the fully removed cartridge placed parallel with the collection device to illustrate the positioning of the cartridge within the device. Once removed, a cartridge can be placed in a secondary vessel with desiccant to dry the sample. In instances where the cartridge comprises strips of solid matrix for storing the sample, the strips can be removed with an extraction tool or other mechanism prior to analysis.

Figure 35:
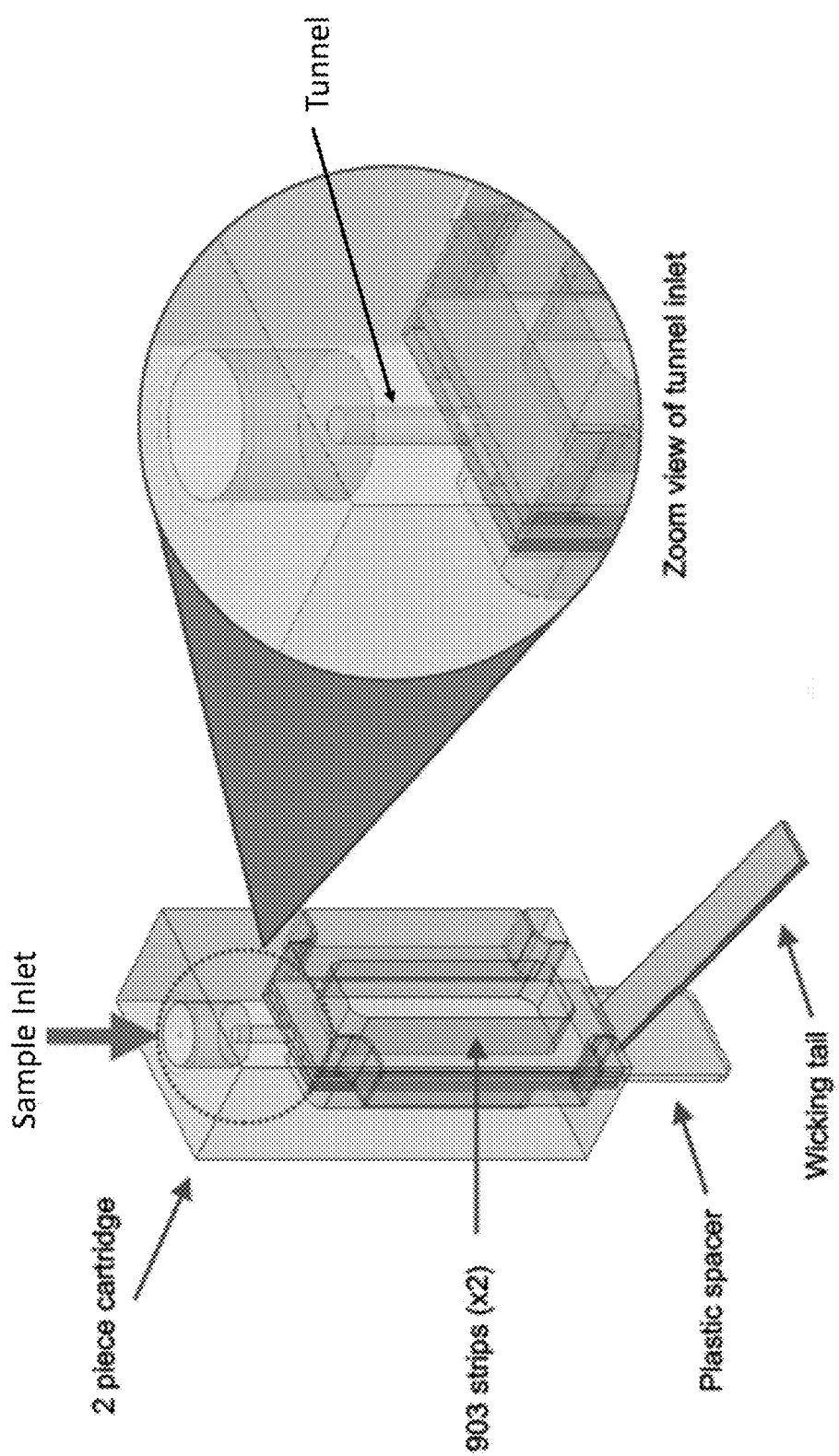
FIG. 35 illustrates an inside view of a removable cartridge that can be used with any of the disclosed sample collection devices (e.g., sample collection devices illustrated in FIGS. 31A-31D, FIGS. 32A-32D, FIGS. 33A-33C, and FIGS. 34A-34D)

A cartridge, for example the cartridge illustrated in FIGS. 34A-D, can comprise multiple components for facilitating accurate and precise sample collection. FIG. 35 illustrates a cross sectional and zoom-in of a cartridge embodiment that can be used in any of the devices disclosed herein. In some instances a cartridge can comprise one or more solid matrices for collecting a blood sample. In embodiments where two or more solid matrices are included in the sample, the matrices can be stacked or arranged in ways that facilitate blood collection, distribution, precision and reproducible volumes of sample or analyte per surface area of solid substrate. In instances where two or more solid matrices are include, the matrices can have different compositions or purposes; for example one matrix can separate cells from a cell free component and collect the cell free component on one matrix, and a second matrix or other matrices can collect raw unseparated sample.

An exemplary sample storage cartridge is depicted in FIG. 35. The cartridge can comprises two pieces, a top piece and a bottom piece which can be merged to form internal chambers. Sample can move through the opening in the concave cavity of the device and into the cylinder shaped sample inlet into a tunnel inlet before entering a chamber. The chamber can comprise solid matrix strips for absorbing the sample and a spacer (e.g., plastic spacer) to separate the two solid matrix strips. The spacer (e.g., plastic spacer) between the two strips can be adjustable and removable, depending on other relevant aspect (e.g. the needs and application of the sample being collected, stability of the analyte, rate of absorption requirements etc). The spacer (e.g., plastic spacer) can comprise a range of widths and coatings. Exemplary widths include widths in the millimeter to centimeter range (e.g. greater than 2 mm, greater than 4 mm, greater than 6 mm, greater than 8 mm, greater than 10 mm, greater than 0.2 cm, greater than 0.4 cm etc.). In further embodiments, the spacer (e.g., plastic spacer) can be coated with materials including hydrophobic coatings, hydrophilic coatings, antimicrobial coatings, coatings that bind to one or more components of a sample, coatings for binding to or inhibiting enzymes that can degrade or otherwise impact the quality of one or more analytes on the sample.

As shown in FIG. 35, after moving thought the sample chamber, excess sample can move out of the storage cartridge through a wicking tail. The wicking tail can be configured to absorb excess sample overflow. The wicking tail can be configured (e.g. composition adjusted) so that the wicking tail can be used as a means to control the volume of the sample absorbed on the solid matrix strips. In further embodiments, the wicking tail can be used as or incorporated into an indicator or be visible through a viewing window configured for informing a user that the collection procedure is complete. The cartridges illustrated in FIG. 35 depict sample stored on a solid matrix; however, this should not be taken to limit the devices disclosed herein—devices can comprise cartridges or means for collecting, treating, stabilizing and storing sample in either a liquid or a solid state.

Figure 36B:
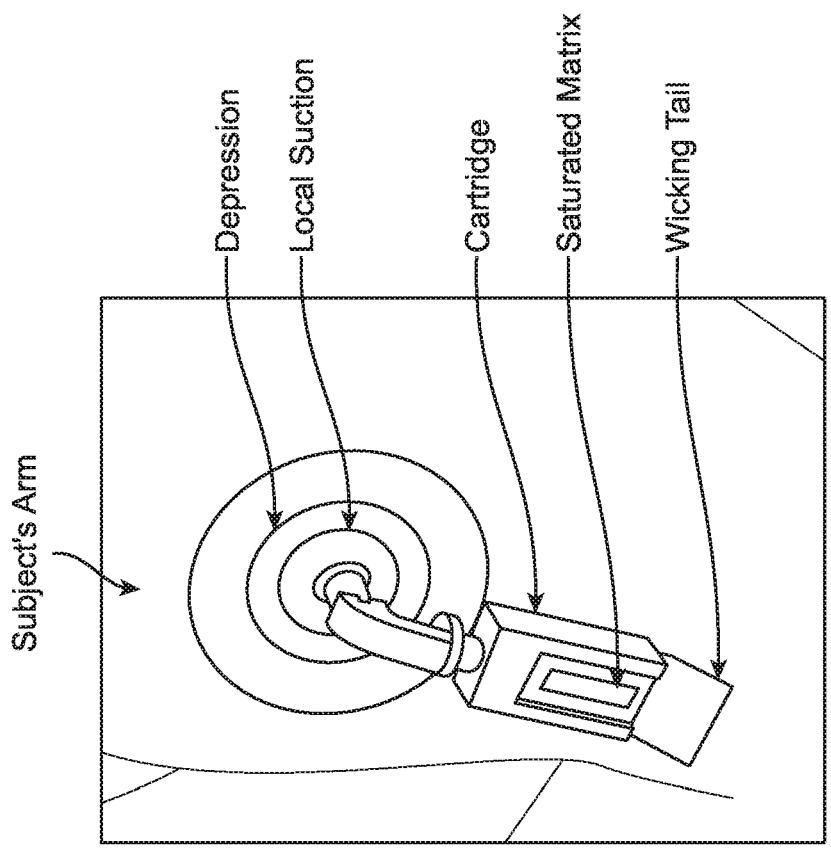
FIG. 36A and FIG. 36B illustrate an exemplary orientation of a device or device configured to use one or more mechanisms (e.g. gravity, capillary action, global vacuum, and local suction) collect and deposit a blood sample on a solid matrix for storage.
Figure 36A:
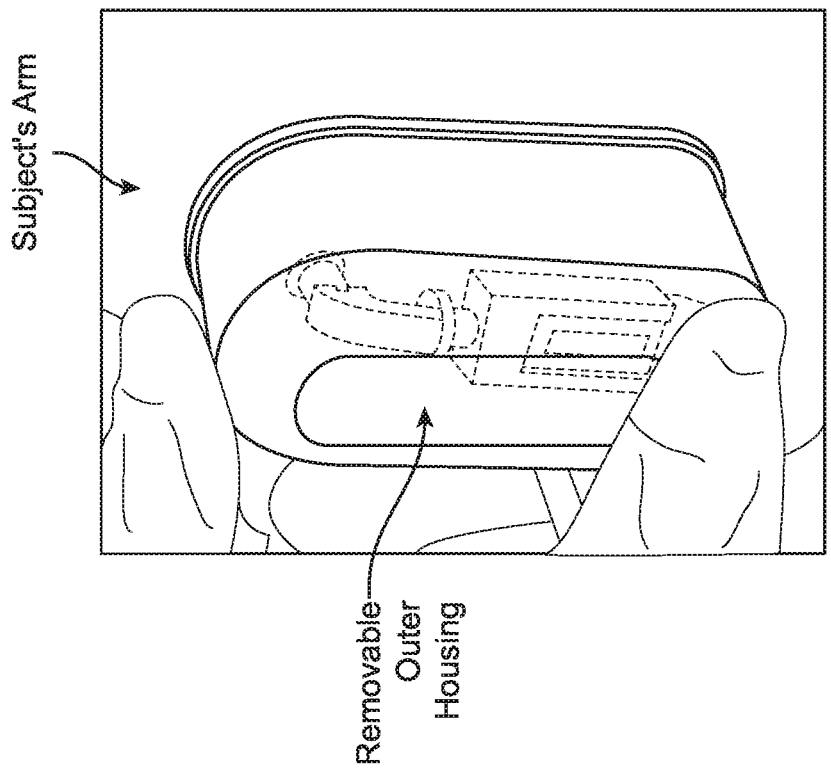

FIG. 36A and FIG. 36B illustrate an exemplary device configured with a sample storage cartridge similar to the cartridge illustrated in FIG. 35. FIG. 36A shows a removable outer housing configured for applying global vacuum to the sample collection site located on a subject's arm. In some embodiments the global vacuum can be applied through a concave cavity for deforming the skin prior to lancing. FIG. 36B illustrates exemplary local suction and blood collection components of the device depicted in FIGS. 36A and 36B. A depression is apparent on the arm of the subject, indicating that global suction was applied. Local suction, through a suction cup, is provided on the surface of the skin around the location where the skin of the subject was lanced. The sample is showing moving from the lanced site into a cartridge comprising a saturated matrix and a wicking tail. The wicking tail can be used to absorb excess sample and standardize or meter the volume of blood deposited on the saturated matrix.

In some embodiments, solid matrices, for example solid matrices included in a cartridge, can be sized to maximize blood collection volume while still fitting into commonly used containers (e.g. a 3 ml BD vacutainer, deep well plate or 2 ml Eppendorf tube). The cartridge can include one solid matrix, two solid matrices, three solid matrices, four solid matrices, or more than four solid matrices. In some embodiments, the cartridge includes two solid matrices. Solid matrix can be configured to meter out, collect and stabilizes fixed volumes of blood or plasma (e.g. greater than 50 uL, greater than 75 uL, greater than 100 uL, greater than 125 uL, greater than 150 uL, greater than 175 uL, greater than 200 uL, or greater than 500 uL of blood or plasma). In some embodiments, the cartridge comprises two solid matrices, wherein each solid matrix stabilizes 75 μL of blood for a total of 150 μL of blood. A solid matrix can comprise cellulose based paper (e.g. Whatman™ 903 paper), paper treated with chemicals or reagents for stabilizing the sample or one or more components of the sample (e.g. RNA stabilization matrix or Protein Stabilization Matrix).

Figure 37A:
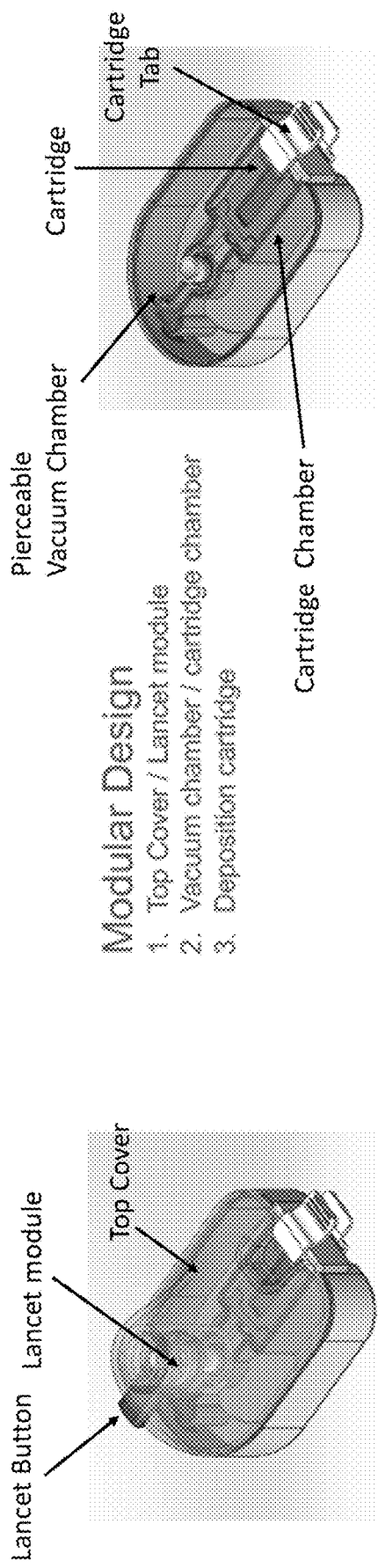
FIG. 37A, FIG. 37B, FIG. 37C, and FIG. 37D illustrate a modular design of an device with components configured for generating a vacuum, lancing a subject's skin, collecting, metering and stabilizing a blood sample from the subject, and storing the collected sample.
Figure 37B:
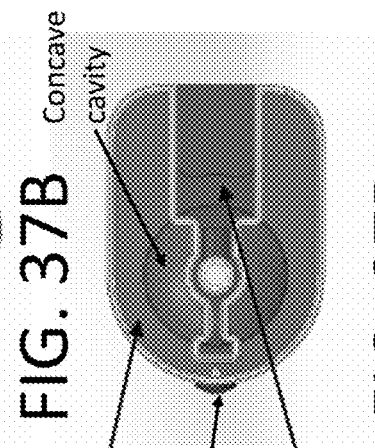
Figure 37C:
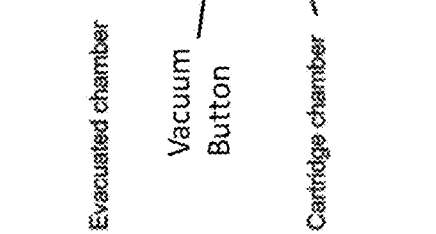
Figure 37D:
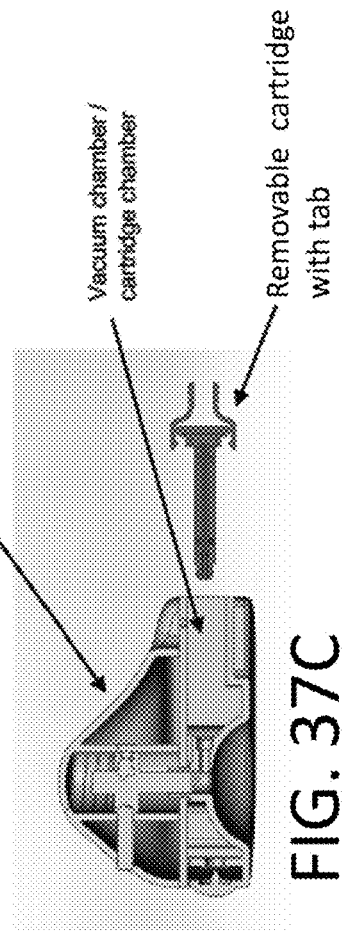

Devices for collecting a blood sample can be modular, with two or more compartments for performing specific actions or functions on the device. An exemplary modular device is depicted in FIG. 37A, FIG. 37B, FIG. 37C, and FIG. 37D. FIG. 37A illustrates the top view of a modular sample acquisition device (e.g. similar to the devices depicted in FIGS. 31A-D, FIGS. 32A-D, and FIGS. 33A-C, and FIGS. 34A-D). Disposed within the top cover of the device illustrated in the FIG. 37A, is a lancet module and a lancet button for activating the lancet module. FIG. 37B illustrates the vacuum chamber and cartridge chamber disposed within the lower portion or "foot" of the device. This module comprises a pierceable vacuum chamber and a cartridge chamber, within the cartridge chamber is a cartridge. Projecting out of the backside of the device is a cartridge tab, which can be used to remove the cartridge as illustrated in FIGS. 34A-D. FIG. 37C illustrates a cross section of the device. The cross section displays the top cover and lancet module also shown in FIG. 37A, and in the bottom of the device the vacuum chamber/cartridge chamber shown in FIG. 37B. Also shown in FIG. 37C is a side view of the removable cartridge with the cartridge tabs, the cartridge is removed from the device and positioned to the side of the cartridge chamber where the cartridge can be inserted or from where the cartridge can be removed. FIG. 37D illustrates a top view of the device in a top down view showing components present in FIG. 37B. FIG. 37D shows the vacuum button, with a sharp end for piercing the evacuated chamber, piercing the evacuated chamber can form suction pulling the sample through the opening of the concave cavity, into the sample inlet of the cartridge and onto the solid matrix strips in the cartridge.

Figure 38A:
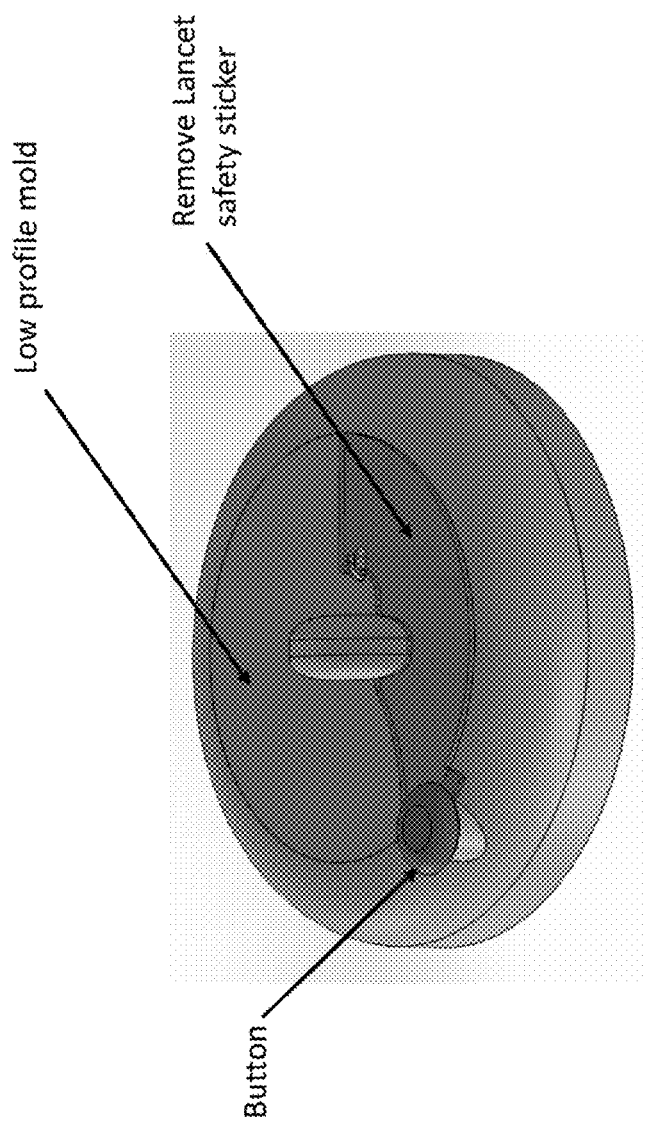
FIG. 38A illustrates external features of an exemplary low profile embodiment of a device provided herein.
Figure 38B:
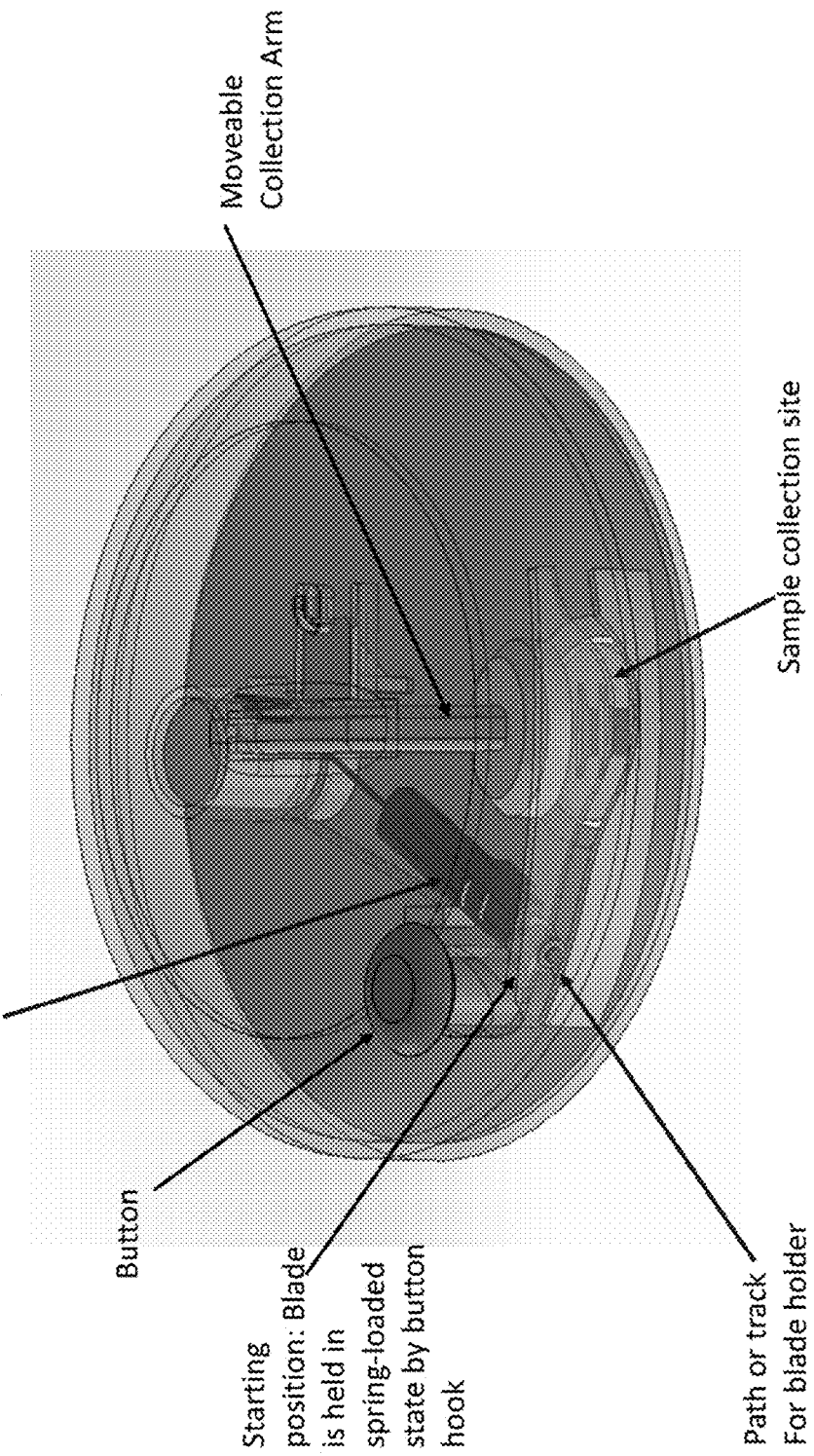
FIG. 38B illustrates internal workings of a device provided herein in an exemplary starting position, when the device is not activated.
Figure 38C:
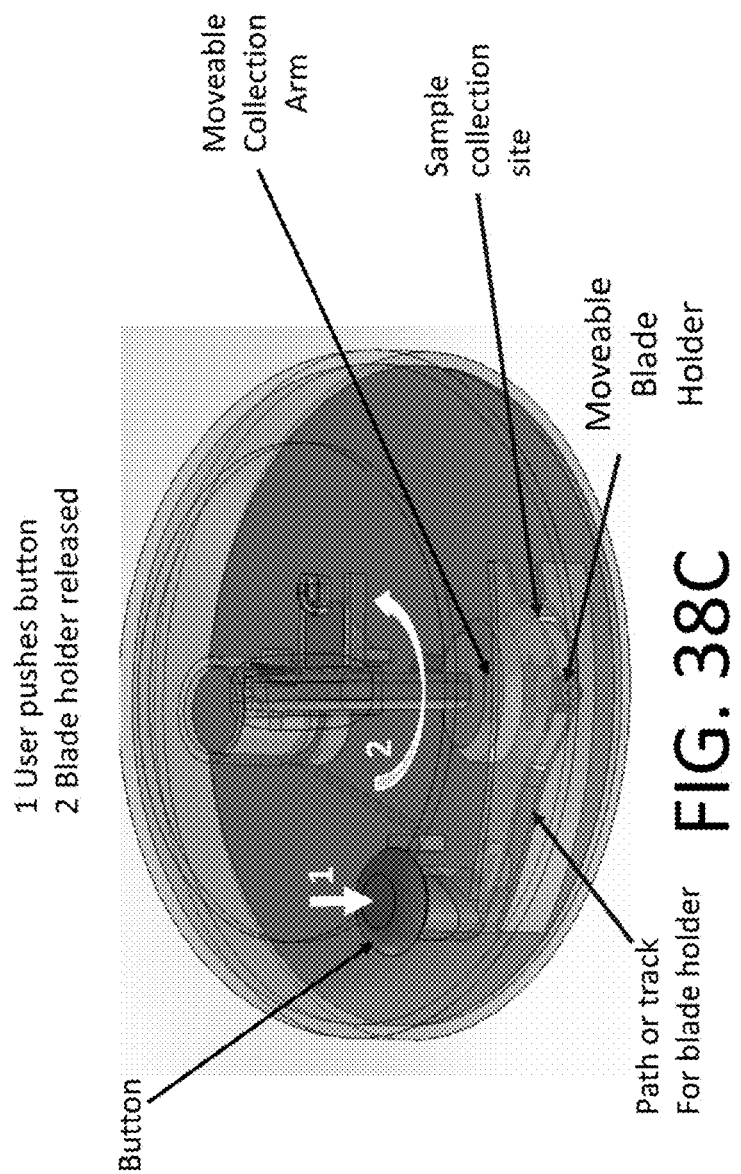
FIG. 38C illustrates internal workings of a device provided herein once the button is depressed (1), and the blade holder is released (2)
Figure 39A:
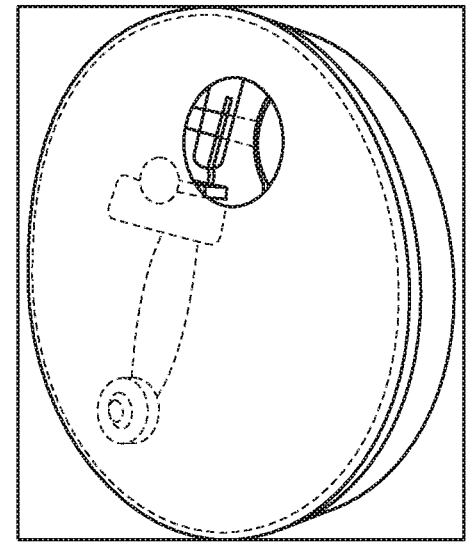
FIG. 39A, FIG. 39B, FIG. 39C, FIG. 39D, and FIG. 39E illustrate top, bottom, side and internal views of an exemplary low profile blood collection device.
Figure 39B:
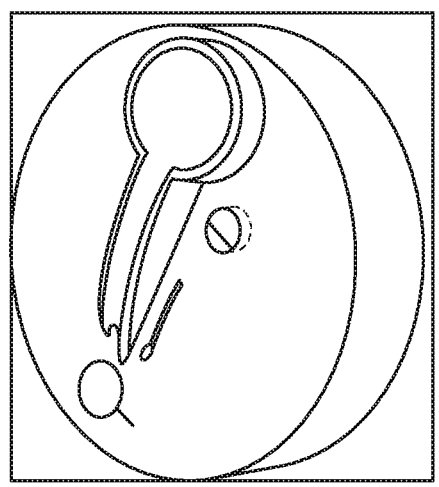
Figure 39C:
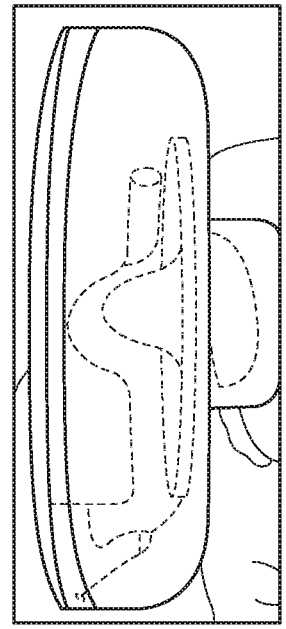
Figure 39E:
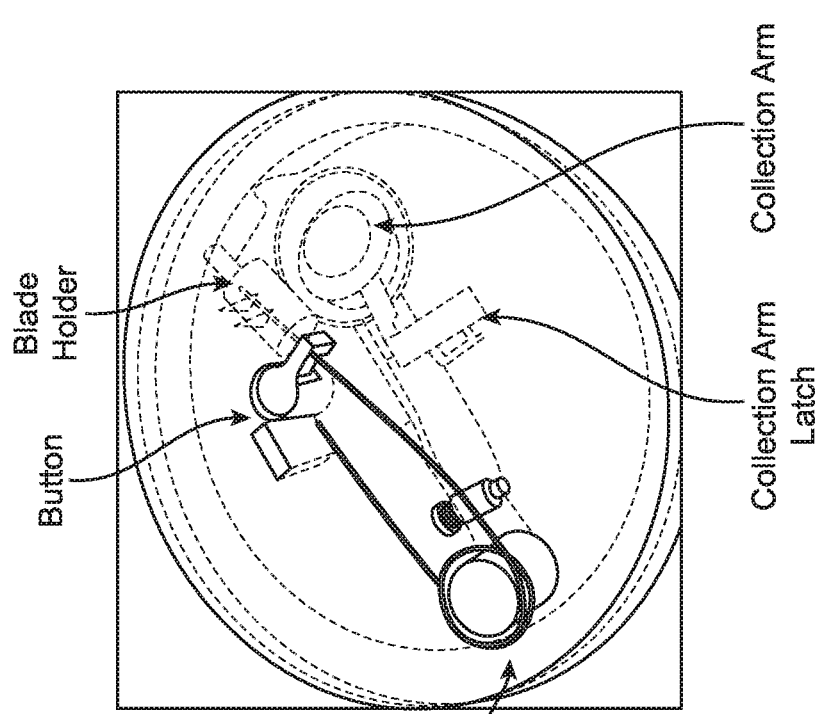
Figure 39D:
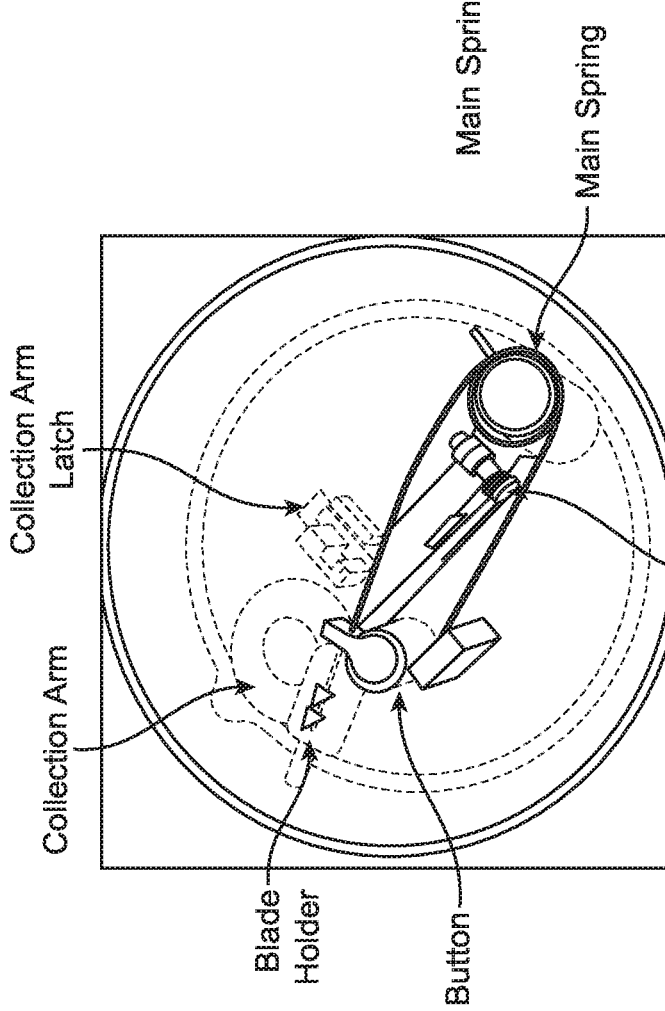

FIGS. 38A-38F shows various views of an exemplary embodiment of a device configured for single activation piercing and collection of a blood sample from a patient. As shown in FIG. 38A the device can comprise a low profile mold with a removable lancet safety sticker, and a button for single activation of the device. FIG. 38B illustrates the internal workings of the device in an exemplary starting position. In the starting position, a moveable blade holder is held in a spring-loaded state by a button hook that releases the blade holder when the button depressed. The device also comprises a path or track for the released blade holder to move along once the blade holder is released. Also illustrated in FIG. 38B is the sample collection site and the moveable collection arm. FIG. 38C illustrates the internal workings of the device once the button is depressed (1), and the blade holder is released (2). When the button is depressed the moveable blade holder is released, and moves down the path or track. At this point in device activation, the moveable collection arm is still in the initial position, disposed above the sample collection site with sufficient space for the moveable blade holder to move between the moveable blade holder and the sample collection site. FIG. 38D illustrates the internal working of the device. Once released, the button actuated moveable blade holder rotates through the device by moving along the path or track. At the end of the path or track it actuates a latch, thereby releasing the blood collection arm. FIG. 38E shows a side view of the device, illustrating the movable blade holder reaching the end of the path or track where the removable blade holder releases a latch that activates the spring loaded blood collection arm resulting in release of the spring loaded collection arm (3). The blood collection arm is released over the sample collection site. Also depicted in FIG. 38E are the blades and an exemplary depth of the blades at a depth by which the blades are configured to project through the bottom of the device and into the subjects skin. The depth of the blades is established by the shape and height of the track or path on which the moveable blade holder travels. FIG. 38F illustrates the formation of a seal by the released blood collection arm over the sample collection site (4). The exemplary device illustrated in FIGS. 38A-38F comprises four steps for activation; first a single button is depressed causing a blade holder to be released and the blade holder moves down the depicted track or path. Along the path, the blades held by the blade holder pierce the skin, and at the end of the blade holder track or path the blade holder activates a latch that releases a spring loaded collection arm over the sample collection site. The collection arm forms a seal with the sample collection site, and the collection arm can draw the blood from the subject. In some instances, the device illustrated in FIGS. 38A-38F can comprise an evacuated chamber or onboard vacuum for creating suction.

An alternate embodiment of a low profile sample acquisition device is shown in FIGS. 39A-39E. A top view (FIG. 39A), bottom view (FIG. 39B), and side view (FIG. 39C) of an exemplary low profile sample acquisition device, along with internal views of the device (FIG. 39D and FIG. 39E), illustrate the button, blade holder with two blades, collection arm, collection arm main spring and release spring, as well as the latch that releases the collection arm. In this embodiment (FIG. 39D and FIG. 39E), the button can be depressed by the user, causing the blade holder and installed blades to rotate, driven by the main spring, and during the rotation pierce the subject's skin, at the end of the rotation the blade holder can activate the collection arm latch that releases the collection arm spring causing the collection arm to release bringing it in contact with the skin of the subject. The collection arm can create contact with the skin, and can be configured to provide suction or vacuum to extract blood sample.

The devices illustrated in FIGS. 38A-38F and FIGS. 39A-39E, and any devices disclosed in the present application, can comprise a single or multiple blades for piercing a subjects skin; for example one or more, two or more, three or more, four or more, five or more, or ten or more blades. Blades can be configured in different shapes or orientations, for example a ring shape, a star shape, a hash shape, square shapes, rectangular shapes, etc.

The devices illustrated in FIGS. 38A-38F and FIGS. 39A-39E, and any devices disclosed in the present application, can be configured to collect, treat, and store the sample. The sample drawn by the device can be stored in liquid or solid form. The sample can undergo optional treatment before being stored. Storage can occur on the device, off the device, or in a removable container, vessel, compartment, or cartridge within the device.

The devices illustrated in FIGS. 38A-38F and FIGS. 39A-39E, and any devices disclosed in the present application can be configured to collect, treat, stabilize, and store a collected sample. A device can be configured to perform one or more of the following processes: collection, treatment, stabilization, and storage of the sample. Collection, treatment, stabilization, and storage can be performed within a single device. Treatment can comprise filtration of the sample to separate components or analytes of interest. Treatment can also comprise exposure to buffers or reagents for stabilizing the sample. In some embodiments the device can be configured to concentrate one or more components of the sample.

In some instances, one or more of the processes (e.g. collection, treatment, stabilization, and storage of the sample) can be performed on the device in response to singe activation of the device by the user. In other instances two or more user actions can need to be performed to move the sample through one or more different processes (e.g. collection, treatment, stabilization, and storage). User actions can comprise pressing a single button, pressing multiple buttons, pressing two or more buttons at the same time, and pressing two or more buttons in a prescribed sequence (e.g. based on a prescribed sequence to perform a set of treatment steps desired by the user.)

Collection of the sample can comprise steps and components configured for lancing the subject's skin and providing or creating a vacuum to extract the sample. In some instances a vacuum can be provided before lancing of the skin, in other instances the vacuum can be provided after lancing of the subject's skin, in further instances the vacuum can be provided simultaneously with lancing the subject's skin.

Treatment of the device can comprise concentrating the sample, adjusting or metering the flow of the sample, exposing the sample to one or more reagents, and depositing the sample on a solid substrate or matrix. Embodiments the device can comprise a removable cartridge or enclosure for storing a liquid sample or solid matrix for removing the sample once it has been collected. A solid matrix can comprise cellulose based paper (e.g. Whatman™ 903 paper), paper treated with chemicals or reagents for stabilizing the sample or one or more components of the sample (e.g. RNA stabilization matrix or Protein Stabilization Matrix).

Devices for collecting a blood sample from a subject can also rely on a vertically oriented device, as shown in FIGS. 40A-40D, FIGS. 41A-41B, and FIGS. 42A-42C.

FIG. 40A illustrates an exemplary embodiment of a sample acquisition device with a vertical cutting modality. The device can comprise a syringe with syringe plunger, connected to a housing comprising a plunger and a blade. The device can comprise a housing within which a plunger and blade or disposed. The housing can be oriented towards the skin of the subject with the syringe and syringe plunger oriented away from the subject. FIG. 40B shows the same device positioned on its side to illustrate the cup shaped shield with slits for the blades. FIG. 40C illustrates a side view of the housing portion of the device in the starting position. The view illustrates the presence of a chamber sealed between the housing and a plunder disposed within the housing. The blade is held in a spring-loaded state by a ridge disposed within the housing. On the bottom of the device, a cup-shaped shield with slits allows blades to move through the cup-shaped shield to pierce the skin of the subject and, through micro-channels cut into the cup-shaped shield, direct blood flow to the center of the cup. FIG. 40D is a side view of the device with a view of the housing and the plunder disposed within. Also visible on the bottom of the device is the cup-shaped shield with blades projecting through the slits of the cup-shaped shield, showing how cutting of the skin of the subject is performed.

Figure 41A:
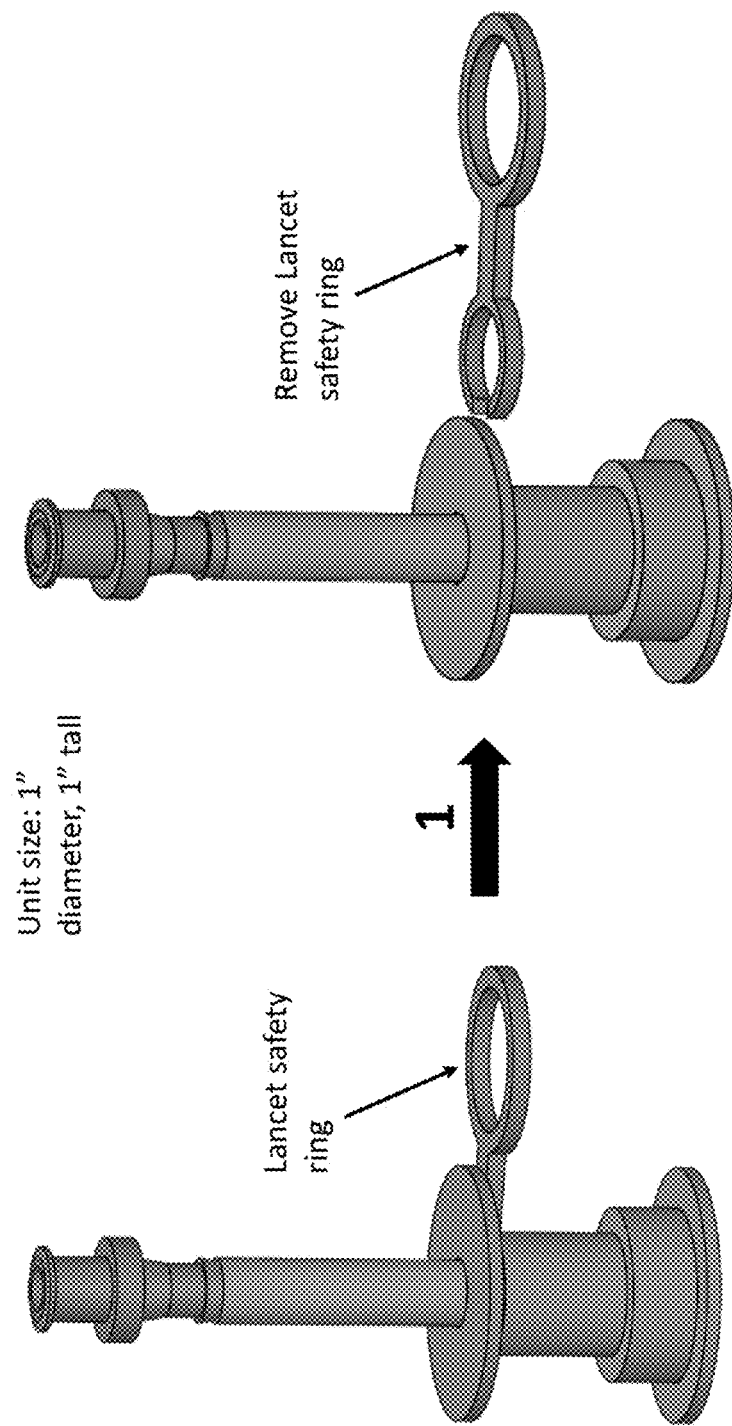
FIG. 41A illustrates a safety mechanism that can be used to prevent inadvertent blade deployment of a blood sample collection device for collecting a sample that relies on vertical cutting using a rotatable blade.
Figure 41B:
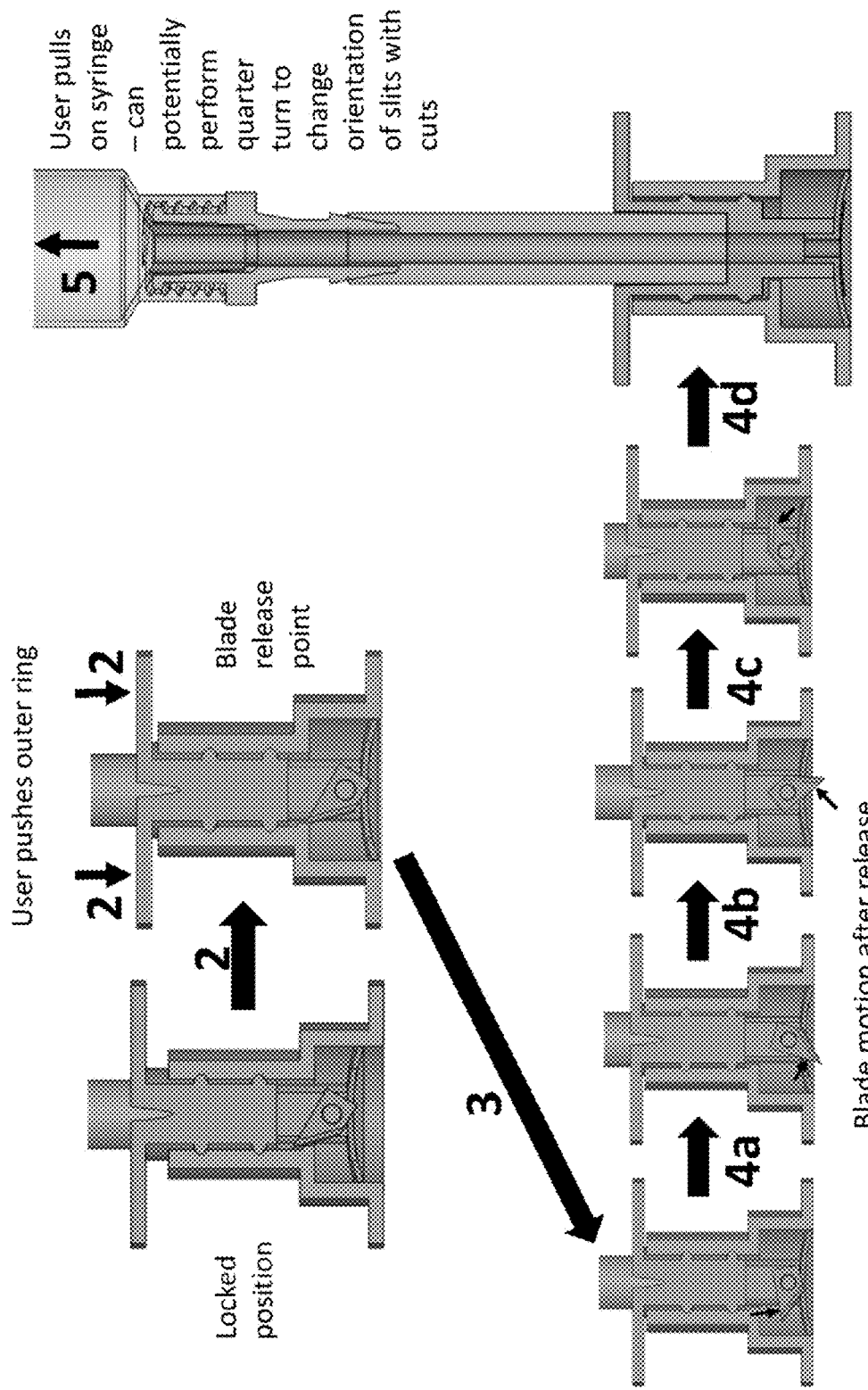
FIG. 41B illustrates a mechanism for collecting a sample using a blood collection device that relies on vertical cutting using a rotatable blade.

Methods for using the device illustrated in FIGS. 40A-40D, are illustrated in FIG. 41A and FIG. 41B. As shown in FIG. 41A, a lancet safety ring is then removed from the device (1). At this point, the device is still in the locked position with the blade resting on a ridge within the device (See FIG. 41B). Then a user pushes down on the outer ring (2), depressing an internal spring and releasing the blade (3). The blade then rotates (4a-4d) cutting the skin of the user and exposing blood that moves into the cup-shaped shield. Finally, the user pulls on the syringe plunger (5) to create negative pressure and draw the sample through the micro channels and slits in the bottom of the cup-shaped shield, and into the syringe.

FIG. 42A, FIG. 42B, and FIG. 42C illustrate a device with a vertical rotational cutter similar to those illustrated in FIGS. 40A-40D, and FIGS. 41A-41B, however a wound spring mechanism is used to control a blade holder and thus drive rotation of the blade in the device. FIG. 42A illustrates the blade and spring, with the blade in the locked position—resting on a features within the housing, with the spring loaded. A force is applied to the top of the device to depress the spring (1a), and the blade is free to rotate (1b). As shown in FIG. 42B, the blade rotates through the path (2a-2d) during which it cuts the skin of the subject, until it reaches an unloaded state. The cut skin of the subject releases blood sample which moves through the shield which directs blood follow towards the center, as shown in FIG. 42C (side view). A possible flap "valve" can be included that covers the blade access slits and form a seal to close the suction. Finally, as shown in FIG. 42C, the syringe can be retracted and the sample can be draw into a sample storage compartment disposed within the device.

Sample acquisition devices (e.g. devices illustrated in FIGS. 40A-40D, FIGS. 41A-41B, and FIGS. 42A-42C, can comprise a single or multiple blades for piercing a subjects skin; for example one or more, two or more, three or more, four or more, five or more, or ten or more blades. Blades can be configured in different shapes or orientations, for example a ring shape, a star shape, a hash shape, square shapes, rectangular shapes, etc.

Sample acquisition devices (e.g. devices illustrated in FIGS. 40A-40D, FIGS. 41A-41B, and FIGS. 42A-42C, can be configured to collect, treat, and store the sample. The sample drawn by the device can be stored in liquid or solid form. The sample can undergo optional treatment before being stored. Storage can occur on the device, off the device, or in a removable container, vessel, compartment, or cartridge within the device.

Sample acquisition devices (e.g. devices illustrated in FIGS. 40A-40D, FIGS. 41A-41B, and FIGS. 42A-42C, can be configured to collect, treat, stabilize, and store a collected sample. A device can be configured to perform one or more of the following processes: collection, treatment, stabilization, and storage of the sample. Collection, treatment, stabilization, and storage can be performed within a single device. Treatment can comprise filtration of the sample to separate components or analytes of interest. In some instances one or more of the processes (e.g. collection, treatment, stabilization, and storage of the sample) can be performed on the device in response to singe activation of the device by the user. In other instances two or more user actions can need to be performed to move the sample through one or more different processes (e.g. collection, treatment, stabilization, and storage). User actions can comprise pressing a single button, pressing multiple buttons, pressing two or more buttons at the same time, and pressing two or more buttons in a prescribed sequence (e.g. based on a prescribed sequence to perform a set of treatment steps desired by the user.)

Collection of the sample can comprise steps and components configured for lancing the subject's skin and providing or creating a vacuum or suction to extract the sample. In some instances a vacuum or suction can be provided before lancing of the skin, in other instances the vacuum or suction can be provided after lancing of the subject's skin, in further instances the vacuum can be provided simultaneously with lancing the subject's skin.

Treatment of the device can comprise concentrating the sample, adjusting or metering the flow of the sample, exposing the sample to one or more reagents, and depositing the sample on a solid substrate or matrix. Embodiments the device can comprise a removable cartridge or enclosure for storing a liquid sample or solid matrix for removing the sample once it has been collected. A solid matrix can comprise cellulose based paper (e.g. Whatman™ 903 paper), paper treated with chemicals or reagents for stabilizing the sample or one or more components of the sample (e.g. RNA stabilization matrix or Protein Stabilization Matrix).

Figures 43A, 43B:
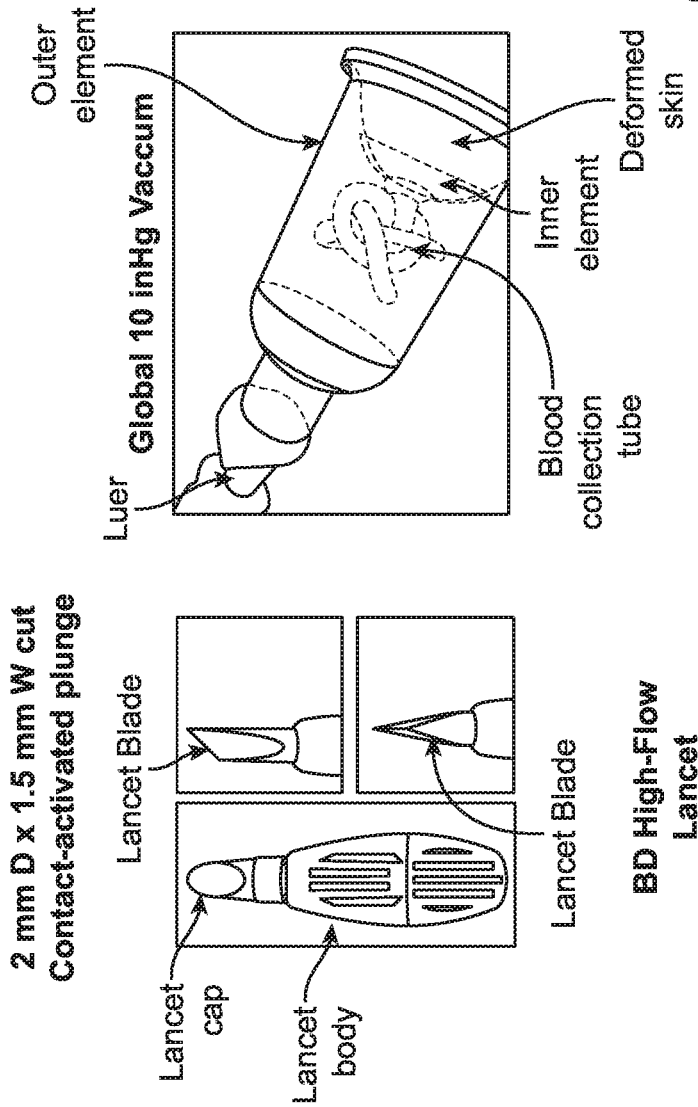
FIG. 43A and FIG. 43B illustrates a device for applying global vacuum and local suction to collect an appropriate amount of sample within a desired period of time (e.g. at a rate that falls within a desired range)

FIG. 43B illustrates a device configured for applying global vacuum and local suction to collect a sample. Lancet blades can be used to pierce the skin of a subject prior to applying the device to collect the sample. Lancets can comprise high flow or low flow. After lancing, a device for applying global vacuum and local suction is applied to the location of the cut. The device, as shown in FIG. 43B, can comprise two nested components, an outer element for applying global vacuum to deform the skin and an inner element for providing local suction. Connected to the inner element is a tube with a luer adaptor at the end of it, suction is provided through the luer adaptor, enabling sample to be drawn into the collection tube. The suction provided through the luer adaptor is used to both deform the skin and to extract the sample.

The method and device for collecting a blood sample, as illustrated in FIG. 43B is configured to collect a targeted volume of blood in under 5 minutes. Examples of blood volumes and corresponding collection times for seven samples are presented in Table 1. The average blood volume drawn was 245 uL+/−12.2 uL in an average of 1.9 minutes+/−0.8 minutes. The average rate for blood collection was 127 uL per minutes. Blood samples collected methods and devices comprising global vacuum and local suction can cover the range of greater than 50 uL per minute, greater than 75 uL per minute, greater than 100 uL per minute, greater than 125 uL per minute, greater than 150 uL per minute, greater than 175 uL per minute and greater than 200 uL per minute. Examples of the pressure generate by the global vacuum can include greater than 5 inHg, greater than 8 inHg, greater than 10 inHg, greater than 12 inHb, and any pressures or ranges of pressures sufficient to pull skin into chamber of the outer element and create overall vacuum on skin in the tube.

Mechanisms that incorporate global vacuum and local suction can increase the rate of sample collection over methods that do not have global vacuum and local suction. Table 1 below illustrates draw times for global vacuum and local suction device illustrated in FIG. 43B. Global vacuum and local suction can comprise any method or device configured for, under negative pressure, sucking or deforming skin into a larger cavity and drawing blood sample out of the surface of the sample. In mechanisms that rely on global vacuum and local suction there can be two or more contacts; for example the outer element (e.g. the bell shaped cup) and the inner element (e.g. inner local suction cup). These nested elements can be configured such that the ratio of the effected surface areas (e.g. ratio generated by the surface area of the global vacuum area divided by the local suction area) are present at a particular ratio. The ratio can be configured to deform the skin and then disrupt the site above the incision to facilitate extraction of the sample.

| Draw times for Global Vacuum Local Suction Blood Collection Method Global Vacuum with 25 mm Cup and Suction Cup + Measured Tubing (2× Becton Dickinson (BD) High Flow lancets) | | |
| --- | --- | --- |
| Draw | Blood Volumes (uL) | Draw Times (min) |
| 1 | 232 | 2.2 |
| 2 | 236 | 3.5 |
| 3 | 246 | 1.7 |
| 4 | 245 | 1.8 |
| 5 | 262 | 1.8 |
| 6 | 236 | 1.0 |
| 7 | 261 | 1.5 |
| Ave | 245 | 1.9 |
| Std Dev: | 12.2 | 0.8 |
| | Ave Draw Rate: | 127 |

The devices illustrated in FIGS. 43A and 43B, and any sample acquisition devices disclosed in the present application, can comprise a single or multiple blades for piercing a subjects skin; for example one or more, two or more, three or more, four or more, five or more, or ten or more blades. Blades can be configured in different shapes or orientations, for example a ring shape, a star shape, a hash shape, square shapes, rectangular shapes, etc.

The devices illustrated in FIGS. 43A and 43B, and any sample acquisition devices disclosed in the present application, can be configured to collect, treat, and store the sample. The sample drawn by the device can be stored in liquid or solid form. The sample can undergo optional treatment before being stored. Storage can occur on the device, off the device, or in a removable container, vessel, compartment, or cartridge within the device.

The devices illustrated in FIGS. 43A and 43B, and any sample acquisition devices disclosed in the present application can be configured to collect, treat, stabilize, and store a collected sample. A device can be configured to perform one or more of the following processes: collection, treatment, stabilization, and storage of the sample. Collection, treatment, stabilization, and storage can be performed within a single device. Treatment can comprise filtration of the sample to separate components or analytes of interest.

In some instances one or more of the processes (e.g. collection, treatment, stabilization, and storage of the sample) can be performed on the device in response to singe activation of the device by the user. In other instances two or more user actions can need to be performed to move the sample through one or more different processes (e.g. collection, treatment, stabilization, and storage). User actions can comprise pressing a single button, pressing multiple buttons, pressing two or more buttons at the same time, and pressing two or more buttons in a prescribed sequence (e.g. based on a prescribed sequence to perform a set of treatment steps desired by the user.)

The device can be adhered to the skin of a patient with an adhesive. In some embodiments, any suitable adhesive is used. The adhesive can be a hydrogel, an acrylic, a polyurethane gel, a hydrocolloid, or a silicone gel.

The adhesive can be a hydrogel. In some embodiments, the hydrogel comprises a synthetic polymer, a natural polymer, a derivative thereof, or a combination thereof. Examples of synthetic polymers include, but are not limited to poly(acrylic acid), poly(vinyl alcohol) (PVA), poly(vinyl pyrrolidone) (PVP), poly (ethylene glycol) (PEG), and polyacrylamide. Examples of natural polymers include, but are not limited to alginate, cellulose, chitin, chitosan, dextran, hyaluronic acid, pectin, starch, xanthan gum, collagen, silk, keratin, elastin, resilin, gelatin, and agar. The hydrogel can comprise a derivatized polyacrylamide polymer.

In some embodiments, the adhesive comes attached to the device. The device can comprise a protective film or backing covering the adhesive on the base of the device, wherein prior to use the protective film is removed. In another embodiment, an adhesive in the form of a gel, a hydrogel, a paste, or a cream is applied to skin of the subject or the base of the device prior in order to adhere the skin to the device. The adhesive can be in contact with the patient for less than about 10 minutes. In some embodiments, the adhesive is a pressure-sensitive adhesive. In some embodiments, the adhesive is hypoallergenic.

Collection of the sample can comprise steps and components configured for lancing the subject's skin and providing or creating a vacuum to extract the sample. In some instances a vacuum can be provided before lancing of the skin, in other instances the vacuum can be provided after lancing of the subject's skin, in further instances the vacuum can be provided simultaneously with lancing the subject's skin.

Treatment of the device can comprise concentrating the sample, adjusting or metering the flow of the sample, exposing the sample to one or more reagents, and depositing the sample on a solid substrate or matrix. Embodiments the device can comprise a removable cartridge or enclosure for storing a liquid sample or solid matrix for removing the sample once it has been collected. A solid matrix can comprise cellulose based paper (e.g. Whatman™ 903 paper), paper treated with chemicals or reagents for stabilizing the sample or one or more components of the sample (e.g. RNA stabilization matrix or Protein Stabilization Matrix).

FIGS. 44A and 44B illustrate a device configured for horizontal cutting, with simultaneous seal formation. The device can comprise a square shaped outer casing. A blade holder can be installed on a track, and the blade can be arranged to move on a semi-circular track. When the actuator is depressed, the blade moves along the semi-circular track, cutting an elastomeric material (e.g. polyurethane) and creating a seal between an adhesive (e.g. hydrogel) circle or donut shaped material disposed from the base of the device. In this embodiment the activation of the actuator triggers the blade which cuts the elastomeric material forming a seal, while simultaneously lancing the subject's skin. FIG. 44A shows the blade before it is actuated, and FIG. 44B shows the blade after it has cut the elastomeric material and formed a seal with the subject's skin.

The devices illustrated in FIGS. 44A-44B, and any sample acquisition devices disclosed in the present application, can comprise a single or multiple blades for piercing a subjects skin; for example one or more, two or more, three or more, four or more, five or more, or ten or more blades. Blades can be configured in different shapes or orientations, for example a ring shape, a star shape, a hash shape, square shapes, rectangular shapes, etc.

The devices illustrated in FIGS. 44A-44B, and any sample acquisition devices disclosed in the present application, can be configured to collect, treat, and store the sample. The sample drawn by the device can be stored in liquid or solid form. The sample can undergo optional treatment before being stored. Storage can occur on the device, off the device, or in a removable container, vessel, compartment, or cartridge within the device.

The devices illustrated in FIGS. 44A-44B, and any sample acquisition devices disclosed in the present application can be configured to collect, treat, stabilize, and store a collected sample. A device can be configured to perform one or more of the following processes: collection, treatment, stabilization, and storage of the sample. Collection, treatment, stabilization, and storage can be performed within a single device. Treatment can comprise filtration of the sample to separate components or analytes of interest.

In some instances, one or more of the processes (e.g. collection, treatment, stabilization, and storage of the sample) can be performed on the device in response to singe activation of the device by the user. In other instances two or more user actions can need to be performed to move the sample through one or more different processes (e.g. collection, treatment, stabilization, and storage). User actions can comprise pressing a single button, pressing multiple buttons, pressing two or more buttons at the same time, and pressing two or more buttons in a prescribed sequence (e.g. based on a prescribed sequence to perform a set of treatment steps desired by the user.)

Collection of the sample can comprise steps and components configured for lancing the subject's skin and providing or creating a vacuum to extract the sample. In some instances a vacuum can be provided before lancing of the skin, in other instances the vacuum can be provided after lancing of the subject's skin, in further instances the vacuum can be provided simultaneously with lancing the subject's skin.

Treatment of the device can comprise concentrating the sample, adjusting or metering the flow of the sample, exposing the sample to one or more reagents, and depositing the sample on a solid substrate or matrix. Embodiments the device can comprise a removable cartridge or enclosure for storing a liquid sample or solid matrix for removing the sample once it has been collected. A solid matrix can comprise cellulose based paper (e.g. Whatman™ 903 paper), paper treated with chemicals or reagents for stabilizing the sample or one or more components of the sample (e.g. RNA or DNA).

Figure 45B:
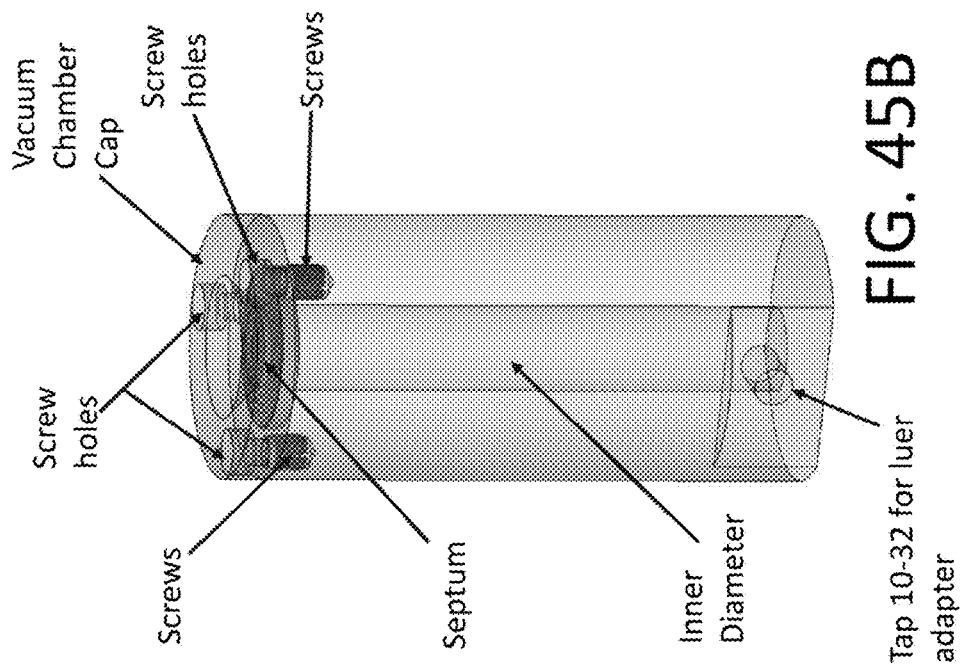
FIG. 45A, FIG. 45B, and FIG. 45C illustrate an exemplary vacuum chamber that can be used with any of the devices and methods disclosed herein.
Figure 45A:
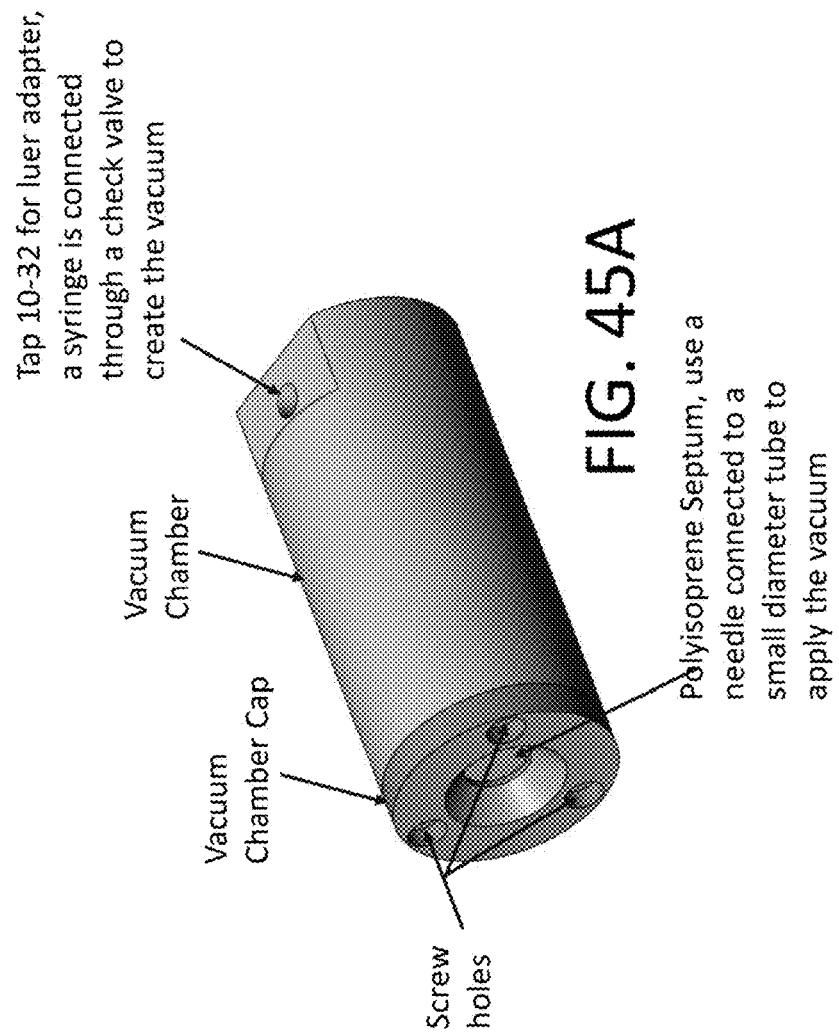
Figure 45C:
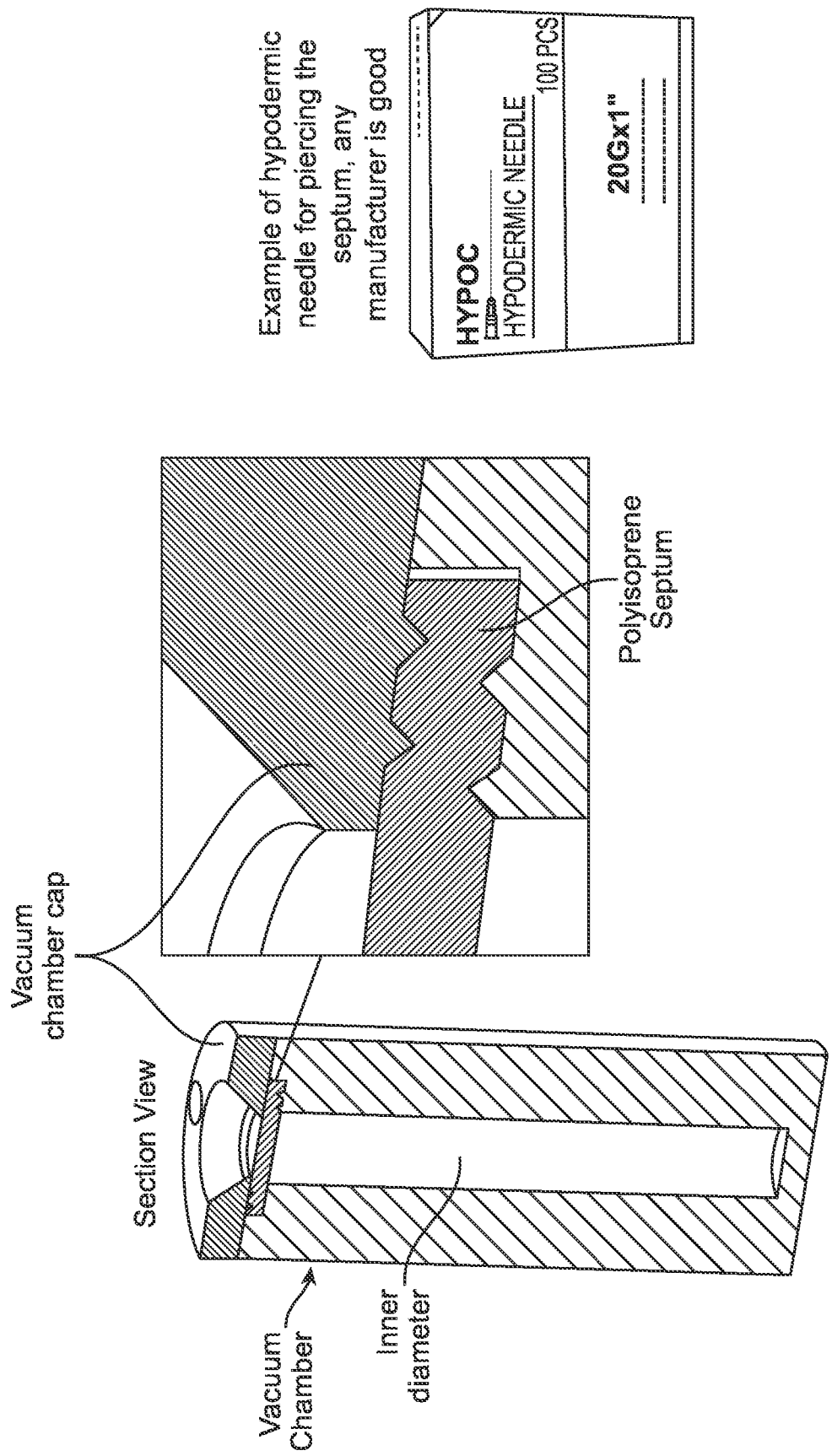

Any of the embodiments disclosed in the present application can comprise a vacuum chamber. Vacuum chambers can vary in size, shape, pressure, and can have structural variations as well as a variety of mechanisms for generating the vacuum. A vacuum chamber can come pre-charged using an onboard evacuated chamber (e.g. a chamber installed on the device using a membrane that when penetrated generates negative pressure in contiguous enclosures), or generated through user action by way of a syringe or other means of generating negative pressure. The vacuum chamber (e.g. evacuated chamber) can seal on one end with foil or elastomer (e.g. polyisoprene) on the other end, such that piercing the foil or septum allows the vacuum to generate within the device. Vacuum chamber sizes can vary, for example the vacuum chamber can be greater than 2 mL, greater than 4 mL, greater than 6 mL, greater than 8 mL, or greater than 10 mL in volume. One embodiment of a vacuum chamber is illustrated in FIGS. 45A-45C. FIGS. 45A and 45B illustrates a side view of a vacuum chamber that could be used in the disclosed devices. The vacuum chamber can comprise a Polyisoprene septum with a needle connected to a small diameter tube to apply the vacuum. The chamber can also comprise, on the opposite side, a luer adaptor so that a syringe can be connected through a check valve to create the vacuum. The vacuum chamber can comprise an opening, a vacuum chamber cap, and one or more screw holes with screws for holding the cap in place. FIG. 45C shows a side view of a vacuum chamber, as well as a zoom-in view of the groves that hold the septum in place and illustration of the type of needles that can be used with the vacuum chamber.

Once a device lances the skin of a subject and the blood sample is drawn into the device, the sample can be optionally treated then stored on a sample collection matrix. The storage and sample treatment methods can comprise treating the sample to fix the volume, uniformity, or concentration of the sample deposited on sample collection matrix. Methods and devices for collecting and storing the sample on the matrix can comprise a cartridge or compartment that can be removed from the device. An exemplary cartridge or compartment for depositing and storing the collected sample is illustrated in FIGS. 46A-46C.

Figure 46A:
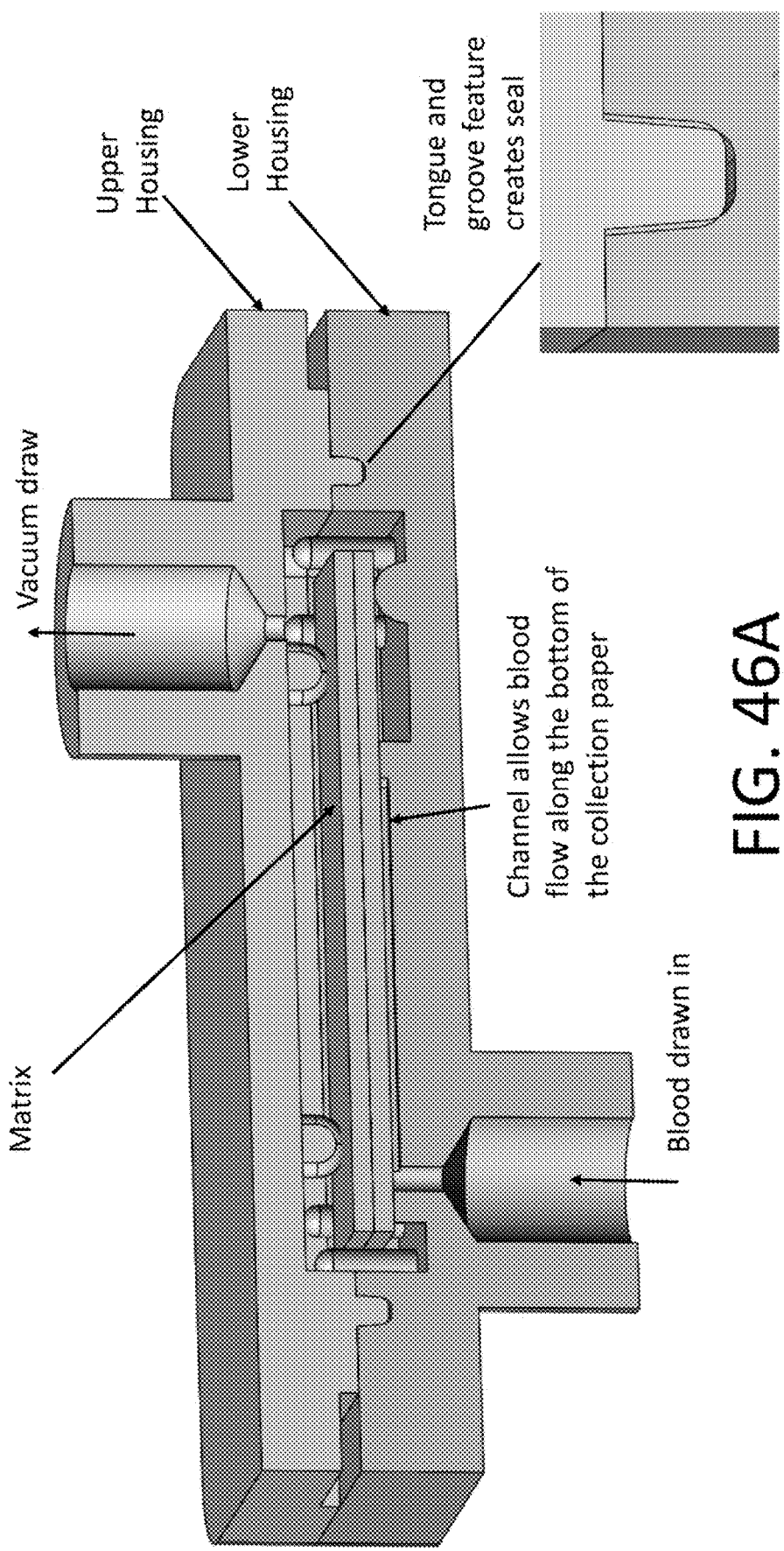
FIG. 46A, FIG. 46B, and FIG. 46C illustrate an exemplary chamber for collecting, metering, storing and stabilizing a sample, and mechanisms for driving sample through the chamber and onto the solid matrices for storing the sample.
Figure 46C:
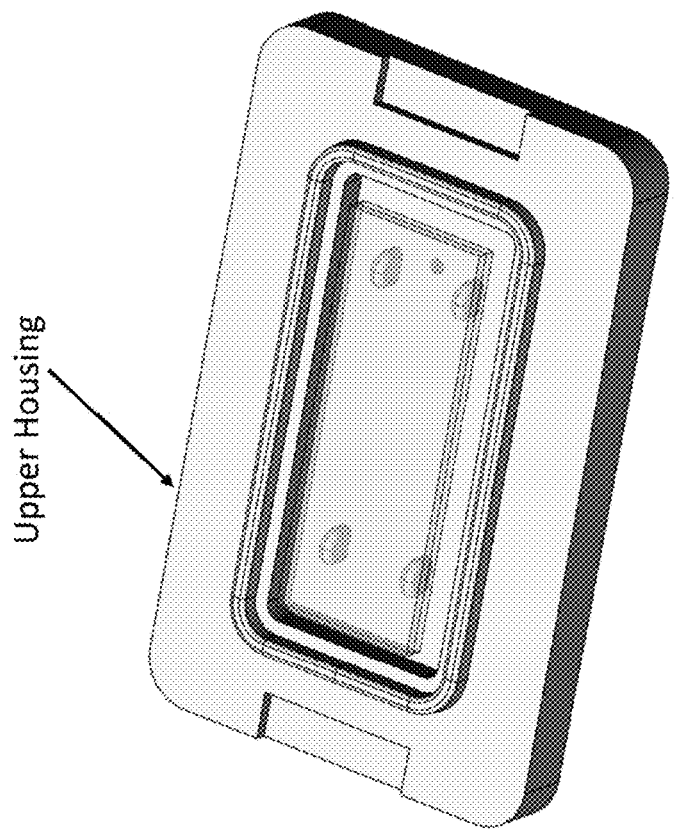
Figure 46B:
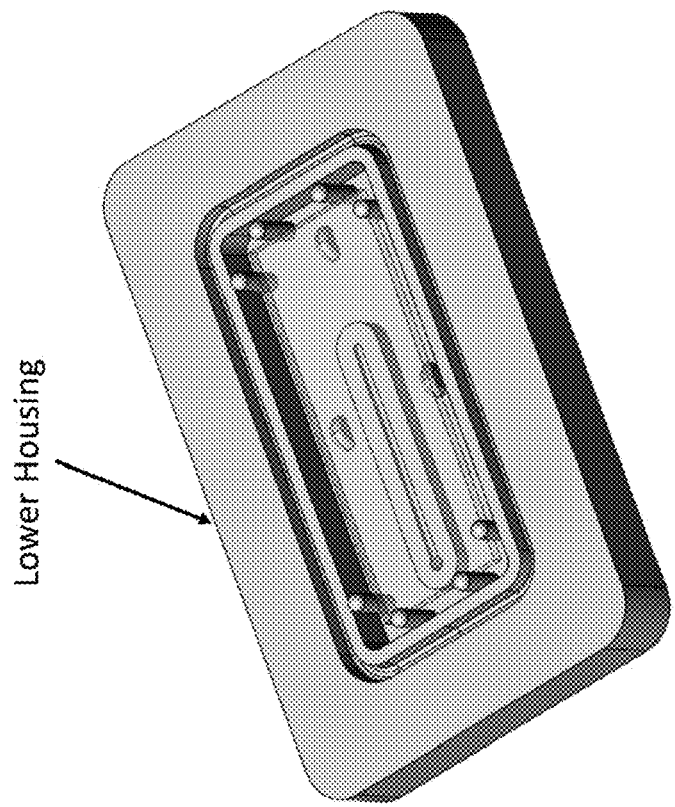

FIG. 46A, FIG. 46B, and FIG. 46C illustrate a sample collection matrix for collecting and storing sample on a stabilization matrix. As shown in FIG. 46A, the sample collection matrix can comprise an inlet where the blood sample is drawn into a channel within the device that allows blood to flow along the bottom of the solid matrix. A vacuum draw is present on the other side of the device to draw the sample into the solid matrix. The sample collection housing can comprise a upper housing and a lower housing (as shown in FIGS. 46B and 46C) with the matrix and channel moving sample within the housing, disposed between the upper and lower housing. A tongue and groove feature can create a seal between the upper and lower housing.

Figure 47:
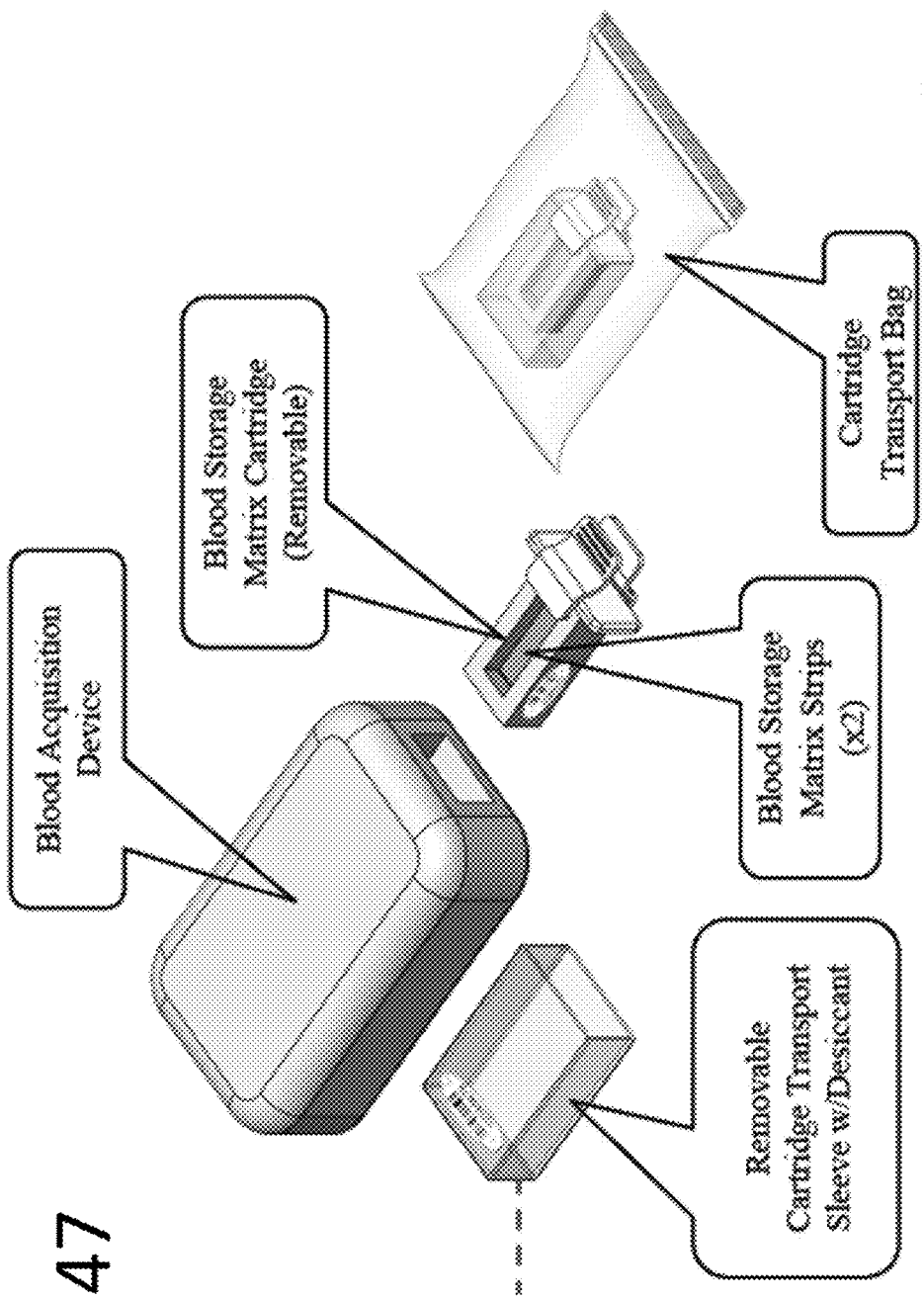
FIG. 47 illustrates the components of a system configured for collecting a blood sample using a sample collection device and a removable sample storage cartridge.

FIG. 47 illustrates components of a device or kit for collecting a sample from a subject. The kit can comprise a sample collection device, a removable cartridge transport sleeve with desiccant (with or without a barcode or label), a removable blood storage matrix cartridge, blood storage matrix strips, and a cartridge transport bag.

Figure 48:
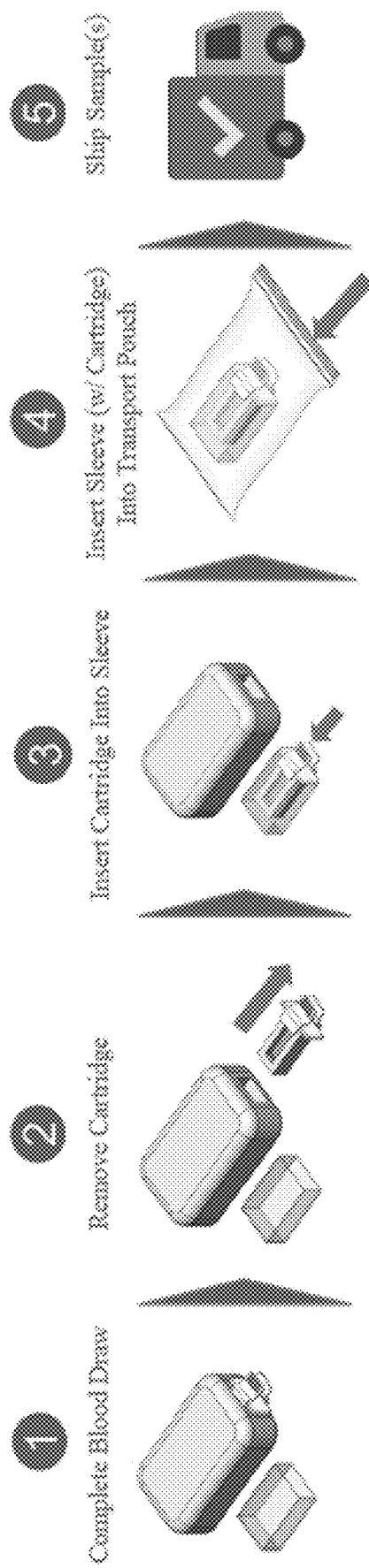
FIG. 48 illustrates steps that a subject or clinician might take to collect and provide a sample to a facility for analysis.

FIG. 48 illustrates methods by which a user can acquire a sample using the kit. The kit can be obtained and the user can insert the cartridge into the device. Steps executed by the user can comprise using the device to collect a sample, remove the cartridge once sample collection is complete, place the removable cartridge into the transportation sleeve with desiccant, and place it in the cartridge transport bag. Multiple samples can be taken by the user, and then the user can ship the sample(s) to a facility for analysis.

Figure 49:
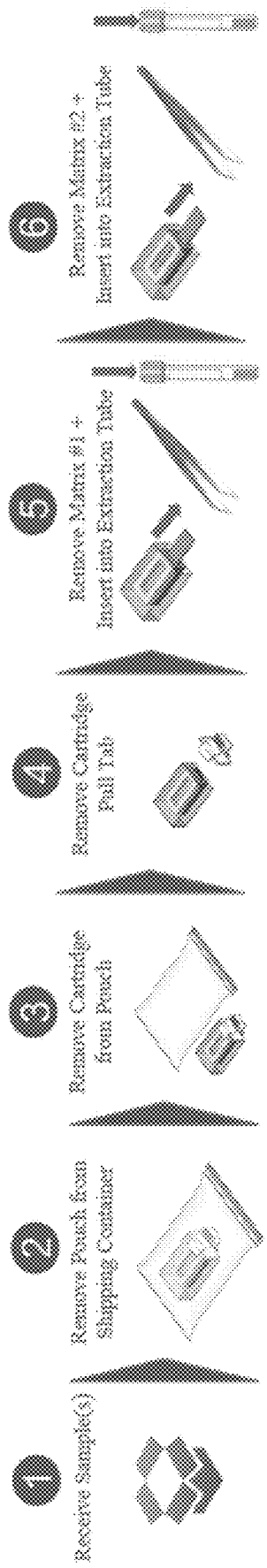
FIG. 49 illustrates steps that a lab (e.g. a CLIA certified lab or other facility) might perform to prepare a sample for analysis.

FIG. 49 illustrates exemplary method steps that a laboratory can perform upon receipt of a shipping container containing the sample(s). The sample pouch can be removed from the shipping container, the sample cartridge can be removed from the sample pouch, and the pull tab can then be removed from the cartridge. Matrix #1 can be removed from the cartridge and placed in an extraction tube, then matrix #2 can be removed from the cartridge and placed in an extraction tube. The extraction tube matrix #2 is placed in can be a different extraction tube from the extraction tube matrix #1 is placed in. The extraction tube matrix #2 is placed in can be the same extraction tube from the extraction tube matrix #1 is placed in. The extraction tube can be a microfuge tube. From there any number of tests or analyses can be performed on the sample.

The devices, systems, and methods disclosed herein can stabilize sample on a matrix (e.g. blood storage matrix, sample collection matrix, matrix, sample stabilization matrix, stabilization matrix (e.g. RNA Stabilization Matrix, Protein Stabilization Matrix), solid matrix, solid substrate, solid support matrix, or solid support). The matrix can be integrated into the device, or external to the device. In some embodiments the matrix can be incorporated into a cartridge for removal (e.g. after sample collection). In some embodiments the matrix can matrix comprise a planar dimensional that is at least 176 mm$^2$. A matrix can be prepared according to the methods of U.S. Pat. Nos. 9,040,675, 9,040,679, 9,044,738, or U.S. Pat. No. 9,480,966 of which are all herein incorporated by reference in their entirety.

In some embodiments, a system, a method, or a device can comprise a high surface area matrix that selectively stabilizes nucleic acids or proteins. In some instances the matrix can be configured to comprise a planar sheet with total dimensional area (length multiplied by width) greater than 176 mm$^2$.

The matrix can be configured to selectively stabilize sample preparation reagents comprising protein and/or nucleic acids. The matrix can be configured to stabilize protein and nucleic acids can comprise an oligosaccharide (e.g. a trisaccharide) under a substantially dry state. The oligosaccharide or trisaccharide can be selected from a group comprising: melezitose, raffinose, maltotriulose, isomaltotriose, nigerotriose, maltotriose, ketose, cyclodextrin, trehalose or combinations thereof. In some embodiments the matrix can comprise melezitose. In further embodiments the melezitose can be under a substantially dry state. In some embodiments, melezitose under a substantially dry state can have less than 2% of water content. In the matrix, the concentration of the melezitose can be in range of about 10% to about 30% weight percent by mass (e.g. calculates as the mass of the solute divided by the mass of the solution where the solution comprises both the solute and the solvent together. The concentration of melezitose can be 15% weight percent by mass. The melezitose can be impregnated in the matrix. In some embodiments, the impregnated melezitose concentration in the matrix results from immersing the matrix in a melezitose solution comprising between about 10 to about 30%. In some other embodiments, 15% melezitose is impregnated into the matrix in a dried state. The matrix can be passively coated or covalently-modified with melezitose. In other embodiments the melezitose can be applied to the surface of the matrix (e.g. with dipping, spraying, brushing etc.). In some other embodiments, the matrix can be coated with a 15% solution of melezitose. In some embodiments the matrix can matrix comprise a planar dimensional with a surface area that is at least 176 mm$^2$. In some embodiments the melezitose can be present at greater than 0.01 ng/mm$^2$, greater than 0.05 ng/mm$^2$, greater than 0.1 ng/mm$^2$, greater than 0.5 ng/mm$^2$, greater than 1 ng/mm$^2$, greater than 5 ng/mm$^2$, greater than 0.01 μg/mm$^2$, greater than 0.05 μg/mm$^2$, greater than 0.1 μg/mm$^2$, greater than 1 μg/mm$^2$, greater than 5 μg/mm$^2$, greater than 0.01 mg/mm$^2$, greater than 0.05 mg/mm$^2$, greater than 0.1 mg/mm$^2$, greater than 1 mg/mm$^2$, greater than 5 mg/mm$^2$, greater than 10 mg/mm$^2$, greater than 50 mg/mm$^2$, greater than 1 μg/mm$^2$, greater than 5 μg/mm$^2$, or greater than 10 μg/mm$^2$. The matrix can comprise additional components to stabilize protein and/or nucleic acids, including various stabilization molecules. A non-limiting example of a stabilization molecule is validamycin. In some embodiments the matrix can comprise 31-ETF (e.g. cellulose based matrix) and melezitose.

The matrix can comprise a buffer reagent. A buffer reagent can be impregnated into the matrix. Buffers can stabilize sample preparation reagents and/or various sample components. The matrix can further include at least one buffer disposed on or impregnated within the matrix, wherein the matrix can be substantially dry with a water content of less than 2%. The buffer can be an acid-titrated buffer reagent that generates a pH in a range from about 3 to about 6, or about 2 to about 7. The matrix can contain any one of the following: 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), phosphate buffers or combinations thereof, or Tris-Hydrochloride (TrisHCl). The matrix can be configured to yield a solution upon rehydration comprising about 20 to about 70 mM Tris-HCl and about 5 to about 30 mM $MgCl_2$. The amount of various dehydrated buffer reagents impregnated into a matrix can be configured for stabilizing sample preparation reagent(s).

The matrix can comprise a reagent or compound that minimizes nuclease activity, e.g., a nuclease inhibitor. Examples of nuclease inhibitors include RNase inhibitor, compounds able to alter pH such as mineral acids or bases such as HCl, NaOH, $HNO_3$, KOH, $H_2SO_4$, or combinations thereof; denaturants including urea, guanidine hydrochloride, guanidinium thiocyanate, a one metal thiocyanate salt that is not guanidinium thiocyanate (GuSCN) beta-mercaptoethanol, dithiothreitol; inorganic salts including lithium bromide, potassium thiocyanate, sodium iodide, or detergents including sodium dodecyl sulfate (SDS).

The matrix can comprise a reagent or compound that minimizes or inhibits protease activity, e.g., a protease inhibitor. A protease inhibitor can be synthetic or naturally-occurring (e.g., a naturally-occurring peptide or protein). Examples of protease inhibitors include aprotinin, bestatin, chymostatin, leupeptin, alpha-2-macroglobulin, pepstatin, phenylmethanesulfonyl fluoride, N-ethylmaleimide, ethylenediaminetetraacetid acid, antithrombin, or combinations thereof. In one example, protease inhibitors enhance the stability of the proteins by inhibiting proteases or peptidases in a sample.

The matrix can comprise one or more free radical scavengers. The matrix can comprise a UV protectant or a free-radical trap. Exemplary UV protectants include hydroquinone monomethyl ether (MEHQ), hydroquinone (HQ), toluhydroquinone (THQ), and ascorbic acid. In certain aspects, the free-radical trap can be MEHQ. The matrix can also comprise oxygen scavengers, e.g. ferrous carbonate and metal halides. Other oxygen scavengers can include ascorbate, sodium hydrogen carbonate and citrus.

The matrix can comprise a cell lysis reagent. Cell lysis reagents can include guanidinium thiocyanate, guanidinium hydrochloride, sodium thiocyanate, potassium thiocyanate, arginine, sodium dodecyl sulfate (SDS), urea or a combination thereof. Cell lysis reagents can include detergents, wherein exemplary detergents can be categorized as ionic detergents, non-ionic detergents, or zwitterionic detergents. The ionic detergents can comprise anionic detergent such as, sodium dodecylsulphate (SDS) or cationic detergent, such as ethyl trimethyl ammonium bromide. Examples of non-ionic detergent for cell lysis include TritonX-100, NP-40, Brij 35, Tween 20, Octyl glucoside, Octyl thioglucoside or digitonin. Some zwitterionic detergents can comprise 3-[(3-Cholamidopropyl)dimethylammonio]-1-propanesulfonate (CHAPS) and 3-[(3-Cholamidopropyl)dimethylammonio]-2-hydroxy-1-propanesulfonate (CHAPSO). The cell lysis reagent can comprise a thiocyanate salt. One or more embodiments of the solid support matrix comprises a thiocyanate salt impregnated in a dry state. Exemplary thiocyanate salts include, but are not limited to, guanidinium thiocyanate, sodium thiocyanate, potassium thiocyanate or combinations thereof. In some other embodiments, the cell lysis reagent is selected from guanidinium thiocyanate, sodium thiocyanate, sodium dodecyl sulfate (SDS) or combinations thereof.

A solid support matrix can comprise a reducing agent. Reducing agents can include dithiothreitol (DTT), 2-mercaptoethanol (2-ME), tris(2-carboxyethyl)phosphine (TCEP) and combinations thereof. Reducing agents can further comprise oxygen scavengers. Oxygen scavengers or reducing agents can comprise ferrous carbonate and metal halides. A solid support matrix can comprise a chelating agent. Chelating agents can include ethylenediaminetetraacetic acid (EDTA), citric acid, ethylene glycol tetraacetic acid (EGTA), or combinations thereof. The solid support matrix can be configured to provide an acidic pH upon hydration and/or preserve nucleic acids in a substantially dry state at ambient temperature. The solid support matrix can be configured to provide a pH between about 2 and about 7 upon hydration. The solid matrix can be configured to provide a pH between about 3 and about 6 upon hydration.

In some embodiments, a sample can be filtered or separated before being deposited on a matrix. Liquid sample can collect or pool into a collection chamber, after the collection chamber or in lieu of a collection chamber the sample can optionally be absorbed through one or more particles, materials, structures or filters with optimized porosity and absorptivity for drawing the sample into the device. Materials for drawing the sample into the devices herein can consist of any absorptive or adsorptive surfaces, or materials with modified surfaces; optional materials including but not limited to paper-based media, gels, beads, membranes, matrices including polymer based matrices, or any combination thereof.

In some embodiments, the device or cartridge can comprise a sample separation unit comprising one or more substrates, membranes, or filters for separating sample components. The sample separation unit can be integrated within the sample stabilization component, or it can be attached to or separate from the sample stabilization component. In some embodiments, sample separation can occur as an intermediate step between sample acquisition and transfer of sample to the matrix. In some instances sample separation and stabilization can occur in one step without the need for user intervention. Sample separation can further occur sequentially or simultaneously with sample stabilization.

In some embodiments, sample acquisition and stabilization can require user action to proceed between one or more phases of the sample collection, optional separation, and stabilization process. A device can require user action to activate sample acquisition, and move sample between separation, stabilization, and storage. Alternatively, user action can be required to initiate sample acquisition as well as one or more additional steps of the sample collection, separation or stabilization process. User action can include any number of actions, including pushing a button, tapping, shaking, rupture of internal parts, turning or rotating components of the device, forcing sample through one or more chambers and any number of other mechanisms. Movement through the phases can occur in tandem with sample collection, or can occur after sample collection. Anytime during or prior to the processing phases the entire sample or components of the sample can be exposed to any number of techniques or treatment strategies for pre-treatment of cells of biological components of the sample; potential treatment includes but is not limited to treatment with reagents, detergents, evaporative techniques, mechanical stress or any combination thereof.

In some embodiments, the devices described herein are configured to draw capillary blood.

In some embodiments, the devices disclosed herein are designed to be used once and then discarded. Resterilization or reuse can compromise the structural integrity of the device or increase the risk of contamination or infection leading to device failure, cross-infection, or patient injury, illness, or death.

Figure 53:
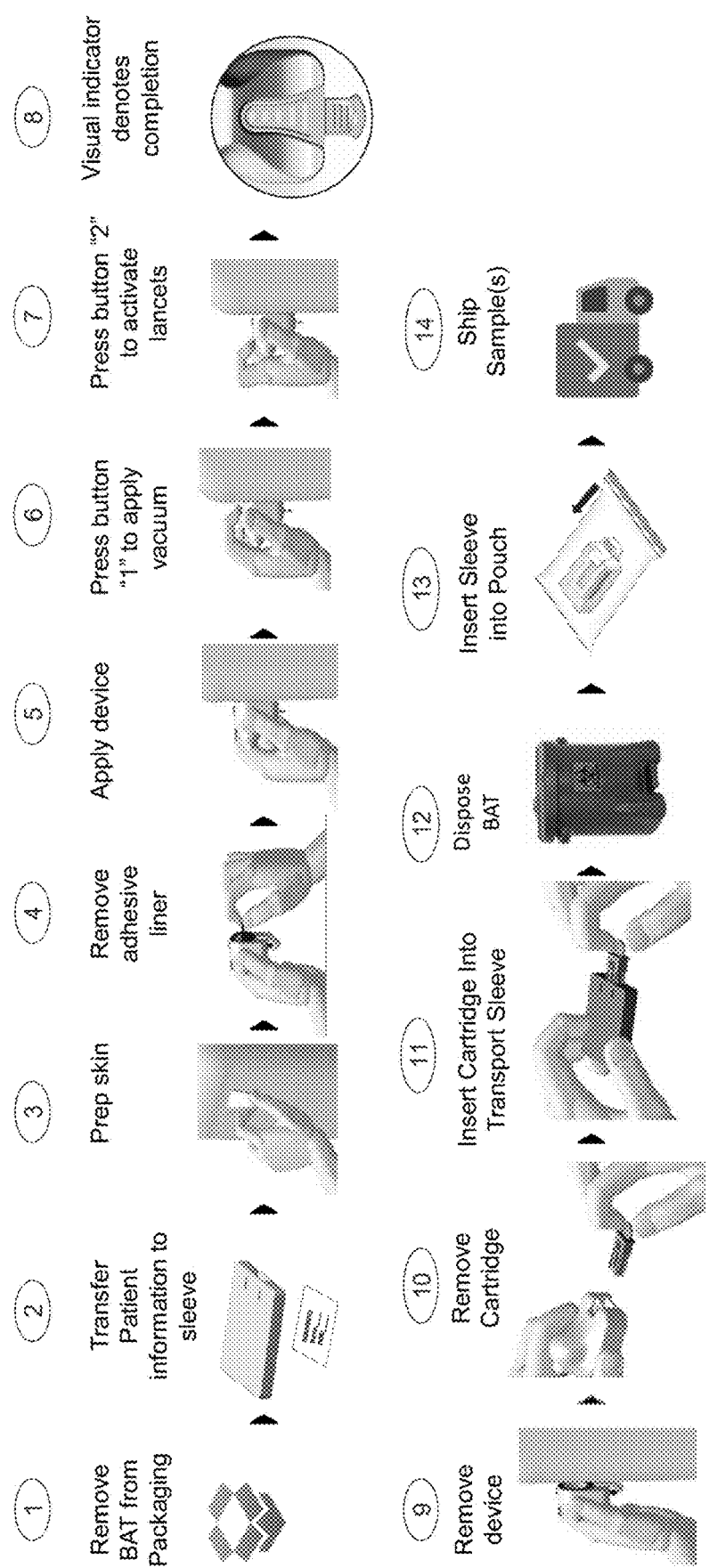
FIG. 53 illustrates principles of operation and use flow of a device.
Figure 54:
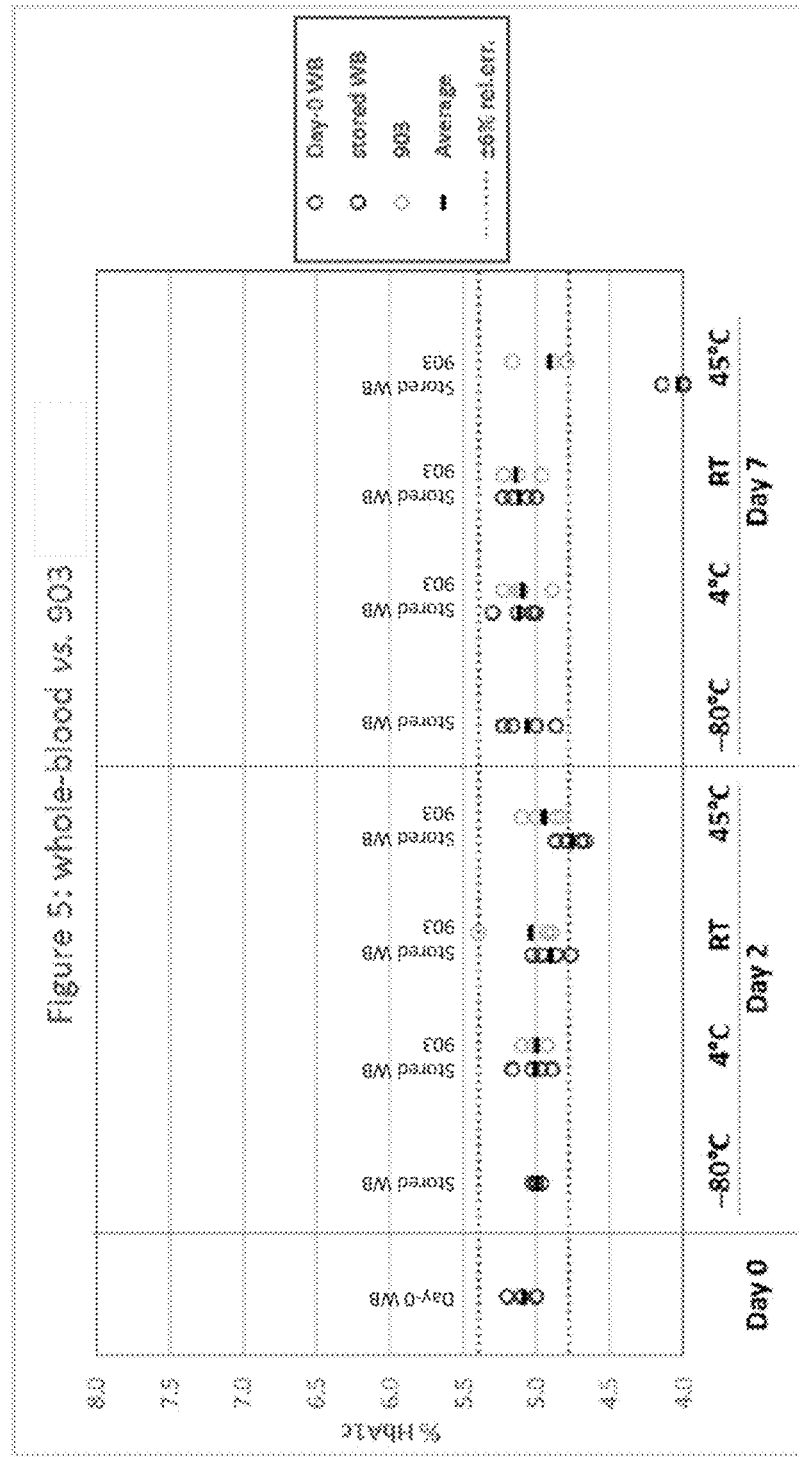
FIG. 54 illustrates HbA1c as a percent of total hemoglobin (Y-axis) for various experimental conditions (X-axis) (For each condition, the average of the replicate measurements is plotted as a black bar and sample measurements are shown as open circles. The dotted lines delineate ±6% relative error around the Day-0 average measurement.)
Figure 55:
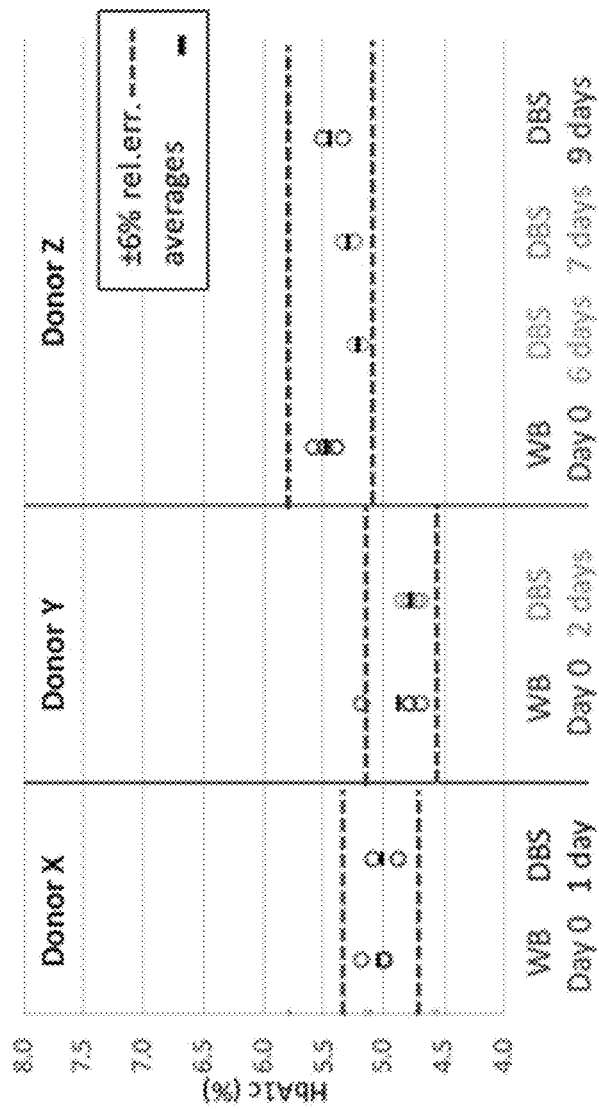
FIG. 55 illustrates HbA1c as a percent of total hemoglobin (Y-axis) for various experimental conditions (X-axis) (Four individual, Day-0, liquid whole-blood, replicates for each donor are plotted as circles. Two technical replicates for each dried blood spot (DBS)-strip are averaged and the resulting DBS-strip averages are also plotted as circles. For each experimental condition, the average of all measurements is plotted as a black bar. Dotted lines delineate ±% relative error around the donor-specific, Day-0, average measurements.)

FIG. 53 and FIG. 56 illustrate exemplary procedures to collect and store blood using a device described herein.

Disclosed herein, in certain embodiments, are kits for use with one or methods described herein. A kit can include the device for blood sample collection described herein. The kit can comprise a sample pouch or transportation sleeve, wherein the pouch or sleeve is used to store a cartridge comprising at least one solid matrix strip. A desiccant can be added to the pouch or sleeve. In some embodiments, the desiccant is a silica gel desiccant. The kit can further comprise a sample return envelope, a bandage, an alcohol prep pad, a gauze pad, or a combination thereof.

A kit can include labels listing contents and/or instructions for use, and package inserts with instructions for use. A set of instructions can be included.

In one embodiment, a label is on or associated with the pouch or sleeve. In one embodiment, a label is on a pouch or sleeve when letters, numbers or other characters forming the label are attached, molded or etched into the pouch or sleeve itself, a label can be associated with a pouch or sleeve when it is present within a receptacle or carrier that also holds the pouch or sleeve, e.g., as a package insert. The label can indicate directions for use of the contents, such as in the methods described herein.

The devices, methods, systems and kits disclosed herein can comprise one or more sample separation units. Sample separation units can be used, e.g., to separate plasma from blood, cells from a water sample, or cells from cell free components. The solid matrix can be used to store circulating or cell-free nucleic acids (e.g. DNA or RNA) separated from a sample, e.g., a blood sample, after filtration. The circulating DNA can be tumor circulating DNA. For blood samples one or more components can be used to separate plasma or specific cells from other components of a blood sample. Alternatively, devices, methods and systems can selectively separate any number of sample components including cells, plasma, platelets, specific cell types, DNA, RNA, protein, inorganic materials, drugs, or any other components.

Non-limiting embodiments of the sample stabilization unit can employ sample separation components to separate other non-plasma components as well. Sample separation components can be connected to the sample acquisition component e.g., through channels, including microchannels, wicking of absorbent materials or other means that allow sample to flow through the device. The systems and methods for separating the sample are exemplary and non-limiting.

There are many methods for performing separation, some of which use size, deformability, shape or any combination thereof. Separation can occur through one or more membranes, chambers, filters, polymers, or other materials. Membranes, substrates, filters and other components of the device can be chemically treated to selectively stabilize components, facilitate flow of sample, dry the sample, or any combination thereof. Alternative separation mechanisms can include liquid-liquid extraction, solid-liquid extraction, and selective precipitation of target or non-target elements, charge separation, binding affinity, or any combination thereof. Separation phase can be comprised of one or more steps, with each step relying on different mechanisms to separate the sample. One such mechanism can utilize size, shape or deformation to separate larger components from smaller ones. Cell separation can occur through a sorter that can, for example, rely on one or more filters or other size exclusion methods to separate components of the sample. Separation can also be conducted through selective binding wherein specific components are separated by binding events while the unbound elutant moves into or through alternate chambers.

In some devices, systems, methods, or kits, a single membrane, substrate, or filter can be used for separation and collection of one or more sample components from the bulk sample. Single membrane, substrate, or filter methods can comprise a device wherein samples can be applied to one end of the membrane, substrate, or filter and as the sample flows through a first component of the sample, for example cells, can be separated from a second component of the sample, for example plasma, based on the size of the membrane, substrate, or filter pores. After operation of the device the membrane, substrate, or filter containing the first component of the sample, cells in this example, can be severed from the portion containing the second component of the sample, plasma in this example, necessitating an additional step of severing the membranes, substrates, or filters. In another method, two separate membranes, substrates, or filters can be used for the separation and collection sample components; specifically, a first membrane, substrate, or filter for the separation of one component, for example blood cells, and a second membrane, substrate, or filter for collection of other components, for example plasma. These membranes, substrates, or filters can be arranged such that a distal end of the first membrane, substrate, or filter contacts a proximal end of the second membrane to facilitate the separation of a large component, for example cells, via the first membrane, substrate, or filter and the collection of a second smaller component, for example plasma, via the second membrane, substrate, or filter.

Generally, a sample can contain or is suspected of containing one or more analytes. The term "analyte" as used herein can refer to any substance that can be analyzed using the assays or immunoassay devices. As an example, an immunoassay device can be configured to detect the presence of 1, 2, 3, 4, 5, 6, 7, 8, 9, 10 or more analytes in a sample. Non-limiting examples of analytes can include proteins, haptens, immunoglobulins, hormones, polynucleotides, steroids, drugs, infectious disease agents (e.g., of bacterial or viral origin), drugs of abuse, environmental agents, biological markers, and the like.

As used in the specification and claims, the singular form "a", "an" and "the" include plural references unless the context clearly dictates otherwise. For example, the term "a cell" includes a plurality of cells, including mixtures thereof.

As used herein, the term "about" a number refers to that number plus or minus 10%, 9%, 8%, 7%, 6%, 5%, 4%, 3%, 2%, 1%, of that number.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A carrier for storing a blood sample during transportation, the carrier comprising:
a cartridge assembly comprising a cartridge and a cartridge holder releasably coupled to the cartridge, wherein the cartridge comprises one or more porous matrices on which the blood sample is collected;
a chamber having an opening configured to receive the cartridge assembly; and
a release mechanism configured to release the cartridge from the cartridge holder to provide a released cartridge;
wherein the chamber is configured to store the released cartridge in a secured position.

2. The carrier of claim 1, wherein the blood sample is in a substantially dried state.

3. The carrier of claim 1, wherein the blood sample is in a liquid state.

4. The carrier of claim 1, wherein the cartridge holder is configured to releasably couple to the carrier.

5. The carrier of claim 4, wherein the cartridge is partially released from the cartridge holder when the cartridge holder is coupled to the carrier.

6. The carrier of claim 4, wherein the cartridge is fully released from the cartridge holder when the cartridge holder is decoupled from the carrier.

7. The carrier of claim 4, wherein the one or more porous matrices are removable from the opening of the dumber when the cartridge holder is decoupled from the carrier.

8. The carrier of claim 1, wherein the cartridge assembly further comprises a gasket configured to close the opening and seal the chamber when the cartridge holder is coupled to the carrier.

9. The carrier of claim 8, further comprising a desiccant in the chamber.

10. The carrier of claim 9, wherein the desiccant comprises silica gel.

11. The carrier of claim 9, wherein the desiccant and the sealing of the chamber collectively aid in improving a stability of one or more components of the blood sample when the blood sample is being stored in the chamber.

12. The carrier of claim 1, further comprising: a retention mechanism configured to engage with at least one mating feature on the cartridge to secure the cartridge within the chamber.

13. The carrier of claim 12, wherein the retention mechanism and the release mechanism collectively provide a dual support-release mechanism.

14. The carrier of claim 13, wherein the dual support-release mechanism permits the cartridge holder to be removed from the carrier while the cartridge is secured in place within the chamber.

15. The carrier of claim 12, wherein the cartridge holder is releasably coupled to the cartridge via spring clips, and the release mechanism is configured to cause the spring clips on the cartridge holder to partially release the cartridge from the cartridge holder.

16. The carrier of claim 15, wherein the release mechanism comprises a first set of posts that pushes apart the spring clips to partially release the cartridge when the cartridge assembly is coupled to the carrier.

17. The carrier of claim 16, wherein the retention mechanism comprises the first set of posts and a second set of posts, wherein the first and second sets of posts contact different portions of the cartridge to constrain the cartridge in the secured position.

18. The carrier of claim 17, wherein at least two of the different portions of the cartridge are non-coplanar with each other.

19. The carrier of claim 17, wherein at least two of the different portions of the cartridge are coplanar with each other.

20. The carrier of claim 17, wherein at least two of the different portions of the cartridge are substantially parallel with each other.

21. The carrier of claim 17, wherein the second set of posts is configured to limit a travel distance of the cartridge into the chamber.

22. The carrier of claim 17, wherein the first set of posts is in contact with laterally opposite side portions of the cartridge.

23. The carrier of claim 22, wherein the at least one mating feature is located on the laterally opposite side portions of the cartridge.

24. The carrier of claim 17, wherein the second set of posts is in contact with a distal portion of the cartridge.

25. The carrier of claim 17, wherein the cartridge comprises a fluid access port, and wherein the fluid access port is disposed between the second set of posts when the released cartridge is stored in the secured position within the chamber.

26. The carrier of claim 1, wherein the carrier is sized and shaped to accommodate user or patient identity (ID) labels.

27. The carrier of claim 1, further comprising: a peelable foil for sealing the opening of the chamber prior to coupling the cartridge assembly to the carrier.

28. The carrier of claim 27, wherein the peelable foil is configured to protect the chamber of the carrier from moisture and contamination prior to use of the carrier for storing and transporting the blood sample.

* * * * *